(12) United States Patent
Chen

(10) Patent No.: US 8,026,359 B2
(45) Date of Patent: Sep. 27, 2011

(54) FUNGICIDAL HETEROCYCLIC AMINES

(75) Inventor: Yuzhong Chen, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/741,047

(22) PCT Filed: May 14, 2009

(86) PCT No.: PCT/US2008/082398
§ 371 (c)(1),
(2), (4) Date: May 3, 2010

(87) PCT Pub. No.: WO2009/061761
PCT Pub. Date: May 14, 2009

(65) Prior Publication Data
US 2010/0267729 A1  Oct. 21, 2010

Related U.S. Application Data

(60) Provisional application No. 61/002,129, filed on Nov. 6, 2007.

(51) Int. Cl.
*C07D 403/04* (2006.01)
*C07D 403/14* (2006.01)
*C07D 401/04* (2006.01)
*C07D 401/14* (2006.01)
*C07D 407/14* (2006.01)
*C07D 409/14* (2006.01)
*C07D 413/14* (2006.01)
*C07D 417/14* (2006.01)
*A01N 43/66* (2006.01)
*A01N 43/54* (2006.01)

(52) U.S. Cl. .................. 544/194; 544/209; 514/245
(58) Field of Classification Search ............. 544/194, 544/209; 514/245
See application file for complete search history.

(56) References Cited

U.S. PATENT DOCUMENTS
2004/0043388 A1  3/2004  Come et al.

FOREIGN PATENT DOCUMENTS

| WO | 01/25220 A1 | 4/2001 |
|---|---|---|
| WO | 01/93682 A1 | 12/2001 |
| WO | 03/037891 A1 | 5/2003 |
| WO | 2004/084634 A1 | 10/2004 |
| WO | 2004/089286 A2 | 10/2004 |
| WO | 2005/033095 A1 | 4/2005 |
| WO | 2006/044732 A2 | 4/2006 |
| WO | 2008/148889 A1 | 12/2008 |

OTHER PUBLICATIONS

Database registry, Chemical Abstracts Service, Columbus, Ohio; XP002523618; published Dec. 20, 2007.
C. Pillonel, "Evaluation of Phenylaminopyrimidines as Antifungal Protein Kinase Inhibitors", *Pest Management Science*, 2005, vol. 61, pp. 1069-1076.

*Primary Examiner* — Venkataraman Balasubramanian
(74) *Attorney, Agent, or Firm* — Renee M. Lett

(57) ABSTRACT

Disclosed are compounds of Formula 1, N-oxides, and salts thereof,

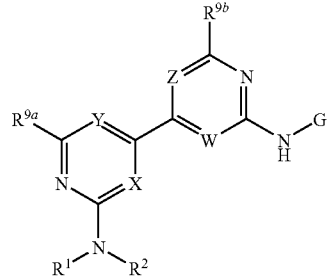

wherein
$R^1$, $R^2$, $R^{9a}$, $R^{9b}$, G, W, X, Y, and Z are as defined in the disclosure.

Also disclosed are compositions containing the compounds of Formula 1 and methods for controlling plant disease caused by a fungal pathogen comprising applying an effective amount of a compound or a composition of the invention.

10 Claims, No Drawings

US 8,026,359 B2

FUNGICIDAL HETEROCYCLIC AMINES

FIELD OF THE INVENTION

This invention relates to certain amines, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds which are more effective, less costly, less toxic, environmentally safer or have different sites of action.

Certain N-phenyl amines have been previously described. World Patent Publication WO 05/033095 discloses amine derivatives of Formula i as fungicides

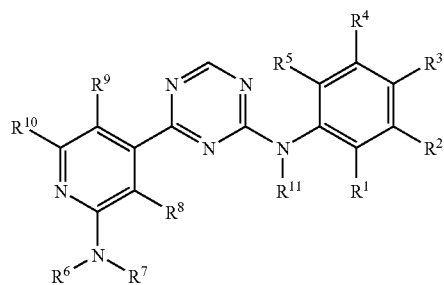

wherein, inter alia, each of $R^1$, $R^2$, $R^3$, $R^4$, $R^5$, $R^8$, $R^9$ and $R^{10}$ are independently H, halogen or alkyl; and each of $R^6$, $R^7$ and $R^{11}$ are independently H or alkyl. World Patent Publication WO 04/084634 discloses amine derivatives of Formula ii as fungicides

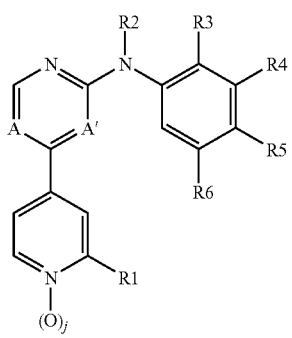

wherein, inter alia, A and A' are both N or A and A' are both CH or A is CH and A' is N; each of R3, R4, R5 and R6 are independently H, halogen or alkyl; R2 is H or alkyl; and R1 is hydrazino or optionally substituted amino. World Patent Publication WO 01/93682 discloses amine derivatives of Formula iii as fungicides

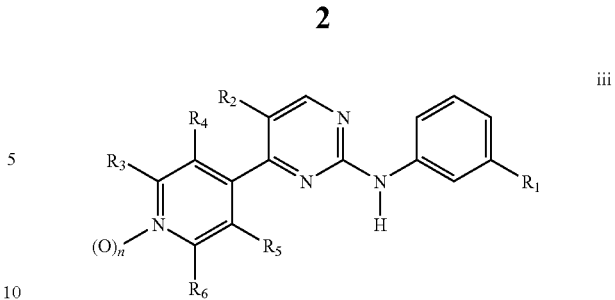

wherein, inter alia, each of $R_1$, $R_2$, $R_3$, $R_4$ and $R_5$ are independently H, halogen or alkyl; and $R_6$ is hydrazino or optionally substituted amino.

The amines of the present invention are not disclosed in these publications.

SUMMARY OF THE INVENTION

This invention is directed to compounds of Formula 1 (including all geometric and stereoisomers), N-oxides, and salts thereof, agricultural compositions containing them and their use as fungicides:

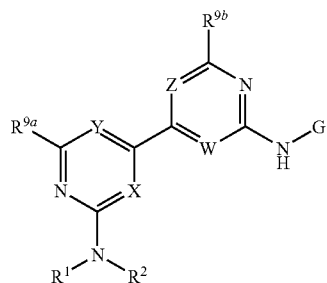

wherein
$R^1$ is H, halogen, cyano, hydroxy, amino, nitro, —CHO or —C(=O)NH$_2$; or C$_1$-C$_6$ alkyl, C$_2$-C$_6$ alkenyl, C$_2$-C$_6$ alkynyl, C$_2$-C$_8$ alkylcarbonyl, C$_2$-C$_8$ alkoxycarbonyl, C$_2$-C$_8$ alkylaminocarbonyl, C$_3$-C$_{10}$ dialkylaminocarbonyl, C$_1$-C$_6$ alkoxy, C$_3$-C$_8$ cycloalkoxy, C$_2$-C$_8$ alkylcarbonyloxy, C$_4$-C$_{10}$ cycloalkylcarbonyloxy, C$_1$-C$_6$ alkylthio, C$_3$-C$_8$ cycloalkylthio, C$_1$-C$_6$ alkylsulfinyl, C$_1$-C$_6$ alkylsulfonyl, C$_3$-C$_8$ cycloalkylsulfonyl, C$_1$-C$_6$ alkylamino, C$_2$-C$_8$ dialkylamino, C$_3$-C$_8$ cycloalkylamino, C$_2$-C$_8$ alkylcarbonylamino, C$_1$-C$_6$ alkylsulfonylamino, G$^A$, G$^N$ or naphthalenyl, each optionally substituted with one or more substituents selected from the group consisting of halogen, cyano, hydroxy, amino, nitro, —CHO, —C(=O)OH, —C(=O)NH$_2$, C$_1$-C$_6$ alkyl, C$_2$-C$_6$ alkenyl, C$_2$-C$_6$ alkynyl, C$_1$-C$_6$ haloalkyl, C$_2$-C$_8$ alkylcarbonyl, C$_2$-C$_8$ haloalkylcarbonyl, C$_4$-C$_{10}$ cycloalkylcarbonyl, C$_2$-C$_8$ alkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_{10}$ cycloalkylaminocarbonyl, C$_1$-C$_6$ alkoxy, C$_1$-C$_6$ haloalkoxy, C$_3$-C$_8$ cycloalkoxy, C$_3$-C$_8$ halocycloalkoxy, C$_4$-C$_{10}$ cycloalkylalkoxy, C$_2$-C$_6$ alkenyloxy, C$_2$-C$_6$ haloalkenyloxy, C$_2$-C$_6$ alkynyloxy, C$_3$-C$_6$ haloalkynyloxy, C$_2$-C$_8$ alkoxyalkoxy, C$_2$-C$_8$ alkylcarbonyloxy, C$_2$-C$_8$ haloalkylcarbonyloxy, C$_4$-C$_{10}$ cycloalkylcarbonyloxy, C$_1$-C$_6$ alkylthio, C$_1$-C$_6$ haloalkylthio, C$_3$-C$_8$ cycloalkylthio, C$_1$-C$_6$ alkylsulfinyl, C$_1$-C$_6$ haloalkylsulfinyl, C$_1$-C$_6$ alkylsulfonyl, C$_1$-C$_6$ haloalkylsulfonyl, C$_3$-C$_8$ cycloalkylsulfonyl, $C_3$-$C_{10}$ trialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, $G^A$, $G^N$ and phenyl;

$R^2$ is H, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_2$-$C_8$ alkoxyalkyl, $C_4$-$C_{10}$ cycloalkoxyalkyl or $C_3$-$C_{10}$ alkoxyalkoxyalkyl; or $R^1$ and $R^2$ are taken together with the nitrogen to which they are attached to form a 3- to 7-membered ring, containing ring members, in addition to the nitrogen, selected from the group consisting of $C(R^8)_2$, O, S, $NR^3$, —$C(R^8)$=$C(CR^8)$—, —$C(R^8)$=N—, —N=N—, $C(=O)$, $C(=S)$, $C(=NR^4)$, $S(=O)_p(=NR^4)_q$ and $SiR^{5a}R^{5b}$;

each $G^A$ is independently benzoyl, phenoxy or phenylsulfonyl or a 5- or 6-membered heteroaromatic ring;

each $G^N$ is independently a 3- to 7-membered nonaromatic carbocyclic or heterocyclic ring, containing ring members selected from the group consisting of $C(R^8)_2$, O, S, $NR^3$, —$C(R^8)$=$C(CR^8)$—, —$C(R^8)$=N—, —N=N—, $C(=O)$, $C(=S)$, $C(=NR^4)$, $S(=O)_p(=NR^4)_q$ and $SiR^{5a}R^{5b}$;

each $R^3$ is independently H, cyano, hydroxy, —$C(=O)NH_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_3$-$C_8$ cycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_4$-$C_{10}$ dialkylaminoalkyl, $C_3$-$C_8$ haloalkylaminoalkyl, $C_4$-$C_{10}$ cycloalkylaminoalkyl, $C_2$-$C_{10}$ alkylcarbonyl, $C_2$-$C_{10}$ haloalkylcarbonyl, $C_4$-$C_{10}$ cycloalkylcarbonyl, $C_2$-$C_{10}$ alkoxycarbonyl, $C_4$-$C_{10}$ cycloalkoxycarbonyl, $C_2$-$C_{10}$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkoxyalkoxy, $C_1$-$C_6$ alkylthio, $C_1$-$C_6$ haloalkylthio, $C_3$-$C_8$ cycloalkylthio, $C_1$-$C_6$ alkylsulfonyl, $C_1$-$C_6$ haloalkylsulfonyl, $C_3$-$C_8$ cycloalkylsulfonyl, $C_3$-$C_5$ trialkylsilyl or $C_3$-$C_5$ halotrialkylsilyl;

each $R^4$ is independently H, cyano, amino, hydroxy, $C_1$-$C_6$ alkyl, $C_3$-$C_{10}$ cycloalkyl, $C_2$-$C_6$ alkylcarbonyl, $C_2$-$C_6$ haloalkylcarbonyl, $C_1$-$C_6$ alkoxy, phenyl or benzoyl;

each $R^{5a}$ and $R^{5b}$ is independently $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_4$-$C_{10}$ cycloalkylalkyl, $C_4$-$C_{10}$ alkylcycloalkyl, $C_5$-$C_{12}$ alkylcycloalkylalkyl, $C_1$-$C_6$ haloalkyl, $C_1$-$C_6$ alkoxy or $C_1$-$C_6$ haloalkoxy;

G is benzoyl, phenoxy, phenylethynyl, phenylsulfonyl or —$(CR^{6a}R^{6b})_nG^B$;

$G^B$ is a phenyl ring, naphthalenyl or a 5- to 6-membered heteroaromatic ring, each ring optionally substituted with 1 to 5 substituents independently selected from $R^7$;

each $R^{6a}$ and $R^{6b}$ is independently H, halogen, —$C(=O)OH$, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_4$-$C_{10}$ cycloalkylalkyl, $C_4$-$C_8$ alkylcycloalkyl, $C_5$-$C_{12}$ alkylcycloalkylalkyl, $C_1$-$C_6$ haloalkyl, $C_2$-$C_8$ alkoxycarbonyl, $C_1$-$C_6$ alkoxy or $C_1$-$C_6$ haloalkoxy; or $R^{6a}$ and $R^{6b}$ in geminal configuration are taken together with the carbon atom to which they are attached to form a 3- to 7-membered ring, containing ring members, in addition to the carbon atom, selected from the group consisting of $C(R^8)_2$, O, S, $NR^3$, —$C(R^8)$=$C(CR^8)$—, —$C(R^8)$=N—, —N=N—, $C(=O)$, $C(=S)$, $C(=NR^4)$, $S(=O)_p(=NR^4)_q$ and $SiR^{5a}R^{5b}$;

$R^7$ is halogen, cyano, hydroxy, amino, nitro, —CHO, —$C(=O)OH$, —$C(=O)NH_2$, —$SO_2NH_2$, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^8$ is independently H, halogen, CN, $C_1$-$C_3$ alkyl or $C_1$-$C_3$ alkoxy;

X is N or $CR^{9c}$;
Y is N or $CR^{9d}$;
W is N or $CR^{9e}$;
Z is N or $CR^{9f}$;

each $R^{9a}$, $R^{9b}$, $R^{9c}$, $R^{9d}$, $R^{9e}$ and $R^{9f}$ is independently H, halogen, nitro, CN, $C_1$-$C_3$ alkyl, $C_1$-$C_3$ haloalkyl, $C_3$-$C_6$ cycloalkyl, $C_1$-$C_3$ alkoxy or $C_1$-$C_3$ haloalkoxy;

n is an integer selected from 0 through 6; and p and q are independently 0, 1 or 2 in each instance of $S(=O)_p(=NR^4)_q$, provided that the sum of p and q is 0, 1 or 2;

provided that:
(a) when $R^1$ is hydroxy, then $R^2$ is other than hydroxy; and
(b) at least one of X or Y is N.

More particularly, this invention pertains to a compound of Formula 1 (including all geometric and stereoisomers), an N-oxide, or a salt thereof.

This invention also relates to a fungicidal composition comprising a fungicidally effective amount of a compound of Formula 1 and at least one additional component selected from the group consisting of surfactants, solid diluents or liquid diluents.

This invention also relates to a fungicidal composition comprising a mixture of a compound of Formula 1 and at least one other fungicide.

This invention further relates to a method for controlling plant diseases caused by fungal plant pathogens comprising applying to the plant or portion thereof, or to the plant seed or seedling, a fungicidally effective amount of a compound of the invention (e.g., as a composition described herein).

DETAILS OF THE INVENTION

As used herein, the terms "comprises," "comprising," "includes," "including," "has," "having" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and Both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $CH_3CH=CHCH_2O$, $CH_3CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(=O)$, $CH_3CH_2S(=O)$, $CH_3CH_2CH_2S(=O)$, $(CH_3)_2CHS(=O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers.

"Alkylamino includes an NH radical substituted with straight-chain or branched alkyl. Examples of "alkylamino" include $CH_3CH_2NH$, $CH_3CH_2CH_2NH$, and $(CH_3)_2CHCH_2NH$. Examples of "dialkylamino" include $(CH_3)_2N$, $(CH_3CH_2CH_2)_2N$ and $CH_3CH_2(CH_3)N$. "Alkylaminoalkyl" denotes alkylamino substitution on alkyl. Examples of "alkylaminoalkyl" include $CH_3NHCH_2$, $CH_3NHCH_2CH_2$, $CH_3CH_2NHCH_2$, $CH_3CH_2CH_2NHCH_2$ and $CH_3CH_2NHCH_2CH_2$. Examples of "dialkylaminoalkyl" include $(CH_3)_2CH(CH_3)N$, $(CH_3CH_2CH_2)_2N$ and $CH_3CH_2(CH_3)N$. The term "alkylcarbonylamino" denotes alkyl bonded to a $C(=O)NH$ moiety. Examples of "alkylcarbonylamino" include $CH_3CH_2C(=O)NH$ and $CH_3CH_2CH_2C(=O)NH$.

The term "cycloalkyl" includes, for example, cyclopropyl, cyclobutyl, cyclopentyl, and cyclohexyl. The term "cycloalkylalkyl" denotes cycloalkyl substitution on an alkyl group. Examples of "cycloalkylalkyl" include cyclopropylmethyl, cyclopentylethyl, and other cycloalkyl moieties bonded to straight-chain or branched alkyl groups. "Alkylcycloalkyl" denotes alkyl substitution on a cycloalkyl moiety. Examples include 4-methylcyclohexyl and 3-ethylcyclopentyl. "Cycloalkenyl" includes groups such as cyclopentenyl and cyclohexenyl as well as groups with more than one double bond such as 1,3- and 1,4-cyclohexadienyl. The term "cycloalkoxy" denotes cycloalkyl attached to and linked through an oxygen atom such as cyclopentyloxy and cyclohexyloxy. The term "cycloalkoxyalkyl" denotes cycloalkoxy substitution on an alkyl moiety. Examples of "cycloalkoxyalkyl" include cyclopropyloxymethyl, cyclopentyloxyethyl, and other cycloalkoxy moieties bonded to straight-chain or branched alkyl groups. "Cycloalkylalkoxy" denotes cycloalkylalkyl attached to and linked through an oxygen atom. Examples of "cycloalkylalkoxy" include cyclopropylmethoxy, cyclopentylethoxy, and other cycloalkyl moieties bonded to straight-chain or branched alkoxy groups. The term "cycloalkylthio" denotes cycloalkyl attached to and linked through a sulfur atom such as cyclopropylthio and cyclopentylthio; "cycloalkylsulfonyl" includes the corresponding sulfones. "Cycloalkylamino" denotes an NH radical substituted with cycloalkyl. Examples of "cycloalkylamino" include cyclopropylamino and cyclohexylamino. The term "cycloalkylaminoalkyl" denotes cycloalkylamino substitution on an alkyl group. Examples of "cycloalkylaminoalkyl" include cyclopropylaminomethyl, cyclopentylaminoethyl, and other cycloalkylamino moieties bonded to straight-chain or branched alkyl groups. "Cycloalkylcarbonyl" denotes cycloalkyl bonded to a $C(=O)$ group including, for example, cyclopropylcarbonyl and cyclopentylcarbonyl.

"Trialkylsilyl" includes three branched and/or straight-chain alkyl radicals attached to and linked through a silicon atom such as trimethylsilyl, triethylsilyl and t-butyl-dimethylsilyl.

The term "alkylcarbonyl" denotes straight-chain or branched alkyl bonded to a $C(=O)$ moiety. Examples of "alkylcarbonyl" include $CH_3C(O)$, $CH_3CH_2CH_2C(O)$ and $(CH_3)_2CHC(O)$. Examples of "alkoxycarbonyl" include $CH_3OC(=O)$, $CH_3CH_2OC(=O)$, $CH_3CH_2CH_2C(=O)$, $(CH_3)_2CHOC(=O)$ and the different butoxy- or pentoxycarbonyl isomers. Examples of "alkylaminocarbonyl" include $CH_3NHC(=O)$, $CH_3CH_2NHC(=O)$, $CH_3CH_2CH_2NHC(=O)$, $(CH_3)_2CHNHC(=O)$ and the different butylamino- or pentylaminocarbonyl isomers. Examples of "dialkylaminocarbonyl" include $(CH_3)_2NC(=O)$, $(CH_3CH_2)_2NC(=O)$, $CH_3CH_2(CH_3)NC(=O)$, $(CH_3)_2CHN(CH_3)C(=O)$ and $CH_3CH_2CH_2(CH_3)NC(=O)—$.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "halocycloalkyl", "haloalkoxy", "haloalkylthio", haloalkylamino and the like, are defined analogously to the term "haloalkyl". Examples of "haloalkenyl" include $(Cl)_2C=CHCH_2$ and $CF_3CH_2CH=CHCH_2$. Examples of "haloalkynyl" include HC≡CCHCl, CF$_3$C≡C, CCl$_3$C≡C and FCH$_2$C≡CCH$_2$. Examples of "haloalkoxy" include CF$_3$O, CCl$_3$CH$_2$O, HCF$_2$CH$_2$CH$_2$O and CF$_3$CH$_2$O. Examples of "haloalkylthio" include CCl$_3$S, CF$_3$S, CCl$_3$CH$_2$S and ClCH$_2$CH$_2$CH$_2$S. Examples of "haloalkylsulfinyl" include CF$_3$S(=O), CCl$_3$S(=O), CF$_3$CH$_2$S(=O) and CF$_3$CF$_2$S(=O). Examples of "haloalkylsulfonyl" include CF$_3$S(O)$_2$, CCl$_3$S(O)$_2$, CF$_3$CH$_2$S(O)$_2$ and CF$_3$CF$_2$S(O)$_2$. Examples of "haloalkylamino" include CF$_3$(CH$_3$)CHNH, (CF$_3$)$_2$CHNH and CH$_2$ClCH$_2$NH. Examples of "halodialkylamino" include (BrCH$_2$CH$_2$)$_2$N and BrCH$_2$CH$_2$(ClCH$_2$CH$_2$)N.

The total number of carbon atoms in a substituent group is indicated by the "$C_i$-$C_j$" prefix where i and j are numbers from 1 to 12. For example, $C_1$-$C_4$ alkylsulfonyl designates methylsulfonyl through butylsulfonyl; $C_2$ alkoxyalkyl designates CH$_3$OCH$_2$; $C_3$ alkoxyalkyl designates, for example, CH$_3$CH(OCH$_3$), CH$_3$OCH$_2$CH$_2$ or CH$_3$CH$_2$OCH$_2$; and $C_4$ alkoxyalkyl designates the various isomers of an alkyl group substituted with an alkoxy group containing a total of four carbon atoms, examples including CH$_3$CH$_2$CH$_2$OCH$_2$ and CH$_3$CH$_2$OCH$_2$CH$_2$. $C_2$ alkylaminoalkyl designates CH$_3$NHCH$_2$—; $C_3$ alkylaminoalkyl designates, for example, CH$_3$(CH$_3$NH)CH—, CH$_3$NHCH$_2$CH$_2$— or CH$_3$CH$_2$NHCH$_2$—; and $C_4$ alkylaminoalkyl designates the various isomers of an alkyl group substituted with an alkylamino group containing a total of four carbon atoms, examples including CH$_3$CH$_2$CH$_2$NHCH$_2$— and CH$_3$CH$_2$NHCH$_2$CH$_2$—.

When a compound is substituted with a substituent bearing a subscript that indicates the number of said substituents can vary, when the number of said substituents is greater than 1, said substituents are independently selected from the group of defined substituents. Further, when the subscript indicates a range, e.g. $(R)_{i-j}$, then the number of substituents may be selected from the integers between i and j inclusive. Also, one skilled in the art recognizes that the number of available points of attachment is a limit of the number of substituents possible and may be lower than the broad definition.

When a group contains a substituent which can be hydrogen, for example $R^1$, $R^2$, $R^3$, $R^4$, $R^{6a}$, $R^{6b}$, $R^8$ or $R^9$ then, when this substituent is taken as hydrogen, it is recognized that this is equivalent to said group being unsubstituted at that position. The term "optionally substituted" without recitation of limitation in connection with the groups listed for $R^1$ refers to groups that are unsubstituted or have at least 1 non-hydrogen substituent. These groups may be substituted with as many optional substituents as can be accommodated by replacing a hydrogen atom with a non-hydrogen substituent on any available carbon or nitrogen atom. When the term "optionally substituted" is accompanied by a limit as for the groups listed for $G^B$, the number of optional substituents cannot exceed the limit even if further positions for substitution are available. Therefore, for example, the phrase "optionally substituted with 1 to 5 substituents" means than no substituent may be present, 1 substituent may be present, or up to 5 substituents may be present if accommodated by the number of positions available for substitution.

Naming of substituents in the present disclosure uses recognized terminology providing conciseness in precisely conveying to those skilled in the art the chemical structure. For sake of conciseness, locant descriptors may be omitted; "pyrazol-1-yl" means "1H-pyrazol-1-yl" according to the Chemical Abstracts system of nomenclature. The term "pyridyl" is synonymous with "pyridinyl". The order of listing substituents may be different from the Chemical Abstracts system if the difference does not affect the meaning.

Unless otherwise indicated, a "ring" as a component of Formula 1 (e.g., substituent $G^N$) is carbocyclic or heterocyclic. The term "ring member" refers to an atom or other moiety (e.g., C(=O), C(=S), S(O) or S(O)$_2$) forming the backbone of a ring or ring system.

"Aromatic" refers to a ring wherein each of the ring atoms is essentially in the same plane and has a p-orbital perpendicular to the ring plane, and in which (4n+2) π electrons, where n is a positive integer, are associated with the ring to comply with Hückel's rule. When a fully unsaturated carbocyclic ring satisfies Hückel's rule, then said ring is also called an "aromatic ring". "Saturated carbocyclic" refers to a ring having a backbone consisting of carbon atoms linked to one another by single bonds; unless otherwise specified, the remaining carbon valences are occupied by hydrogen atoms. The term "saturated ring" denotes a ring having a backbone consisting of atoms linked to one another by single bonds; unless otherwise specified, the remaining valences are occupied by hydrogen atoms. In regards to degree of saturation, a "partially saturated ring" (alternatively described as a "partially unsaturated ring") is intermediate between a saturated ring and a fully unsaturated ring (which may be aromatic). Therefore the term "partially saturated ring" (which may be carbocyclic or heterocyclic unless otherwise stated) denotes a ring comprising at least one ring member bonded to an adjacent ring member through a double bond and also comprising at least one ring member bonded to an adjacent ring member through a single bond that conceptually could be replaced by a double bond to form a less saturated ring.

The terms "carbocyclic ring" or "carbocycle" denote a ring wherein the atoms forming the ring backbone are selected only from carbon. Unless otherwise indicated, a carbocyclic ring can be a saturated, partially saturated, or fully unsaturated ring. When a fully unsaturated carbocyclic ring satisfies Hückel's rule, then said ring is also called an "aromatic ring". A carbocyclic ring that does not satisfy Hückel's rule is described as a "nonaromatic carbocyclic ring".

The terms "heterocyclic ring" or "heterocycle" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially saturated, or fully unsaturated ring. When a fully unsaturated heterocyclic ring satisfies Hückel's rule, then said ring is also called a "heteroaromatic ring" or "aromatic heterocyclic ring". A heterocyclic ring that does not satisfy Hückel's rule is described as a "nonaromatic heterocyclic ring". The term "saturated heterocyclic ring" denotes a heterocyclic ring in which no ring member is bonded to an adjacent ring member through a double bond. The term "partially saturated heterocyclic ring" denotes a heterocyclic ring comprising at least one ring member bonded to an adjacent ring member through a double bond and also comprising at least one ring member bonded to an adjacent ring member through a single bond that conceptually could be replaced by a double bond to form a less saturated heterocyclic ring. Unless otherwise indicated, heterocyclic rings can be attached through any available carbon or nitrogen by replacement of a hydrogen on said carbon or nitrogen. In the above recitations, when a compound of Formula 1 is comprised of one or more heterocyclic rings, substituents (if present) are attached to these rings through any available carbon or nitrogen by replacement of a hydrogen on said carbon or nitrogen.

As noted above, $G^A$ can be (among others) a 5- or 6-membered heteroaromatic ring, optionally substituted with one or more substituents independently selected from a group of substituents as defined in the Summary of the Invention. Examples of 5- or 6-membered heteroaromatic rings optionally substituted with one or more substituents include the rings G-2 through G-61 illustrated in Exhibit 1 wherein $R^v$ is any substitutent as defined in the Summary of the Invention for $G^A$ (i.e. as defined in $R^1$).

As noted above, $G^B$ can be (among others) phenyl optionally substituted with up to 5 substituents selected from a group of substituents as defined in the Summary of Invention. An example of phenyl optionally substituted with up to five substituents is the ring illustrated as G-1 in Exhibit 1, wherein $R^v$ is selected from a group of substituents as defined in the Summary of the Invention for $G^B$ (i.e., $R^7$) and r is an integer from 0 to 5.

As noted above, $G^B$ can be (among others) naphthalenyl, each ring of which is stated to be optionally substituted with 1 to 5 substituents (independently selected from $R^7$), which one skilled in the art recognizes is limited by the number of available ring positions. As is well known in the art, the naphthalenyl ring system consists of two phenyl rings fused together at adjacent carbon atoms. The ring of naphthalenyl attached to the remainder of Formula 1 has 3 positions available for $R^7$ substituents, and the other ring of naphthalenyl has 4 positions available for $R^7$ substituents.

As noted above, $G^B$ can be (among others) a 5- or 6-membered heteroaromatic ring, optionally substituted with up to 1 to 5 substituents independently selected from a group of substituents as defined in the Summary of the Invention. Examples of 5- or 6-membered heteroaromatic rings optionally substituted with one or more substituents include the rings G-2 through G-61 illustrated in Exhibit 1 wherein $R^v$ is any substituent as defined in the Summary of the Invention for $G^B$ (i.e., $R^7$) and r is an integer from 0 to 5, limited by the number of available positions on each G group. As G-29, G-30, G-36, G-37, G-38, G-39, G-40, G-41, G-42 and G-43 have only one available position, for these G groups r is limited to the integers 0 or 1, and r being 0 means that the G group is unsubstituted and a hydrogen is present at the position indicated by $(R^v)_r$.

Exhibit 1

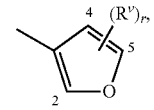
G-1

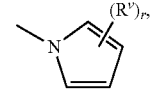
G-2

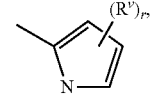
G-3

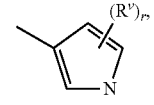
G-4

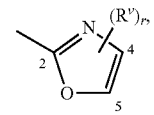
G-5

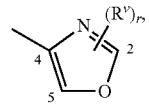
G-6

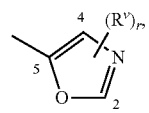
G-7

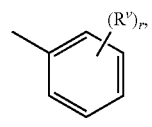
G-8

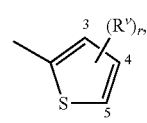
G-9

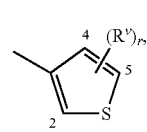
G-10

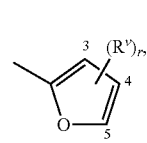
G-11

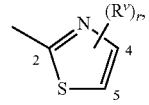
G-12

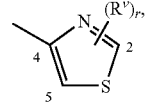
G-13

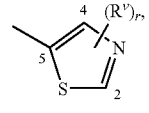
G-14

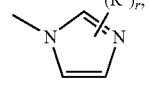
G-15

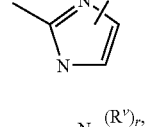
G-16

G-17

-continued
G-18 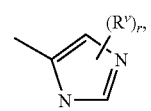
G-19 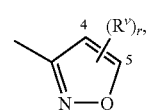
G-20 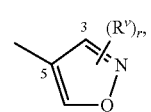
G-21 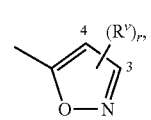
G-22 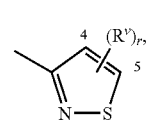
G-23 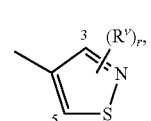
G-24 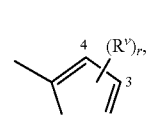
G-25 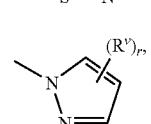
G-26 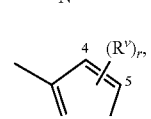
G-27 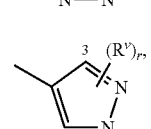
G-28 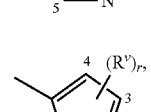
G-29 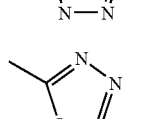
G-30 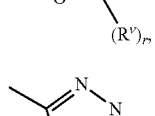
-continued
G-31 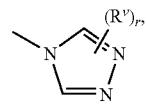
G-32 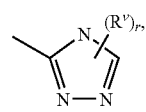
G-33 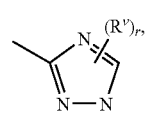
G-34 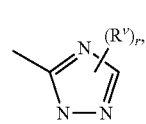
G-35 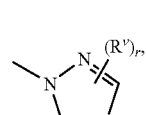
G-36 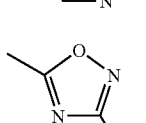
G-37 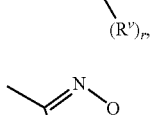
G-38 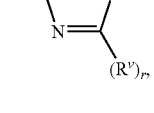
G-39 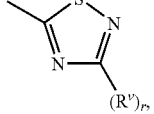
G-40 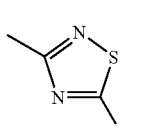
G-41 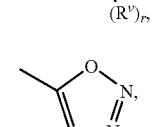
G-42 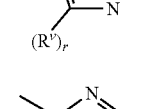

-continued

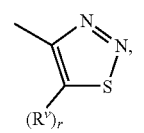 G-43

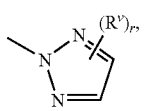 G-44

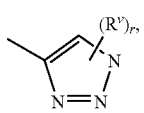 G-45

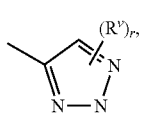 G-46

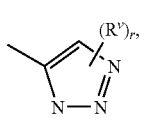 G-47

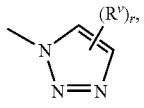 G-48

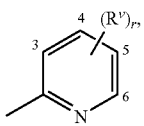 G-49

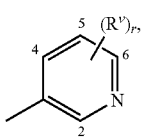 G-50

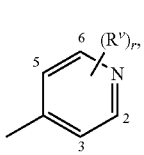 G-51

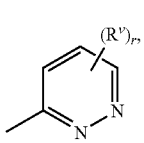 G-52

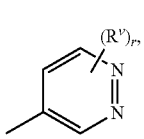 G-53

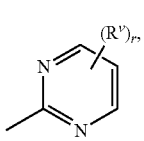 G-54

-continued

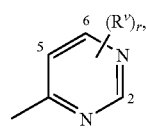 G-55

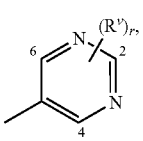 G-56

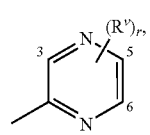 G-57

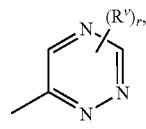 G-58

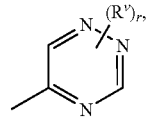 G-59

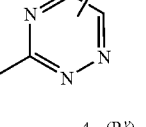 G-60 and

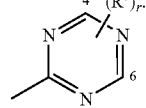 G-61

As noted above, $G^N$ can be (among others) a 3- to 7-membered nonaromatic heterocyclic ring. Examples of a 3-, 4-, 5- or 6-membered saturated or partially unsaturated heterocyclic ring include the rings H-1 through H-48 as illustrated in Exhibit 2 wherein $R^v$ is any substituent as defined in the Summary of the Invention for $G^N$ (e.g. $R^3$ on nitrogen ring members, $R^4$ on double-bonded nitrogen substituents, $R^{5a}$ and $R^{5b}$ on silicon ring members and $R^8$ on carbon ring members) and r is typically an integer from 0 to 5, limited by the number of available positions on each H-ring. The optional substituents corresponding to $(R^v)_r$ can be attached to any available carbon or nitrogen by replacing a hydrogen atom. Note that when the attachment point on the H-ring is illustrated as floating, the H-ring can be attached to the remainder of Formula 1 through any available carbon or nitrogen of the H-ring by replacement of a hydrogen atom.

Note that when $G^N$ comprises a ring selected from H-33, H-34, H-35 and H-41 through H-45, $G^2$ is O, S or N. Note that when $G^2$ is N, the nitrogen atom can complete its valence by substitution with either H or the substituents corresponding to R³ as defined in the Summary of Invention.
Exhibit 2
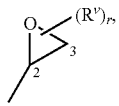
H-1
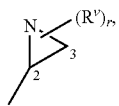
H-2
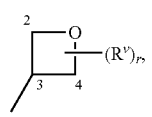
H-3
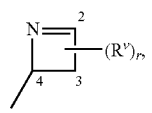
H-4
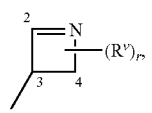
H-5
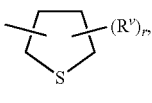
H-6
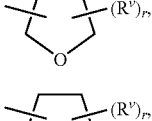
H-7
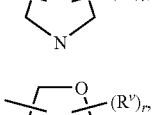
H-8
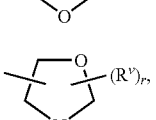
H-9
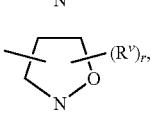
H-10
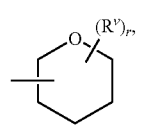
H-11
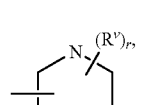
H-12
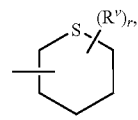
H-13
-continued
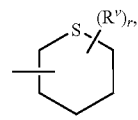
H-14
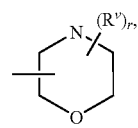
H-15
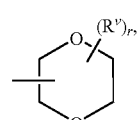
H-16
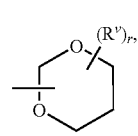
H-17
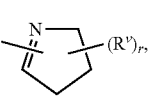
H-18
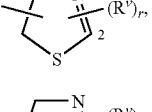
H-19
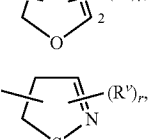
H-20
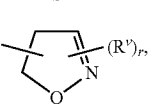
H-21
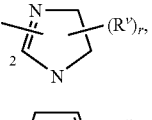
H-22
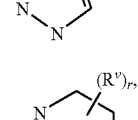
H-23
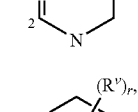
H-24
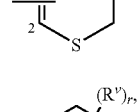
H-25
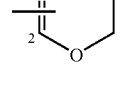
H-26
H-27

-continued
H-28 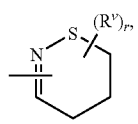
H-29 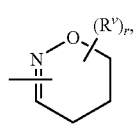
H-30 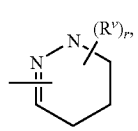
H-31 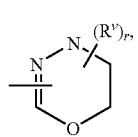
H-32 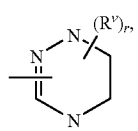
H-33 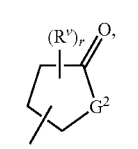
H-34 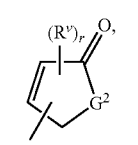
H-35 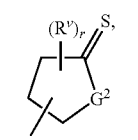
H-36 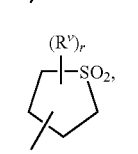
H-37 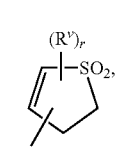
H-38 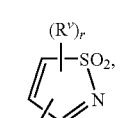
H-39 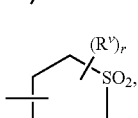
-continued
H-40 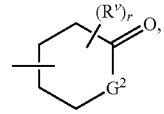
H-41 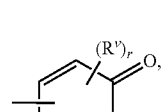
H-42 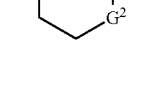
H-43 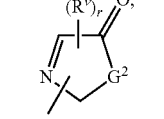
H-44 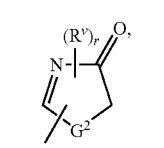
H-45 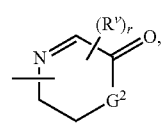
H-46 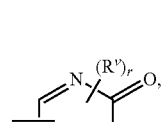
H-47 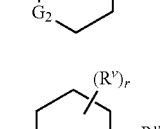
H-48 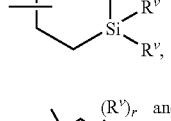
As noted above, $G^N$ can be (among others) a 3- to 7-membered nonaromatic carbocyclic ring. Examples of 3- to 7-membered nonaromatic carbocyclic rings include the rings J-1 through J-9 as illustrated in Exhibit 3 wherein $R^v$ is any substituent on carbon as defined in the Summary of the Invention for $G^N$ (i.e. $R^8$).

Exhibit 3

 J-1

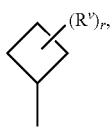 J-2

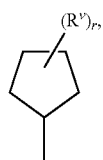 J-3

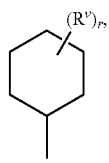 J-4

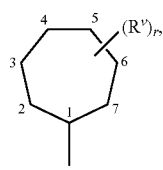 J-5

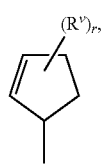 J-6

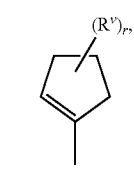 J-7

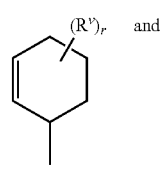 J-8 and

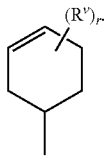 J-9

One skilled in the art will appreciate that not all nitrogen-containing heterocycles can form N-oxides since the nitrogen requires an available lone pair of electrons for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds of Formula 1, N-oxides or salts thereof. The compounds of the invention may be present as a mixture of stereoisomers, individual stereoisomers, or as an optically active form. Compounds of Formula 1 can comprise chiral centers. For example, the substituents $R^1$, $R^2$, $R^{9a}$, $R^{9b}$, $R^{9c}$, $R^{9d}$, $R^{9e}$, $R^{9f}$ and G may contain chiral centers. This invention comprises racemic mixtures as well as enriched and essentially pure stereoconfigurations at these additional chiral centers.

When enantiomerically enriched, one enantiomer is present in greater amounts than the other, and the extent of enrichment can be defined by an expression of enantiomeric excess ("ee"), which is defined as $(2x-1)\cdot 100\%$, where x is the mole fraction of the dominant enantiomer in the mixture (e.g., an ee of 20% corresponds to a 60:40 ratio of enantiomers).

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of this invention can exist as one or more conformational isomers due to the amide bonds in the compounds of Formula 1 as known by one skilled in the art. This invention comprises mixtures of conformational isomers. In addition, this invention includes compounds that are enriched compared to the mixture of a conformer of Formula 1.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of plant diseases caused by fungal plant pathogens (i.e., are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include those described below. In the following Embodiments, Formula 1 includes N-oxides and salts thereof, and reference to "a compound of Formula 1" includes the definitions of substituents specified in the Summary of the Invention unless further defined in the Embodiments.

Embodiment 1

A compound of Formula 1 wherein $R^1$ is $C_1$-$C_6$ alkyl, $C_2$-$C_6$ alkenyl, $C_2$-$C_6$ alkynyl, $C_2$-$C_8$ alkylcarbonyl, $C_2$-$C_8$ alkoxycarbonyl, $C_2$-$C_8$ alkylaminocarbonyl, $C_3$-$C_{10}$ dialkylaminocarbonyl, $C_1$-$C_6$ alkoxy, $C_3$-$C_8$ cycloalkoxy, $C_1$-$C_6$ alkylthio, $C_3$-$C_8$ cycloalkylthio, $C_1$-$C_6$ alkylsulfinyl, $C_1$-$C_6$ alkylsulfonyl, $C_3$-$C_8$ cycloalkylsulfonyl, $G^A$ or $G^N$, each optionally substituted with one or more substituents selected from the group consisting of halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylamino carbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, $G^A$, $G^N$ and phenyl.

Embodiment 2

A compound of Embodiment 1 wherein $R^1$ is $C_1$-$C_6$ alkyl, $C_2$-$C_6$ alkenyl, $C_2$-$C_6$ alkynyl or $G^N$, each optionally substituted with one or more substituents selected from the group consisting of halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, $G^A$, $G^N$ and phenyl.

Embodiment 3

A compound of Embodiment 2 wherein $R^1$ is $C_1$-$C_6$ alkyl, $C_2$-$C_6$ alkenyl, $C_2$-$C_6$ alkynyl or $G^N$, each optionally substituted with one or more substituents selected from the group consisting of halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl and $G^N$.

Embodiment 4

A compound of Embodiment 3 wherein $R^1$ is $C_1$-$C_6$ alkyl, $C_2$-$C_6$ alkenyl, $C_2$-$C_6$ alkynyl or $G^N$, each optionally substituted with one or more substituents selected from the group consisting of halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy and $G^N$.

Embodiment 5

A compound of Embodiment 4 wherein $R^1$ is 2-methoxy-1-methylethyl, 2-ethoxy-1-methylethyl, 2-methoxy-1-ethylethyl, 2-ethoxy-1-ethylethyl, 3-methoxy-1-methylpropyl, 3-ethoxy-1-methylpropyl, 1-ethyl-3-methoxypropyl, 3-ethoxy-1-ethylpropyl or tetrahydro-2H-pyran-4-yl.

Embodiment 6

A compound of Embodiment 5 wherein $R^1$ is 2-methoxy-1-methylethyl or tetrahydro-2H-pyran-4-yl.

Embodiment 7

A compound of Embodiment 6 wherein $R^1$ is 2-methoxy-1-methylethyl.

Embodiment 8

A compound of Embodiment 6 wherein $R^1$ is tetrahydro-2H-pyran-4-yl.

Embodiment 9

A compound of Formula 1 or any one of Embodiments 1 through 8 wherein $R^2$ is H, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, $C_2$-$C_8$ alkoxyalkyl, $C_4$-$C_{10}$ cycloalkoxyalkyl or $C_3$-$C_{10}$ alkoxyalkoxyalkyl.

Embodiment 10

A compound of Embodiment 9 wherein $R^2$ is H or $C_1$-$C_6$ alkyl.

Embodiment 11

A compound of Embodiment 10 wherein $R^2$ is H.

Embodiment 12

A compound of Formula 1 wherein $R^1$ and $R^2$ are taken together with the nitrogen to which they are attached to form a 5- to 6-membered ring containing ring members, in addition to the nitrogen, selected from the group consisting of $C(R^8)_2$, O, S, NR$^3$, —C($R^8$)=C(CR$^8$)—, —C($R^8$)=N—, —N=N—, C(=O), C(=S), C(=NR$^4$), S(=O)$_p$(=NR$^4$)$_q$ and SiR$^{5a}$R$^{5b}$.

Embodiment 13

A compound of Embodiment 12 wherein $R^1$ and $R^2$ are taken together with the nitrogen to which they are attached to form a 5-membered ring, containing ring members, in addition to the nitrogen, selected from the group consisting of $C(R^8)_2$, O, S, NR$^3$, —C($R^8$)=C(CR$^8$)—, —C($R^8$)=N—, —N=N—, C(=O), C(=S), C(=NR$^4$), S(=O)$_p$(=NR$^4$)$_q$ and SiR$^{5a}$R$^{5b}$;

Embodiment 14

A compound of Embodiment 13 wherein $R^1$ and $R^2$ are taken together to form a 4-methyl-2-oxo-3-oxazolidin-3-yl ring.

Embodiment 14A

A compound of Formula 1 wherein when $R^1$ and $R^2$ are taken together with the nitrogen to which they are attached to form a ring, the ring is 5- or 6-membered.

Embodiment 14B

A compound of Embodiment 14A wherein when $R^1$ and $R^2$ are taken together with the nitrogen to which they are attached to form a ring, the ring is 5-membered.

Embodiment 15

A compound of Formula 1 or any one of Embodiments 1 through 14B wherein each $R^3$ is independently H, cyano, hydroxy, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_3$-$C_8$ cycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_4$-$C_{10}$ dialkylaminoalkyl, $C_3$-$C_8$ haloalkylaminoalkyl or $C_4$-$C_{10}$ cycloalkylaminoalkyl.

Embodiment 16

A compound of Embodiment 15 wherein each $R^3$ is independently H, cyano, —C(=O)NH$_2$, $C_1$-$C_6$ alkyl, $C_2$-$C_6$ alkenyl, $C_2$-$C_6$ alkynyl, $C_1$-$C_6$ haloalkyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_2$-$C_8$ alkoxyalkyl, $C_4$-$C_{10}$ cycloalkoxyalkyl or $C_3$-$C_{10}$ alkoxyalkoxyalkyl.

Embodiment 17

A compound of Formula 1 or any one of Embodiments 1 through 16 wherein G is —(CR$^{6a}$R$^{6b}$)$_n$G$^B$.

Embodiment 18

A compound of Embodiment 17 wherein G is G$^B$.

Embodiment 19

A compound of Formula 1, or any one of Embodiments 1 through 18 wherein G$^B$ is a phenyl ring, naphthalenyl or 5- to 6-membered heteroaromatic ring, each ring optionally substituted with from 1 to 3 substituents independently selected from R$^7$.

Embodiment 19A

A compound of Embodiment 19 wherein G$^B$ is naphthalenyl or a phenyl or pyridinyl ring, each optionally substituted

Embodiment 20

A compound of Embodiment 19 wherein $G^B$ is a 5-membered heteroaromatic ring, optionally substituted with from 1 to 3 substituents independently selected from $R^7$.

Embodiment 21

A compound of Embodiment 19 wherein $G^B$ is a phenyl ring or 6-membered heteroaromatic ring, each ring optionally substituted with up to 3 substituents independently selected from $R^7$.

Embodiment 22

A compound of Embodiment 19A or 21 wherein $G^B$ is a phenyl or pyridinyl ring, each optionally substituted with up to 3 substituents independently selected from halogen, $C_1$-$C_6$ alkyl, $C_1$-$C_6$ haloalkyl and $C_1$-$C_6$ alkoxy.

Embodiment 23

A compound of Embodiment 22 wherein $G^B$ is phenyl optionally substituted at the 3 and 5 positions with substituents selected from halogen and $C_1$-$C_6$ alkyl.

Embodiment 24

A compound of Embodiment 23 wherein $G^B$ is phenyl optionally substituted at the 3 and 5 positions with halogen.

Embodiment 25

A compound of Embodiment 22 wherein $G^B$ is phenyl optionally substituted at the 3 position with substituents selected from halogen and $C_1$-$C_6$ alkyl.

Embodiment 26

A compound of Embodiment 25 wherein $G^B$ is phenyl optionally substituted at the 3 position with halogen.

Embodiment 27

A compound of Embodiment 22 wherein $G^B$ is 3-pyridinyl or 4-pyridinyl, each optionally substituted with up to 3 substituents independently selected from halogen, $C_1$-$C_6$ alkyl, $C_1$-$C_6$ haloalkyl and $C_1$-$C_6$ alkoxy.

Embodiment 28

A compound of Embodiment 27 wherein $G^B$ is 3-pyridinyl or 4-pyridinyl, each optionally substituted with up to 3 substituents independently selected from halogen and $C_1$-$C_6$ alkyl.

Embodiment 29

A compound of Formula 1 or any one of Embodiments 1 through 28 wherein each $R^{6a}$ and $R^{6b}$ is independently H.

Embodiment 30

A compound of Formula 1 or any one of Embodiments 1 through 29 wherein each $R^{9a}$, $R^{9b}$, $R^{9c}$, $R^{9d}$, $R^{9e}$ and $R^{9f}$ is independently H or halogen.

Embodiment 31

A compound of Embodiment 30 wherein each $R^{9a}$, $R^{9b}$, $R^{9c}$, $R^{9d}$, $R^{9e}$ and $R^{9f}$ is H.

Embodiment 32

A compound of Formula 1 or any one of Embodiments 1 through 31 wherein each X, W and Z is N and Y is CH; X is N and each Y, W and Z is CH; each X, Y and W is N and Z is CH; each X and Z is N and each Y and W is CH; or each X and Z is CH and each Y and W is N.

Embodiment 33

A compound of Embodiment 32 wherein each X, W and Z is N and Y is CH.

Embodiment 34

A compound of Embodiment 32 wherein X is N and each Y, W and Z is CH.

Embodiment 35

A compound of Embodiment 32 wherein each X, Y and W is N and Z is CH.

Embodiment 36

A compound of Embodiment 32 wherein each X and Z is N and each Y and W is CH.

Embodiment 37

A compound of Embodiment 32 wherein each X and Z is independently CH and each Y and W is N.

Embodiments of this invention, including Embodiments 1-37 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-37 above as well as any other embodiments described herein, and any combination thereof, pertain to the compositions and methods of the present invention.

Combinations of Embodiments 1-37 are illustrated by:

Embodiment A1

A compound of Formula 1 wherein
$R^1$ is $C_1$-$C_6$ alkyl, $C_2$-$C_6$ alkenyl, $C_2$-$C_6$ alkynyl or $G^N$, each optionally substituted with one or more substituents selected from the group consisting of halogen, cyano, hydroxy, amino,
nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy and $G^N$;

$R^2$ is H or $C_1$-$C_6$ alkyl;

G is $G^B$; and each X, W and Z is N and Y is CH; X is N and each Y, W and Z is CH; each X, Y and W is N and Z is CH; each X and Z is N and each Y and W is CH; or each X and Z is CH and each Y and W is N.

Embodiment A2

A compound of Embodiment A1 wherein $R^1$ is 2-methoxy-1-methylethyl, 2-ethoxy-1-methylethyl, 2-methoxy-1-ethylethyl, 2-ethoxy-1-ethylethyl, 3-methoxy-1-methylpropyl, 3-ethoxy-1-methylpropyl, 1-ethyl-3-methoxypropyl, 3-ethoxy-1-ethylpropyl or tetrahydro-2H-pyran-4-yl;

$R^2$ is H; and $G^B$ is naphthalenyl or a phenyl or pyridinyl ring, each optionally substituted with up to 3 substituents independently selected from halogen, $C_1$-$C_6$ alkyl, $C_1$-$C_6$ haloalkyl and $C_1$-$C_6$ alkoxy.

Embodiment A3

A compound of Embodiment A2 wherein $R^1$ is 2-methoxy-1-methylethyl or tetrahydro-2H-pyran-4-yl; and $G^B$ is phenyl optionally substituted at the 3 and 5 positions with halogen.

Embodiment A4

A compound of Embodiment A3 wherein $G^B$ is phenyl optionally substituted at the 3 position with halogen.

Specific embodiments include compounds of Formula 1 selected from the group consisting of:

N-(3,5-difluorophenyl)-4-[2-[[(1S)-2-methoxy-1-methylethyl]amino]-4-pyrimidinyl]-1,3,5-triazin-2-amine;

4-[2-[(3-chlorophenyl)amino]-4-pyridinyl]-N-(2-methoxy-1-methylethyl)-2-pyrimidinamine;

N-(3-fluorophenyl)-4-[2-[[(1S)-2-methoxy-1-methylethyl]amino]-4-pyrimidinyl]-1,3,5-triazin-2-amine;

N-(3-fluorophenyl)-4-[2-[(2-methoxy-1-methylethyl)amino]-4-pyrimidinyl]-1,3,5-triazin-2-amine; and 4-[2-[(2-chloro-6-methylphenyl)amino]-4-pyridinyl]-N-(tetrahydro-2H-pyran-4-yl)-2-pyrimidinamine.

Of note are the above embodiments, including Embodiments 1 through 37 and A1 through A4, wherein Formula 1 does not include N-oxides and salts thereof.

This invention provides a fungicidal composition comprising a compound of Formula 1 (including all geometric and stereoisomers, N-oxides, and salts thereof), and at least one other fungicide. Of note as embodiments of such compositions are compositions comprising a compound corresponding to any of the compound embodiments describe above.

This invention provides a fungicidal composition comprising a fungicidally effective amount of a compound of Formula 1 (including all geometric and stereoisomers, N-oxides, and salts thereof), and at least one additional component selected from the group consisting of surfactants, solid diluents and liquid diluents. Of note as embodiment of such compositions are compositions comprising a compound corresponding to any of the compound embodiments describe above.

This invention provides a method for controlling plant diseases caused by fungal plant pathogens comprising applying to the plant or portion thereof, or to the plant seed or seedling, a fungicidally effective amount of a compound of Formula 1 (including all geometric and stereoisomers, N-oxides, and salts thereof). Of note as embodiment of such methods are methods comprising applying a fungicidally effective amount of a compound corresponding to any of the compound embodiments describe above. Of particular notes are embodiments where the compounds are applied as compositions of this invention.

One or more of the following methods and variations as described in Schemes 1-23 can be used to prepare the compounds of Formula 1. The definitions of $R^1$, $R^2$, $R^{9a}$, $R^{9b}$, $R^{9c}$, $R^{9d}$, $R^{9e}$, $R^{9f}$ and G in the compounds of Formulae 1-25a below are as defined above in the Summary of the Invention unless otherwise noted. Formulae 1a-1e are various subsets of Formula 1, and all substituents for Formulae 1a-1e are as defined above for Formula 1.

Scheme 1

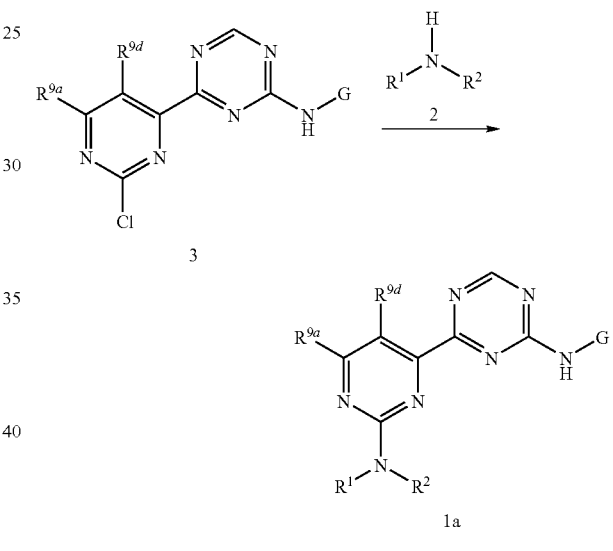

As shown in Scheme 1, compounds of Formula 1a (Formula 1 wherein Y is $CR^{9d}$ and X, W and Z are N) can be prepared by coupling of a compound of Formula 3 with an amine of Formula 2 in the presence of acid scavenger. An excess of the amine of Formula 2 can also be used as an acid scavenger. Typical acid scavengers include amine bases such as triethylamine, N,N-diisopropylethylamine and pyridine. The reaction is typically conducted in a common organic solvent such as tetrahydrofuran, acetone, ethyl acetate, acetonitrile, N,N-dimethylformamide or dimethylsulfoxide in the presence of excess of the amine of Formula 2, usually in 2 to 10 equivalents relative to the compound of Formula 3. The reaction is typically conducted at a temperature of about 50° C. to about 120° C. over a period of 0.5 to 20 h. When $R^1$ and $R^2$ are taken together with the nitrogen to which they are attached to form substituted oxazolidin-2-ones, a palladium catalyst is needed to effectively catalyze the reaction. Similar methods of displacing chloride from 2-chloropyridinyl-1,3,5-triazinyl derivatives with 4-methyl-oxazolidin-2-one have been described in PCT Patent Publication WO 2005/033095 A1.

Scheme 2

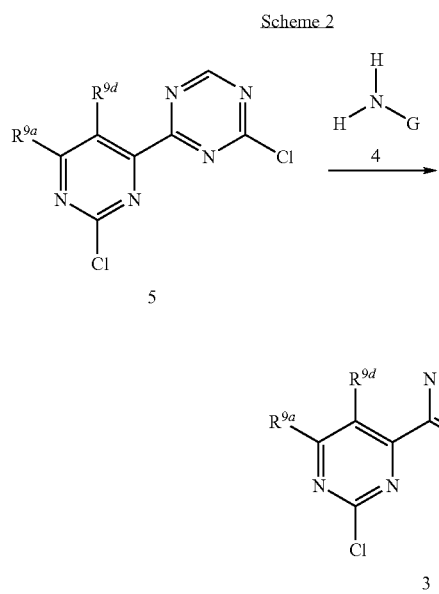

As shown in Scheme 2, compounds of Formula 3 can be prepared by coupling a compound of Formula 5 with an amine of Formula 4 in a common organic solvent such as tetrahydrofuran, acetone, ethyl acetate, acetonitrile, N,N-dimethylformamide or dimethylsulfoxide in the presence of excess of the amine of Formula 4, usually in 2 to 10 equivalents relative to the compound of Formula 5. The reaction is typically run at room temperature to about 60° C. over a period of about 1 to 20 h.

Scheme 3

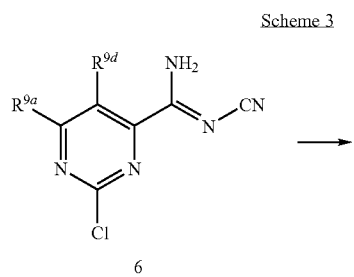

As shown in Scheme 3, compounds of Formula 5 can be prepared from compounds of Formula 6 by adding a solution prepared from mixing phosphorus(V) oxychloride and N,N-dimethylformamide to the compound of Formula 6 to in acetonitrile at a temperature range from about −20° C. to 10° C. The reaction is typically run at 0° C. over a period of about 12 to 20 h.

Scheme 4

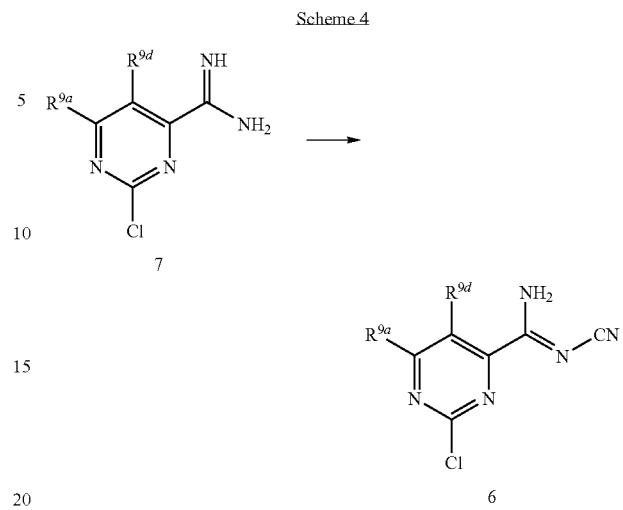

As shown in Scheme 4, the compound of Formula 6 can be prepared by treatment of the compound of Formula 7 with cyanamide in a mixture of water and isopropanol in a ratio in the range of 1:1 to 4:1. The reaction is typically run at room temperature over a period of about 10 to 20 h.

Scheme 5

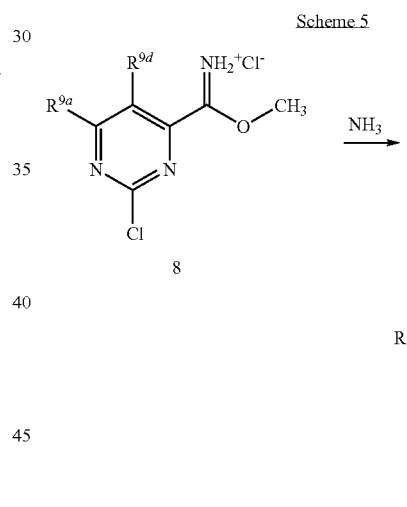

As shown in Scheme 5, the compound of Formula 7 can be prepared by treatment of the compound of Formula 8 with ammonia in methyl alcohol at room temperature over a period of about 3 to 10 h.

Scheme 6

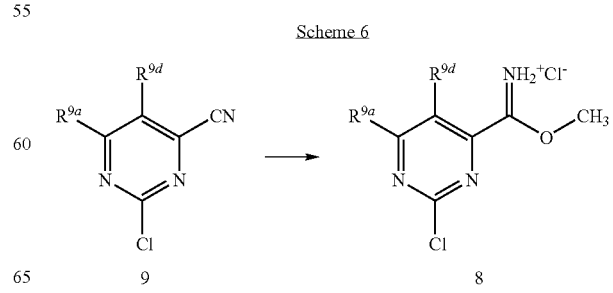

As shown in Scheme 6, the compound of Formula 8 can be prepared by treatment of commercially available compound 9 with hydrochloric acid in the presence of methanol in a suitable organic solvent, such as toluene, benzene or methylene chloride. The reaction is typically run at a temperature from about 0° C. to about 20° C. over a period of about 8 to 20 h.

Scheme 7

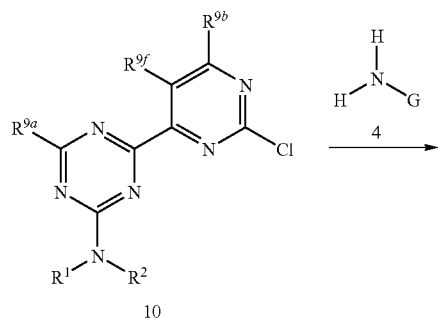

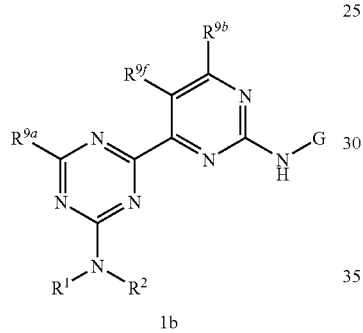

1b

As shown in Scheme 7, compounds of Formula 1b (Formula 1 wherein Z is $CR^{9f}$ and W, X and Y are N) can be prepared by coupling a compound of Formula 10 with an amine of Formula 4. The reaction is conducted in the presence of 0.5 to 5 mol % of a palladium catalyst, such as palladium (II) acetate or tris(dibenzylideneacetone)dipalladium(0), and 1 to 10% of a ligand such as (±)-2,2'-bis(diphenylphosphino)-1,1'-binaphthalene, and a base such as cesium carbonate. The reaction is typically run in a common organic solvent such as tetrahydrofuran, toluene, or 1,4-dioxane at a temperature range from about 70° C. to about 120° C. over a period of about 0.5 to 20 h.

Scheme 8

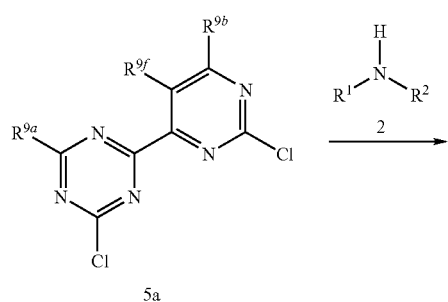

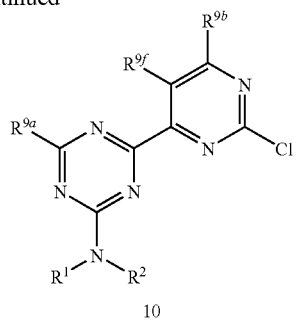

10

As shown in Scheme 8, compounds of Formula 10 can be prepared by coupling a compound of Formula 5a with an amine of Formula 2. The reaction is conducted in an organic solvent such as tetrahydrofuran, acetone, ethyl acetate, acetonitrile, N,N-dimethylformamide or dimethylsulfoxide in the presence of excess of the amine of Formula 2, usually in 2 to 10 equivalents relative to the compound of Formula 5a. The reaction is usually run at a temperature from about 0° C. to about 30° C. over a period of about 0.5 to 20 h. Compounds of Formula 5a can be prepared by methods analogous to methods for preparing compounds of Formula 5 (e.g. Scheme 3).

Scheme 9

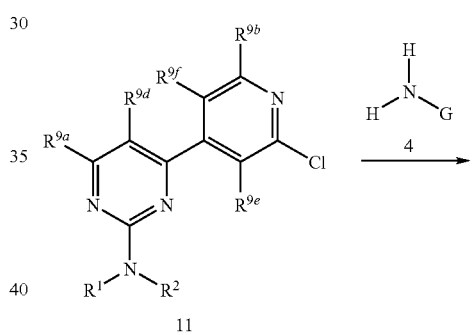

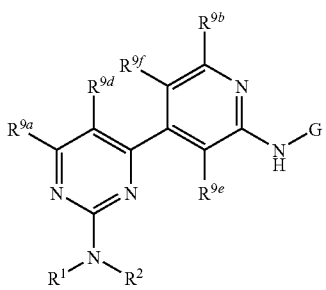

1c

As shown in Scheme 9, compounds of Formula 1c (Formula 1 wherein X is N, W is $CR^{9e}$, Y is $CR^{9d}$ and Z is $CR^{9f}$) can be prepared by coupling a compound of Formula 11 with an amine of Formula 4. The reaction is conducted with an excess of the amine of Formula 4, relative to compound of Formula 11, in common organic solvents such as toluene and 1,4-dioxane with heating at a temperature range of about 80° C. to about 110° C. for 5 to 24 hours. The method typically involves palladium catalysts such as palladium(II) acetate or tris(dibenzylideneacetone)dipalladium(0) and ligands such as (±)-2,2'-bis(diphenylphosphino)-1,1'-binaphthalene ((±)-BINAP), 4,5-bis(diphenylphosphino)-9,9-dimethylxanthene (Xantphos) or 2-(di-t-butyl or dicyclohexylphosphino)biphenyl. An excess amount (usually 2 to 3 equivalents relative to the compound of Formula 11) of base, such as sodium t-butoxide, cesium carbonate or tribasic potassium phosphate, is employed in these reactions. This Buchwald-Hartwig C—N bond forming reactions are well known in the literature; general methods for forming C—N bonds can be found in Buchwald, S. L. et al, *J. Org. Chem.* 2000, 65, 1158-1174.

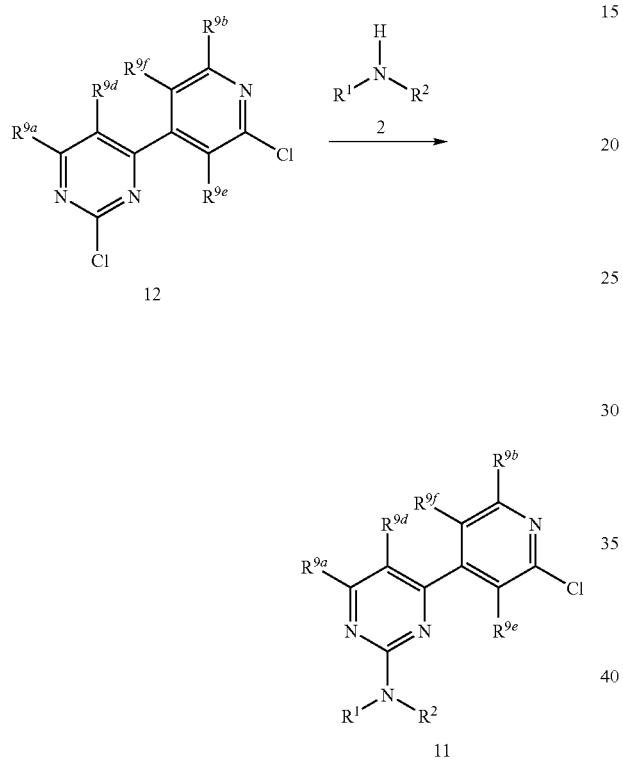

As shown in Scheme 10, compounds of Formula 11 can be prepared by heating compounds of Formula 12 with an excess amount of an amine of Formula 2. The reaction is conducted neat or in common organic solvents such as tetrahydrofuran, acetone, ethyl acetate, acetonitrile, N,N-dimethylformamide or dimethylsulfoxide, typically at temperatures ranging from about 50° C. to about 120° C. over a period of about 1 to 20 h.

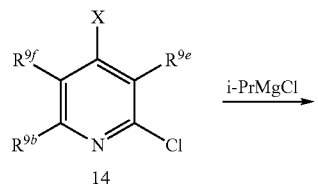

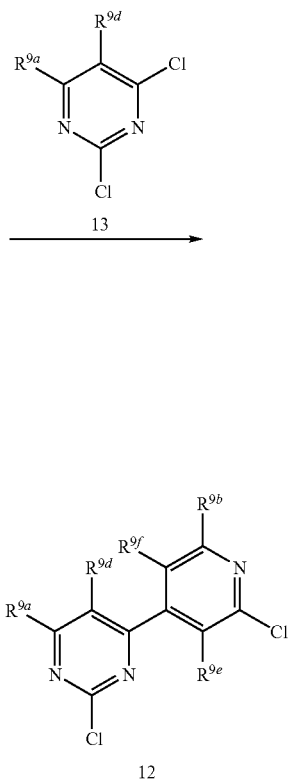

As shown in Scheme 11, compounds of Formula 12 can be prepared by treatment of compounds of Formula 15 with a compound of Formula 13 in the presence of palladium cross-coupling catalyst PdCl$_2$(dppf). General procedures can be found from Negishi, E., et al. *Handbook of Organopalladium Chemistry for Organic Synthesis Volumes* 1 *and* 2, (2002). The intermediate compound of Formula 15 can be prepared from the compound of Formula 14 (wherein X is Br or I) using isopropylmagnesium chloride as reported by Queguiner, G. et al. *Tetrahedron* 2000, 56, 1349. Compounds of Formula 14 can be prepared by methods reported in Swahn, B. M. et al, *Bioorg. Med. Chem. Lett.* 2006, 16, 1397-1401.

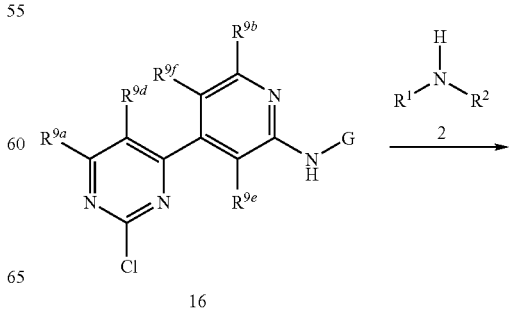

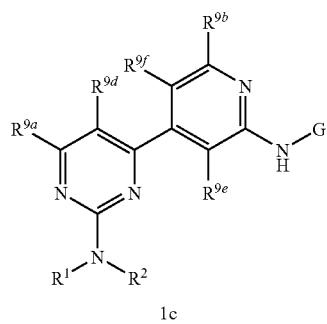

1c

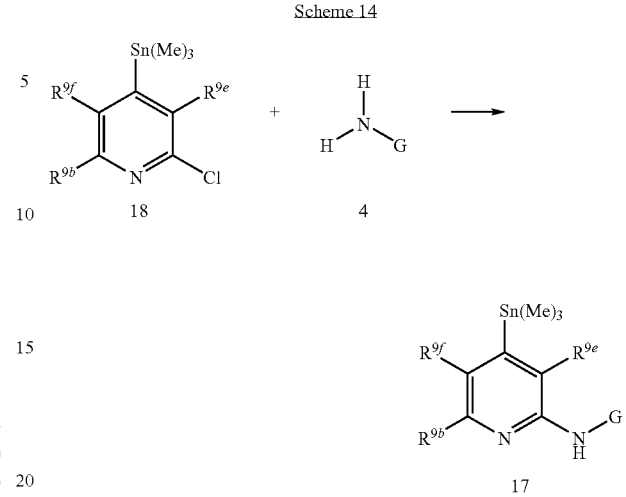

As shown in Scheme 12, compounds of Formula 1c (Formula 1 wherein X is N, W is $CR^{9e}$, Y is $CR^{9d}$ and Z is $CR^{9f}$) can be prepared by treatment of intermediates of Formula 16 with amines of Formula 2 under conditions as described in Scheme 1. When $R^1$ and $R^2$ are taken together with the nitrogen to which they are attached to form substituted oxazolidin-2-ones, a palladium catalyst is needed to effectively catalyze the reactions. Similar methods of displacing chloride from 2-chloropyridinyl-1,3,5-triazinyl derivatives with 4-methyl-oxazolidin-2-one have been described in PCT Patent Publication WO 2005/033095 A1.

As shown in Scheme 14, compounds of Formula 17 can be prepared by Buchwald-Hartwig C—N bond-forming reactions involving treatment of compounds of Formula 18 with amines of Formula 4 analogous to the method of Scheme 9.

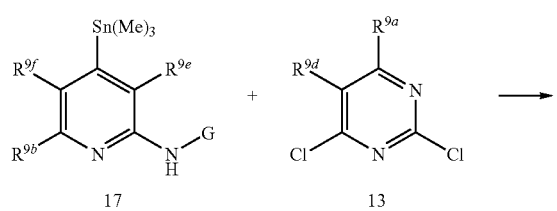

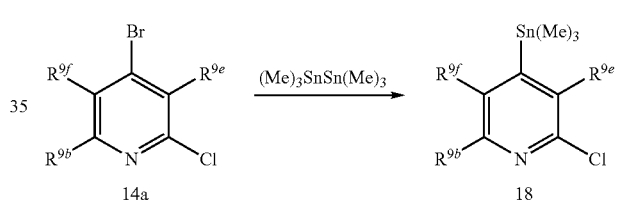

As shown in Scheme 15, compounds of Formula 18 can be prepared by treatment of the pyridine of Formula 14a (Formula 14 wherein X is Br) with hexamethylditin in the presence of palladium catalyst such as tetrakis(triphenylphosphine)palladium(0) or bis(triphenylphosphine)palladium(II) dichloride in organic solvents, such as 1,4-dioxane or tetrahydrofuran, at temperatures ranging from about 70° C. to about 120° C. over a period of 10 minutes to 5 h. A similar procedure was reported by Zhang, Y. et al. *J. Med. Chem.*, 2004, 47(10), 2453.

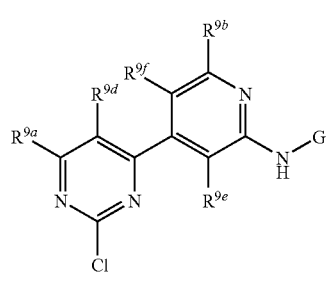

16

As shown in Scheme 13, compounds of Formula 16 can be prepared by cross-coupling of compounds of Formula 17 with a compound of Formula 13. This method is typically conducted in a solvent such as 1,4-dioxane, toluene or N-methyl-2-pyrrolidinone at temperatures from about 80° C. to about 110° C. over a period from about 1 to 20 h in the presence of palladium catalysts such as bis(triphenylphosphine)palladium(II) dichloride or tetrakis(triphenylphosphine)palladium(0) and catalytic amounts of copper salts such as copper iodide.

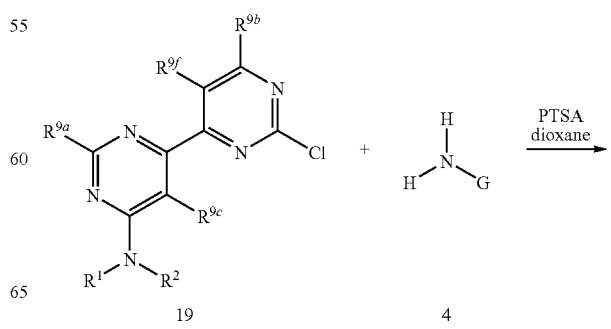

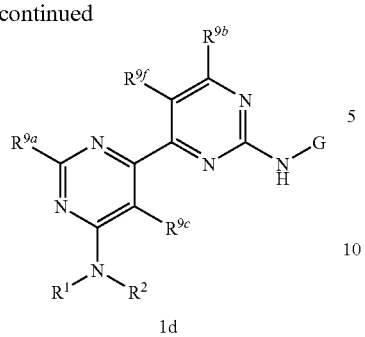

1d

As shown in Scheme 16, compounds of Formula 1d (Formula 1 wherein X is $CR^{9c}$, Z is $CR^{9f}$ and W and Y are N) are prepared by heating intermediates of Formula 19 with an excess amount of the amine of Formula 4. Typically the reaction is conducted in the presence of a catalytic amount of p-toluenesulfonic acid monohydrate (PTSA) in 1,4-dioxane at temperatures ranging from about 80° C. to about 120° C. over a period of 5 to 20 h. This method is disclosed in GB 2369359.

Scheme 17

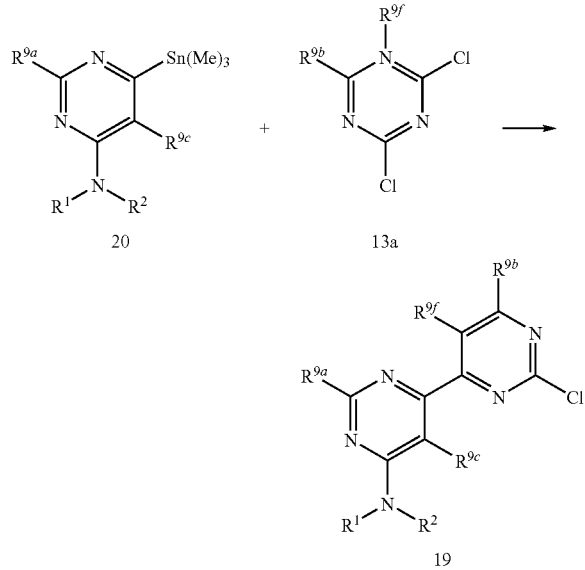

As shown in Scheme 17, compounds of Formula 19 can be prepared by cross-coupling a compound of Formula 20 with a compound of Formula 13a analogous to the method of Scheme 13.

Scheme 18

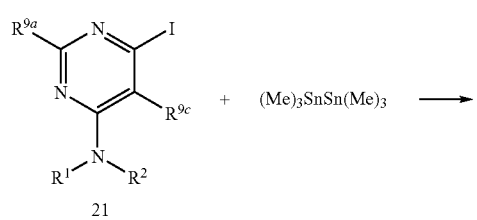

As shown in Scheme 18, compounds of Formula 20 can be prepared by treatment of compounds of Formula 21 with hexamethylditin in the presence of a palladium catalyst such as bis(triphenylphosphine)palladium(II) dichloride or tetrakis(triphenylphosphine)-palladium(0). Representative procedures can be found in the literature, e.g., Undheim, K. et al. *Tetrahedron* 1989, 45, 993-1006.

Scheme 19

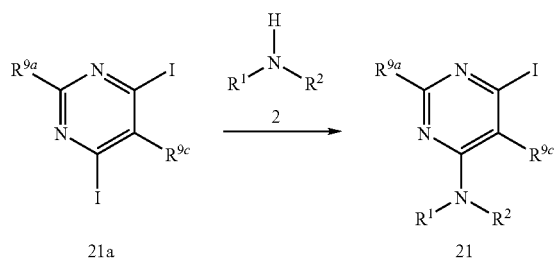

As shown in Scheme 19, compounds of Formula 21 can be prepared by treatment of compounds of Formula 21a with an excess of amine of Formula 2. Introduction of the amino group can be achieved by heating in a "closed vessel", such as a microwave vial or pressure/bomb vessel, with organic solvents such as 1,4-dioxane or N-methylpyrrolidinone in the presence of a hindered base such as triethylamine or N,N-diisopropylethylamine at temperatures ranging from about 80° C. to about 220° C. over a period of 0.3 to 20 h. Compounds of Formula 21a can be prepared according to Boucher, E. et al, *J. Org. Chem.* 1995, 60, 1408-1412.

Scheme 20

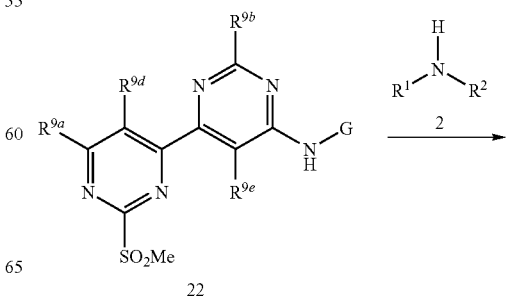

-continued

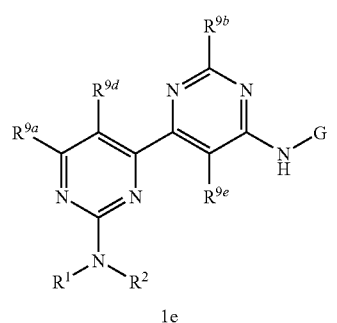

1e

As shown in Scheme 20, compounds of Formula 1e (Formula 1 wherein W is $CR^{9e}$, Y is $CR^{9d}$ and X and Z are N) can be prepared by coupling of compounds of Formula 22 with an excess amount of the amine of Formula 2. The reaction is conducted neat or in organic solvents such as tetrahydrofuran, acetone, acetonitrile, N,N-dimethylformamide or dimethylsulfoxide typically at temperatures ranging from about 50° C. to about 120° C. over a period of 1 to 20 h.

Scheme 21

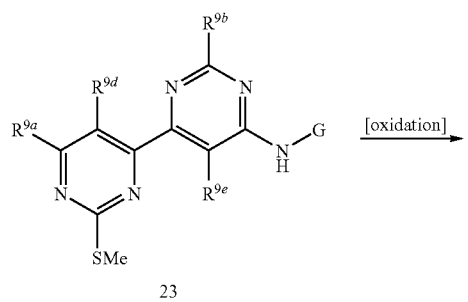

As shown in Scheme 21, compounds of Formula 22 can be prepared by treatment of compounds of Formula 23 with an oxidizing reagent such as m-chloroperbenzoic acid (MCPBA) or Oxone® in organic solvents such as chloroform or dichloromethane at temperatures ranging from about 0° C. to about 20° C. over a period of 2 to 20 h.

Scheme 22

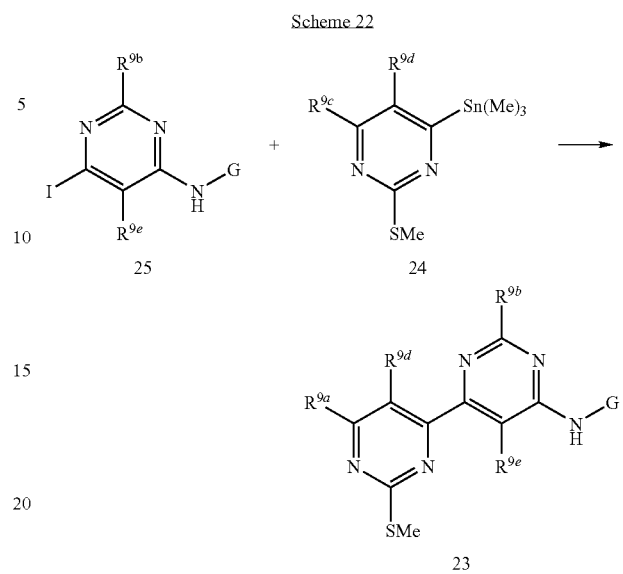

As shown in Scheme 22, compounds of Formula 23 can be prepared by treatment of compounds of Formula 25 with a compound of Formula 24 analogous to the coupling method of Scheme 17. For a method of preparation of compounds of Formula 24 see Undheim, K. et al. *Tetrahedron* 1989, 45, 993-1006.

Scheme 23

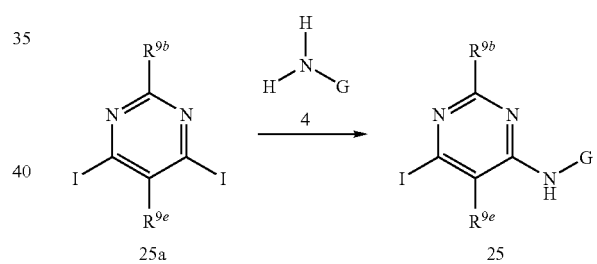

As shown in Scheme 23, compounds of Formula 25 can be prepared by coupling a compound of Formula 25a with an amine of Formula 4. The reaction is conducted in the presence of a hindered base such as triethylamine or N,N-diisopropylethylamine in solvents such as n-butanol, typically at temperatures ranging from about 50° C. to about 120° C. over a period of 2 to 20 h.

Schemes 1 through 23 illustrate methods to prepare compounds of Formula 1 having a wide variety of combinations of nitrogen and carbon radicals for X, Y, W and Z. Compounds of Formula 1 having other combinations of nitrogen and carbon radicals for X, Y, W and Z can be prepared by general methods known in the art of synthetic organic chemistry, including methods analogous to those described for Schemes 1 to 23.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, T. W. Greene and P. G. M. Wuts, *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. Unless otherwise indicated, $^1$H NMR spectra are reported in ppm downfield from tetramethylsilane; "s" means singlet, "d" means doublet, "t" means triplet, "m" means multiplet, "q" means quartet, "dd" means doublet of doublets, "dt" means doublet of triplets, and "br s" means broad singlet. The abbreviation "m.p." means melting point.

Example 1

Preparation of N-(3-chlorophenyl)-4-[2-[(2-methoxy-1-methylethyl)amino]-4-pyrimidinyl]-1,3,5-triazine-2-amine (a compound of Formula 1)

Step A: Preparation of 2-chloro-N-cyano-4-pyrimidinecarboximidamide

To an ice-cooled solution of 2-chloro-4-pyrimidinecarbonitrile (23 g, 0.16 mol) in toluene (500 mL) was added methanol (7.5 mL, 0.18 mol), followed by treatment with gaseous hydrogen chloride for 2 h. The HCl-saturated solution was sealed and stirred overnight at room temperature, and then the white solid was collected by filtration and washed with diethyl ether (200 mL) and ethyl acetate (200 mL). The solid was then dissolved in methanol (400 mL) and treated with ammonia solution (100 mL, 7 M in MeOH) at room temperature. After stirring 4 h, the solution was concentrated in vacuo and the residue washed with ethyl acetate (200 mL). The resulting crude solid was dissolved in a mixture of water (150 mL) and isopropanol (50 mL), and to this solution was added cyanamide (8.5 g, 0.2 mol), and sodium bicarbonate (9 g, 0.1 mol). The mixture was stirred at room temperature for 5 h, cooled to 0° C. and stirred for an additional 5 h. The resulting grey mixture was filtered, rinsed with water, and dried in vacuo for 24 h to give 13 g of the title compound as a white solid.

$^1$H NMR (DMSO-$d_6$) δ 9.32 (br s, 2H), 8.97 (d, 1H), 8.05 (d, 1H).

Step B: Preparation of 2-chloro-4-(2-chloro-4-pyrimidinyl)-1,3,5-triazine

To an ice-cooled solution of N,N-dimethylformamide (8.5 mL, 110 mmol) in methylene chloride (100 mL) was added phosphorus oxychloride (8.0 mL, 87 mmol) dropwise, and the mixture was stirred for 0.5 h. The resulting mixture was poured into a cold (0° C.) suspension of 2-chloro-N-cyano-4-pyrimidinecarboximidamide (i.e., the product of Step A) (13 g, 73 mmol) in acetonitrile (200 mL). The resulting mixture was stirred overnight in an ice bath. The mixture was passed through a short silica gel pad, eluted with 30% ethyl acetate in hexanes, and concentrated under reduced pressure to give 7 g of the title compound as a white solid.

$^1$H NMR (CDCl$_3$) δ 9.30 (s, 1H), 8.97 (d, 1H), 8.43 (d, 1H).

Step C: Preparation of N-(3-chlorophenyl)-4-[2-[(2-methoxy-1-methylethyl)amino]-4-pyrimidinyl]-1,3,5-triazin-2-amine To a solution of 2-chloro-4-(2-chloro-4-pyrimidinyl)-1,3,5-triazine (i.e., the product of Step B) (25 mg, 0.11 mmol) in tetrahydrofuran (1.0 mL) was added 3-chloroaniline (0.1 mL). The resulting mixture was stirred at room temperature for 3 h to generate a yellow suspension. To this suspension was added 1-methoxy-2-propylamine (0.2 mL), and the resulting mixture was refluxed for 5 h. The solution was concentrated and purified using column chromatography on silica gel eluted with 70% ethyl acetate in hexanes to give 30 mg of the title compound as a yellow solid.

$^1$H NMR (CDCl$_3$) δ 8.96 (s, 1H), 8.54 (d, 1H), 7.87 (br s, 2H), 7.55 (d, 1H), 7.45 (br s, 1H), 7.28 (t, 1H), 7.12 (d, 1H), 5.83 (br s, 1H), 4.37 (br s, 1H), 3.47 (m, 2H), 3.37 (s, 3H), 1.28 (d, 3H).

Example 2

Preparation of N-(3-chlorophenyl)-4-[2-[(tetrahydro-2H-pyran-4-yl)amino]-4-pyrimidinyl]-1,3,5-triazin-2-amine (a compound of Formula 1)

To a solution of 2-chloro-4-(2-chloro-4-pyrimidinyl)-1,3,5-triazine (i.e., the product of Example 1, Step B) (25 mg, 0.11 mmol) in tetrahydrofuran (1.0 mL) was added 3-chloroaniline (0.1 mL), and the resulting mixture was stirred at room temperature for 3 h to provide a yellow suspension. To this suspension added 4-aminotetrahydropyran (0.2 mL), and the mixture was refluxed for 5 h. The solution was concentrated and purified using column chromatography on silica gel eluted with 70% ethyl acetate in hexanes to give 25 mg of the title compound as a yellow solid.

$^1$H NMR (CDCl$_3$) δ 8.94 (s, 1H), 8.56 (d, 1H), 7.88 (br s, 1H), 7.75 (br s, 1H), 7.59 (d, 1H), 7.46 (d, 1H), 7.31 (t, 1H), 7.16 (d, 1H), 5.49 (br s, 1H), 4.15 (br s, 1H), 4.00 (m, 2H), 3.57 (m, 2H), 2.05 (m, 2H), 1.59 (m, 2H).

Example 3

Preparation of 5-[[4-[2-[[(1S)-2-methoxy-1-methylethyl]amino]-4-pyrimidinyl]-1,3,5-triazinyl]amino]-2-pyridinecarbonitrile (a compound of Formula 1)

To a solution of 2-chloro-4-(2-chloro-4-pyrimidinyl)-1,3,5-triazine (i.e., the product of Example 1, Step B) (100 mg, 0.43 mmol) in tetrahydrofuran (2.0 mL) was added 5-amino-2-pyridinecarbonitrile (86 mg, 0.72 mmol), and the resulting mixture was stirred at 40° C. for 3 h. To this mixture was added (S)-1-methoxy-2-propylamine (0.2 mL), and the resulting mixture was refluxed for 2 h. The solution was concentrated and purified using column chromatography on silica gel eluted with a gradient of 70% to 80% ethyl acetate in hexanes to give 84 mg of the title compound as a yellow solid.

$^1$H NMR (CDCl$_3$) δ 9.10 (s, 1H), 8.97 (s, 1H), 8.57 (d, 1H), 8.39 (br s, 2H), 7.75 (d, 1H), 7.57 (d, 1H), 5.84 (br s, 1H), 4.37 (br s, 1H), 3.50 (m, 2H), 3.40 (s, 3H), 1.31 (d, 3H).

Example 4

Preparation of N-(3-fluoro-5-nitrophenyl)-4-[2-[[(1S)-2-methoxy-1-methylethyl]amino]-4-pyrimidinyl]-1,3,5-triazin-2-amine (a compound of Formula 1)

To a solution of 2-chloro-4-(2-chloro-4-pyrimidinyl)-1,3,5-triazine (i.e., the product of Example 1, Step B) (68 mg, 0.30 mmol) in tetrahydrofuran (2.0 mL) was added 3-fluoro-5-nitroaniline (72 mg, 0.46 mmol), and the resulting mixture was stirred at 50° C. for 1 h to form a yellow suspension. To this suspension was added (S)-1-methoxy-2-propylamine (0.2 mL), and the resulting mixture was refluxed for 3 h. The solution was concentrated and purified using column chromatography on silica gel eluted with 70% ethyl acetate in hexanes to give 93 mg of the title compound as yellow solid.

$^1$H NMR (CDCl$_3$) δ 9.04 (s, 1H), 8.56 (d, 1H), 8.47 (br s, 2H), 7.99 (br s, 1H), 7.67 (m, 1H), 7.59 (d, 1H), 5.81 (br s, 1H), 4.38 (br s, 1H), 3.50 (d, 2H), 3.40 (s, 3H), 1.30 (d, 3H).

Example 5

Preparation of 4-[2-[(2-chloro-6-methylphenyl)amino]-4-pyrimidinyl]-N-(tetrahydro-2H-pyran-4yl)-1,3,5-triazin-2-amine (a compound of Formula 1)

Step A: Preparation of the 4-(2-chloro-4-pyrimidinyl)-N-(tetrahydro-2H-pyran-4-yl)-1,3,5-triazin-2-amine To an ice-cooled solution of 2-chloro-4-(2-chloro-4-pyrimidinyl)-1,3,5-triazine (i.e., the product of Example 1, Step B) (290 mg, 1.27 mmol) in tetrahydrofuran (20 mL) was added 4-aminotetrahydrofuran (284 mg, 2.8 mmol). The resulting mixture was stirred at room temperature overnight and then concentrated and purified using column chromatography on silica gel eluted with 60% ethyl acetate in hexanes to give 300 mg of the title compound as a white solid.

$^1$H NMR (CDCl$_3$) δ 8.87 (d, 1H), 8.79 (s, 1H), 8.31 (d, 1H), 5.87 (d, 1H), 4.20 (m, 1H), 4.02 (m, 2H), 3.56 (m, 2H), 2.06 (m, 2H), 1.63 (m, 2H).

Step B: Preparation of 4-[2-[(2-chloro-6-methylphenyl)amino]-4-pyrimidinyl]-N-(tetrahydro-2H-pyran-4yl)-1,3,5-triazin-2-amine To a solution of 4-(2-chloro-4-pyrimidinyl)-N-(tetrahydro-2H-pyran-4-yl)-1,3,5-triazin-2-amine (i.e., the product of Step A) (125 mg, 0.42 mmol) in toluene (4.0 mL) under nitrogen was added 2-chloro-6-methylaniline (180 mg, 1.27 mmol), cesium carbonate (273 mg, 0.84 mmol), tris(dibenzylideneacetone)dipalladium(0) (20 mg, 0.022 mmol), and ((±)-BINAP) (28 mg, 0.044 mmol), and the resulting mixture was stirred and heated at reflux for 6 h. After cooling to room temperature, the mixture was concentrated and purified using column chromatography on silica gel eluted with 40% acetone in hexanes to give 57 mg of the title compound as a yellow solid.

$^1$H NMR (CDCl$_3$) δ 8.79 (s, 1H), 8.53 (d, 1H), 7.70 (d, 1H), 7.31 (d, 1H), 7.20 (m, 2H), 7.10 (s, 1H), 5.79 (d, 1H), 4.20 (m, 1H), 4.03 (m, 2H), 3.55 (m, 2H), 2.29 (s, 3H), 2.06 (m, 2H), 1.62 (m, 2H).

Example 6

Preparation of 4-[2-[(2-chloro-6-methylphenyl)amino]-4-pyridinyl]-N-(2-methoxy-1-methylethyl)-2-pyrimidinamine (a compound of Formula 1)

Step A: Preparation of 2-chloro-4-(2-chloro-4-pyridinyl)pyrimidine

Method A: To a cold solution (−40° C.) of 2-chloro-4-bromopyridine (9.5 g, 49 mmol) in tetrahydrofuran (200 mL) was added isopropylmagnesium chloride solution (25 mL, 2 M in THF) via syringe over 10 min. The resulting light yellow solution was warmed to 0° C. over 2 h and stirred at 0° C. for 1 h under nitrogen to form a white suspension. To this suspension was added [1,1-bis(diphenylphosphino)ferrocene] dichloropalladium(II) (PdCl$_2$ (dppf)) (2.0 g, 2.0 mmol), followed by 2,4-dichloropyrimidine (7.4 g, 49 mmol). After stirring at 0° C. for 10 min, the cold bath was removed. The mixture was allowed to stir overnight under nitrogen and then diluted with ethyl acetate (300 mL). The resulting mixture was washed with saturated aqueous ammonium chloride solution, dried over anhydrous magnesium sulfate, and purified using column chromatography on silica gel eluted with 35% ethyl acetate in hexanes to give 6.3 g of the title compound as an off-white solid.

$^1$H NMR (CDCl$_3$) δ 8.80 (d, 1H), 8.60 (d, 1H), 8.01 (s, 1H), 7.86 (d, 1H), 7.70 (d, 1H).

Method B: Under a nitrogen atmosphere, to a mixture of 2,4-dichloropyrimidine (473 mg, 3.18 mmol), 2-chloro-4-pyridineboronic acid (500 mg, 3.18 mmol) and bis(triphenylphosphine)palladium(II) dichloride (67 mg, 0.095 mmol) in glyme (6.4 mL) was added 2 N aqueous sodium carbonate (3.35 mL) and methanol (1.67 mL), and the resulting mixture was stirred at 80° C. for 6 h. The solution was then cooled to room temperature and diluted with de-ionized water and ethyl acetate. The layers were separated, and the aqueous layer was extracted twice with ethyl acetate. The organic layers were combined and washed with saturated sodium chloride solution, dried and concentrated to afford 760 mg of crude residue, which was subjected to silica gel chromatographic purification using 35% ethyl acetate in hexanes as eluant to give 435 mg of the title compound as an off-white solid.

Step B: Preparation of 4-(2-chloro-4-pyridinyl)-N-(2-methoxy-1-methylethyl)-2-pyrimidinamine A solution of 2-chloro-4-(2-chloro-4-pyridinyl)pyrimidine (i.e., the product of Step A) (1.6 g, 7.0 mmol) in 1-methoxy-2-propylamine (5 mL) was stirred at reflux for 45 minutes. After cooling to room temperature, the mixture was purified using column chromatography on silica gel eluted with 40% ethyl acetate in hexanes to give 1.4 g of the title compound as a white solid.

¹H NMR (CDCl₃) δ 8.51 (d, 1H), 8.43 (d, 1H), 7.94 (s, 1H), 7.78 (d, 1H), 6.96 (d, 1H), 5.45 (d, 1H), 4.35 (m, 1H), 3.50 (d, 2H), 3.41 (s, 3H), 1.33 (d, 3H).

Step C: Preparation of 4-[2-[(2-chloro-6-methylphenyl)amino]-4-pyridinyl]-N-(2-methoxy-1-methylethyl)-2-pyrimidinamine To a solution of 4-(2-chloro-4-pyridinyl)-N-(2-methoxy-1-methylethyl)-2-pyrimidinamine (i.e., the product of Step B) (100 mg, 0.35 mmol) in toluene (10 mL) was added 2-chloro-6-methylaniline (102 mg, 0.72 mmol), cesium carbonate (350 mg, 1.07 mmol), palladium(II) acetate (4 mg, 0.017 mmol) and ((±)-BINAP) (22 mg, 0.035 mmol), and the resulting mixture was stirred at reflux for 30 h. After cooling to room temperature, the mixture was concentrated, and purified using column chromatography on silica gel eluted with 40% ethyl acetate in hexanes to give 30 mg of the title compound as a solid.
¹H NMR (CDCl₃) δ 8.33 (d, 1H), 8.29 (d, 1H), 7.36 (d, 1H), 7.25 (m, 2H), 7.14 (t, 1H), 6.84 (m, 2H), 6.60 (s, 1H), 5.43 (d, 1H), 4.24 (m, 1H), 3.45 (d, 2H), 3.36 (s, 3H), 2.30 (s, 3H), 1.24 (d, 2H).

Example 7

Preparation of 4-[2-[(3-fluorophenyl)amino]-4-pyridinyl]-N-[1-methyl-2-(methylthio)ethyl]-2-pyrimidinamine (a compound of Formula 1)

Step A: Preparation of 1-(methylthio)-2-propanone oxime

To a solution of 1-(methylthio)-2-propanone (10.2 mL, 99.7 mmol) in 120 mL water was added hydroxylamine hydrochloride (8.9 g, 122 mmol) followed by the addition of sodium bicarbonate (8.4 g, 99.9 mmol) portion-wise over 15 min. The resulting suspension was stirred at room temperature for 72 h and then extracted with diethyl ether (200 mL). The organic layer was washed twice with brine (150 mL), dried over MgSO₄, filtered and concentrated to give 11.0 g of the title compound as a clear oil.
¹H NMR (CDCl₃) δ 3.17 (s, 2H), 2.03 (s, 3H), 2.00 (s, 3H).

Step B: Preparation of 1-(methylthio)-2-propanamine

To a stirred solution of 1-(methylthio)-2-propanone oxime (i.e., the product of Step A) (8.3 g, 64.2 mmol) in diethyl ether (150 mL) was added lithium aluminum hydride (2.4 g, 64.2 mmol) portion-wise over 15 minutes, while maintaining the temperature of the reaction mixture below 30° C. The stirred mixture was allowed to warm to room temperature for 24 h. To this mixture was added sequentially over 0.5 h, water (2.4 g), 15% aqueous sodium hydroxide (2.4 g) and water (7.2 g). The resulting mixture was then stirred at room temperature for 1.5 h. The resulting suspension was filtered through a pad of Celite® filter aid, and the filtrate was concentrated under reduced pressure to give 6.9 g of the title compound as an oil.
¹H NMR (CDCl₃) δ 3.04-3.13 (m, 1H), 2.56-2.63 (m, 1H), 2.34-2.42 (m, 1H), 2.11 (s, 3H), 1.17 (d, 3H).

Step C: Preparation 4-(2-chloro-4-pyridinyl)-N-[1-methyl-2-(methylthio)ethyl]-2-pyrimidinamine To a solution of 2-chloro-4-(2-chloro-4-pyridinyl)pyrimidine (i.e., the product of Example 6, Step A) (350 mg, 1.5 mmol) in toluene (4.0 mL) was added 1-(methylthio)-2-propanamine (i.e., the product of Step B) (1 mL, 9.5 mmol) in one portion; this mixture was heated at 60° C. for 18 h. The mixture was allowed to cool and silica gel (300 mg) was added. The excess solvent was removed under reduced pressure, and the resulting solid was chromatographed on silica gel eluted with a solvent gradient of 5% to 60% ethyl acetate in hexanes to give 400 mg (88%) of the title compound as a tan solid, m.p. 103-106° C.
¹H NMR (CDCl₃) δ 8.50 (d, 1H), 8.43 (d, 1H), 7.94 (s, 1H) 7.77 (d, 1H), 6.98 (d, 1H), 5.32-5.43 (m, 1H), 4.31-4.45 (m, 1H), 2.78-2.88 (m, 1H), 2.65-2.75 (m, 1H), 2.18 (s, 3H), 1.39 (d, 3H).

Step D: Preparation of 4-[2-[(3-fluorophenyl)amino]-4-pyridinyl]-N-[1-methyl-2-(methylthio)ethyl]-2-pyrimidinamine To a solution of 4-(2-chloro-4-pyridinyl)-N-[1-methyl-2-(methylthio)ethyl]-2-pyrimidinamine (i.e., the product of Step C) (150 mg, 0.5 mmol) in toluene (6.0 mL) was added 3-fluoroaniline (108 μL, 1.1 mmol), palladium(II) acetate (24 mg, 0.12 mmol), (±)-2,2'-bis(diphenylphosphino)-1,1'-binaphthalene ((±)-BINAP) (40 mg, 0.06 mmol) and cesium carbonate (700 mg, 2.2 mmol); the resulting mixture was stirred at 110° C. for 13 h. The mixture was allowed to cool and silica gel (300 mg) was added. The excess solvent was removed under reduced pressure, and the resulting solid was chromatographed on silica gel eluted with 5% to 60% ethyl acetate in hexanes to give 60 mg of the title compound as a yellow solid, m.p. 104-107° C.
¹H NMR (CDCl₃) δ 8.40 (d, 1H), 8.35 (d, 1H), 7.52 (s, 1H), 7.25-7.38 (m, 3H), 7.07-7.12 (m, 1H), 6.96 (d, 1H), 6.71-6.79 (m, 2H), 5.32 (d, 1H), 4.33-4.44 (m, 1H), 2.79-2.86 (m, 1H), 2.68-2.75 (m, 1H), 2.15 (s, 3H), 1.38 (d, 3H).

Example 8

Preparation of 4-[2-[(3-chlorophenyl)amino]-4-pyridinyl]-N-[1-methyl-2-(methylthio)ethyl]-2-pyrimidinamine (a compound of Formula 1)

The title compound was prepared in the same fashion as described in Example 7, Step D using 3-chloroaniline in place of 3-fluoroaniline.
¹H NMR (CDCl₃) δ 8.39 (d, 1H), 8.34 (d, 1H), 7.48-7.61 (m, 2H), 7.27-7.32 (m, 2H), 7.24-7.26 (m, 1H), 6.99-7.04 (m, 1H), 6.94 (d, 1H), 6.77 (s, 1H), 5.36 (d, 1H), 4.32-4.43 (m, 1H), 2.77-2.85 (m, 1H), 2.67-2.75 (m, 1H), 2.13 (s, 3H), 1.37 (d, 3H).

Example 9

Preparation of N-cyclopentyl-4-[2-[(3-fluorophenyl)amino]-4-pyridinyl]-2-pyrimidinamine (a compound of Formula 1)

Step A: Preparation of 4-(2-chloro-4-pyridinyl)-N-cyclopentyl-2-pyrimidinamine

Cyclopentylamine (3 mL) was combined with 2-chloro-4-(2-chloro-4-pyridinyl)pyrimidine (i.e., the product of Example 6, Step A) (300 mg, 1.3 mmol) and stirred at 55° C. for 2 hours. The resulting suspension was filtered, and the collected solid was oven dried at 50° C. in vacuo to give 340 mg of the title compound as a brown solid.

¹H NMR (CDCl₃) δ 8.51 (d, 1H), 8.43 (d, 1H), 7.94 (s, 1H), 7.79 (d, 1H), 6.95 (d, 1H), 5.27 (d, 1H), 4.32-4.42 (m, 1H), 2.07-2.19 (m, 2H), 1.64-1.83 (m, 4H), 1.49-1.59 (m, 2H).

Step B: Preparation of N-cyclopentyl-4-[2-[(3-fluorophenyl)amino]-4-pyridinyl]-2-pyrimidinamine The title compound was prepared in the same fashion as described in Example 7, Step D using 4-(2-chloro-4-pyridinyl)-N-cyclopentyl-2-pyrimidinamine (i.e., the product of Step A) and 3-fluoroaniline.
¹H NMR (CDCl₃) δ 8.39 (d, 1H), 8.34 (d, 1H), 7.56 (br s, 1H), 7.35-7.37 (m, 1H), 7.29-7.34 (m, 2H), 7.09 (d, 1H), 6.93 (d, 1H), 6.71-6.79 (m, 2H), 5.22 (d, 1H), 4.30-4.39 (m, 1H), 2.04-2.16 (m, 2H), 1.64-1.79 (m, 4H), 1.50-1.57 (m, 2H).

Example 10

Preparation of 4-[2-[(3-fluorophenyl)amino]-4-pyridinyl]-N-(tetrahydro-2H-pyran-4-yl)-2-pyrimidinamine (a compound of Formula 1)

Step A: Preparation of 4-(2-chloro-4-pyridinyl)-N-(tetrahydro-2H-pyran-4-yl)-2-pyrimidinamine The title compound was prepared in the same fashion as described in Example 9, Step A using 4-aminotetrahydrofuran in place of cyclopentylamine to obtain 300 mg of the title compound as a tan solid, m.p. 156-158° C.
¹H NMR (CDCl₃) δ 8.51 (d, 1H), 8.43 (d, 1H), 7.90-7.93 (m, 1H), 7.77 (d, 1H), 6.98 (d, 1H), 5.22 (d, 1H), 4.09-4.17 (m, 1H), 3.99-4.06 (m, 2H), 3.54-3.63 (m, 2H), 2.09 (d, 2H), 1.59-1.67 (m, 2H).

Step B: Preparation of 4-[2-[(3-fluorophenyl)amino]-4-pyridinyl]-N-(tetrahydro-2H-pyran-4-yl)-2-pyrimidinamine To a solution of 4-(2-chloro-4-pyridinyl)-N-(tetrahydro-2H-pyran-4-yl)-2-pyrimidinamine (i.e., the product of Step A) (500 mg, 1.7 mmol) in toluene (15 mL) was added 3-fluoroaniline (400 uL, 4.1 mmol), palladium(II) acetate (50 mg, 0.20 mmol), (±)-BINAP (100 mg, 0.16 mmol) and cesium carbonate (1.9 g, 5.8 mmol), and the resulting mixture was stirred at reflux for 4.5 h. The cooled mixture was partitioned between ethyl acetate and water, and the organic layer was washed with brine, dried over MgSO₄ and filtered. The solvent was removed under reduced pressure to give a residue that was chromatographed on silica gel eluted with 15% to 85% ethyl acetate in hexanes to afford 330 mg of title compound as a solid, m.p. 190-192° C.
¹H NMR (CDCl₃) δ 8.40 (d, 1H), 8.36 (d, 1H), 7.53 (br s, 1H), 7.33-7.38 (m, 1H), 7.28-7.32 (m, 2H), 7.08 (d, 1H), 6.96 (d, 1H), 6.73-6.82 (m, 1H), 6.71 (s, 1H), 5.17 (d, 1H), 4.09-4.20 (m, 1H), 3.97-4.07 (m, 2H), 3.51-3.61 (m, 2H), 2.06-2.12 (m, 2H), 1.59-1.67 (m, 2H).

Example 11

Preparation of 4-[2-[(3-chlorophenyl)amino]-4-pyridinyl]-N-(tetrahydro-2H-pyran-4-yl)-2-pyrimidinamine (a compound of Formula 1)

The title compound was prepared in the same fashion as described in Example 10, Step B using 4-(2-chloro-4-pyridinyl)-N-(tetrahydro-2H-pyran-4-yl)-2-pyrimidinamine (i.e., the product of Example 10, Step A) and 3-chloroaniline to give 75 mg of the title compound as a tan solid.
¹H NMR (CDCl₃) δ 8.40 (d, 1H), 8.35 (d, 1H), 7.53 (s, 1H), 7.50 (br s, 1H), 7.30 (d, 1H), 7.02-7.06 (m, 1H), 6.96 (d, 1H), 6.67 (br s, 1H), 5.17 (d, 1H), 4.10-4.17 (m, 1H), 3.98-4.05 (m, 2H), 3.52-3.60 (m, 2H), 2.08 (d, 2H), 1.59-1.65 (m, 2H).

Example 12

Preparation of 4-[2-[(2-chlorophenyl)amino]-4-pyridinyl]-N-(tetrahydro-2H-pyran-4-yl)-2-pyrimidinamine (a compound of Formula 1)

The title compound was prepared in the same fashion as described in Example 10, Step B using 4-(2-chloro-4-pyridinyl)-N-(tetrahydro-2H-pyran-4-yl)-2-pyrimidinamine (i.e., the product of Example 10, Step A) and 2-chloroaniline to give 124 mg of the title compound as a tan solid, m.p. 153-156° C.
¹H NMR (CDCl₃) δ 8.40 (d, 1H), 8.37 (d, 1H), 8.11 (d, 1H), 7.50 (s, 1H), 7.42 (dd, 1H), 7.28-7.33 (m, 1H), 7.25-7.28 (m, 1H), 6.97-7.04 (m, 1H), 6.95-6.97 (m, 2H), 5.20 (d, 1H), 4.06-4.18 (m, 1H), 4.01 (dt, 2H), 3.55 (t, 2H), 2.08 (d, 2H), 1.53-1.64 (m, 2H).

Example 13

Preparation of 4-[2-[(4-chloro-2-methylphenyl)amino]-4-pyridinyl]-N-(tetrahydro-2H-pyran-4-yl)-2-pyrimidinamine (a compound of Formula 1)

The title compound was prepared in the same fashion as described in Example 10, Step B using 4-(2-chloro-4-pyridinyl)-N-(tetrahydro-2H-pyran-4-yl)-2-pyrimidinamine (i.e., the product of Example 10, Step A) and 2-methyl-4-chloroaniline to give 40 mg of the title compound as a solid, m.p. 196-198° C.
¹H NMR (CDCl₃) δ 8.36 (d, 1H), 8.28 (d, 2H), 7.43 (d, 1H), 7.16-7.26 (m, 3H), 6.90 (d, 1H), 6.49 (br s, 1H), 5.25 (d, 1H), 3.97-4.08 (m, 3H), 3.51 (t, 2H), 2.27 (s, 3H), 2.01 (br s, 2H), 1.51-1.63 (m, 2H).

Example 14

Preparation of 4-[2-[(2-chloro-4-methylphenyl)amino]-4-pyridinyl]-N-(tetrahydro-2H-pyran-4-yl)-2-pyrimidinamine (a compound of Formula 1)

The title compound was prepared in the same as described in Example 10, Step B using 4-(2-chloro-4-pyridinyl)-N-(tetrahydro-2H-pyran-4-yl)-2-pyrimidinamine (i.e., the product of Example 10, Step A) and 2-chloro-4-methylaniline to give 137 mg of the title compound as a tan solid, m.p. 184-186° C.
¹H NMR (CDCl₃) δ 8.39 (d, 1H), 8.35 (d, 1H), 7.89 (d, 1H), 7.44 (s, 1H), 7.25-7.30 (m, 2H), 7.09 (dd, 1H), 6.96 (d, 1H), 6.85 (s, 1H), 5.16 (d, 1H), 3.98-4.05 (m, 2H), 3.55 (dt, 2H), 2.33 (s, 3H), 2.03-2.11 (m, 2H), 1.54-1.64 (m, 2H).

Example 15

Preparation of 4-[2-[(3-fluorophenyl)amino]-4-pyridinyl]-N-[(tetrahydro-3-furanyl)methyl]-2-pyrimidinamine (a compound of Formula 1)

Step A: Preparation of (tetrahydro-3-furanyl)methyl 4-methylbenzenesulfonate

To a solution of tetrahydro-3-furanmethanol (6.2 g, 60.8 mmol) in 60 mL tetrahydrofuran was added p-toluenesulfonyl chloride (11.6 g, 60.9 mmol) in one portion, followed by the drop-wise addition of triethylamine (9.2 mL, 66.4 mol) over 10 min. The resulting mixture was stirred at reflux for 16 h and then treated with triethylamine (1.6 mL, 11.5 mmol). Heating was continued for an additional 18 h. The cooled mixture was diluted with diethyl ether, washed with water and brine, and dried over MgSO$_4$. The mixture was then filtered and concentrated under reduced pressure. The resulting residue was placed on a column of silica gel (30 g) and eluted with 5% to 80% ethyl acetate in hexanes to give 11.0 g (72%) of the title compound as an orange oil.

$^1$H NMR (CDCl$_3$) δ 7.79 (m, 2H), 7.36 (m, 2H), 3.88-4.04 (m, 2H), 3.64-3.84 (m, 3H), 3.50 (dd, 1H), 2.53-2.67 (m, 1H), 2.46 (s, 3H), 1.96-2.05 (m, 1H), 1.50-1.64 (m, 1H).

Step B: Preparation of 2-[(tetrahydro-3-furanyl)methyl]-1H-isoindole-1,3(2H)-dione To a solution of (tetrahydro-3-furanyl)methyl 4-methylbenzenesulfonate (i.e., the product of Step A) (11.0 g, 42.9 mmol) in N,N-dimethylformamide (160 mL) was added potassium phthalimide (7.9 g, 42.7 mmol) in one portion, and the resulting mixture was stirred at 80° C. for 6 h. Additional potassium phthalimide (5 g, 27 mmol) was added, and stirring was continued at 100° C. for 18 h. The cooled reaction mixture was partitioned between water and ethyl acetate and the aqueous layer was separated and extracted with ethyl acetate (5×75 mL). The combined extracts were dried over MgSO$_4$ and filtered, and the solvent was removed under reduced pressure to give a residue which was chromatographed on silica gel (40 g) eluted with 5% to 100% ethyl acetate in hexanes to give 4.5 g of the title compound as a white solid, m.p. 114-118° C.

$^1$H NMR (CDCl$_3$) δ 7.87 (dd, 2H), 7.74 (dd, 2H), 3.94 (dt, 1H), 3.67-3.87 (m, 4H), 3.62 (dd, 1H), 2.70-2.79 (m, 1H), 1.97-2.07 (m, 1H), 1.74 (dt, 1H).

Step C: Preparation of tetrahydro-3-furanmethanamine

To a solution of 2-[(tetrahydro-3-furanyl)methyl]-1H-isoindole-1,3(2H)-dione (i.e., the product of Step B) (4.5 g, 19.5 mmol) in ethanol (150 mL) was added hydrazine monohydrate (4.75 mL, 97.5 mmol) drop-wise over 5 minutes. The resulting mixture was stirred at reflux for 90 minutes during which time a suspension formed, followed by dissolution to form a solution. The cooled solution was diluted with 200 mL diethyl ether, and the resulting suspension was filtered. Excess solvent was removed under reduced pressure to give a residue, which was filtered through a pad of Celite®. The solvent was removed under reduced pressure to give 2.5 g of the title compound as a clear oil.

$^1$H NMR (CDCl$_3$) δ 3.82-3.91 (m, 1H), 3.72-3.78 (m, 1H), 3.51 (dd, 1H), 2.72 (d, 2H), 2.23-2.35 (m, 2H), 1.99-2.10 (m, 1H), 1.53-1.63 (m, 1H).

Step D: Preparation of 4-(2-chloro-4-pyridinyl)-N-[(tetrahydro-3-furanyl)methyl]-2-pyrimidinamine The title compound was prepared from 2-chloro-4-(2-chloro-4-pyridinyl)pyrimidine (i.e., the product of Example 6, Step A) and tetrahydro-3-furanmethanamine (i.e., the product of Step C) in the same fashion as described in Example 9, Step A.

$^1$H NMR (CDCl$_3$) δ 8.51 (d, 1H), 8.43 (d, 1H), 7.93 (s, 1H), 7.78 (d, 1H), 6.99 (d, 1H), 5.46 (br s, 1H), 3.86-3.98 (m, 2H), 3.79 (dt, 1H), 3.66 (dd, 1H), 3.54 (t, 2H), 2.58-2.72 (m, 1H), 2.03-2.18 (m, 1H), 1.73 (dt, 1H).

Step E: Preparation of 4-[2-[(3-fluorophenyl)amino]-4-pyridinyl]-N-[(tetrahydro-3-furanyl)methyl]-2-pyrimidinamine The title compound was prepared in the same fashion as described in Example 10, Step B using 4-(2-chloro-4-pyridinyl)-N-[(tetrahydro-3-furanyl)methyl]-2-pyrimidinamine (i.e., the product of Step D) and 3-fluoroaniline to give 115 mg of the title compound as a tan solid, m.p. 154-156° C.

$^1$H NMR (CDCl$_3$) δ 8.40 (d, 1H), 8.36 (d, 1H), 7.53 (br s, 1H), 7.33-7.39 (m, 1H), 7.27-7.33 (m, 2H), 7.10 (dd, 1H), 6.97 (d, 1H), 6.71-6.79 (m, 2H), 5.35 (t, 1H), 3.85-3.97 (m, 2H), 3.74-3.82 (m, 1H), 3.65 (dd, 1H), 3.53 (t, 2H), 2.59-2.70 (m, 1H), 2.06-2.15 (m, 1H), 1.67-1.77 (m, 1H).

Example 16

Preparation of 4-[2-[(3-fluorophenyl)amino]-4-pyridinyl]-N-[(tetrahydro-2-furanyl)methyl]-2-pyrimidinamine (a compound of Formula 1)

Step A: Preparation of 4-(2-chloro-4-pyridinyl)-N-[(tetrahydro-2-furanyl)methyl]-2-pyrimidinamine The title compound was prepared from 2-chloro-4-(2-chloro-4-pyridinyl)pyrimidine (i.e., the product of Example 6, Step A) and tetrahydrofurfurylamine in the same fashion as described in Example 9, Step A, m.p. 74-75° C.

$^1$H NMR (CDCl$_3$) δ 8.51 (d, 1H), 8.43 (d, 1H), 7.94 (s, 1H), 7.79 (dd, 1H), 6.97 (d, 1H), 5.61 (br s, 1H), 4.08-4.19 (m, 1H), 3.94 (dt, 1H), 3.79-3.85 (m, 1H), 3.71-3.79 (m, 1H), 3.55 (br s, 1H), 1.90-2.11 (m, 3H), 1.62-1.73 (m, 1H).

Step B: 4-[2-[(3-fluorophenyl)amino]-4-pyridinyl]-N-[(tetrahydro-2-furanyl)methyl]-2-pyrimidinamine The title compound was prepared in the same fashion as described in Example 10, Step B using 4-(2-chloro-4-pyridinyl)-N-[(tetrahydro-2-furanyl)methyl]-2-pyrimidinamine (i.e., the product Step A) and 3-fluoroaniline to give 90 mg of the title compound as a brown solid.

$^1$H NMR (CDCl$_3$) δ 8.38 (d, 1H), 8.31 (d, 1H), 7.24-7.37 (m, 3H), 7.21 (br s, 1H), 7.09 (dd, 1H), 6.92 (d, 1H), 6.75 (dt, 1H), 5.67 (br s, 1H), 4.08-4.18 (m, 1H), 3.87-3.98 (m, 1H), 3.76-3.85 (m, 1H), 3.68-3.76 (m, 1H), 3.52 (br s, 1H), 1.88-2.06 (m, 3H), 1.60-1.71 (m, 1H).

Example 17

Preparation of 4-[2-[(3-fluorophenyl)amino]-4-pyridinyl]-N-(2-methoxypropyl)-2-pyrimidinamine (a compound of Formula 1)

Step A: Preparation of 2-chloro-4-trimethylstannylpyridine

To a solution of 2-chloro-4-bromopyridine (16 g, 83 mmol) in 1,4-dioxane (250 mL) was added hexamethyldistannane (30 g, 91 mmol) and bis(triphenylphosphine)palladium(II) dichloride (2.6 g, 3 mmol). The resulting mixture was stirred at reflux for 30 min under nitrogen. After cooling to room temperature, the solution was concentrated and the residue was purified via column chromatography on silica gel eluted with 10% ethyl acetate in hexanes to give 30 g of title compound as colorless oil.

$^1$H NMR (CDCl$_3$) δ 8.26 (d, 1H), 7.40 (s, 1H), 7.28 (d, 1H), 0.35 (s, 9H).

Step B: Preparation of N-(3-fluorophenyl)-4-trimethylstannyl-2-pyridinamine

To a solution of 2-chloro-4-trimethylstannylpyridine (i.e., the product of Step A) (10 g, 36 mmol) in toluene (200 mL) was added 3-fluoroaniline (6.0 g, 54 mmol), cesium carbonate (23 g, 70 mmol), palladium(II) acetate (406 mg, 1.8 mmol) and (±)-BINAP (2.2 g, 3.4 mmol). The resulting mixture was stirred at 100° C. for 5 h. After cooling to room temperature, the mixture was diluted with ethyl acetate (200 mL), washed with water and brine, and dried over anhydrous magnesium sulfate. The mixture was filtered, concentrated under reduced pressure and purified using column chromatography on silica gel eluted with 10% ethyl acetate in hexanes to afford 4.5 g of title compound as colorless oil.

$^1$H NMR (CDCl$_3$) δ 8.16 (m, 1H), 7.33 (d, 1H), 7.24 (m, 1H), 7.06 (d, 1H), 6.96 (s, 1H), 6.88 (d, 1H), 6.68 (t, 1H), 6.60 (br s, 1H), 0.31 (s, 9H).

Step C: Preparation of 4-(2-chloro-4-pyrimidinyl)-N-(3-fluorophenyl)-2-pyridinamine To a solution of N-(3-fluorophenyl)-4-trimethylstannyl)-2-pyridinamine (i.e., the product of Step B) (4.0 g, 11 mmol) in 1,4-dioxane (100 mL) under nitrogen was added 2,4-dichloropyrimidine (2.26 g, 15 mmol), copper iodide (216 mg, 1.1 mmol) and bis(triphenylphosphine)palladium(II) dichloride (400 mg, 0.57 mmol). The resulting mixture was stirred at reflux for 4 h. After cooling to room temperature, the solution was concentrated under reduced pressure. The resulting residue was purified using column chromatography on silica gel eluted with 25% ethyl acetate in hexanes to afford 2.3 g of title compound as a yellow solid.

$^1$H NMR (CDCl$_3$) δ 8.75 (d, 1H), 8.41 (d, 1H), 7.65 (d, 1H), 7.53 (s, 1H), 7.43 (m, 1H), 7.32 (m, 1H), 7.29 (m, 1H), 7.11 (m, 1H), 6.77 (m, 2H).

Step D: Preparation of 4-[2-[(3-fluorophenyl)amino]-4-pyridinyl]-N-(2-methoxypropyl)-2-pyrimidinamine To a solution of 4-(2-chloro-4-pyrimidinyl)-N-(3-fluorophenyl)-2-pyridinamine (i.e., the product of Step C) (55 mg, 0.18 mmol) in toluene (3.0 mL) was added 2-methoxy-1-aminopropane hydrochloride (125 mg, 1.0 mmol) and potassium carbonate (200 mg, 1.5 mmol). The mixture was stirred at 100° C. for 2 h and then allowed to cool to room temperature. The mixture was partitioned with water and ethyl acetate and the water layer was decanted. The organic layer was washed with brine and passed through a Celite® containing drying tube. The solvent was evaporated, and the resulting residue was chromatographed using 5% to 60% ethyl acetate in hexanes as eluant to give an oil which solidified upon standing. This solid was suspended in hexanes, filtered and washed with hexanes to give 25 mg of the title compound as a yellow solid, m.p. 103-105° C.

$^1$H NMR (CDCl$_3$) δ 8.39 (d, 1H), 8.34 (d, 1H), 7.52 (br s, 1H), 7.33-7.39 (m, 1H), 7.26-7.32 (m, 2H), 7.09 (d, 1H), 6.94 (d, 1H), 6.74 (dt, 1H), 6.68 (br s, 1H), 5.52-5.62 (m, 1H), 3.73 (m, 1H), 3.58 (dt, 1H), 3.38-3.41 (m, 3H), 3.32-3.38 (m, 1H), 1.22 (d, 3H).

Example 18

Preparation of 4-[2-[(3-fluorophenyl)amino]-4-pyridinyl]-N-(3-methoxy-1-methylpropyl)-2-pyrimidinamine (a compound of Formula 1)

Step A: Preparation of 4-methoxy-2-butanone oxime

To a 1 N solution of hydrogen chloride (2 mL) was added 1,3,3-trimethyoxybutane (15 g, 101 mmol) drop-wise over 5 minutes, and the resulting mixture was stirred at 50° C. for 30 min. Sodium bicarbonate (5 g) was added to the cooled mixture, followed by diethyl ether, and MgSO$_4$. Filtration followed by the evaporation of the solvent yielded 8.5 g of a yellow oil. This oil was dissolved in methanol (100 mL) and cooled to 15° C. Hydroxylamine hydrochloride (8 g, 115 mmol) and aqueous sodium hydroxide (50%, 15 mL, 192 mmol) were added alternately at a rate to maintaining the internal temperature below 30° C. The mixture was stirred at room temperature for 72 h and then partitioned between diethyl ether and water. The organic layer was dried over MgSO$_4$ and filtered. The solvent was removed under reduced pressure to give 2.0 g of the title compound as a yellow oil.

$^1$H NMR (CDCl$_3$) δ 8.32 (br s, 1H), 3.54-3.61 (m, 2H), 3.35 (s, 3H), 2.47 (t, 2H), 1.92 (s, 3H).

Step B: Preparation of 3-methoxy-1-methylpropylamine

3-Methoxy-1-methyl-propylamine was prepared from 4-methoxy-2-butanone oxime (i.e., the product of Step B) in the same fashion as described in Example 7, Step B to give the title compound as an oil.

$^1$H NMR (CDCl$_3$) δ 3.40-3.53 (m, 2H), 3.33 (s, 3H), 3.01-3.11 (m, 1H), 1.51-1.69 (m, 2H), 1.06-1.12 (m, 3H).

Step C: Preparation of 4-[2-[(3-fluorophenyl)amino]-4-pyridinyl]-N-(3-methoxy-1-methylpropyl)-2-pyrimidinamine The title compound was prepared from 3-methoxy-1-methylpropylamine (i.e., the product of Step B) and 4-(2-chloro-4-pyrimidinyl)-N-(3-fluorophenyl)-2-pyridinamine (i.e., the product of Example 17, Step C) in the same fashion as described in Example 17, Step D to give the title compound as a yellow solid, m.p. 104-106° C.

$^1$H NMR (CDCl$_3$) δ 8.39 (d, 1H), 8.35 (d, 1H), 7.56 (br s, 1H), 7.37 (dt, 1H), 7.25-7.34 (m, 2H), 7.10 (dd, 1H), 6.92 (d, 1H), 6.70-6.78 (m, 2H), 5.41 (d, 1H), 4.32 (m, 1H), 3.46-3.62 (m, 2H), 3.34 (s, 3H), 1.88 (dt, 2H), 1.31 (d, 3H).

Example 19

Preparation of $N^2$-(3-chlorophenyl)-$N^{6'}$-(2-methoxy-1-methylethyl) [4,4'-bipyrimidine]-2,6'-diamine (a compound of Formula 1)

Step A: Preparation of 6-iodo-N-(2-methoxy-1-methylethyl)-4-pyrimidinamine 4,6-Diiodo-pyrimidine is a known compound and was prepared according to Taft, W. E. et al. *J. Med. Pharm. Chem.*, 1962, 5, 1335.

A microwave vial was charged with 4,6-diiodopyrimidine (2.0 g, 6.02 mmol), 2-aminomethoxypropane (763 μL, 7.23 mmol), triethylamine (2.1 mL, 15.06 mmol) and N-methylpyrrolidinone (16 mL). The resulting solution was microwaved for 20 min at 200° C., then poured into water and extracted with diethyl ether (3×30 mL). The organic layers were combined and washed three times with de-ionized water, then dried and concentrated. The residue was subjected to silica gel chromatographic purification using a gradient of hexanes to 40% ethyl acetate in hexanes as eluant to afford 2.0 g of the title compound as an oil.

$^1$H NMR (CDCl$_3$) δ 8.2 (s, 1H), 6.8 (s, 1H), 5.1 (br s, 1H), 4.1 (br s, 1H), 3.4 (m, 2H), 3.3 (s, 3H), 1.2 (d, 3H).

Step B: Preparation of N-(2-methoxy-1-methylethyl)-6-(trimethylstannyl)-4-pyrimidinamine To a solution of 6-iodo-N-(2-methoxy-1-methylethyl)-4-pyrimidinamine (i.e., the product of Step A) (2.0 g, 6.82 mmol) and hexamethyldistannane (2.34 g, 7.16 mmol) in 1,4-dioxane (70 mL) under a nitrogen atmosphere was added bis(triphenyl phosphine)palladium(II) dichloride (0.14 g, 0.205 mmol). The resulting mixture was stirred at reflux for 3 h. After cooling to room temperature the solution was diluted with water and extracted with ethyl acetate. The organic layers were combined and washed three times with water, dried and concentrated to give 2.2 g of the title compound.

$^1$H NMR (CDCl$_3$) δ 8.6 (s, 1H), 6.5 (s, 1H), 4.8 (br s, 1H), 4.1 (br s, 1H), 3.4 (m, 2H), 3.3 (s, 3H), 1.2 (d, 3H), 0.3 (s, 9H).

Step C: Preparation of 2'-chloro-N-(2-methoxy-1-methylethyl) [4,4'-bipyrimidine]-6-amine To a solution of N-(2-methoxy-1-methylethyl)-6-(trimethylstannyl)-4-pyrimidinamine (i.e., the product of Step B) (0.5 g, 1.51 mmol), 2,4-dichloropyrimidine (0.22 g, 1.51 mmol) and copper iodide (12 mg, 0.061 mmol) in N-methylpyrrolidinone (12 mL) under a nitrogen atmosphere was added bis (triphenylphosphine)palladium(II) dichloride (53 mg, 0.076 mmol). The resulting mixture was stirred at reflux for 2 h. After cooling to room temperature, the solution was diluted with water and extracted with diethyl ether 3 times. The organic layers were combined and washed three times with water, then dried and concentrated. The residue was purified on silica gel using a gradient of 100% hexanes to 40% ethyl acetate in hexanes to afford 270 mg of title compound as a solid.

$^1$H NMR (CDCl$_3$) δ 8.8 (d, 1H), 8.6 (s, 1H), 8.2 (d, 1H), 7.46 (s, 1H), 5.4 (br s, 1H), 4.3 (br s, 1H), 3.4 (m, 2H), 3.3 (s, 3H), 1.3 (d, 3H).

Step D: Preparation of N$^2$-(3-chlorophenyl)-N$^{6'}$-(2-methoxy-1-methylethyl) [4,4'-bipyrimidine]-2,6'-diamine To a solution of 2'-chloro-N-(2-methoxy-1-methylethyl) [4,4'-bipyrimidine]-6-amine (i.e., the product of Step C) (100 mg, 0.357 mmol) and 3-chloroaniline (57 mg, 0.45 mmol) in 1,4-dioxane (3.5 mL) under a nitrogen atmosphere was added p-toluenesulfonic acid monohydrate (57 mg, 0.30 mmol). The resulting mixture was stirred at 100° C. for 18 h. The solution was concentrated under reduced pressure to give a yellow solid residue. The residue was then purified on silica gel eluted with 40% ethyl acetate in hexanes, followed by acetone to give 113 mg of title compound as a solid.

$^1$H NMR (CDCl$_3$) δ 9.8 (s, 1H), 8.4 (s, 1H), 8.3 (d, 1H), 7.9 (d, 2H), 7.8 (s, 1H), 7.5 (d, 1H), 7.1-7.2 (m, 2H), 6.9 (d, 1H), 4.4 (m, 1H), 3.4 (m, 2H), 3.3 (s, 3H), 1.2 (d, 3H).

Example 20

Preparation of N$^2$-(3-fluorophenyl)-N$^{6'}$-(2-methoxy-1-methylethyl) [4,4'-bipyrimidine]-2,6'-diamine (a compound of Formula 1)

The title compound was prepared in the same manner as described in Example 19, Step D using 2'-chloro-N-(2-methoxy-1-methylethyl) [4,4'-bipyrimidine]-6-amine (i.e., the product of Example 19, Step C) and 3-fluoroaniline to give the title compound as a solid.

$^1$H NMR (DMSO-d$_6$) δ 10.1 (br s, NH), 8.9 (d, 1H), 8.7 (d, 2H), 7.6-7.8 (m, 2H), 7.4 (m, 2H), 7.3 (m, 1H), 7.1 (d, 1H), 6.8 (m, 1H), 6.6 (m, 1H), 4.4 (m, 1H), 3.4 (m, 2H), 3.3 (s, 3H), 1.2 (d, 3H).

Example 21

Preparation of N$^{6'}$-(2-methoxy-1-methylethyl)-N$^2$-(3-nitrophenyl) [4,4'-bipyrimidine]-2,6'-diamine (a compound of Formula 1)

The title compound was prepared in the same manner as described in Example 19, Step D using 2'-chloro-N-(2-methoxy-1-methylethyl) [4,4'-bipyrimidine]-6-amine (i.e., the product of Example 19, Step C) and 3-nitroaniline to give the title compound as a solid.

$^1$H NMR (acetone-d$_6$) δ 10.8 (br s, 1H), 9.4 (br s, 1H), 8.9 (s, 1H), 8.7 (d, 2H), 8.1 (d, 1H), 7.9 (s, 1H), 7.8 (d, 2H), 7.5-7.6 (m, 2H), 7.2 (d, 2H), 4.6 (m, 1H), 3.4 (m, 2H), 3.3 (s, 3H), 1.2 (d, 3H).

Example 22

Preparation of N$^{6'}$-(2-methoxy-1-methylethyl)-N$^2$-phenyl) [4,4'-bipyrimidine]-2,6'-diamine (a compound of Formula 1)

The title compound was prepared in the same manner as described in Example 19, Step D using 2'-chloro-N-(2-methoxy-1-methylethyl) [4,4'-bipyrimidine]-6-amine (i.e., the product of Example 19, Step C) and aniline to give the title compound as a solid.

$^1$H NMR (CDCl$_3$) δ 9.6 (s, 1H), 8.4 (s, 1H), 8.3 (br s, 1H), 7.9 (d, 2H), 7.6 (br s, 2H), 7.2 (m, 3H), 6.9 (br s, 1H), 4.4 (br s, 1H), 3.4 (m, 2H), 3.3 (s, 3H), 1.2 (d, 3H).

Example 23

Preparation of N$^2$-(2-chloro-6-methylphenyl)-N$^{6'}$-(2-methoxy-1-methylethyl) [4,4'-bipyrimidine]-2,6'-diamine (a compound of Formula 1)

The title compound was prepared in the same manner as described in Example 19, Step D using 2'-chloro-N-(2-methoxy-1-methylethyl) [4,4'-bipyrimidine]-6-amine (i.e., the product of Example 19, Step C) and 2-chloro-6-methylaniline to give the title compound as a solid.

$^1$H NMR (CDCl$_3$) δ 8.6 (br s, 1H), 8.3 (br s, 1H), 7.9 (br s, 2H), 7.6 (br s, 1H), 7.4 (br s, 1H), 7.1-7.2 (m, 2H), 4.4 (br s, 1H), 3.4 (m, 2H), 3.3 (s, 3H), 2.35 (m, 3H), 1.2 (d, 3H).

Example 24

Preparation of N⁶'-(3-fluorophenyl)-N²-(2-methoxy-1-methylethyl) [4,4'-bipyrimidine]-2,6'-diamine (a compound of Formula 1)

Step A: Preparation of N-(3-fluorophenyl)-6-iodo-4-pyrimidinamine

A mixture of 4,6-diiodopyrimidine (1.0 g, 3.01 mmol), 3-fluoroaniline (290 μL, 3.01 mmol), N,N-diisopropylethylamine (782 μL, 4.52 mmol) and n-butanol (3 mL) under nitrogen was stirred at 120° C. for 4 h. After cooling to room temperature, the solution was poured into water and extracted with ethyl acetate. The organic layer was washed once with 1 N hydrochloric acid, followed by brine, dried and concentrated to yield 0.68 g of title compound.

¹H NMR (DMSO-d₆) δ 9.8 (s, 1H), 8.3 (s, 1H), 7.7 (d, 1H), 7.3-7.4 (m, 2H), 6.8 (m, 1H).

Step B: Preparation of 2'-methylthio-N-(3-fluorophenyl) [4,4'-bipyrimidine]-6-amine 2-Methylthio-4-tri-n-butylstannylpyrimidine was prepared according to Undheim, K. et al. *Tetrahedron* 1989, 45, 993-1006.

To a solution of 2-methylthio-4-(tri-n-butylstannyl)pyrimidine (0.29 g, 1.0 mmol) and N-(3-fluorophenyl)-6-iodo-4-pyrimidinamine (i.e., the product of Step A) (0.67 g, 2.12 mmol) in N-methylpyrrolidinone (10 mL) under nitrogen was added copper iodide (16 mg, 0.085 mmol) and bis(triphenylphosphine)palladium(II) dichloride (149 mg, 0.21 mmol). The resulting mixture was stirred at 100° C. for 2.5 h. After cooling to room temperature, the solution was diluted with ethyl acetate and washed with water. The aqueous layer was extracted two times with ethyl acetate, and the combined organic layers were washed with water and brine, dried and concentrated to give 259 mg of the title compound as a light brown solid.

¹H NMR (DMSO-d₆) δ 10.2 (br s, 1H), 8.8 (m, 2H), 8.0 (d, 1H), 7.8 (m, 2H), 7.3-7.4 (m, 2H), 6.8 (m, 1H), 2.64 (s, 3H).

Step C: Preparation of 2'-methylsulfonyl-N-(3-fluorophenyl) [4,4'-bipyrimidine]-6-amine To a solution of 2'-methylthio-N-(3-fluorophenyl) [4,4'-bipyrimidine]-6-amine (i.e., the product of Step B) (259 mg, 0.826 mmol) in dichloromethane (6 mL) and chloroform (12 mL) was added m-chloroperoxybenzoic acid (370 mg, 77%). The resulting mixture was stirred at room temperature for 3 h. The mixture was then diluted with dichloromethane and washed with saturated sodium bisulfite solution, followed by saturated sodium bicarbonate solution, dried and concentrated to provide 390 mg of the title compound a yellow solid.

¹H NMR (DMSO-d₆) δ 10.4 (br s, 1H), 9.3 (d, 1H), 8.9 (s, 1H), 8.6 (d, 1H), 7.96 (s, 1H), 7.9 (d, 1H), 7.3-7.4 (m, 2H), 6.8 (m, 1H), 3.51 (s, 3H).

Step D: Preparation of N⁶'-(3-fluorophenyl)-N²-(2-methoxy-1-methylethyl) [4,4'-bipyrimidine]-2,6'-diamine A mixture of 2'-methylsulfonyl-N-(3-fluorophenyl) [4,4'-bipyrimidine]-6-amine (i.e., the product of Step C) (290 mg, 0.841 mmol) and 2-aminomethoxypropane (5 mL) was stirred at 100° C. for 2 h under a nitrogen atmosphere. The solution was concentrated and the residue was dissolved in dichloromethane and washed with water and brine. The organic layer was dried, and concentrated, and the solid residue was washed with diethyl ether to give 122 mg of title compound was obtained as a solid.

¹H NMR (DMSO-d₆) δ 8.8 (s, 1H), 8.4 (d, 1H), 7.8 (s, 1H), 7.5 (d, 1H), 7.3-7.4 (m, 2H), 7.2 (m, 1H), 6.8 (t, 1H), 5.4 (d, 1H), 4.3 (m, 1H), 3.48 (m, 2H), 3.38 (s, 3H), 1.3 (d, 3H).

By the procedures described herein, together with methods known in the art, the following compounds of Tables 1 to 7 can be prepared. The following abbreviations are used in the Tables which follow: t means tertiary, s means secondary, n means normal, means iso, c means cyclo, Me means methyl, Et means ethyl, Pr means propyl, i-Pr means isopropyl, c-Pr means cyclopropyl, Bu means butyl, Hex means hexyl, Ph means phenyl, MeO means methoxy, CN means cyano, SO₂ means S(O)₂, and NO₂ means nitro. (R) or (S) denotes the absolute chirality of the asymmetric carbon center. The radicals CH₂-2-tetrahydrofuranyl, CH₂-2-tetrahydropyranyl, CH₂-2-dioxolanyl, CH₂-2-thienyl, CH₂-2-pyridinyl and CH₂-3-pyridinyl are bonded to the remainder of the molecule through the CH₂ moiety.

The invention includes but is not limited to the following exemplary species.

TABLE 1

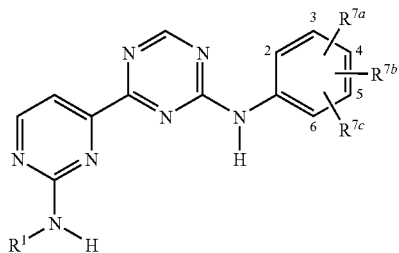

| R¹ | R⁷ᵃ | R⁷ᵇ | R⁷ᶜ |
|---|---|---|---|
| Me | H | 3-F | H |
| Et | H | 3-F | H |
| i-Pr | H | 3-F | H |
| n-Pr | H | 3-F | H |
| i-Bu | H | 3-F | H |
| n-Bu | H | 3-F | H |
| s-Bu | H | 3-F | H |
| t-butyl | H | 3-F | H |
| n-Hex | H | 3-F | H |
| cyclopropyl | H | 3-F | H |
| cyclopentyl | H | 3-F | H |
| cyclohexyl | H | 3-F | H |
| 2-cyclohexenyl | H | 3-F | H |
| 3-cyclohexenyl | H | 3-F | H |
| CH₂-c-Pr | H | 3-F | H |
| 4-tetrahydropyranyl | H | 3-F | H |
| 3-tetrahydropyranyl | H | 3-F | H |
| (R)-3-tetrahydropyranyl | H | 3-F | H |
| (S)-3-tetrahydropyranyl | H | 3-F | H |
| 3-tetrahydrofuranyl | H | 3-F | H |
| (R)-3-tetrahydrofuranyl | H | 3-F | H |
| (S)-3-tetrahydrofuranyl | H | 3-F | H |
| Ph | H | 3-F | H |
| 2-Cl-phenyl | H | 3-F | H |
| 3-Cl-phenyl | H | 3-F | H |
| 4-Cl-phenyl | H | 3-F | H |
| 2-pyridinyl | H | 3-F | H |
| 2-pyrimidinyl | H | 3-F | H |
| Me | 3-Cl | 5-F | H |
| Et | 3-Cl | 5-F | H |
| i-Pr | 3-Cl | 5-F | H |
| n-Pr | 3-Cl | 5-F | H |
| i-Bu | 3-Cl | 5-F | H |
| n-Bu | 3-Cl | 5-F | H |
| s-Bu | 3-Cl | 5-F | H |

TABLE 1-continued

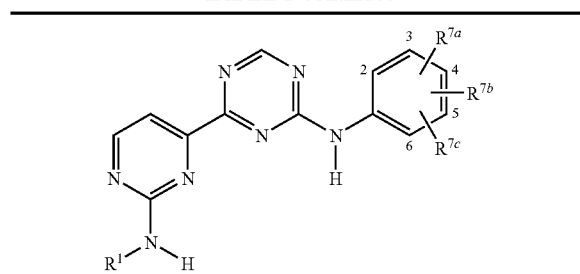

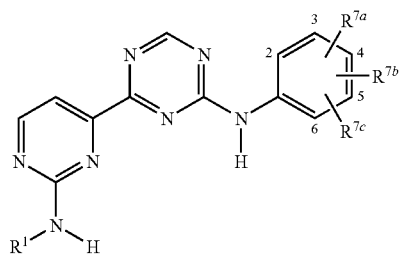

| R¹ | R⁷ᵃ | R⁷ᵇ | R⁷ᶜ |
|---|---|---|---|
| t-butyl | 3-Cl | 5-F | H |
| n-Hex | 3-Cl | 5-F | H |
| cyclopropyl | 3-Cl | 5-F | H |
| cyclopentyl | 3-Cl | 5-F | H |
| cyclohexyl | 3-Cl | 5-F | H |
| 2-cyclohexenyl | 3-Cl | 5-F | H |
| 3-cyclohexenyl | 3-Cl | 5-F | H |
| CH₂-c-Pr | 3-Cl | 5-F | H |
| 4-tetrahydropyranyl | 3-Cl | 5-F | H |
| 3-tetrahydropyranyl | 3-Cl | 5-F | H |
| (R)-3-tetrahydropyranyl | 3-Cl | 5-F | H |
| (S)-3-tetrahydropyranyl | 3-Cl | 5-F | H |
| 3-tetrahydrofuranyl | 3-Cl | 5-F | H |
| (R)-3-tetrahydrofuranyl | 3-Cl | 5-F | H |
| (S)-3-tetrahydrofuranyl | 3-Cl | 5-F | H |
| Ph | 3-Cl | 5-F | H |
| 2-Cl-phenyl | 3-Cl | 5-F | H |
| 3-Cl-phenyl | 3-Cl | 5-F | H |
| 4-Cl-phenyl | 3-Cl | 5-F | H |
| 2-pyridinyl | 3-Cl | 5-F | H |
| 2-pyrimidinyl | 3-Cl | 5-F | H |
| 2-pyrazinyl | H | 3-F | H |
| 2-thiazolyl | H | 3-F | H |
| 2-oxazolyl | H | 3-F | H |
| 2-chloro-2-propenyl | H | 3-F | H |
| 3,3-dichloro-2-propenyl | H | 3-F | H |
| CH₂-2-tetrahydrofuranyl | H | 3-F | H |
| CH₂-2-tetrahydropyranyl | H | 3-F | H |
| CH₂CH₂OH | H | 3-F | H |
| CH₂OMe | H | 3-F | H |
| CH₂CH₂OMe | H | 3-F | H |
| CH₂CH₂CH₂OMe | H | 3-F | H |
| CH₂CH(Me)OMe | H | 3-F | H |
| CH(Me)OMe | H | 3-F | H |
| CH(Me)OEt | H | 3-F | H |
| CH(Me)CH₂OMe | H | 3-F | H |
| C(Me)₂CH₂OMe | H | 3-F | H |
| CH(Me)CH₂CH₂OMe | H | 3-F | H |
| (R)—CH(Me)CH₂OMe | H | 3-F | H |
| (S)—CH(Me)CH₂OMe | H | 3-F | H |
| CH(Me)CH₂OH | H | 3-F | H |
| CH(Me)CH₂OC(=O)Me | H | 3-F | H |
| CH(Me)CH(OMe)₂ | H | 3-F | H |
| CH₂-2-dioxolanyl | H | 3-F | H |
| CH₂CH₂OCF₃ | H | 3-F | H |
| CH₂CH(Me)SMe | H | 3-F | H |
| CH(Me)CH₂SMe | H | 3-F | H |
| CH₂CH₂S(=O)Me | H | 3-F | H |
| CH₂CH₂S(O)₂Me | H | 3-F | H |
| CH₂CO₂Me | H | 3-F | H |
| CH(Me)CO₂Me | H | 3-F | H |
| CH₂C(=O)Me | H | 3-F | H |
| CH₂CH₂C(=O)Me | H | 3-F | H |
| 2-pyrazinyl | 3-Cl | 5-F | H |
| 2-thiazolyl | 3-Cl | 5-F | H |
| 2-oxazolyl | 3-Cl | 5-F | H |
| 2-chloro-2-propenyl | 3-Cl | 5-F | H |
| 3,3-dichloro-2-propenyl | 3-Cl | 5-F | H |
| CH₂-2-tetrahydrofuranyl | 3-Cl | 5-F | H |
| CH₂-2-tetrahydropyranyl | 3-Cl | 5-F | H |
| CH₂CH₂OH | 3-Cl | 5-F | H |
| CH₂OMe | 3-Cl | 5-F | H |
| CH₂CH₂OMe | 3-Cl | 5-F | H |
| CH₂CH₂CH₂OMe | 3-Cl | 5-F | H |
| CH₂CH(Me)OMe | 3-Cl | 5-F | H |
| CH(Me)OMe | 3-Cl | 5-F | H |
| CH(Me)OEt | 3-Cl | 5-F | H |
| CH(Me)CH₂OMe | 3-Cl | 5-F | H |
| C(Me)₂CH₂OMe | 3-Cl | 5-F | H |
| CH(Me)CH₂CH₂OMe | 3-Cl | 5-F | H |
| (R)—CH(Me)CH₂OMe | 3-Cl | 5-F | H |
| (S)—CH(Me)CH₂OMe | 3-Cl | 5-F | H |
| CH(Me)CH₂OH | 3-Cl | 5-F | H |
| CH(Me)CH₂OC(=O)Me | 3-Cl | 5-F | H |
| CH(Me)CH(OMe)₂ | 3-Cl | 5-F | H |
| CH₂-2-dioxolanyl | 3-Cl | 5-F | H |
| CH₂CH₂OCF₃ | 3-Cl | 5-F | H |
| CH₂CH(Me)SMe | 3-Cl | 5-F | H |
| CH(Me)CH₂SMe | 3-Cl | 5-F | H |
| CH₂CH₂S(=O)Me | 3-Cl | 5-F | H |
| CH₂CH₂S(O)₂Me | 3-Cl | 5-F | H |
| CH₂CO₂Me | 3-Cl | 5-F | H |
| CH(Me)CO₂Me | 3-Cl | 5-F | H |
| CH₂C(=O)Me | 3-Cl | 5-F | H |
| CH₂CH₂C(=O)Me | 3-Cl | 5-F | H |
| CH₂SiMe₃ | H | 3-F | H |
| CH₂CH₂SiMe₃ | H | 3-F | H |
| CH₂-2-thienyl | H | 3-F | H |
| CH₂-2-pyridinyl | H | 3-F | H |
| CH₂-3-pyridinyl | H | 3-F | H |
| NH₂ | H | 3-F | H |
| NHCH₃ | H | 3-F | H |
| NHCH₂CF₃ | H | 3-F | H |
| NHCH₂CH₃ | H | 3-F | H |
| NHCH(Me)CH₃ | H | 3-F | H |
| NHCH₂CH(Me)₂ | H | 3-F | H |
| NHC(Me)₃ | H | 3-F | H |
| N(CH₃)₂ | H | 3-F | H |
| N(CH₃)CH₂CH₃ | H | 3-F | H |
| N(CH₂CH₃)CH₂CH₃ | H | 3-F | H |
| Me | 3-F | 4-F | H |
| Et | 3-F | 4-F | H |
| i-Pr | 3-F | 4-F | H |
| n-Pr | 3-F | 4-F | H |
| i-Bu | 3-F | 4-F | H |
| n-Bu | 3-F | 4-F | H |
| s-Bu | 3-F | 4-F | H |
| t-butyl | 3-F | 4-F | H |
| n-Hex | 3-F | 4-F | H |
| cyclopropyl | 3-F | 4-F | H |
| cyclopentyl | 3-F | 4-F | H |
| cyclohexyl | 3-F | 4-F | H |
| 2-cyclohexenyl | 3-F | 4-F | H |
| 3-cyclohexenyl | 3-F | 4-F | H |
| CH₂-c-Pr | 3-F | 4-F | H |
| 4-tetrahydropyranyl | 3-F | 4-F | H |
| CH₂SiMe₃ | 3-Cl | 5-F | H |
| CH₂CH₂SiMe₃ | 3-Cl | 5-F | H |
| CH₂-2-thienyl | 3-Cl | 5-F | H |
| CH₂-2-pyridinyl | 3-Cl | 5-F | H |
| CH₂-3-pyridinyl | 3-Cl | 5-F | H |
| NH₂ | 3-Cl | 5-F | H |
| NHCH₃ | 3-Cl | 5-F | H |
| NHCH₂CF₃ | 3-Cl | 5-F | H |
| NHCH₂CH₃ | 3-Cl | 5-F | H |
| NHCH(Me)CH₃ | 3-Cl | 5-F | H |
| NHCH₂CH(Me)₂ | 3-Cl | 5-F | H |

TABLE 1-continued

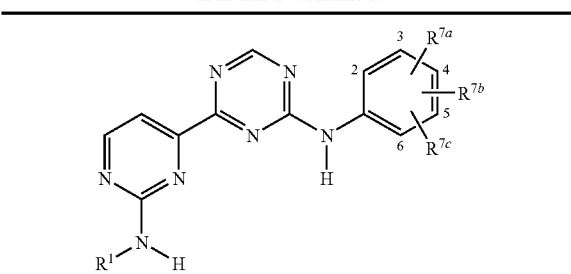

| R¹ | R⁷ᵃ | R⁷ᵇ | R⁷ᶜ |
|---|---|---|---|
| NHC(Me)₃ | 3-Cl | 5-F | H |
| N(CH₃)₂ | 3-Cl | 5-F | H |
| N(CH₃)CH₂CH₃ | 3-Cl | 5-F | H |
| N(CH₂CH₃)CH₂CH₃ | 3-Cl | 5-F | H |
| Me | 3-F | 5-F | H |
| Et | 3-F | 5-F | H |
| i-Pr | 3-F | 5-F | H |
| n-Pr | 3-F | 5-F | H |
| i-Bu | 3-F | 5-F | H |
| n-Bu | 3-F | 5-F | H |
| s-Bu | 3-F | 5-F | H |
| t-butyl | 3-F | 5-F | H |
| n-Hex | 3-F | 5-F | H |
| cyclopropyl | 3-F | 5-F | H |
| cyclopentyl | 3-F | 5-F | H |
| cyclohexyl | 3-F | 5-F | H |
| 2-cyclohexenyl | 3-F | 5-F | H |
| 3-cyclohexenyl | 3-F | 5-F | H |
| CH₂-c-Pr | 3-F | 5-F | H |
| 4-tetrahydropyranyl | 3-F | 5-F | H |
| 3-tetrahydropyranyl | 3-F | 4-F | H |
| (R)-3-tetrahydropyranyl | 3-F | 4-F | H |
| (S)-3-tetrahydropyranyl | 3-F | 4-F | H |
| 3-tetrahydrofuranyl | 3-F | 4-F | H |
| (R)-3-tetrahydrofuranyl | 3-F | 4-F | H |
| (S)-3-tetrahydrofuranyl | 3-F | 4-F | H |
| Ph | 3-F | 4-F | H |
| 2-Cl-phenyl | 3-F | 4-F | H |
| 3-Cl-phenyl | 3-F | 4-F | H |
| 4-Cl-phenyl | 3-F | 4-F | H |
| 2-pyridinyl | 3-F | 4-F | H |
| 2-pyrimidinyl | 3-F | 4-F | H |
| 2-pyrazinyl | 3-F | 4-F | H |
| 2-thiazolyl | 3-F | 4-F | H |
| 2-oxazolyl | 3-F | 4-F | H |
| 2-chloro-2-propenyl | 3-F | 4-F | H |
| 3,3-dichloro-2-propenyl | 3-F | 4-F | H |
| CH₂-2-tetrahydrofuranyl | 3-F | 4-F | H |
| CH₂-2-tetrahydropyranyl | 3-F | 4-F | H |
| CH₂CH₂OH | 3-F | 4-F | H |
| CH₂OMe | 3-F | 4-F | H |
| CH₂CH₂OMe | 3-F | 4-F | H |
| CH₂CH₂CH₂OMe | 3-F | 4-F | H |
| CH₂CH(Me)OMe | 3-F | 4-F | H |
| CH(Me)OMe | 3-F | 4-F | H |
| CH(Me)OEt | 3-F | 4-F | H |
| CH(Me)CH₂OMe | 3-F | 4-F | H |
| C(Me)₂CH₂OMe | 3-F | 4-F | H |
| CH(Me)CH₂CH₂OMe | 3-F | 4-F | H |
| (R)—CH(Me)CH₂OMe | 3-F | 4-F | H |
| (S)—CH(Me)CH₂OMe | 3-F | 4-F | H |
| 3-tetrahydropyranyl | 3-F | 5-F | H |
| (R)-3-tetrahydropyranyl | 3-F | 5-F | H |
| (S)-3-tetrahydropyranyl | 3-F | 5-F | H |
| 3-tetrahydrofuranyl | 3-F | 5-F | H |
| (R)-3-tetrahydrofuranyl | 3-F | 5-F | H |
| (S)-3-tetrahydrofuranyl | 3-F | 5-F | H |
| Ph | 3-F | 5-F | H |
| 2-Cl-phenyl | 3-F | 5-F | H |
| 3-Cl-phenyl | 3-F | 5-F | H |
| 4-Cl-phenyl | 3-F | 5-F | H |
| 2-pyridinyl | 3-F | 5-F | H |
| 2-pyrimidinyl | 3-F | 5-F | H |
| 2-pyrazinyl | 3-F | 5-F | H |
| 2-thiazolyl | 3-F | 5-F | H |

TABLE 1-continued

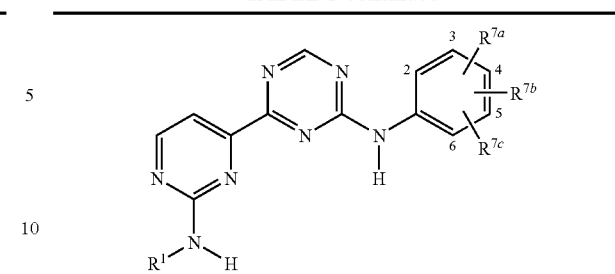

| R¹ | R⁷ᵃ | R⁷ᵇ | R⁷ᶜ |
|---|---|---|---|
| 2-oxazolyl | 3-F | 5-F | H |
| 2-chloro-2-propenyl | 3-F | 5-F | H |
| 3,3-dichloro-2-propenyl | 3-F | 5-F | H |
| CH₂-2-tetrahydrofuranyl | 3-F | 5-F | H |
| CH₂-2-tetrahydropyranyl | 3-F | 5-F | H |
| CH₂CH₂OH | 3-F | 5-F | H |
| CH₂OMe | 3-F | 5-F | H |
| CH₂CH₂OMe | 3-F | 5-F | H |
| CH₂CH₂CH₂OMe | 3-F | 5-F | H |
| CH₂CH(Me)OMe | 3-F | 5-F | H |
| CH(Me)OMe | 3-F | 5-F | H |
| CH(Me)OEt | 3-F | 5-F | H |
| CH(Me)CH₂OMe | 3-F | 5-F | H |
| C(Me)₂CH₂OMe | 3-F | 5-F | H |
| CH(Me)CH₂CH₂OMe | 3-F | 5-F | H |
| (R)—CH(Me)CH₂OMe | 3-F | 5-F | H |
| (S)—CH(Me)CH₂OMe | 3-F | 5-F | H |
| CH(Me)CH₂OH | 3-F | 4-F | H |
| CH(Me)CH₂OC(=O)Me | 3-F | 4-F | H |
| CH(Me)CH(OMe)₂ | 3-F | 4-F | H |
| CH₂-2-dioxolanyl | 3-F | 4-F | H |
| CH₂CH₂OCF₃ | 3-F | 4-F | H |
| CH₂CH(Me)SMe | 3-F | 4-F | H |
| CH(Me)CH₂SMe | 3-F | 4-F | H |
| CH₂CH₂S(=O)Me | 3-F | 4-F | H |
| CH₂CH₂S(O)₂Me | 3-F | 4-F | H |
| CH₂CO₂Me | 3-F | 4-F | H |
| CH(Me)CO₂Me | 3-F | 4-F | H |
| CH₂C(=O)Me | 3-F | 4-F | H |
| CH₂CH₂C(=O)Me | 3-F | 4-F | H |
| CH₂SiMe₃ | 3-F | 4-F | H |
| CH₂CH₂SiMe₃ | 3-F | 4-F | H |
| CH₂-2-thienyl | 3-F | 4-F | H |
| CH₂-2-pyridinyl | 3-F | 4-F | H |
| CH₂-3-pyridinyl | 3-F | 4-F | H |
| NH₂ | 3-F | 4-F | H |
| NHCH₃ | 3-F | 4-F | H |
| NHCH₂CF₃ | 3-F | 4-F | H |
| NHCH₂CH₃ | 3-F | 4-F | H |
| NHCH(Me)CH₃ | 3-F | 4-F | H |
| NHCH₂CH(Me)₂ | 3-F | 4-F | H |
| NHC(Me)₃ | 3-F | 4-F | H |
| N(CH₃)₂ | 3-F | 4-F | H |
| N(CH₃)CH₂CH₃ | 3-F | 4-F | H |
| N(CH₂CH₃)CH₂CH₃ | 3-F | 4-F | H |
| Me | H | 3-Cl | H |
| Et | H | 3-Cl | H |
| i-Pr | H | 3-Cl | H |
| n-Pr | H | 3-Cl | H |
| i-Bu | H | 3-Cl | H |
| n-Bu | H | 3-Cl | H |
| s-Bu | H | 3-Cl | H |
| CH(Me)CH₂OH | 3-F | 5-F | H |
| CH(Me)CH₂OC(=O)Me | 3-F | 5-F | H |
| CH(Me)CH(OMe)₂ | 3-F | 5-F | H |
| CH₂-2-dioxolanyl | 3-F | 5-F | H |
| CH₂CH₂OCF₃ | 3-F | 5-F | H |
| CH₂CH(Me)SMe | 3-F | 5-F | H |
| CH(Me)CH₂SMe | 3-F | 5-F | H |
| CH₂CH₂S(=O)Me | 3-F | 5-F | H |
| CH₂CH₂S(O)₂Me | 3-F | 5-F | H |
| CH₂CO₂Me | 3-F | 5-F | H |
| CH(Me)CO₂Me | 3-F | 5-F | H |
| CH₂C(=O)Me | 3-F | 5-F | H |
| CH₂CH₂C(=O)Me | 3-F | 5-F | H |

TABLE 1-continued

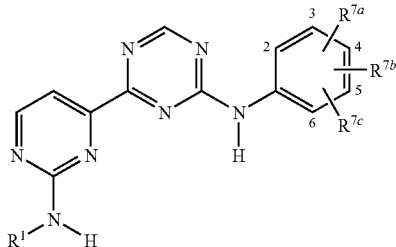

| R¹ | R⁷ᵃ | R⁷ᵇ | R⁷ᶜ |
|---|---|---|---|
| CH₂SiMe₃ | 3-F | 5-F | H |
| CH₂CH₂SiMe₃ | 3-F | 5-F | H |
| CH₂-2-thienyl | 3-F | 5-F | H |
| CH₂-2-pyridinyl | 3-F | 5-F | H |
| CH₂-3-pyridinyl | 3-F | 5-F | H |
| NH₂ | 3-F | 5-F | H |
| NHCH₃ | 3-F | 5-F | H |
| NHCH₂CF₃ | 3-F | 5-F | H |
| NHCH₂CH₃ | 3-F | 5-F | H |
| NHCH(Me)CH₃ | 3-F | 5-F | H |
| NHCH₂CH(Me)₂ | 3-F | 5-F | H |
| NHC(Me)₃ | 3-F | 5-F | H |
| N(CH₃)₂ | 3-F | 5-F | H |
| N(CH₃)CH₂CH₃ | 3-F | 5-F | H |
| N(CH₂CH₃)CH₂CH₃ | 3-F | 5-F | H |
| Me | 3-CN | 5-F | H |
| Et | 3-CN | 5-F | H |
| i-Pr | 3-CN | 5-F | H |
| n-Pr | 3-CN | 5-F | H |
| i-Bu | 3-CN | 5-F | H |
| n-Bu | 3-CN | 5-F | H |
| s-Bu | 3-CN | 5-F | H |
| t-butyl | H | 3-Cl | H |
| n-Hex | H | 3-Cl | H |
| cyclopropyl | H | 3-Cl | H |
| cyclopentyl | H | 3-Cl | H |
| cyclohexyl | H | 3-Cl | H |
| 2-cyclohexenyl | H | 3-Cl | H |
| 3-cyclohexenyl | H | 3-Cl | H |
| CH₂-c-Pr | H | 3-Cl | H |
| 4-tetrahydropyranyl | H | 3-Cl | H |
| 3-tetrahydropyranyl | H | 3-Cl | H |
| (R)-3-tetrahydropyranyl | H | 3-Cl | H |
| (S)-3-tetrahydropyranyl | H | 3-Cl | H |
| 3-tetrahydrofuranyl | H | 3-Cl | H |
| (R)-3-tetrahydrofuranyl | H | 3-Cl | H |
| (S)-3-tetrahydrofuranyl | H | 3-Cl | H |
| Ph | H | 3-Cl | H |
| 2-Cl-phenyl | H | 3-Cl | H |
| 3-Cl-phenyl | H | 3-Cl | H |
| 4-Cl-phenyl | H | 3-Cl | H |
| 2-pyridinyl | H | 3-Cl | H |
| 2-pyrimidinyl | H | 3-Cl | H |
| 2-pyrazinyl | H | 3-Cl | H |
| 2-thiazolyl | H | 3-Cl | H |
| 2-oxazolyl | H | 3-Cl | H |
| 2-chloro-2-propenyl | H | 3-Cl | H |
| 3,3-dichloro-2-propenyl | H | 3-Cl | H |
| CH₂-2-tetrahydrofuranyl | H | 3-Cl | H |
| CH₂-2-tetrahydropyranyl | H | 3-Cl | H |
| CH₂CH₂OH | H | 3-Cl | H |
| CH₂OMe | H | 3-Cl | H |
| CH₂CH₂OMe | H | 3-Cl | H |
| CH₂CH₂CH₂OMe | H | 3-Cl | H |
| CH₂CH(Me)OMe | H | 3-Cl | H |
| CH(Me)OMe | H | 3-Cl | H |
| CH(Me)OEt | H | 3-Cl | H |
| CH(Me)CH₂OMe | H | 3-Cl | H |
| C(Me)₂CH₂OMe | H | 3-Cl | H |
| t-butyl | 3-CN | 5-F | H |
| n-Hex | 3-CN | 5-F | H |
| cyclopropyl | 3-CN | 5-F | H |
| cyclopentyl | 3-CN | 5-F | H |
| cyclohexyl | 3-CN | 5-F | H |
| 2-cyclohexenyl | 3-CN | 5-F | H |

TABLE 1-continued

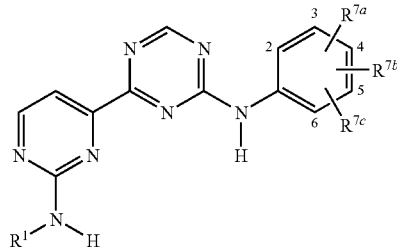

| R¹ | R⁷ᵃ | R⁷ᵇ | R⁷ᶜ |
|---|---|---|---|
| 3-cyclohexenyl | 3-CN | 5-F | H |
| CH₂-c-Pr | 3-CN | 5-F | H |
| 4-tetrahydropyranyl | 3-CN | 5-F | H |
| 3-tetrahydropyranyl | 3-CN | 5-F | H |
| (R)-3-tetrahydropyranyl | 3-CN | 5-F | H |
| (S)-3-tetrahydropyranyl | 3-CN | 5-F | H |
| 3-tetrahydrofuranyl | 3-CN | 5-F | H |
| (R)-3-tetrahydrofuranyl | 3-CN | 5-F | H |
| (S)-3-tetrahydrofuranyl | 3-CN | 5-F | H |
| Ph | 3-CN | 5-F | H |
| 2-Cl-phenyl | 3-CN | 5-F | H |
| 3-Cl-phenyl | 3-CN | 5-F | H |
| 4-Cl-phenyl | 3-CN | 5-F | H |
| 2-pyridinyl | 3-CN | 5-F | H |
| 2-pyrimidinyl | 3-CN | 5-F | H |
| 2-pyrazinyl | 3-CN | 5-F | H |
| 2-thiazolyl | 3-CN | 5-F | H |
| 2-oxazolyl | 3-CN | 5-F | H |
| 2-chloro-2-propenyl | 3-CN | 5-F | H |
| 3,3-dichloro-2-propenyl | 3-CN | 5-F | H |
| CH₂-2-tetrahydrofuranyl | 3-CN | 5-F | H |
| CH₂-2-tetrahydropyranyl | 3-CN | 5-F | H |
| CH₂CH₂OH | 3-CN | 5-F | H |
| CH₂OMe | 3-CN | 5-F | H |
| CH₂CH₂OMe | 3-CN | 5-F | H |
| CH₂CH₂CH₂OMe | 3-CN | 5-F | H |
| CH₂CH(Me)OMe | 3-CN | 5-F | H |
| CH(Me)OMe | 3-CN | 5-F | H |
| CH(Me)OEt | 3-CN | 5-F | H |
| CH(Me)CH₂OMe | 3-CN | 5-F | H |
| C(Me)₂CH₂OMe | 3-CN | 5-F | H |
| CH(Me)CH₂CH₂OMe | H | 3-Cl | H |
| (R)—CH(Me)CH₂OMe | H | 3-Cl | H |
| (S)—CH(Me)CH₂OMe | H | 3-Cl | H |
| CH(Me)CH₂OH | H | 3-Cl | H |
| CH(Me)CH₂OC(=O)Me | H | 3-Cl | H |
| CH(Me)CH(OMe)₂ | H | 3-Cl | H |
| CH₂-2-dioxolanyl | H | 3-Cl | H |
| CH₂CH₂OCF₃ | H | 3-Cl | H |
| CH₂CH(Me)SMe | H | 3-Cl | H |
| CH(Me)CH₂SMe | H | 3-Cl | H |
| CH₂CH₂S(=O)Me | H | 3-Cl | H |
| CH₂CH₂S(O)2Me | H | 3-Cl | H |
| CH₂CO₂Me | H | 3-Cl | H |
| CH(Me)CO₂Me | H | 3-Cl | H |
| CH₂C(=O)Me | H | 3-Cl | H |
| CH₂CH₂C(=O)Me | H | 3-Cl | H |
| CH₂SiMe₃ | H | 3-Cl | H |
| CH₂CH₂SiMe₃ | H | 3-Cl | H |
| CH₂-2-thienyl | H | 3-Cl | H |
| CH₂-2-pyridinyl | H | 3-Cl | H |
| CH₂-3-pyridinyl | H | 3-Cl | H |
| NH₂ | H | 3-Cl | H |
| NHCH₃ | H | 3-Cl | H |
| NHCH₂CF₃ | H | 3-Cl | H |
| NHCH₂CH₃ | H | 3-Cl | H |
| NHCH(Me)CH₃ | H | 3-Cl | H |
| NHCH₂CH(Me)₂ | H | 3-Cl | H |
| NHC(Me)₃ | H | 3-Cl | H |
| N(CH₃)₂ | H | 3-Cl | H |
| N(CH₃)CH₂CH₃ | H | 3-Cl | H |
| N(CH₂CH₃)CH₂CH₃ | H | 3-Cl | H |
| Me | H | 3-CN | H |
| Et | H | 3-CN | H |
| i-Pr | H | 3-CN | H |

TABLE 1-continued

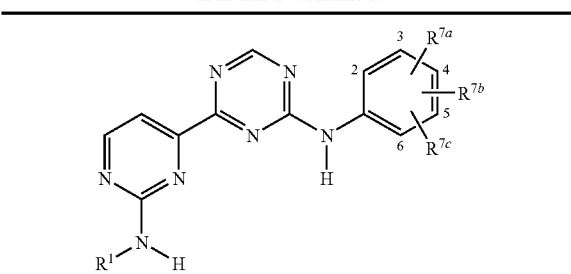

| R¹ | R⁷ᵃ | R⁷ᵇ | R⁷ᶜ |
|---|---|---|---|
| n-Pr | H | 3-CN | H |
| i-Bu | H | 3-CN | H |
| n-Bu | H | 3-CN | H |
| CH(Me)CH₂CH₂OMe | 3-CN | 5-F | H |
| (R)—CH(Me)CH₂OMe | 3-CN | 5-F | H |
| (S)—CH(Me)CH₂OMe | 3-CN | 5-F | H |
| CH(Me)CH₂OH | 3-CN | 5-F | H |
| CH(Me)CH₂OC(=O)Me | 3-CN | 5-F | H |
| CH(Me)CH(OMe)₂ | 3-CN | 5-F | H |
| CH₂-2-dioxolanyl | 3-CN | 5-F | H |
| CH₂CH₂OCF₃ | 3-CN | 5-F | H |
| CH₂CH(Me)SMe | 3-CN | 5-F | H |
| CH(Me)CH₂SMe | 3-CN | 5-F | H |
| CH₂CH₂S(=O)Me | 3-CN | 5-F | H |
| CH₂CH₂S(O)2Me | 3-CN | 5-F | H |
| CH₂CO₂Me | 3-CN | 5-F | H |
| CH(Me)CO₂Me | 3-CN | 5-F | H |
| CH₂C(=O)Me | 3-CN | 5-F | H |
| CH₂CH₂C(=O)Me | 3-CN | 5-F | H |
| CH₂SiMe₃ | 3-CN | 5-F | H |
| CH₂CH₂SiMe₃ | 3-CN | 5-F | H |
| CH₂-2-thienyl | 3-CN | 5-F | H |
| CH₂-2-pyridinyl | 3-CN | 5-F | H |
| CH₂-3-pyridinyl | 3-CN | 5-F | H |
| NH₂ | 3-CN | 5-F | H |
| NHCH₃ | 3-CN | 5-F | H |
| NHCH₂CF₃ | 3-CN | 5-F | H |
| NHCH₂CH₃ | 3-CN | 5-F | H |
| NHCH(Me)CH₃ | 3-CN | 5-F | H |
| NHCH₂CH(Me)₂ | 3-CN | 5-F | H |
| NHC(Me)₃ | 3-CN | 5-F | H |
| N(CH₃)₂ | 3-CN | 5-F | H |
| N(CH₃)CH₂CH₃ | 3-CN | 5-F | H |
| N(CH₂CH₃)CH₂CH₃ | 3-CN | 5-F | H |
| Me | H | 3-NO₂ | H |
| Et | H | 3-NO₂ | H |
| i-Pr | H | 3-NO₂ | H |
| n-Pr | H | 3-NO₂ | H |
| i-Bu | H | 3-NO₂ | H |
| n-Bu | H | 3-NO₂ | H |
| s-Bu | H | 3-CN | H |
| t-butyl | H | 3-CN | H |
| n-Hex | H | 3-CN | H |
| cyclopropyl | H | 3-CN | H |
| cyclopentyl | H | 3-CN | H |
| cyclohexyl | H | 3-CN | H |
| 2-cyclohexenyl | H | 3-CN | H |
| 3-cyclohexenyl | H | 3-CN | H |
| CH₂-c-Pr | H | 3-CN | H |
| 4-tetrahydropyranyl | H | 3-CN | H |
| 3-tetrahydropyranyl | H | 3-CN | H |
| (R)-3-tetrahydropyranyl | H | 3-CN | H |
| (S)-3-tetrahydropyranyl | H | 3-CN | H |
| 3-tetrahydrofuranyl | H | 3-CN | H |
| (R)-3-tetrahydrofuranyl | H | 3-CN | H |
| (S)-3-tetrahydrofuranyl | H | 3-CN | H |
| Ph | H | 3-CN | H |
| 2-Cl-phenyl | H | 3-CN | H |
| 3-Cl-phenyl | H | 3-CN | H |
| 4-Cl-phenyl | H | 3-CN | H |
| 2-pyridinyl | H | 3-CN | H |
| 2-pyrimidinyl | H | 3-CN | H |
| 2-pyrazinyl | H | 3-CN | H |
| 2-thiazolyl | H | 3-CN | H |
| 2-oxazolyl | H | 3-CN | H |

TABLE 1-continued

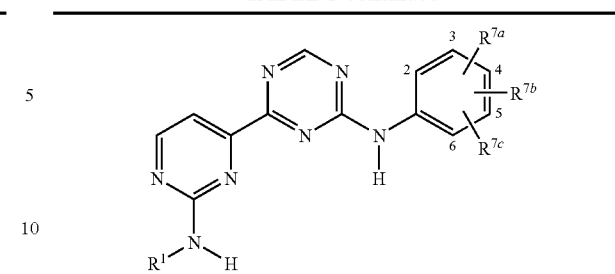

| R¹ | R⁷ᵃ | R⁷ᵇ | R⁷ᶜ |
|---|---|---|---|
| 2-chloro-2-propenyl | H | 3-CN | H |
| 3,3-dichloro-2-propenyl | H | 3-CN | H |
| CH₂-2-tetrahydrofuranyl | H | 3-CN | H |
| CH₂-2-tetrahydropyranyl | H | 3-CN | H |
| CH₂CH₂OH | H | 3-CN | H |
| CH₂OMe | H | 3-CN | H |
| CH₂CH₂OMe | H | 3-CN | H |
| CH₂CH₂CH₂OMe | H | 3-CN | H |
| CH₂CH(Me)OMe | H | 3-CN | H |
| CH(Me)OMe | H | 3-CN | H |
| CH(Me)OEt | H | 3-CN | H |
| CH(Me)CH₂OMe | H | 3-CN | H |
| s-Bu | H | 3-NO₂ | H |
| t-butyl | H | 3-NO₂ | H |
| n-Hex | H | 3-NO₂ | H |
| cyclopropyl | H | 3-NO₂ | H |
| cyclopentyl | H | 3-NO₂ | H |
| cyclohexyl | H | 3-NO₂ | H |
| 2-cyclohexenyl | H | 3-NO₂ | H |
| 3-cyclohexenyl | H | 3-NO₂ | H |
| CH₂-c-Pr | H | 3-NO₂ | H |
| 4-tetrahydropyranyl | H | 3-NO₂ | H |
| 3-tetrahydropyranyl | H | 3-NO₂ | H |
| (R)-3-tetrahydropyranyl | H | 3-NO₂ | H |
| (S)-3-tetrahydropyranyl | H | 3-NO₂ | H |
| 3-tetrahydrofuranyl | H | 3-NO₂ | H |
| (R)-3-tetrahydrofuranyl | H | 3-NO₂ | H |
| (S)-3-tetrahydrofuranyl | H | 3-NO₂ | H |
| Ph | H | 3-NO₂ | H |
| 2-Cl-phenyl | H | 3-NO₂ | H |
| 3-Cl-phenyl | H | 3-NO₂ | H |
| 4-Cl-phenyl | H | 3-NO₂ | H |
| 2-pyridinyl | H | 3-NO₂ | H |
| 2-pyrimidinyl | H | 3-NO₂ | H |
| 2-pyrazinyl | H | 3-NO₂ | H |
| 2-thiazolyl | H | 3-NO₂ | H |
| 2-oxazolyl | H | 3-NO₂ | H |
| 2-chloro-2-propenyl | H | 3-NO₂ | H |
| 3,3-dichloro-2-propenyl | H | 3-NO₂ | H |
| CH₂-2-tetrahydrofuranyl | H | 3-NO₂ | H |
| CH₂-2-tetrahydropyranyl | H | 3-NO₂ | H |
| CH₂CH₂OH | H | 3-NO₂ | H |
| CH₂OMe | H | 3-NO₂ | H |
| CH₂CH₂OMe | H | 3-NO₂ | H |
| CH₂CH₂CH₂OMe | H | 3-NO₂ | H |
| CH₂CH(Me)OMe | H | 3-NO₂ | H |
| CH(Me)OMe | H | 3-NO₂ | H |
| CH(Me)OEt | H | 3-NO₂ | H |
| CH(Me)CH₂OMe | H | 3-NO₂ | H |
| C(Me)₂CH₂OMe | H | 3-CN | H |
| CH(Me)CH₂OMe | H | 3-CN | H |
| (R)—CH(Me)CH₂OMe | H | 3-CN | H |
| (S)—CH(Me)CH₂OMe | H | 3-CN | H |
| CH(Me)CH₂OH | H | 3-CN | H |
| CH(Me)CH₂OC(=O)Me | H | 3-CN | H |
| CH(Me)CH(OMe)₂ | H | 3-CN | H |
| CH₂-2-dioxolanyl | H | 3-CN | H |
| CH₂CH₂OCF₃ | H | 3-CN | H |
| CH₂CH(Me)SMe | H | 3-CN | H |
| CH(Me)CH₂SMe | H | 3-CN | H |
| CH₂CH₂S(=O)Me | H | 3-CN | H |
| CH₂CH₂S(O)₂Me | H | 3-CN | H |
| CH₂CO₂Me | H | 3-CN | H |
| CH(Me)CO₂Me | H | 3-CN | H |
| CH₂C(=O)Me | H | 3-CN | H |

TABLE 1-continued

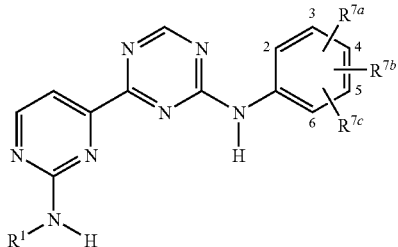

| R¹ | R⁷ᵃ | R⁷ᵇ | R⁷ᶜ |
|---|---|---|---|
| CH₂CH₂C(=O)Me | H | 3-CN | H |
| CH₂SiMe₃ | H | 3-CN | H |
| CH₂CH₂SiMe₃ | H | 3-CN | H |
| CH₂-2-thienyl | H | 3-CN | H |
| CH₂-2-pyridinyl | H | 3-CN | H |
| CH₂-3-pyridinyl | H | 3-CN | H |
| NH₂ | H | 3-CN | H |
| NHCH₃ | H | 3-CN | H |
| NHCH₂CF₃ | H | 3-CN | H |
| NHCH₂CH₃ | H | 3-CN | H |
| NHCH(Me)CH₃ | H | 3-CN | H |
| NHCH₂CH(Me)₂ | H | 3-CN | H |
| NHC(Me)₃ | H | 3-CN | H |
| N(CH₃)₂ | H | 3-CN | H |
| N(CH₃)CH₂CH₃ | H | 3-CN | H |
| N(CH₂CH₃)CH₂CH₃ | H | 3-CN | H |
| Me | H | 3-Br | H |
| Et | H | 3-Br | H |
| i-Pr | H | 3-Br | H |
| n-Pr | H | 3-Br | H |
| i-Bu | H | 3-Br | H |
| C(Me)₂CH₂OMe | H | 3-NO₂ | H |
| CH(Me)CH₂CH₂OMe | H | 3-NO₂ | H |
| (R)—CH(Me)CH₂OMe | H | 3-NO₂ | H |
| (S)—CH(Me)CH₂OMe | H | 3-NO₂ | H |
| CH(Me)CH₂OH | H | 3-NO₂ | H |
| CH(Me)CH₂OC(=O)Me | H | 3-NO₂ | H |
| CH(Me)CH(OMe)₂ | H | 3-NO₂ | H |
| CH₂-2-dioxolanyl | H | 3-NO₂ | H |
| CH₂CH₂OCF₃ | H | 3-NO₂ | H |
| CH₂CH(Me)SMe | H | 3-NO₂ | H |
| CH(Me)CH₂SMe | H | 3-NO₂ | H |
| CH₂CH₂S(=O)Me | H | 3-NO₂ | H |
| CH₂CH₂S(O)₂Me | H | 3-NO₂ | H |
| CH₂CO₂Me | H | 3-NO₂ | H |
| CH(Me)CO₂Me | H | 3-NO₂ | H |
| CH₂C(=O)Me | H | 3-NO₂ | H |
| CH₂CH₂C(=O)Me | H | 3-NO₂ | H |
| CH₂SiMe₃ | H | 3-NO₂ | H |
| CH₂CH₂SiMe₃ | H | 3-NO₂ | H |
| CH₂-2-thienyl | H | 3-NO₂ | H |
| CH₂-2-pyridinyl | H | 3-NO₂ | H |
| CH₂-3-pyridinyl | H | 3-NO₂ | H |
| NH₂ | H | 3-NO₂ | H |
| NHCH₃ | H | 3-NO₂ | H |
| NHCH₂CF₃ | H | 3-NO₂ | H |
| NHCH₂CH₃ | H | 3-NO₂ | H |
| NHCH(Me)CH₃ | H | 3-NO₂ | H |
| NHCH₂CH(Me)₂ | H | 3-NO₂ | H |
| NHC(Me)₃ | H | 3-NO₂ | H |
| N(CH₃)₂ | H | 3-NO₂ | H |
| N(CH₃)CH₂CH₃ | H | 3-NO₂ | H |
| N(CH₂CH₃)CH₂CH₃ | H | 3-NO₂ | H |
| Me | H | 3-I | H |
| Et | H | 3-I | H |
| i-Pr | H | 3-I | H |
| n-Pr | H | 3-I | H |
| i-Bu | H | 3-I | H |
| n-Bu | H | 3-Br | H |
| s-Bu | H | 3-Br | H |
| t-butyl | H | 3-Br | H |
| n-Hex | H | 3-Br | H |
| cyclopropyl | H | 3-Br | H |
| cyclopentyl | H | 3-Br | H |
| cyclohexyl | H | 3-Br | H |

TABLE 1-continued

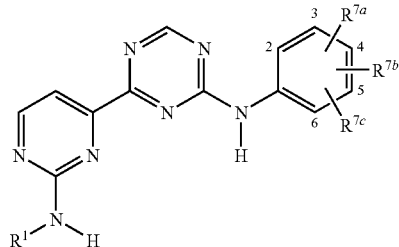

| R¹ | R⁷ᵃ | R⁷ᵇ | R⁷ᶜ |
|---|---|---|---|
| 2-cyclohexenyl | H | 3-Br | H |
| 3-cyclohexenyl | H | 3-Br | H |
| CH₂-c-Pr | H | 3-Br | H |
| 4-tetrahydropyranyl | H | 3-Br | H |
| 3-tetrahydropyranyl | H | 3-Br | H |
| (R)-3-tetrahydropyranyl | H | 3-Br | H |
| (S)-3-tetrahydropyranyl | H | 3-Br | H |
| 3-tetrahydrofuranyl | H | 3-Br | H |
| (R)-3-tetrahydrofuranyl | H | 3-Br | H |
| (S)-3-tetrahydrofuranyl | H | 3-Br | H |
| Ph | H | 3-Br | H |
| 2-Cl-phenyl | H | 3-Br | H |
| 3-Cl-phenyl | H | 3-Br | H |
| 4-Cl-phenyl | H | 3-Br | H |
| 2-pyridinyl | H | 3-Br | H |
| 2-pyrimidinyl | H | 3-Br | H |
| 2-pyrazinyl | H | 3-Br | H |
| 2-thiazolyl | H | 3-Br | H |
| 2-oxazolyl | H | 3-Br | H |
| 2-chloro-2-propenyl | H | 3-Br | H |
| 3,3-dichloro-2-propenyl | H | 3-Br | H |
| CH₂-2-tetrahydrofuranyl | H | 3-Br | H |
| CH₂-2-tetrahydropyranyl | H | 3-Br | H |
| CH₂CH₂OH | H | 3-Br | H |
| CH₂OMe | H | 3-Br | H |
| CH₂CH₂OMe | H | 3-Br | H |
| CH₂CH₂CH₂OMe | H | 3-Br | H |
| CH₂CH(Me)OMe | H | 3-Br | H |
| CH(Me)OMe | H | 3-Br | H |
| CH(Me)OEt | H | 3-Br | H |
| n-Bu | H | 3-I | H |
| s-Bu | H | 3-I | H |
| t-butyl | H | 3-I | H |
| n-Hex | H | 3-I | H |
| cyclopropyl | H | 3-I | H |
| cyclopentyl | H | 3-I | H |
| cyclohexyl | H | 3-I | H |
| 2-cyclohexenyl | H | 3-I | H |
| 3-cyclohexenyl | H | 3-I | H |
| CH₂-c-Pr | H | 3-I | H |
| 4-tetrahydropyranyl | H | 3-I | H |
| 3-tetrahydropyranyl | H | 3-I | H |
| (R)-3-tetrahydropyranyl | H | 3-I | H |
| (S)-3-tetrahydropyranyl | H | 3-I | H |
| 3-tetrahydrofuranyl | H | 3-I | H |
| (R)-3-tetrahydrofuranyl | H | 3-I | H |
| (S)-3-tetrahydrofuranyl | H | 3-I | H |
| Ph | H | 3-I | H |
| 2-Cl-phenyl | H | 3-I | H |
| 3-Cl-phenyl | H | 3-I | H |
| 4-Cl-phenyl | H | 3-I | H |
| 2-pyridinyl | H | 3-I | H |
| 2-pyrimidinyl | H | 3-I | H |
| 2-pyrazinyl | H | 3-I | H |
| 2-thiazolyl | H | 3-I | H |
| 2-oxazolyl | H | 3-I | H |
| 2-chloro-2-propenyl | H | 3-I | H |
| 3,3-dichloro-2-propenyl | H | 3-I | H |
| CH₂-2-tetrahydrofuranyl | H | 3-I | H |
| CH₂-2-tetrahydropyranyl | H | 3-I | H |
| CH₂CH₂OH | H | 3-I | H |
| CH₂OMe | H | 3-I | H |
| CH₂CH₂OMe | H | 3-I | H |
| CH₂CH₂CH₂OMe | H | 3-I | H |
| CH₂CH(Me)OMe | H | 3-I | H |

TABLE 1-continued

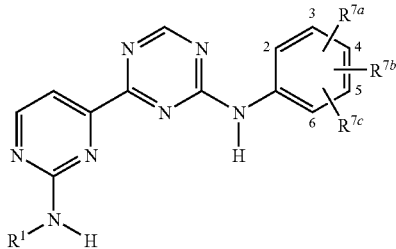

| R¹ | R⁷ᵃ | R⁷ᵇ | R⁷ᶜ |
|---|---|---|---|
| CH(Me)OMe | H | 3-I | H |
| CH(Me)OEt | H | 3-I | H |
| CH(Me)CH₂OMe | H | 3-Br | H |
| C(Me)₂CH₂OMe | H | 3-Br | H |
| CH(Me)CH₂CH₂OMe | H | 3-Br | H |
| (R)—CH(Me)CH₂OMe | H | 3-Br | H |
| (S)—CH(Me)CH₂OMe | H | 3-Br | H |
| CH(Me)CH₂OH | H | 3-Br | H |
| CH(Me)CH₂OC(=O)Me | H | 3-Br | H |
| CH(Me)CH(OMe)₂ | H | 3-Br | H |
| CH₂-2-dioxolanyl | H | 3-Br | H |
| CH₂CH₂OCF₃ | H | 3-Br | H |
| CH₂CH(Me)SMe | H | 3-Br | H |
| CH(Me)CH₂SMe | H | 3-Br | H |
| CH₂CH₂S(=O)Me | H | 3-Br | H |
| CH₂CH₂S(O)₂Me | H | 3-Br | H |
| CH₂CO₂Me | H | 3-Br | H |
| CH(Me)CO₂Me | H | 3-Br | H |
| CH₂C(=O)Me | H | 3-Br | H |
| CH₂CH₂C(=O)Me | H | 3-Br | H |
| CH₂SiMe₃ | H | 3-Br | H |
| CH₂CH₂SiMe₃ | H | 3-Br | H |
| CH₂-2-thienyl | H | 3-Br | H |
| CH₂-2-pyridinyl | H | 3-Br | H |
| CH₂-3-pyridinyl | H | 3-Br | H |
| NH₂ | H | 3-Br | H |
| NHCH₃ | H | 3-Br | H |
| NHCH₂CF₃ | H | 3-Br | H |
| NHCH₂CH₃ | H | 3-Br | H |
| NHCH(Me)CH₃ | H | 3-Br | H |
| NHCH₂CH(Me)₂ | H | 3-Br | H |
| NHC(Me)₃ | H | 3-Br | H |
| N(CH₃)₂ | H | 3-Br | H |
| N(CH₃)CH₂CH₃ | H | 3-Br | H |
| N(CH₂CH₃)CH₂CH₃ | H | 3-Br | H |
| Me | H | 3-Me | H |
| Et | H | 3-Me | H |
| i-Pr | H | 3-Me | H |
| n-Pr | H | 3-Me | H |
| CH(Me)CH₂OMe | H | 3-I | H |
| C(Me)₂CH₂OMe | H | 3-I | H |
| CH(Me)CH₂CH₂OMe | H | 3-I | H |
| (R)—CH(Me)CH₂OMe | H | 3-I | H |
| (S)—CH(Me)CH₂OMe | H | 3-I | H |
| CH(Me)CH₂OH | H | 3-I | H |
| CH(Me)CH₂OC(=O)Me | H | 3-I | H |
| CH(Me)CH(OMe)₂ | H | 3-I | H |
| CH₂-2-dioxolanyl | H | 3-I | H |
| CH₂CH₂OCF₃ | H | 3-I | H |
| CH₂CH(Me)SMe | H | 3-I | H |
| CH(Me)CH₂SMe | H | 3-I | H |
| CH₂CH₂S(=O)Me | H | 3-I | H |
| CH₂CH₂S(O)₂Me | H | 3-I | H |
| CH₂CO₂Me | H | 3-I | H |
| CH(Me)CO₂Me | H | 3-I | H |
| CH₂C(=O)Me | H | 3-I | H |
| CH₂CH₂C(=O)Me | H | 3-I | H |
| CH₂SiMe₃ | H | 3-I | H |
| CH₂CH₂SiMe₃ | H | 3-I | H |
| CH₂-2-thienyl | H | 3-I | H |
| CH₂-2-pyridinyl | H | 3-I | H |
| CH₂-3-pyridinyl | H | 3-I | H |
| NH₂ | H | 3-I | H |
| NHCH₃ | H | 3-I | H |
| NHCH₂CF₃ | H | 3-I | H |

TABLE 1-continued

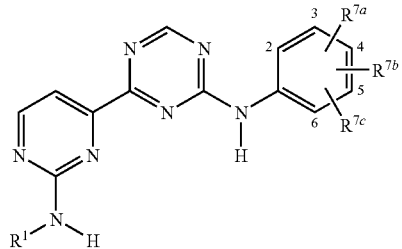

| R¹ | R⁷ᵃ | R⁷ᵇ | R⁷ᶜ |
|---|---|---|---|
| NHCH₂CH₃ | H | 3-I | H |
| NHCH(Me)CH₃ | H | 3-I | H |
| NHCH₂CH(Me)₂ | H | 3-I | H |
| NHC(Me)₃ | H | 3-I | H |
| N(CH₃)₂ | H | 3-I | H |
| N(CH₃)CH₂CH₃ | H | 3-I | H |
| N(CH₂CH₃)CH₂CH₃ | H | 3-I | H |
| Me | H | 4-Me | H |
| Et | H | 4-Me | H |
| i-Pr | H | 4-Me | H |
| n-Pr | H | 4-Me | H |
| i-Bu | H | 3-Me | H |
| n-Bu | H | 3-Me | H |
| s-Bu | H | 3-Me | H |
| t-butyl | H | 3-Me | H |
| n-Hex | H | 3-Me | H |
| cyclopropyl | H | 3-Me | H |
| cyclopentyl | H | 3-Me | H |
| cyclohexyl | H | 3-Me | H |
| 2-cyclohexenyl | H | 3-Me | H |
| 3-cyclohexenyl | H | 3-Me | H |
| CH₂-c-Pr | H | 3-Me | H |
| 4-tetrahydropyranyl | H | 3-Me | H |
| 3-tetrahydropyranyl | H | 3-Me | H |
| (R)-3-tetrahydropyranyl | H | 3-Me | H |
| (S)-3-tetrahydropyranyl | H | 3-Me | H |
| 3-tetrahydrofuranyl | H | 3-Me | H |
| (R)-3-tetrahydrofuranyl | H | 3-Me | H |
| (S)-3-tetrahydrofuranyl | H | 3-Me | H |
| Ph | H | 3-Me | H |
| 2-Cl-phenyl | H | 3-Me | H |
| 3-Cl-phenyl | H | 3-Me | H |
| 4-Cl-phenyl | H | 3-Me | H |
| 2-pyridinyl | H | 3-Me | H |
| 2-pyrimidinyl | H | 3-Me | H |
| 2-pyrazinyl | H | 3-Me | H |
| 2-thiazolyl | H | 3-Me | H |
| 2-oxazolyl | H | 3-Me | H |
| 2-chloro-2-propenyl | H | 3-Me | H |
| 3,3-dichloro-2-propenyl | H | 3-Me | H |
| CH₂-2-tetrahydrofuranyl | H | 3-Me | H |
| CH₂-2-tetrahydropyranyl | H | 3-Me | H |
| CH₂OH | H | 3-Me | H |
| CH₂OMe | H | 3-Me | H |
| CH₂CH₂OMe | H | 3-Me | H |
| CH₂CH₂CH₂OMe | H | 3-Me | H |
| CH₂CH(Me)OMe | H | 3-Me | H |
| CH(Me)OMe | H | 3-Me | H |
| i-Bu | H | 4-Me | H |
| n-Bu | H | 4-Me | H |
| s-Bu | H | 4-Me | H |
| t-butyl | H | 4-Me | H |
| n-Hex | H | 4-Me | H |
| cyclopropyl | H | 4-Me | H |
| cyclopentyl | H | 4-Me | H |
| cyclohexyl | H | 4-Me | H |
| 2-cyclohexenyl | H | 4-Me | H |
| 3-cyclohexenyl | H | 4-Me | H |
| CH₂-c-Pr | H | 4-Me | H |
| 4-tetrahydropyranyl | H | 4-Me | H |
| 3-tetrahydropyranyl | H | 4-Me | H |
| (R)-3-tetrahydropyranyl | H | 4-Me | H |
| (S)-3-tetrahydropyranyl | H | 4-Me | H |
| 3-tetrahydrofuranyl | H | 4-Me | H |
| (R)-3-tetrahydrofuranyl | H | 4-Me | H |

TABLE 1-continued

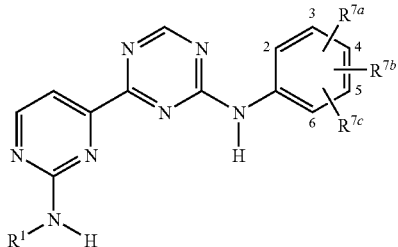

| R¹ | R⁷ᵃ | R⁷ᵇ | R⁷ᶜ |
|---|---|---|---|
| (S)-3-tetrahydrofuranyl | H | 4-Me | H |
| Ph | H | 4-Me | H |
| 2-Cl-phenyl | H | 4-Me | H |
| 3-Cl-phenyl | H | 4-Me | H |
| 4-Cl-phenyl | H | 4-Me | H |
| 2-pyridinyl | H | 4-Me | H |
| 2-pyrimidinyl | H | 4-Me | H |
| 2-pyrazinyl | H | 4-Me | H |
| 2-thiazolyl | H | 4-Me | H |
| 2-oxazolyl | H | 4-Me | H |
| 2-chloro-2-propenyl | H | 4-Me | H |
| 3,3-dichloro-2-propenyl | H | 4-Me | H |
| CH₂-2-tetrahydrofuranyl | H | 4-Me | H |
| CH₂-2-tetrahydropyranyl | H | 4-Me | H |
| CH₂CH₂OH | H | 4-Me | H |
| CH₂OMe | H | 4-Me | H |
| CH₂CH₂OMe | H | 4-Me | H |
| CH₂CH₂CH₂OMe | H | 4-Me | H |
| CH₂CH(Me)OMe | H | 4-Me | H |
| CH(Me)OMe | H | 4-Me | H |
| CH(Me)OEt | H | 3-Me | H |
| CH(Me)CH₂OMe | H | 3-Me | H |
| C(Me)₂CH₂OMe | H | 3-Me | H |
| CH(Me)CH₂CH₂OMe | H | 3-Me | H |
| (R)—CH(Me)CH₂OMe | H | 3-Me | H |
| (S)—CH(Me)CH₂OMe | H | 3-Me | H |
| CH(Me)CH₂OH | H | 3-Me | H |
| CH(Me)CH₂OC(=O)Me | H | 3-Me | H |
| CH(Me)CH(OMe)₂ | H | 3-Me | H |
| CH₂-2-dioxolanyl | H | 3-Me | H |
| CH₂CH₂OCF₃ | H | 3-Me | H |
| CH₂CH(Me)SMe | H | 3-Me | H |
| CH(Me)CH₂SMe | H | 3-Me | H |
| CH₂CH₂S(=O)Me | H | 3-Me | H |
| CH₂CH₂S(O)₂Me | H | 3-Me | H |
| CH₂CO₂Me | H | 3-Me | H |
| CH(Me)CO₂Me | H | 3-Me | H |
| CH₂C(=O)Me | H | 3-Me | H |
| CH₂CH₂C(=O)Me | H | 3-Me | H |
| CH₂SiMe₃ | H | 3-Me | H |
| CH₂CH₂SiMe₃ | H | 3-Me | H |
| CH₂-2-thienyl | H | 3-Me | H |
| CH₂-2-pyridinyl | H | 3-Me | H |
| CH₂-3-pyridinyl | H | 3-Me | H |
| NH₂ | H | 3-Me | H |
| NHCH₃ | H | 3-Me | H |
| NHCH₂CF₃ | H | 3-Me | H |
| NHCH₂CH₃ | H | 3-Me | H |
| NHCH(Me)CH₃ | H | 3-Me | H |
| NHCH₂CH(Me)₂ | H | 3-Me | H |
| NHC(Me)₃ | H | 3-Me | H |
| N(CH₃)₂ | H | 3-Me | H |
| N(CH₃)CH₂CH₃ | H | 3-Me | H |
| N(CH₂CH₃)CH₂CH₃ | H | 3-Me | H |
| Me | 3-F | 4-Me | H |
| Et | 3-F | 4-Me | H |
| i-Pr | 3-F | 4-Me | H |
| CH(Me)OEt | H | 4-Me | H |
| CH(Me)CH₂OMe | H | 4-Me | H |
| C(Me)₂CH₂OMe | H | 4-Me | H |
| CH(Me)CH₂CH₂OMe | H | 4-Me | H |
| (R)—CH(Me)CH₂OMe | H | 4-Me | H |
| (S)—CH(Me)CH₂OMe | H | 4-Me | H |
| CH(Me)CH₂OH | H | 4-Me | H |
| CH(Me)CH₂OC(=O)Me | H | 4-Me | H |

TABLE 1-continued

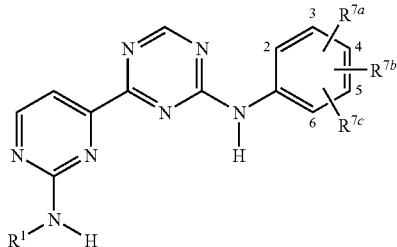

| R¹ | R⁷ᵃ | R⁷ᵇ | R⁷ᶜ |
|---|---|---|---|
| CH(Me)CH(OMe)₂ | H | 4-Me | H |
| CH₂-2-dioxolanyl | H | 4-Me | H |
| CH₂CH₂OCF₃ | H | 4-Me | H |
| CH₂CH(Me)SMe | H | 4-Me | H |
| CH(Me)CH₂SMe | H | 4-Me | H |
| CH₂CH₂S(=O)Me | H | 4-Me | H |
| CH₂CH₂S(O)₂Me | H | 4-Me | H |
| CH₂CO₂Me | H | 4-Me | H |
| CH(Me)CO₂Me | H | 4-Me | H |
| CH₂C(=O)Me | H | 4-Me | H |
| CH₂CH₂C(=O)Me | H | 4-Me | H |
| CH₂SiMe₃ | H | 4-Me | H |
| CH₂CH₂SiMe₃ | H | 4-Me | H |
| CH₂-2-thienyl | H | 4-Me | H |
| CH₂-2-pyridinyl | H | 4-Me | H |
| CH₂-3-pyridinyl | H | 4-Me | H |
| NH₂ | H | 4-Me | H |
| NHCH₃ | H | 4-Me | H |
| NHCH₂CF₃ | H | 4-Me | H |
| NHCH₂CH₃ | H | 4-Me | H |
| NHCH(Me)CH₃ | H | 4-Me | H |
| NHCH₂CH(Me)₂ | H | 4-Me | H |
| NHC(Me)₃ | H | 4-Me | H |
| N(CH₃)₂ | H | 4-Me | H |
| N(CH₃)CH₂CH₃ | H | 4-Me | H |
| N(CH₂CH₃)CH₂CH₃ | H | 4-Me | H |
| Me | 3-Me | 4-Me | H |
| Et | 3-Me | 4-Me | H |
| i-Pr | 3-Me | 4-Me | H |
| n-Pr | 3-F | 4-Me | H |
| i-Bu | 3-F | 4-Me | H |
| n-Bu | 3-F | 4-Me | H |
| s-Bu | 3-F | 4-Me | H |
| t-butyl | 3-F | 4-Me | H |
| n-Hex | 3-F | 4-Me | H |
| cyclopropyl | 3-F | 4-Me | H |
| cyclopentyl | 3-F | 4-Me | H |
| cyclohexyl | 3-F | 4-Me | H |
| 2-cyclohexenyl | 3-F | 4-Me | H |
| 3-cyclohexenyl | 3-F | 4-Me | H |
| CH₂-c-Pr | 3-F | 4-Me | H |
| 4-tetrahydropyranyl | 3-F | 4-Me | H |
| 3-tetrahydropyranyl | 3-F | 4-Me | H |
| (R)-3-tetrahydropyranyl | 3-F | 4-Me | H |
| (S)-3-tetrahydropyranyl | 3-F | 4-Me | H |
| 3-tetrahydrofuranyl | 3-F | 4-Me | H |
| (R)-3-tetrahydrofuranyl | 3-F | 4-Me | H |
| (S)-3-tetrahydrofuranyl | 3-F | 4-Me | H |
| Ph | 3-F | 4-Me | H |
| 2-Cl-phenyl | 3-F | 4-Me | H |
| 3-Cl-phenyl | 3-F | 4-Me | H |
| 4-Cl-phenyl | 3-F | 4-Me | H |
| 2-pyridinyl | 3-F | 4-Me | H |
| 2-pyrimidinyl | 3-F | 4-Me | H |
| 2-pyrazinyl | 3-F | 4-Me | H |
| 2-thiazolyl | 3-F | 4-Me | H |
| 2-oxazolyl | 3-F | 4-Me | H |
| 2-chloro-2-propenyl | 3-F | 4-Me | H |
| 3,3-dichloro-2-propenyl | 3-F | 4-Me | H |
| CH₂-2-tetrahydrofuranyl | 3-F | 4-Me | H |
| CH₂-2-tetrahydropyranyl | 3-F | 4-Me | H |
| CH₂CH₂OH | 3-F | 4-Me | H |
| CH₂OMe | 3-F | 4-Me | H |
| CH₂CH₂OMe | 3-F | 4-Me | H |
| CH₂CH₂CH₂OMe | 3-F | 4-Me | H |

TABLE 1-continued

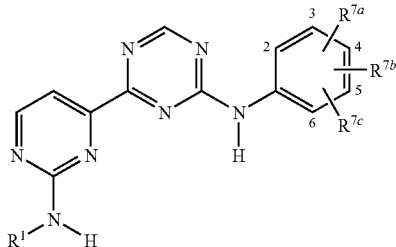

| R¹ | R⁷ᵃ | R⁷ᵇ | R⁷ᶜ |
|---|---|---|---|
| CH₂CH(Me)OMe | 3-F | 4-Me | H |
| n-Pr | 3-Me | 4-Me | H |
| i-Bu | 3-Me | 4-Me | H |
| n-Bu | 3-Me | 4-Me | H |
| s-Bu | 3-Me | 4-Me | H |
| t-butyl | 3-Me | 4-Me | H |
| n-Hex | 3-Me | 4-Me | H |
| cyclopropyl | 3-Me | 4-Me | H |
| cyclopentyl | 3-Me | 4-Me | H |
| cyclohexyl | 3-Me | 4-Me | H |
| 2-cyclohexenyl | 3-Me | 4-Me | H |
| 3-cyclohexenyl | 3-Me | 4-Me | H |
| CH₂-c-Pr | 3-Me | 4-Me | H |
| 4-tetrahydropyranyl | 3-Me | 4-Me | H |
| 3-tetrahydropyranyl | 3-Me | 4-Me | H |
| (R)-3-tetrahydropyranyl | 3-Me | 4-Me | H |
| (S)-3-tetrahydropyranyl | 3-Me | 4-Me | H |
| 3-tetrahydrofuranyl | 3-Me | 4-Me | H |
| (R)-3-tetrahydrofuranyl | 3-Me | 4-Me | H |
| (S)-3-tetrahydrofuranyl | 3-Me | 4-Me | H |
| Ph | 3-Me | 4-Me | H |
| 2-Cl-phenyl | 3-Me | 4-Me | H |
| 3-Cl-phenyl | 3-Me | 4-Me | H |
| 4-Cl-phenyl | 3-Me | 4-Me | H |
| 2-pyridinyl | 3-Me | 4-Me | H |
| 2-pyrimidinyl | 3-Me | 4-Me | H |
| 2-pyrazinyl | 3-Me | 4-Me | H |
| 2-thiazolyl | 3-Me | 4-Me | H |
| 2-oxazolyl | 3-Me | 4-Me | H |
| 2-chloro-2-propenyl | 3-Me | 4-Me | H |
| 3,3-dichloro-2-propenyl | 3-Me | 4-Me | H |
| CH₂-2-tetrahydrofuranyl | 3-Me | 4-Me | H |
| CH₂-2-tetrahydropyranyl | 3-Me | 4-Me | H |
| CH₂CH₂OH | 3-Me | 4-Me | H |
| CH₂OMe | 3-Me | 4-Me | H |
| CH₂CH₂OMe | 3-Me | 4-Me | H |
| CH₂CH₂CH₂OMe | 3-Me | 4-Me | H |
| CH₂CH(Me)OMe | 3-Me | 4-Me | H |
| CH(Me)OMe | 3-F | 4-Me | H |
| CH(Me)OEt | 3-F | 4-Me | H |
| CH(Me)CH₂OMe | 3-F | 4-Me | H |
| C(Me)₂CH₂OMe | 3-F | 4-Me | H |
| CH(Me)CH₂CH₂OMe | 3-F | 4-Me | H |
| (R)—CH(Me)CH₂OMe | 3-F | 4-Me | H |
| (S)—CH(Me)CH₂OMe | 3-F | 4-Me | H |
| CH(Me)CH₂OH | 3-F | 4-Me | H |
| CH(Me)CH₂OC(=O)Me | 3-F | 4-Me | H |
| CH(Me)CH(OMe)₂ | 3-F | 4-Me | H |
| CH₂-2-dioxolanyl | 3-F | 4-Me | H |
| CH₂CH₂OCF₃ | 3-F | 4-Me | H |
| CH₂CH(Me)SMe | 3-F | 4-Me | H |
| CH(Me)CH₂SMe | 3-F | 4-Me | H |
| CH₂CH₂S(=O)Me | 3-F | 4-Me | H |
| CH₂CH₂S(O)₂Me | 3-F | 4-Me | H |
| CH₂CO₂Me | 3-F | 4-Me | H |
| CH(Me)CO₂Me | 3-F | 4-Me | H |
| CH₂C(=O)Me | 3-F | 4-Me | H |
| CH₂CH₂C(=O)Me | 3-F | 4-Me | H |
| CH₂SiMe₃ | 3-F | 4-Me | H |
| CH₂CH₂SiMe₃ | 3-F | 4-Me | H |
| CH₂-2-thienyl | 3-F | 4-Me | H |
| CH₂-2-pyridinyl | 3-F | 4-Me | H |
| CH₂-3-pyridinyl | 3-F | 4-Me | H |
| NH₂ | 3-F | 4-Me | H |
| NHCH₃ | 3-F | 4-Me | H |

TABLE 1-continued

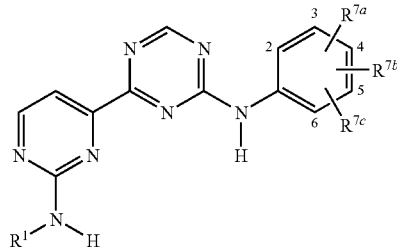

| R¹ | R⁷ᵃ | R⁷ᵇ | R⁷ᶜ |
|---|---|---|---|
| NHCH₂CF₃ | 3-F | 4-Me | H |
| NHCH₂CH₃ | 3-F | 4-Me | H |
| NHCH(Me)CH₃ | 3-F | 4-Me | H |
| NHCH₂CH(Me)₂ | 3-F | 4-Me | H |
| NHC(Me)₃ | 3-F | 4-Me | H |
| N(CH₃)₂ | 3-F | 4-Me | H |
| N(CH₃)CH₂CH₃ | 3-F | 4-Me | H |
| N(CH₂CH₃)CH₂CH₃ | 3-F | 4-Me | H |
| Me | 3-NO₂ | 4-Me | H |
| Et | 3-NO₂ | 4-Me | H |
| CH(Me)OMe | 3-Me | 4-Me | H |
| CH(Me)OEt | 3-Me | 4-Me | H |
| CH(Me)CH₂OMe | 3-Me | 4-Me | H |
| C(Me)₂CH₂OMe | 3-Me | 4-Me | H |
| CH(Me)CH₂CH₂OMe | 3-Me | 4-Me | H |
| (R)—CH(Me)CH₂OMe | 3-Me | 4-Me | H |
| (S)—CH(Me)CH₂OMe | 3-Me | 4-Me | H |
| CH(Me)CH₂OH | 3-Me | 4-Me | H |
| CH(Me)CH₂OC(=O)Me | 3-Me | 4-Me | H |
| CH(Me)CH(OMe)₂ | 3-Me | 4-Me | H |
| CH₂-2-dioxolanyl | 3-Me | 4-Me | H |
| CH₂CH₂OCF₃ | 3-Me | 4-Me | H |
| CH₂CH(Me)SMe | 3-Me | 4-Me | H |
| CH(Me)CH₂SMe | 3-Me | 4-Me | H |
| CH₂CH₂S(=O)Me | 3-Me | 4-Me | H |
| CH₂CH₂S(O)₂Me | 3-Me | 4-Me | H |
| CH₂CO₂Me | 3-Me | 4-Me | H |
| CH(Me)CO₂Me | 3-Me | 4-Me | H |
| CH₂C(=O)Me | 3-Me | 4-Me | H |
| CH₂CH₂C(=O)Me | 3-Me | 4-Me | H |
| CH₂SiMe₃ | 3-Me | 4-Me | H |
| CH₂CH₂SiMe₃ | 3-Me | 4-Me | H |
| CH₂-2-thienyl | 3-Me | 4-Me | H |
| CH₂-2-pyridinyl | 3-Me | 4-Me | H |
| CH₂-3-pyridinyl | 3-Me | 4-Me | H |
| NH₂ | 3-Me | 4-Me | H |
| NHCH₃ | 3-Me | 4-Me | H |
| NHCH₂CF₃ | 3-Me | 4-Me | H |
| NHCH₂CH₃ | 3-Me | 4-Me | H |
| NHCH(Me)CH₃ | 3-Me | 4-Me | H |
| NHCH₂CH(Me)₂ | 3-Me | 4-Me | H |
| NHC(Me)₃ | 3-Me | 4-Me | H |
| N(CH₃)₂ | 3-Me | 4-Me | H |
| N(CH₃)CH₂CH₃ | 3-Me | 4-Me | H |
| N(CH₂CH₃)CH₂CH₃ | 3-Me | 4-Me | H |
| Me | 3-Cl | 5-Cl | H |
| Et | 3-Cl | 5-Cl | H |
| i-Pr | 3-NO₂ | 4-Me | H |
| n-Pr | 3-NO₂ | 4-Me | H |
| i-Bu | 3-NO₂ | 4-Me | H |
| n-Bu | 3-NO₂ | 4-Me | H |
| s-Bu | 3-NO₂ | 4-Me | H |
| t-butyl | 3-NO₂ | 4-Me | H |
| n-Hex | 3-NO₂ | 4-Me | H |
| cyclopropyl | 3-NO₂ | 4-Me | H |
| cyclopentyl | 3-NO₂ | 4-Me | H |
| cyclohexyl | 3-NO₂ | 4-Me | H |
| 2-cyclohexenyl | 3-NO₂ | 4-Me | H |
| 3-cyclohexenyl | 3-NO₂ | 4-Me | H |
| CH₂-c-Pr | 3-NO₂ | 4-Me | H |
| 4-tetrahydropyranyl | 3-NO₂ | 4-Me | H |
| 3-tetrahydropyranyl | 3-NO₂ | 4-Me | H |
| (R)-3-tetrahydropyranyl | 3-NO₂ | 4-Me | H |
| (S)-3-tetrahydropyranyl | 3-NO₂ | 4-Me | H |
| 3-tetrahydrofuranyl | 3-NO₂ | 4-Me | H |

TABLE 1-continued

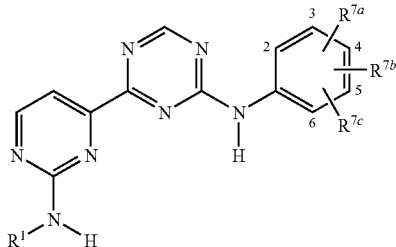 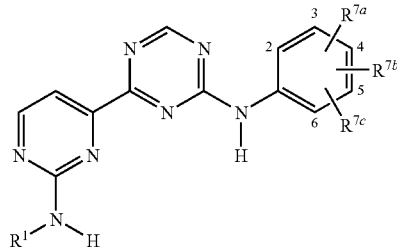

| R¹ | R⁷ᵃ | R⁷ᵇ | R⁷ᶜ |
|---|---|---|---|
| (R)-3-tetrahydrofuranyl | 3-NO₂ | 4-Me | H |
| (S)-3-tetrahydrofuranyl | 3-NO₂ | 4-Me | H |
| Ph | 3-NO₂ | 4-Me | H |
| 2-Cl-phenyl | 3-NO₂ | 4-Me | H |
| 3-Cl-phenyl | 3-NO₂ | 4-Me | H |
| 4-Cl-phenyl | 3-NO₂ | 4-Me | H |
| 2-pyridinyl | 3-NO₂ | 4-Me | H |
| 2-pyrimidinyl | 3-NO₂ | 4-Me | H |
| 2-pyrazinyl | 3-NO₂ | 4-Me | H |
| 2-thiazolyl | 3-NO₂ | 4-Me | H |
| 2-oxazolyl | 3-NO₂ | 4-Me | H |
| 2-chloro-2-propenyl | 3-NO₂ | 4-Me | H |
| 3,3-dichloro-2-propenyl | 3-NO₂ | 4-Me | H |
| CH₂-2-tetrahydrofuranyl | 3-NO₂ | 4-Me | H |
| CH₂-2-tetrahydropyranyl | 3-NO₂ | 4-Me | H |
| CH₂CH₂OH | 3-NO₂ | 4-Me | H |
| CH₂OMe | 3-NO₂ | 4-Me | H |
| CH₂CH₂OMe | 3-NO₂ | 4-Me | H |
| CH₂CH₂CH₂OMe | 3-NO₂ | 4-Me | H |
| i-Pr | 3-Cl | 5-Cl | H |
| n-Pr | 3-Cl | 5-Cl | H |
| i-Bu | 3-Cl | 5-Cl | H |
| n-Bu | 3-Cl | 5-Cl | H |
| s-Bu | 3-Cl | 5-Cl | H |
| t-butyl | 3-Cl | 5-Cl | H |
| n-Hex | 3-Cl | 5-Cl | H |
| cyclopropyl | 3-Cl | 5-Cl | H |
| cyclopentyl | 3-Cl | 5-Cl | H |
| cyclohexyl | 3-Cl | 5-Cl | H |
| 2-cyclohexenyl | 3-Cl | 5-Cl | H |
| 3-cyclohexenyl | 3-Cl | 5-Cl | H |
| CH₂-c-Pr | 3-Cl | 5-Cl | H |
| 4-tetrahydropyranyl | 3-Cl | 5-Cl | H |
| 3-tetrahydropyranyl | 3-Cl | 5-Cl | H |
| (R)-3-tetrahydropyranyl | 3-Cl | 5-Cl | H |
| (S)-3-tetrahydropyranyl | 3-Cl | 5-Cl | H |
| 3-tetrahydrofuranyl | 3-Cl | 5-Cl | H |
| (R)-3-tetrahydrofuranyl | 3-Cl | 5-Cl | H |
| (S)-3-tetrahydrofuranyl | 3-Cl | 5-Cl | H |
| Ph | 3-Cl | 5-Cl | H |
| 2-Cl-phenyl | 3-Cl | 5-Cl | H |
| 3-Cl-phenyl | 3-Cl | 5-Cl | H |
| 4-Cl-phenyl | 3-Cl | 5-Cl | H |
| 2-pyridinyl | 3-Cl | 5-Cl | H |
| 2-pyrimidinyl | 3-Cl | 5-Cl | H |
| 2-pyrazinyl | 3-Cl | 5-Cl | H |
| 2-thiazolyl | 3-Cl | 5-Cl | H |
| 2-oxazolyl | 3-Cl | 5-Cl | H |
| 2-chloro-2-propenyl | 3-Cl | 5-Cl | H |
| 3,3-dichloro-2-propenyl | 3-Cl | 5-Cl | H |
| CH₂-2-tetrahydrofuranyl | 3-Cl | 5-Cl | H |
| CH₂-2-tetrahydropyranyl | 3-Cl | 5-Cl | H |
| CH₂CH₂OH | 3-Cl | 5-Cl | H |
| CH₂OMe | 3-Cl | 5-Cl | H |
| CH₂OMe | 3-Cl | 5-Cl | H |
| CH₂CH₂CH₂OMe | 3-Cl | 5-Cl | H |
| CH₂CH(Me)OMe | 3-NO₂ | 4-Me | H |
| CH(Me)OMe | 3-NO₂ | 4-Me | H |
| CH(Me)OEt | 3-NO₂ | 4-Me | H |
| CH(Me)CH₂OMe | 3-NO₂ | 4-Me | H |
| C(Me)₂CH₂OMe | 3-NO₂ | 4-Me | H |
| CH(Me)CH₂CH₂OMe | 3-NO₂ | 4-Me | H |
| (R)—CH(Me)CH₂OMe | 3-NO₂ | 4-Me | H |
| (S)—CH(Me)CH₂OMe | 3-NO₂ | 4-Me | H |
| CH(Me)CH₂OH | 3-NO₂ | 4-Me | H |
| CH(Me)CH₂OC(=O)Me | 3-NO₂ | 4-Me | H |
| CH(Me)CH(OMe)₂ | 3-NO₂ | 4-Me | H |
| CH₂-2-dioxolanyl | 3-NO₂ | 4-Me | H |
| CH₂CH₂OCF₃ | 3-NO₂ | 4-Me | H |
| CH₂CH(Me)SMe | 3-NO₂ | 4-Me | H |
| CH(Me)CH₂SMe | 3-NO₂ | 4-Me | H |
| CH₂CH₂S(=O)Me | 3-NO₂ | 4-Me | H |
| CH₂CH₂S(O)₂Me | 3-NO₂ | 4-Me | H |
| CH₂CO₂Me | 3-NO₂ | 4-Me | H |
| CH(Me)CO₂Me | 3-NO₂ | 4-Me | H |
| CH₂C(=O)Me | 3-NO₂ | 4-Me | H |
| CH₂CH₂C(=O)Me | 3-NO₂ | 4-Me | H |
| CH₂SiMe₃ | 3-NO₂ | 4-Me | H |
| CH₂CH₂SiMe₃ | 3-NO₂ | 4-Me | H |
| CH₂-2-thienyl | 3-NO₂ | 4-Me | H |
| CH₂-2-pyridinyl | 3-NO₂ | 4-Me | H |
| CH₂-3-pyridinyl | 3-NO₂ | 4-Me | H |
| NH₂ | 3-NO₂ | 4-Me | H |
| NHCH₃ | 3-NO₂ | 4-Me | H |
| NHCH₂CF₃ | 3-NO₂ | 4-Me | H |
| NHCH₂CH₃ | 3-NO₂ | 4-Me | H |
| NHCH(Me)CH₃ | 3-NO₂ | 4-Me | H |
| NHCH₂CH(Me)₂ | 3-NO₂ | 4-Me | H |
| NHC(Me)₃ | 3-NO₂ | 4-Me | H |
| N(CH₃)₂ | 3-NO₂ | 4-Me | H |
| N(CH₃)CH₂CH₃ | 3-NO₂ | 4-Me | H |
| N(CH₂CH₃)CH₂CH₃ | 3-NO₂ | 4-Me | H |
| Me | 3-Cl | 5-CN | H |
| CH₂CH(Me)OMe | 3-Cl | 5-Cl | H |
| CH(Me)OMe | 3-Cl | 5-Cl | H |
| CH(Me)OEt | 3-Cl | 5-Cl | H |
| CH(Me)CH₂OMe | 3-Cl | 5-Cl | H |
| C(Me)₂CH₂OMe | 3-Cl | 5-Cl | H |
| CH(Me)CH₂CH₂OMe | 3-Cl | 5-Cl | H |
| (R)—CH(Me)CH₂OMe | 3-Cl | 5-Cl | H |
| (S)—CH(Me)CH₂OMe | 3-Cl | 5-Cl | H |
| CH(Me)CH₂OH | 3-Cl | 5-Cl | H |
| CH(Me)CH₂OC(=O)Me | 3-Cl | 5-Cl | H |
| CH(Me)CH(OMe)₂ | 3-Cl | 5-Cl | H |
| CH₂-2-dioxolanyl | 3-Cl | 5-Cl | H |
| CH₂CH₂OCF₃ | 3-Cl | 5-Cl | H |
| CH₂CH(Me)SMe | 3-Cl | 5-Cl | H |
| CH(Me)CH₂SMe | 3-Cl | 5-Cl | H |
| CH₂CH₂S(=O)Me | 3-Cl | 5-Cl | H |
| CH₂CH₂S(O)₂Me | 3-Cl | 5-Cl | H |
| CH₂CO₂Me | 3-Cl | 5-Cl | H |
| CH(Me)CO₂Me | 3-Cl | 5-Cl | H |
| CH₂C(=O)Me | 3-Cl | 5-Cl | H |
| CH₂CH₂C(=O)Me | 3-Cl | 5-Cl | H |
| CH₂SiMe₃ | 3-Cl | 5-Cl | H |
| CH₂CH₂SiMe₃ | 3-Cl | 5-Cl | H |
| CH₂-2-thienyl | 3-Cl | 5-Cl | H |
| CH₂-2-pyridinyl | 3-Cl | 5-Cl | H |
| CH₂-3-pyridinyl | 3-Cl | 5-Cl | H |
| NH₂ | 3-Cl | 5-Cl | H |
| NHCH₃ | 3-Cl | 5-Cl | H |
| NHCH₂CF₃ | 3-Cl | 5-Cl | H |
| NHCH₂CH₃ | 3-Cl | 5-Cl | H |
| NHCH(Me)CH₃ | 3-Cl | 5-Cl | H |
| NHCH₂CH(Me)₂ | 3-Cl | 5-Cl | H |
| NHC(Me)₃ | 3-Cl | 5-Cl | H |
| N(CH₃)₂ | 3-Cl | 5-Cl | H |
| N(CH₃)CH₂CH₃ | 3-Cl | 5-Cl | H |
| N(CH₂CH₃)CH₂CH₃ | 3-Cl | 5-Cl | H |
| Me | 3-F | 4-Cl | H |

TABLE 1-continued

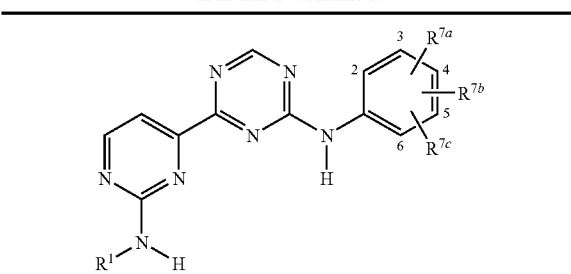

| R¹ | R⁷ᵃ | R⁷ᵇ | R⁷ᶜ |
|---|---|---|---|
| Et | 3-Cl | 5-CN | H |
| i-Pr | 3-Cl | 5-CN | H |
| n-Pr | 3-Cl | 5-CN | H |
| i-Bu | 3-Cl | 5-CN | H |
| n-Bu | 3-Cl | 5-CN | H |
| s-Bu | 3-Cl | 5-CN | H |
| t-butyl | 3-Cl | 5-CN | H |
| n-Hex | 3-Cl | 5-CN | H |
| cyclopropyl | 3-Cl | 5-CN | H |
| cyclopentyl | 3-Cl | 5-CN | H |
| cyclohexyl | 3-Cl | 5-CN | H |
| 2-cyclohexenyl | 3-Cl | 5-CN | H |
| 3-cyclohexenyl | 3-Cl | 5-CN | H |
| $CH_2$-c-Pr | 3-Cl | 5-CN | H |
| 4-tetrahydropyranyl | 3-Cl | 5-CN | H |
| 3-tetrahydropyranyl | 3-Cl | 5-CN | H |
| (R)-3-tetrahydropyranyl | 3-Cl | 5-CN | H |
| (S)-3-tetrahydropyranyl | 3-Cl | 5-CN | H |
| 3-tetrahydrofuranyl | 3-Cl | 5-CN | H |
| (R)-3-tetrahydrofuranyl | 3-Cl | 5-CN | H |
| (S)-3-tetrahydrofuranyl | 3-Cl | 5-CN | H |
| Ph | 3-Cl | 5-CN | H |
| 2-Cl-phenyl | 3-Cl | 5-CN | H |
| 3-Cl-phenyl | 3-Cl | 5-CN | H |
| 4-Cl-phenyl | 3-Cl | 5-CN | H |
| 2-pyridinyl | 3-Cl | 5-CN | H |
| 2-pyrimidinyl | 3-Cl | 5-CN | H |
| 2-pyrazinyl | 3-Cl | 5-CN | H |
| 2-thiazolyl | 3-Cl | 5-CN | H |
| 2-oxazolyl | 3-Cl | 5-CN | H |
| 2-chloro-2-propenyl | 3-Cl | 5-CN | H |
| 3,3-dichloro-2-propenyl | 3-Cl | 5-CN | H |
| $CH_2$-2-tetrahydrofuranyl | 3-Cl | 5-CN | H |
| $CH_2$-2-tetrahydropyranyl | 3-Cl | 5-CN | H |
| $CH_2CH_2OH$ | 3-Cl | 5-CN | H |
| $CH_2OMe$ | 3-Cl | 5-CN | H |
| $CH_2CH_2OMe$ | 3-Cl | 5-CN | H |
| Et | 3-F | 4-Cl | H |
| i-Pr | 3-F | 4-Cl | H |
| n-Pr | 3-F | 4-Cl | H |
| i-Bu | 3-F | 4-Cl | H |
| n-Bu | 3-F | 4-Cl | H |
| s-Bu | 3-F | 4-Cl | H |
| t-butyl | 3-F | 4-Cl | H |
| n-Hex | 3-F | 4-Cl | H |
| cyclopropyl | 3-F | 4-Cl | H |
| cyclopentyl | 3-F | 4-Cl | H |
| cyclohexyl | 3-F | 4-Cl | H |
| 2-cyclohexenyl | 3-F | 4-Cl | H |
| 3-cyclohexenyl | 3-F | 4-Cl | H |
| $CH_2$-c-Pr | 3-F | 4-Cl | H |
| 4-tetrahydropyranyl | 3-F | 4-Cl | H |
| 3-tetrahydropyranyl | 3-F | 4-Cl | H |
| (R)-3-tetrahydropyranyl | 3-F | 4-Cl | H |
| (S)-3-tetrahydropyranyl | 3-F | 4-Cl | H |
| 3-tetrahydrofuranyl | 3-F | 4-Cl | H |
| (R)-3-tetrahydrofuranyl | 3-F | 4-Cl | H |
| (S)-3-tetrahydrofuranyl | 3-F | 4-Cl | H |
| Ph | 3-F | 4-Cl | H |
| 2-Cl-phenyl | 3-F | 4-Cl | H |
| 3-Cl-phenyl | 3-F | 4-Cl | H |
| 4-Cl-phenyl | 3-F | 4-Cl | H |
| 2-pyridinyl | 3-F | 4-Cl | H |
| 2-pyrimidinyl | 3-F | 4-Cl | H |
| 2-pyrazinyl | 3-F | 4-Cl | H |

TABLE 1-continued

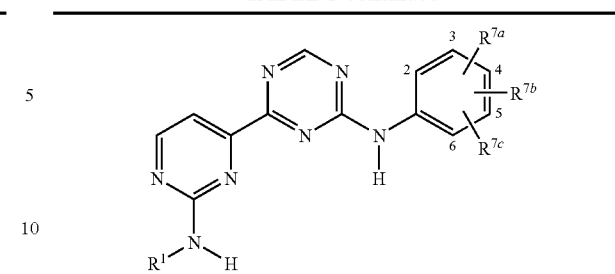

| R¹ | R⁷ᵃ | R⁷ᵇ | R⁷ᶜ |
|---|---|---|---|
| 2-thiazolyl | 3-F | 4-Cl | H |
| 2-oxazolyl | 3-F | 4-Cl | H |
| 2-chloro-2-propenyl | 3-F | 4-Cl | H |
| 3,3-dichloro-2-propenyl | 3-F | 4-Cl | H |
| $CH_2$-2-tetrahydrofuranyl | 3-F | 4-Cl | H |
| $CH_2$-2-tetrahydropyranyl | 3-F | 4-Cl | H |
| $CH_2CH_2OH$ | 3-F | 4-Cl | H |
| $CH_2OMe$ | 3-F | 4-Cl | H |
| $CH_2CH_2OMe$ | 3-F | 4-Cl | H |
| $CH_2CH_2CH_2OMe$ | 3-Cl | 5-CN | H |
| $CH_2CH(Me)OMe$ | 3-Cl | 5-CN | H |
| $CH(Me)OMe$ | 3-Cl | 5-CN | H |
| $CH(Me)OEt$ | 3-Cl | 5-CN | H |
| $CH(Me)CH_2OMe$ | 3-Cl | 5-CN | H |
| $C(Me)_2CH_2OMe$ | 3-Cl | 5-CN | H |
| $CH(Me)CH_2CH_2OMe$ | 3-Cl | 5-CN | H |
| (R)—$CH(Me)CH_2OMe$ | 3-Cl | 5-CN | H |
| (S)—$CH(Me)CH_2OMe$ | 3-Cl | 5-CN | H |
| $CH(Me)CH_2OH$ | 3-Cl | 5-CN | H |
| $CH(Me)CH_2OC(=O)Me$ | 3-Cl | 5-CN | H |
| $CH(Me)CH(OMe)_2$ | 3-Cl | 5-CN | H |
| $CH_2$-2-dioxolanyl | 3-Cl | 5-CN | H |
| $CH_2CH_2OCF_3$ | 3-Cl | 5-CN | H |
| $CH_2CH(Me)SMe$ | 3-Cl | 5-CN | H |
| $CH(Me)CH_2SMe$ | 3-Cl | 5-CN | H |
| $CH_2CH_2S(=O)Me$ | 3-Cl | 5-CN | H |
| $CH_2CH_2S(O)_2Me$ | 3-Cl | 5-CN | H |
| $CH_2CO_2Me$ | 3-Cl | 5-CN | H |
| $CH(Me)CO_2Me$ | 3-Cl | 5-CN | H |
| $CH_2C(=O)Me$ | 3-Cl | 5-CN | H |
| $CH_2CH_2C(=O)Me$ | 3-Cl | 5-CN | H |
| $CH_2SiMe_3$ | 3-Cl | 5-CN | H |
| $CH_2CH_2SiMe_3$ | 3-Cl | 5-CN | H |
| $CH_2$-2-thienyl | 3-Cl | 5-CN | H |
| $CH_2$-2-pyridinyl | 3-Cl | 5-CN | H |
| $CH_2$-3-pyridinyl | 3-Cl | 5-CN | H |
| $NH_2$ | 3-Cl | 5-CN | H |
| $NHCH_3$ | 3-Cl | 5-CN | H |
| $NHCH_2CF_3$ | 3-Cl | 5-CN | H |
| $NHCH_2CH_3$ | 3-Cl | 5-CN | H |
| $NHCH(Me)CH_3$ | 3-Cl | 5-CN | H |
| $NHCH_2CH(Me)_2$ | 3-Cl | 5-CN | H |
| $NHC(Me)_3$ | 3-Cl | 5-CN | H |
| $N(CH_3)_2$ | 3-Cl | 5-CN | H |
| $N(CH_3)CH_2CH_3$ | 3-Cl | 5-CN | H |
| $N(CH_2CH_3)CH_2CH_3$ | 3-Cl | 5-CN | H |
| $CH_2CH_2CH_2OMe$ | 3-F | 4-Cl | H |
| $CH_2CH(Me)OMe$ | 3-F | 4-Cl | H |
| $CH(Me)OMe$ | 3-F | 4-Cl | H |
| $CH(Me)OEt$ | 3-F | 4-Cl | H |
| $CH(Me)CH_2OMe$ | 3-F | 4-Cl | H |
| $C(Me)_2CH_2OMe$ | 3-F | 4-Cl | H |
| $CH(Me)CH_2CH_2OMe$ | 3-F | 4-Cl | H |
| (R)—$CH(Me)CH_2OMe$ | 3-F | 4-Cl | H |
| (S)—$CH(Me)CH_2OMe$ | 3-F | 4-Cl | H |
| $CH(Me)CH_2OH$ | 3-F | 4-Cl | H |
| $CH(Me)CH_2OC(=O)Me$ | 3-F | 4-Cl | H |
| $CH(Me)CH(OMe)_2$ | 3-F | 4-Cl | H |
| $CH_2$-2-dioxolanyl | 3-F | 4-Cl | H |
| $CH_2CH_2OCF_3$ | 3-F | 4-Cl | H |
| $CH_2CH(Me)SMe$ | 3-F | 4-Cl | H |
| $CH(Me)CH_2SMe$ | 3-F | 4-Cl | H |
| $CH_2CH_2S(=O)Me$ | 3-F | 4-Cl | H |
| $CH_2CH_2S(O)_2Me$ | 3-F | 4-Cl | H |
| $CH_2CO_2Me$ | 3-F | 4-Cl | H |

TABLE 1-continued

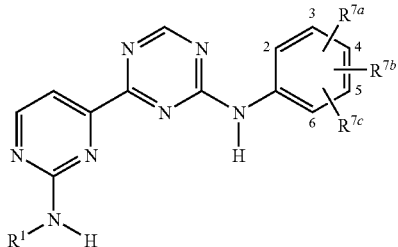

| R¹ | R⁷ᵃ | R⁷ᵇ | R⁷ᶜ |
|---|---|---|---|
| CH(Me)CO₂Me | 3-F | 4-Cl | H |
| CH₂C(=O)Me | 3-F | 4-Cl | H |
| CH₂CH₂C(=O)Me | 3-F | 4-Cl | H |
| CH₂SiMe₃ | 3-F | 4-Cl | H |
| CH₂CH₂SiMe₃ | 3-F | 4-Cl | H |
| CH₂-2-thienyl | 3-F | 4-Cl | H |
| CH₂-2-pyridinyl | 3-F | 4-Cl | H |
| CH₂-3-pyridinyl | 3-F | 4-Cl | H |
| NH₂ | 3-F | 4-Cl | H |
| NHCH₃ | 3-F | 4-Cl | H |
| NHCH₂CF₃ | 3-F | 4-Cl | H |
| NHCH₂CH₃ | 3-F | 4-Cl | H |
| NHCH(Me)CH₃ | 3-F | 4-Cl | H |
| NHCH₂CH(Me)₂ | 3-F | 4-Cl | H |
| NHC(Me)₃ | 3-F | 4-Cl | H |
| N(CH₃)₂ | 3-F | 4-Cl | H |
| N(CH₃)CH₂CH₃ | 3-F | 4-Cl | H |
| N(CH₂CH₃)CH₂CH₃ | 3-F | 4-Cl | H |
| Me | 3-F | 4-CN | H |
| Et | 3-F | 4-CN | H |
| i-Pr | 3-F | 4-CN | H |
| n-Pr | 3-F | 4-CN | H |
| i-Bu | 3-F | 4-CN | H |
| n-Bu | 3-F | 4-CN | H |
| s-Bu | 3-F | 4-CN | H |
| t-butyl | 3-F | 4-CN | H |
| n-Hex | 3-F | 4-CN | H |
| cyclopropyl | 3-F | 4-CN | H |
| cyclopentyl | 3-F | 4-CN | H |
| cyclohexyl | 3-F | 4-CN | H |
| 2-cyclohexenyl | 3-F | 4-CN | H |
| 3-cyclohexenyl | 3-F | 4-CN | H |
| CH₂-c-Pr | 3-F | 4-CN | H |
| 4-tetrahydropyranyl | 3-F | 4-CN | H |
| 3-tetrahydropyranyl | 3-F | 4-CN | H |
| (R)-3-tetrahydropyranyl | 3-F | 4-CN | H |
| (S)-3-tetrahydropyranyl | 3-F | 4-CN | H |
| 3-tetrahydrofuranyl | 3-F | 4-CN | H |
| (R)-3-tetrahydrofuranyl | 3-F | 4-CN | H |
| (S)-3-tetrahydrofuranyl | 3-F | 4-CN | H |
| Ph | 3-F | 4-CN | H |
| 2-Cl-phenyl | 3-F | 4-CN | H |
| 3-Cl-phenyl | 3-F | 4-CN | H |
| 4-Cl-phenyl | 3-F | 4-CN | H |
| 2-pyridinyl | 3-F | 4-CN | H |
| 2-pyrimidinyl | 3-F | 4-CN | H |
| 2-pyrazinyl | 3-F | 4-CN | H |
| 2-thiazolyl | 3-F | 4-CN | H |
| 2-oxazolyl | 3-F | 4-CN | H |
| 2-chloro-2-propenyl | 3-F | 4-CN | H |
| 3,3-dichloro-2-propenyl | 3-F | 4-CN | H |
| CH₂-2-tetrahydrofuranyl | 3-F | 4-CN | H |
| CH₂-2-tetrahydropyranyl | 3-F | 4-CN | H |
| CH₂CH₂OH | 3-F | 4-CN | H |
| CH₂OMe | 3-F | 4-CN | H |
| Me | 3-Cl | 4-F | H |
| Et | 3-Cl | 4-F | H |
| i-Pr | 3-Cl | 4-F | H |
| n-Pr | 3-Cl | 4-F | H |
| i-Bu | 3-Cl | 4-F | H |
| n-Bu | 3-Cl | 4-F | H |
| s-Bu | 3-Cl | 4-F | H |
| t-butyl | 3-Cl | 4-F | H |
| n-Hex | 3-Cl | 4-F | H |
| cyclopropyl | 3-Cl | 4-F | H |

TABLE 1-continued

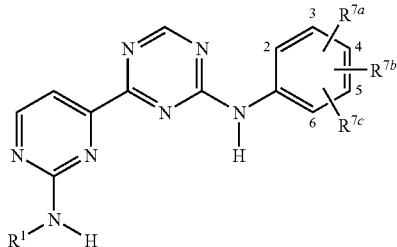

| R¹ | R⁷ᵃ | R⁷ᵇ | R⁷ᶜ |
|---|---|---|---|
| cyclopentyl | 3-Cl | 4-F | H |
| cyclohexyl | 3-Cl | 4-F | H |
| 2-cyclohexenyl | 3-Cl | 4-F | H |
| 3-cyclohexenyl | 3-Cl | 4-F | H |
| CH₂-c-Pr | 3-Cl | 4-F | H |
| 4-tetrahydropyranyl | 3-Cl | 4-F | H |
| 3-tetrahydropyranyl | 3-Cl | 4-F | H |
| (R)-3-tetrahydropyranyl | 3-Cl | 4-F | H |
| (S)-3-tetrahydropyranyl | 3-Cl | 4-F | H |
| 3-tetrahydrofuranyl | 3-Cl | 4-F | H |
| (R)-3-tetrahydrofuranyl | 3-Cl | 4-F | H |
| (S)-3-tetrahydrofuranyl | 3-Cl | 4-F | H |
| Ph | 3-Cl | 4-F | H |
| 2-Cl-phenyl | 3-Cl | 4-F | H |
| 3-Cl-phenyl | 3-Cl | 4-F | H |
| 4-Cl-phenyl | 3-Cl | 4-F | H |
| 2-pyridinyl | 3-Cl | 4-F | H |
| 2-pyrimidinyl | 3-Cl | 4-F | H |
| 2-pyrazinyl | 3-Cl | 4-F | H |
| 2-thiazolyl | 3-Cl | 4-F | H |
| 2-oxazolyl | 3-Cl | 4-F | H |
| 2-chloro-2-propenyl | 3-Cl | 4-F | H |
| 3,3-dichloro-2-propenyl | 3-Cl | 4-F | H |
| CH₂-2-tetrahydrofuranyl | 3-Cl | 4-F | H |
| CH₂-2-tetrahydropyranyl | 3-Cl | 4-F | H |
| CH₂CH₂OH | 3-Cl | 4-F | H |
| CH₂OMe | 3-Cl | 4-F | H |
| CH₂CH₂OMe | 3-F | 4-CN | H |
| CH₂CH₂CH₂OMe | 3-F | 4-CN | H |
| CH₂CH(Me)OMe | 3-F | 4-CN | H |
| CH(Me)OMe | 3-F | 4-CN | H |
| CH(Me)OEt | 3-F | 4-CN | H |
| CH(Me)CH₂OMe | 3-F | 4-CN | H |
| C(Me)₂CH₂OMe | 3-F | 4-CN | H |
| CH(Me)CH₂CH₂OMe | 3-F | 4-CN | H |
| (R)—CH(Me)CH₂OMe | 3-F | 4-CN | H |
| (S)—CH(Me)CH₂OMe | 3-F | 4-CN | H |
| CH(Me)CH₂OH | 3-F | 4-CN | H |
| CH(Me)CH₂OC(=O)Me | 3-F | 4-CN | H |
| CH(Me)CH(OMe)₂ | 3-F | 4-CN | H |
| CH₂-2-dioxolanyl | 3-F | 4-CN | H |
| CH₂CH₂OCF₃ | 3-F | 4-CN | H |
| CH₂CH(Me)SMe | 3-F | 4-CN | H |
| CH(Me)CH₂SMe | 3-F | 4-CN | H |
| CH₂CH₂S(=O)Me | 3-F | 4-CN | H |
| CH₂CH₂S(O)₂Me | 3-F | 4-CN | H |
| CH₂CO₂Me | 3-F | 4-CN | H |
| CH(Me)CO₂Me | 3-F | 4-CN | H |
| CH₂C(=O)Me | 3-F | 4-CN | H |
| CH₂CH₂C(=O)Me | 3-F | 4-CN | H |
| CH₂SiMe₃ | 3-F | 4-CN | H |
| CH₂CH₂SiMe₃ | 3-F | 4-CN | H |
| CH₂-2-thienyl | 3-F | 4-CN | H |
| CH₂-2-pyridinyl | 3-F | 4-CN | H |
| CH₂-3-pyridinyl | 3-F | 4-CN | H |
| NH₂ | 3-F | 4-CN | H |
| NHCH₃ | 3-F | 4-CN | H |
| NHCH₂CF₃ | 3-F | 4-CN | H |
| NHCH₂CH₃ | 3-F | 4-CN | H |
| NHCH(Me)CH₃ | 3-F | 4-CN | H |
| NHCH₂CH(Me)₂ | 3-F | 4-CN | H |
| NHC(Me)₃ | 3-F | 4-CN | H |
| N(CH₃)₂ | 3-F | 4-CN | H |
| N(CH₃)CH₂CH₃ | 3-F | 4-CN | H |
| CH₂CH₂OMe | 3-Cl | 4-F | H |

TABLE 1-continued

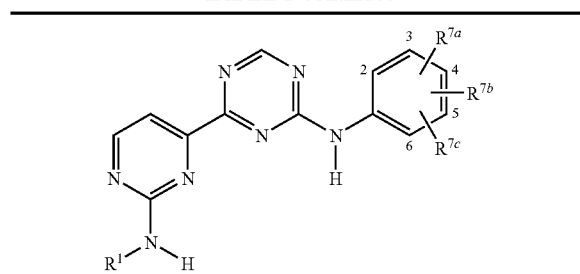

| R¹ | R⁷ᵃ | R⁷ᵇ | R⁷ᶜ |
|---|---|---|---|
| CH₂CH₂CH₂OMe | 3-Cl | 4-F | H |
| CH₂CH(Me)OMe | 3-Cl | 4-F | H |
| CH(Me)OMe | 3-Cl | 4-F | H |
| CH(Me)OEt | 3-Cl | 4-F | H |
| CH(Me)CH₂OMe | 3-Cl | 4-F | H |
| C(Me)₂CH₂OMe | 3-Cl | 4-F | H |
| CH(Me)CH₂CH₂OMe | 3-Cl | 4-F | H |
| (R)—CH(Me)CH₂OMe | 3-Cl | 4-F | H |
| (S)—CH(Me)CH₂OMe | 3-Cl | 4-F | H |
| CH(Me)CH₂OH | 3-Cl | 4-F | H |
| CH(Me)CH₂OC(=O)Me | 3-Cl | 4-F | H |
| CH(Me)CH(OMe)₂ | 3-Cl | 4-F | H |
| CH₂-2-dioxolanyl | 3-Cl | 4-F | H |
| CH₂CH₂OCF₃ | 3-Cl | 4-F | H |
| CH₂CH(Me)SMe | 3-Cl | 4-F | H |
| CH(Me)CH₂SMe | 3-Cl | 4-F | H |
| CH₂CH₂S(=O)Me | 3-Cl | 4-F | H |
| CH₂CH₂S(O)₂Me | 3-Cl | 4-F | H |
| CH₂CO₂Me | 3-Cl | 4-F | H |
| CH(Me)CO₂Me | 3-Cl | 4-F | H |
| CH₂C(=O)Me | 3-Cl | 4-F | H |
| CH₂CH₂C(=O)Me | 3-Cl | 4-F | H |
| CH₂SiMe₃ | 3-Cl | 4-F | H |
| CH₂CH₂SiMe₃ | 3-Cl | 4-F | H |
| CH₂-2-thienyl | 3-Cl | 4-F | H |
| CH₂-2-pyridinyl | 3-Cl | 4-F | H |
| CH₂-3-pyridinyl | 3-Cl | 4-F | H |
| NH₂ | 3-Cl | 4-F | H |
| NHCH₃ | 3-Cl | 4-F | H |
| NHCH₂CF₃ | 3-Cl | 4-F | H |
| NHCH₂CH₃ | 3-Cl | 4-F | H |
| NHCH(Me)CH₃ | 3-Cl | 4-F | H |
| NHCH₂CH(Me)₂ | 3-Cl | 4-F | H |
| NHC(Me)₃ | 3-Cl | 4-F | H |
| N(CH₃)₂ | 3-Cl | 4-F | H |
| N(CH₃)CH₂CH₃ | 3-Cl | 4-F | H |
| N(CH₂CH₃)CH₂CH₃ | 3-F | 4-CN | H |
| Me | H | 4-F | H |
| Et | H | 4-F | H |
| i-Pr | H | 4-F | H |
| n-Pr | H | 4-F | H |
| i-Bu | H | 4-F | H |
| n-Bu | H | 4-F | H |
| s-Bu | H | 4-F | H |
| t-butyl | H | 4-F | H |
| n-Hex | H | 4-F | H |
| cyclopropyl | H | 4-F | H |
| cyclopentyl | H | 4-F | H |
| cyclohexyl | H | 4-F | H |
| 2-cyclohexenyl | H | 4-F | H |
| 3-cyclohexenyl | H | 4-F | H |
| CH₂-c-Pr | H | 4-F | H |
| 4-tetrahydropyranyl | H | 4-F | H |
| 3-tetrahydropyranyl | H | 4-F | H |
| (R)-3-tetrahydropyranyl | H | 4-F | H |
| (S)-3-tetrahydropyranyl | H | 4-F | H |
| 3-tetrahydrofuranyl | H | 4-F | H |
| (R)-3-tetrahydrofuranyl | H | 4-F | H |
| (S)-3-tetrahydrofuranyl | H | 4-F | H |
| Ph | H | 4-F | H |
| 2-Cl-phenyl | H | 4-F | H |
| 3-Cl-phenyl | H | 4-F | H |
| 4-Cl-phenyl | H | 4-F | H |
| 2-pyridinyl | H | 4-F | H |
| 2-pyrimidinyl | H | 4-F | H |

TABLE 1-continued

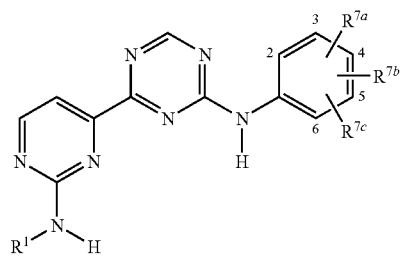

| R¹ | R⁷ᵃ | R⁷ᵇ | R⁷ᶜ |
|---|---|---|---|
| 2-pyrazinyl | H | 4-F | H |
| 2-thiazolyl | H | 4-F | H |
| 2-oxazolyl | H | 4-F | H |
| 2-chloro-2-propenyl | H | 4-F | H |
| 3,3-dichloro-2-propenyl | H | 4-F | H |
| CH₂-2-tetrahydrofuranyl | H | 4-F | H |
| CH₂-2-tetrahydropyranyl | H | 4-F | H |
| CH₂CH₂OH | H | 4-F | H |
| N(CH₂CH₃)CH₂CH₃ | 3-Cl | 4-F | H |
| Me | H | 2-F | H |
| Et | H | 2-F | H |
| i-Pr | H | 2-F | H |
| n-Pr | H | 2-F | H |
| i-Bu | H | 2-F | H |
| n-Bu | H | 2-F | H |
| s-Bu | H | 2-F | H |
| t-butyl | H | 2-F | H |
| n-Hex | H | 2-F | H |
| cyclopropyl | H | 2-F | H |
| cyclopentyl | H | 2-F | H |
| cyclohexyl | H | 2-F | H |
| 2-cyclohexenyl | H | 2-F | H |
| 3-cyclohexenyl | H | 2-F | H |
| CH₂-c-Pr | H | 2-F | H |
| 4-tetrahydropyranyl | H | 2-F | H |
| 3-tetrahydropyranyl | H | 2-F | H |
| (R)-3-tetrahydropyranyl | H | 2-F | H |
| (S)-3-tetrahydropyranyl | H | 2-F | H |
| 3-tetrahydrofuranyl | H | 2-F | H |
| (R)-3-tetrahydrofuranyl | H | 2-F | H |
| (S)-3-tetrahydrofuranyl | H | 2-F | H |
| Ph | H | 2-F | H |
| 2-Cl-phenyl | H | 2-F | H |
| 3-Cl-phenyl | H | 2-F | H |
| 4-Cl-phenyl | H | 2-F | H |
| 2-pyridinyl | H | 2-F | H |
| 2-pyrimidinyl | H | 2-F | H |
| 2-pyrazinyl | H | 2-F | H |
| 2-thiazolyl | H | 2-F | H |
| 2-oxazolyl | H | 2-F | H |
| 2-chloro-2-propenyl | H | 2-F | H |
| 3,3-dichloro-2-propenyl | H | 2-F | H |
| CH₂-2-tetrahydrofuranyl | H | 2-F | H |
| CH₂-2-tetrahydropyranyl | H | 2-F | H |
| CH₂CH₂OH | H | 2-F | H |
| CH₂OMe | H | 4-F | H |
| CH₂CH₂OMe | H | 4-F | H |
| CH₂CH₂CH₂OMe | H | 4-F | H |
| CH₂CH(Me)OMe | H | 4-F | H |
| CH(Me)OMe | H | 4-F | H |
| CH(Me)OEt | H | 4-F | H |
| CH(Me)CH₂OMe | H | 4-F | H |
| C(Me)₂CH₂OMe | H | 4-F | H |
| CH(Me)CH₂CH₂OMe | H | 4-F | H |
| (R)—CH(Me)CH₂OMe | H | 4-F | H |
| (S)—CH(Me)CH₂OMe | H | 4-F | H |
| CH(Me)CH₂OH | H | 4-F | H |
| CH(Me)CH₂OC(=O)Me | H | 4-F | H |
| CH(Me)CH(OMe)₂ | H | 4-F | H |
| CH₂-2-dioxolanyl | H | 4-F | H |
| CH₂CH₂OCF₃ | H | 4-F | H |
| CH₂CH(Me)SMe | H | 4-F | H |
| CH(Me)CH₂SMe | H | 4-F | H |
| CH₂CH₂S(=O)Me | H | 4-F | H |
| CH₂CH₂S(O)₂Me | H | 4-F | H |

TABLE 1-continued

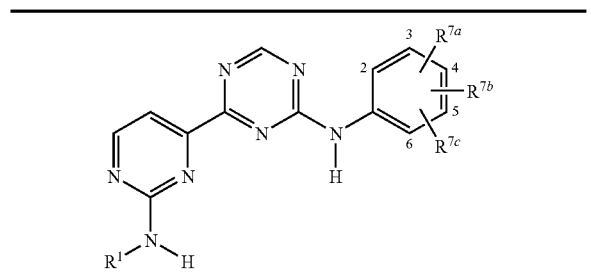

| R¹ | R⁷ᵃ | R⁷ᵇ | R⁷ᶜ |
|---|---|---|---|
| CH₂CO₂Me | H | 4-F | H |
| CH(Me)CO₂Me | H | 4-F | H |
| CH₂C(=O)Me | H | 4-F | H |
| CH₂CH₂C(=O)Me | H | 4-F | H |
| CH₂SiMe₃ | H | 4-F | H |
| CH₂CH₂SiMe₃ | H | 4-F | H |
| CH₂-2-thienyl | H | 4-F | H |
| CH₂-2-pyridinyl | H | 4-F | H |
| CH₂-3-pyridinyl | H | 4-F | H |
| NH₂ | H | 4-F | H |
| NHCH₃ | H | 4-F | H |
| NHCH₂CF₃ | H | 4-F | H |
| NHCH₂CH₃ | H | 4-F | H |
| NHCH(Me)CH₃ | H | 4-F | H |
| NHCH₂CH(Me)₂ | H | 4-F | H |
| NHC(Me)₃ | H | 4-F | H |
| N(CH₃)₂ | H | 4-F | H |
| CH₂OMe | H | 2-F | H |
| CH₂CH₂OMe | H | 2-F | H |
| CH₂CH₂CH₂OMe | H | 2-F | H |
| CH₂CH(Me)OMe | H | 2-F | H |
| CH(Me)OMe | H | 2-F | H |
| CH(Me)OEt | H | 2-F | H |
| CH(Me)CH₂OMe | H | 2-F | H |
| C(Me)₂CH₂OMe | H | 2-F | H |
| CH(Me)CH₂CH₂OMe | H | 2-F | H |
| (R)—CH(Me)CH₂OMe | H | 2-F | H |
| (S)—CH(Me)CH₂OMe | H | 2-F | H |
| CH(Me)CH₂OH | H | 2-F | H |
| CH(Me)CH₂OC(=O)Me | H | 2-F | H |
| CH(Me)CH(OMe)₂ | H | 2-F | H |
| CH₂-2-dioxolanyl | H | 2-F | H |
| CH₂CH₂OCF₃ | H | 2-F | H |
| CH₂CH(Me)SMe | H | 2-F | H |
| CH(Me)CH₂SMe | H | 2-F | H |
| CH₂CH₂S(=O)Me | H | 2-F | H |
| CH₂CH₂S(O)₂Me | H | 2-F | H |
| CH₂CO₂Me | H | 2-F | H |
| CH(Me)CO₂Me | H | 2-F | H |
| CH₂C(=O)Me | H | 2-F | H |
| CH₂CH₂C(=O)Me | H | 2-F | H |
| CH₂SiMe₃ | H | 2-F | H |
| CH₂CH₂SiMe₃ | H | 2-F | H |
| CH₂-2-thienyl | H | 2-F | H |
| CH₂-2-pyridinyl | H | 2-F | H |
| CH₂-3-pyridinyl | H | 2-F | H |
| NH₂ | H | 2-F | H |
| NHCH₃ | H | 2-F | H |
| NHCH₂CF₃ | H | 2-F | H |
| NHCH₂CH₃ | H | 2-F | H |
| NHCH(Me)CH₃ | H | 2-F | H |
| NHCH₂CH(Me)₂ | H | 2-F | H |
| NHC(Me)₃ | H | 2-F | H |
| N(CH₃)₂ | H | 2-F | H |
| N(CH₃)CH₂CH₃ | H | 4-F | H |
| N(CH₂CH₃)CH₂CH₃ | H | 4-F | H |
| Me | 3-F | 5-NO₂ | H |
| Et | 3-F | 5-NO₂ | H |
| i-Pr | 3-F | 5-NO₂ | H |
| n-Pr | 3-F | 5-NO₂ | H |
| i-Bu | 3-F | 5-NO₂ | H |
| n-Bu | 3-F | 5-NO₂ | H |
| s-Bu | 3-F | 5-NO₂ | H |
| t-butyl | 3-F | 5-NO₂ | H |
| n-Hex | 3-F | 5-NO₂ | H |
| cyclopropyl | 3-F | 5-NO₂ | H |
| cyclopentyl | 3-F | 5-NO₂ | H |
| cyclohexyl | 3-F | 5-NO₂ | H |
| 2-cyclohexenyl | 3-F | 5-NO₂ | H |
| 3-cyclohexenyl | 3-F | 5-NO₂ | H |
| CH₂-c-Pr | 3-F | 5-NO₂ | H |
| 4-tetrahydropyranyl | 3-F | 5-NO₂ | H |
| 3-tetrahydropyranyl | 3-F | 5-NO₂ | H |
| (R)-3-tetrahydropyranyl | 3-F | 5-NO₂ | H |
| (S)-3-tetrahydropyranyl | 3-F | 5-NO₂ | H |
| 3-tetrahydrofuranyl | 3-F | 5-NO₂ | H |
| (R)-3-tetrahydrofuranyl | 3-F | 5-NO₂ | H |
| (S)-3-tetrahydrofuranyl | 3-F | 5-NO₂ | H |
| Ph | 3-F | 5-NO₂ | H |
| 2-Cl-phenyl | 3-F | 5-NO₂ | H |
| 3-Cl-phenyl | 3-F | 5-NO₂ | H |
| 4-Cl-phenyl | 3-F | 5-NO₂ | H |
| 2-pyridinyl | 3-F | 5-NO₂ | H |
| 2-pyrimidinyl | 3-F | 5-NO₂ | H |
| 2-pyrazinyl | 3-F | 5-NO₂ | H |
| 2-thiazolyl | 3-F | 5-NO₂ | H |
| 2-oxazolyl | 3-F | 5-NO₂ | H |
| 2-chloro-2-propenyl | 3-F | 5-NO₂ | H |
| 3,3-dichloro-2-propenyl | 3-F | 5-NO₂ | H |
| CH₂-2-tetrahydrofuranyl | 3-F | 5-NO₂ | H |
| CH₂-2-tetrahydropyranyl | 3-F | 5-NO₂ | H |
| N(CH₃)CH₂CH₃ | H | 2-F | H |
| N(CH₂CH₃)CH₂CH₃ | H | 2-F | H |
| Me | 3-F | 4-F | 5-F |
| Et | 3-F | 4-F | 5-F |
| i-Pr | 3-F | 4-F | 5-F |
| n-Pr | 3-F | 4-F | 5-F |
| i-Bu | 3-F | 4-F | 5-F |
| n-Bu | 3-F | 4-F | 5-F |
| s-Bu | 3-F | 4-F | 5-F |
| t-butyl | 3-F | 4-F | 5-F |
| n-Hex | 3-F | 4-F | 5-F |
| cyclopropyl | 3-F | 4-F | 5-F |
| cyclopentyl | 3-F | 4-F | 5-F |
| cyclohexyl | 3-F | 4-F | 5-F |
| 2-cyclohexenyl | 3-F | 4-F | 5-F |
| 3-cyclohexenyl | 3-F | 4-F | 5-F |
| CH₂-c-Pr | 3-F | 4-F | 5-F |
| 4-tetrahydropyranyl | 3-F | 4-F | 5-F |
| 3-tetrahydropyranyl | 3-F | 4-F | 5-F |
| (R)-3-tetrahydropyranyl | 3-F | 4-F | 5-F |
| (S)-3-tetrahydropyranyl | 3-F | 4-F | 5-F |
| 3-tetrahydrofuranyl | 3-F | 4-F | 5-F |
| (R)-3-tetrahydrofuranyl | 3-F | 4-F | 5-F |
| (S)-3-tetrahydrofuranyl | 3-F | 4-F | 5-F |
| Ph | 3-F | 4-F | 5-F |
| 2-Cl-phenyl | 3-F | 4-F | 5-F |
| 3-Cl-phenyl | 3-F | 4-F | 5-F |
| 4-Cl-phenyl | 3-F | 4-F | 5-F |
| 2-pyridinyl | 3-F | 4-F | 5-F |
| 2-pyrimidinyl | 3-F | 4-F | 5-F |
| 2-pyrazinyl | 3-F | 4-F | 5-F |
| 2-thiazolyl | 3-F | 4-F | 5-F |
| 2-oxazolyl | 3-F | 4-F | 5-F |
| 2-chloro-2-propenyl | 3-F | 4-F | 5-F |
| 3,3-dichloro-2-propenyl | 3-F | 4-F | 5-F |
| CH₂-2-tetrahydrofuranyl | 3-F | 4-F | 5-F |
| CH₂-2-tetrahydropyranyl | 3-F | 4-F | 5-F |
| CH₂CH₂OH | 3-F | 5-NO₂ | H |
| CH₂OMe | 3-F | 5-NO₂ | H |

TABLE 1-continued

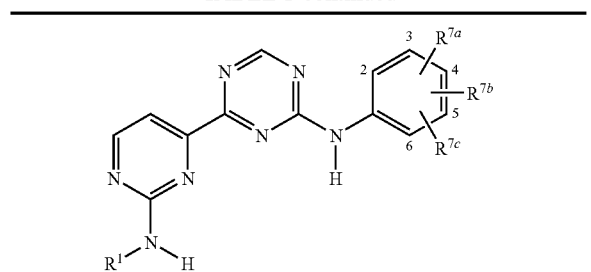

| R¹ | R⁷ᵃ | R⁷ᵇ | R⁷ᶜ |
|---|---|---|---|
| CH₂CH₂OMe | 3-F | 5-NO₂ | H |
| CH₂CH₂CH₂OMe | 3-F | 5-NO₂ | H |
| CH₂CH(Me)OMe | 3-F | 5-NO₂ | H |
| CH(Me)OMe | 3-F | 5-NO₂ | H |
| CH(Me)OEt | 3-F | 5-NO₂ | H |
| CH(Me)CH₂OMe | 3-F | 5-NO₂ | H |
| C(Me)₂CH₂OMe | 3-F | 5-NO₂ | H |
| CH(Me)CH₂CH₂OMe | 3-F | 5-NO₂ | H |
| (R)—CH(Me)CH₂OMe | 3-F | 5-NO₂ | H |
| (S)—CH(Me)CH₂OMe | 3-F | 5-NO₂ | H |
| CH(Me)CH₂OH | 3-F | 5-NO₂ | H |
| CH(Me)CH₂OC(=O)Me | 3-F | 5-NO₂ | H |
| CH(Me)CH(OMe)₂ | 3-F | 5-NO₂ | H |
| CH₂-2-dioxolanyl | 3-F | 5-NO₂ | H |
| CH₂CH₂OCF₃ | 3-F | 5-NO₂ | H |
| CH₂CH(Me)SMe | 3-F | 5-NO₂ | H |
| CH(Me)CH₂SMe | 3-F | 5-NO₂ | H |
| CH₂CH₂S(=O)Me | 3-F | 5-NO₂ | H |
| CH₂CH₂S(O)₂Me | 3-F | 5-NO₂ | H |
| CH₂CO₂Me | 3-F | 5-NO₂ | H |
| CH(Me)CO₂Me | 3-F | 5-NO₂ | H |
| CH₂C(=O)Me | 3-F | 5-NO₂ | H |
| CH₂CH₂C(=O)Me | 3-F | 5-NO₂ | H |
| CH₂SiMe₃ | 3-F | 5-NO₂ | H |
| CH₂CH₂SiMe₃ | 3-F | 5-NO₂ | H |
| CH₂-2-thienyl | 3-F | 5-NO₂ | H |
| CH₂-2-pyridinyl | 3-F | 5-NO₂ | H |
| CH₂-3-pyridinyl | 3-F | 5-NO₂ | H |
| NH₂ | 3-F | 5-NO₂ | H |
| NHCH₃ | 3-F | 5-NO₂ | H |
| NHCH₂CF₃ | 3-F | 5-NO₂ | H |
| NHCH₂CH₃ | 3-F | 5-NO₂ | H |
| NHCH(Me)CH₃ | 3-F | 5-NO₂ | H |
| NHCH₂CH(Me)₂ | 3-F | 5-NO₂ | H |
| NHC(Me)₃ | 3-F | 5-NO₂ | H |
| CH₂CH₂OH | 3-F | 4-F | 5-F |
| CH₂OMe | 3-F | 4-F | 5-F |
| CH₂CH₂OMe | 3-F | 4-F | 5-F |
| CH₂CH₂CH₂OMe | 3-F | 4-F | 5-F |
| CH₂CH(Me)OMe | 3-F | 4-F | 5-F |
| CH(Me)OMe | 3-F | 4-F | 5-F |
| CH(Me)OEt | 3-F | 4-F | 5-F |
| CH(Me)CH₂OMe | 3-F | 4-F | 5-F |
| C(Me)₂CH₂OMe | 3-F | 4-F | 5-F |
| CH(Me)CH₂CH₂OMe | 3-F | 4-F | 5-F |
| (R)—CH(Me)CH₂OMe | 3-F | 4-F | 5-F |
| (S)—CH(Me)CH₂OMe | 3-F | 4-F | 5-F |
| CH(Me)CH₂OH | 3-F | 4-F | 5-F |
| CH(Me)CH₂OC(=O)Me | 3-F | 4-F | 5-F |
| CH(Me)CH(OMe)₂ | 3-F | 4-F | 5-F |
| CH₂-2-dioxolanyl | 3-F | 4-F | 5-F |
| CH₂CH₂OCF₃ | 3-F | 4-F | 5-F |
| CH₂CH(Me)SMe | 3-F | 4-F | 5-F |
| CH(Me)CH₂SMe | 3-F | 4-F | 5-F |
| CH₂CH₂S(=O)Me | 3-F | 4-F | 5-F |
| CH₂CH₂S(O)₂Me | 3-F | 4-F | 5-F |
| CH₂CO₂Me | 3-F | 4-F | 5-F |
| CH(Me)CO₂Me | 3-F | 4-F | 5-F |
| CH₂C(=O)Me | 3-F | 4-F | 5-F |
| CH₂CH₂C(=O)Me | 3-F | 4-F | 5-F |
| CH₂SiMe₃ | 3-F | 4-F | 5-F |
| CH₂CH₂SiMe₃ | 3-F | 4-F | 5-F |
| CH₂-2-thienyl | 3-F | 4-F | 5-F |
| CH₂-2-pyridinyl | 3-F | 4-F | 5-F |
| CH₂-3-pyridinyl | 3-F | 4-F | 5-F |
| NH₂ | 3-F | 4-F | 5-F |
| NHCH₃ | 3-F | 4-F | 5-F |
| NHCH₂CF₃ | 3-F | 4-F | 5-F |
| NHCH₂CH₃ | 3-F | 4-F | 5-F |
| NHCH(Me)CH₃ | 3-F | 4-F | 5-F |
| NHCH₂CH(Me)₂ | 3-F | 4-F | 5-F |
| NHC(Me)₃ | 3-F | 4-F | 5-F |
| N(CH₃)₂ | 3-F | 5-NO₂ | H |
| N(CH₃)CH₂CH₃ | 3-F | 5-NO₂ | H |
| N(CH₂CH₃)CH₂CH₃ | 3-F | 5-NO₂ | H |
| Me | 3-F | 4-Me | 5-F |
| Et | 3-F | 4-Me | 5-F |
| i-Pr | 3-F | 4-Me | 5-F |
| n-Pr | 3-F | 4-Me | 5-F |
| i-Bu | 3-F | 4-Me | 5-F |
| n-Bu | 3-F | 4-Me | 5-F |
| s-Bu | 3-F | 4-Me | 5-F |
| t-butyl | 3-F | 4-Me | 5-F |
| n-Hex | 3-F | 4-Me | 5-F |
| cyclopropyl | 3-F | 4-Me | 5-F |
| cyclopentyl | 3-F | 4-Me | 5-F |
| cyclohexyl | 3-F | 4-Me | 5-F |
| 2-cyclohexenyl | 3-F | 4-Me | 5-F |
| 3-cyclohexenyl | 3-F | 4-Me | 5-F |
| CH₂-c-Pr | 3-F | 4-Me | 5-F |
| 4-tetrahydropyranyl | 3-F | 4-Me | 5-F |
| 3-tetrahydropyranyl | 3-F | 4-Me | 5-F |
| (R)-3-tetrahydropyranyl | 3-F | 4-Me | 5-F |
| (S)-3-tetrahydropyranyl | 3-F | 4-Me | 5-F |
| 3-tetrahydrofuranyl | 3-F | 4-Me | 5-F |
| (R)-3-tetrahydrofuranyl | 3-F | 4-Me | 5-F |
| (S)-3-tetrahydrofuranyl | 3-F | 4-Me | 5-F |
| Ph | 3-F | 4-Me | 5-F |
| 2-Cl-phenyl | 3-F | 4-Me | 5-F |
| 3-Cl-phenyl | 3-F | 4-Me | 5-F |
| 4-Cl-phenyl | 3-F | 4-Me | 5-F |
| 2-pyridinyl | 3-F | 4-Me | 5-F |
| 2-pyrimidinyl | 3-F | 4-Me | 5-F |
| 2-pyrazinyl | 3-F | 4-Me | 5-F |
| 2-thiazolyl | 3-F | 4-Me | 5-F |
| 2-oxazolyl | 3-F | 4-Me | 5-F |
| 2-chloro-2-propenyl | 3-F | 4-Me | 5-F |
| 3,3-dichloro-2-propenyl | 3-F | 4-Me | 5-F |
| CH₂-2-tetrahydrofuranyl | 3-F | 4-Me | 5-F |
| N(CH₃)₂ | 3-F | 4-F | 5-F |
| N(CH₃)CH₂CH₃ | 3-F | 4-F | 5-F |
| N(CH₂CH₃)CH₂CH₃ | 3-F | 4-F | 5-F |
| Me | H | H | H |
| Et | H | H | H |
| i-Pr | H | H | H |
| n-Pr | H | H | H |
| i-Bu | H | H | H |
| n-Bu | H | H | H |
| s-Bu | H | H | H |
| t-butyl | H | H | H |
| n-Hex | H | H | H |
| cyclopropyl | H | H | H |
| cyclopentyl | H | H | H |
| cyclohexyl | H | H | H |
| 2-cyclohexenyl | H | H | H |
| 3-cyclohexenyl | H | H | H |
| CH₂-c-Pr | H | H | H |
| 4-tetrahydropyranyl | H | H | H |
| 3-tetrahydropyranyl | H | H | H |
| (R)-3-tetrahydropyranyl | H | H | H |

TABLE 1-continued

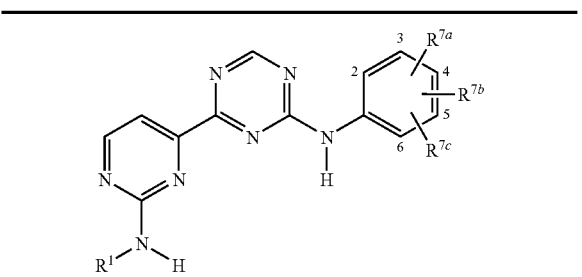

| R¹ | R⁷ᵃ | R⁷ᵇ | R⁷ᶜ |
|---|---|---|---|
| (S)-3-tetrahydropyranyl | H | H | H |
| 3-tetrahydrofuranyl | H | H | H |
| (R)-3-tetrahydrofuranyl | H | H | H |
| (S)-3-tetrahydrofuranyl | H | H | H |
| Ph | H | H | H |
| 2-Cl-phenyl | H | H | H |
| 3-Cl-phenyl | H | H | H |
| 4-Cl-phenyl | H | H | H |
| 2-pyridinyl | H | H | H |
| 2-pyrimidinyl | H | H | H |
| 2-pyrazinyl | H | H | H |
| 2-thiazolyl | H | H | H |
| 2-oxazolyl | H | H | H |
| 2-chloro-2-propenyl | H | H | H |
| 3,3-dichloro-2-propenyl | H | H | H |
| CH₂-2-tetrahydrofuranyl | H | H | H |
| CH₂-2-tetrahydropyranyl | 3-F | 4-Me | 5-F |
| CH₂CH₂OH | 3-F | 4-Me | 5-F |
| CH₂OMe | 3-F | 4-Me | 5-F |
| CH₂CH₂OMe | 3-F | 4-Me | 5-F |
| CH₂CH₂CH₂OMe | 3-F | 4-Me | 5-F |
| CH₂CH(Me)OMe | 3-F | 4-Me | 5-F |
| CH(Me)OMe | 3-F | 4-Me | 5-F |
| CH(Me)OEt | 3-F | 4-Me | 5-F |
| CH(Me)CH₂OMe | 3-F | 4-Me | 5-F |
| C(Me)₂CH₂OMe | 3-F | 4-Me | 5-F |
| CH(Me)CH₂CH₂OMe | 3-F | 4-Me | 5-F |
| (R)—CH(Me)CH₂OMe | 3-F | 4-Me | 5-F |
| (S)—CH(Me)CH₂OMe | 3-F | 4-Me | 5-F |
| CH(Me)CH₂OH | 3-F | 4-Me | 5-F |
| CH(Me)CH₂OC(=O)Me | 3-F | 4-Me | 5-F |
| CH(Me)CH(OMe)₂ | 3-F | 4-Me | 5-F |
| CH₂-2-dioxolanyl | 3-F | 4-Me | 5-F |
| CH₂CH₂OCF₃ | 3-F | 4-Me | 5-F |
| CH₂CH(Me)SMe | 3-F | 4-Me | 5-F |
| CH(Me)CH₂SMe | 3-F | 4-Me | 5-F |
| CH₂CH₂S(=O)Me | 3-F | 4-Me | 5-F |
| CH₂CH₂S(O)₂Me | 3-F | 4-Me | 5-F |
| CH₂CO₂Me | 3-F | 4-Me | 5-F |
| CH(Me)CO₂Me | 3-F | 4-Me | 5-F |
| CH₂C(=O)Me | 3-F | 4-Me | 5-F |
| CH₂CH₂C(=O)Me | 3-F | 4-Me | 5-F |
| CH₂SiMe₃ | 3-F | 4-Me | 5-F |
| CH₂CH₂SiMe₃ | 3-F | 4-Me | 5-F |
| CH₂-2-thienyl | 3-F | 4-Me | 5-F |
| CH₂-2-pyridinyl | 3-F | 4-Me | 5-F |
| CH₂-3-pyridinyl | 3-F | 4-Me | 5-F |
| NH₂ | 3-F | 4-Me | 5-F |
| NHCH₃ | 3-F | 4-Me | 5-F |
| NHCH₂CF₃ | 3-F | 4-Me | 5-F |
| NHCH₂CH₃ | 3-F | 4-Me | 5-F |
| NHCH(Me)CH₃ | 3-F | 4-Me | 5-F |
| NHCH₂CH(Me)₂ | 3-F | 4-Me | 5-F |
| CH₂-2-tetrahydropyranyl | H | H | H |
| CH₂CH₂OH | H | H | H |

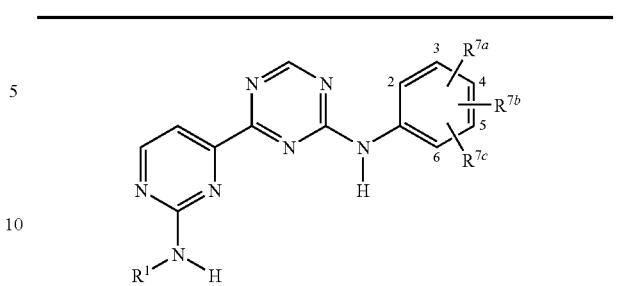

| R¹ | R⁷ᵃ | R⁷ᵇ | R⁷ᶜ |
|---|---|---|---|
| CH₂OMe | H | H | H |
| CH₂CH₂OMe | H | H | H |
| CH₂CH₂CH₂OMe | H | H | H |
| CH₂CH(Me)OMe | H | H | H |
| CH(Me)OMe | H | H | H |
| CH(Me)OEt | H | H | H |
| CH(Me)CH₂OMe | H | H | H |
| C(Me)₂CH₂OMe | H | H | H |
| CH(Me)CH₂CH₂OMe | H | H | H |
| (R)—CH(Me)CH₂OMe | H | H | H |
| (S)—CH(Me)CH₂OMe | H | H | H |
| CH(Me)CH₂OH | H | H | H |
| CH(Me)CH₂OC(=O)Me | H | H | H |
| CH(Me)CH(OMe)₂ | H | H | H |
| CH₂-2-dioxolanyl | H | H | H |
| CH₂CH₂OCF₃ | H | H | H |
| CH₂CH(Me)SMe | H | H | H |
| CH(Me)CH₂SMe | H | H | H |
| CH₂CH₂S(=O)Me | H | H | H |
| CH₂CH₂S(O)₂Me | H | H | H |
| CH₂CO₂Me | H | H | H |
| CH(Me)CO₂Me | H | H | H |
| CH₂C(=O)Me | H | H | H |
| CH₂CH₂C(=O)Me | H | H | H |
| CH₂SiMe₃ | H | H | H |
| CH₂CH₂SiMe₃ | H | H | H |
| CH₂-2-thienyl | H | H | H |
| CH₂-2-pyridinyl | H | H | H |
| CH₂-3-pyridinyl | H | H | H |
| NH₂ | H | H | H |
| NHCH₃ | H | H | H |
| NHCH₂CF₃ | H | H | H |
| NHCH₂CH₃ | H | H | H |
| NHCH(Me)CH₃ | H | H | H |
| NHCH₂CH(Me)₂ | H | H | H |
| NHC(Me)₃ | 3-F | 4-Me | 5-F |
| N(CH₃)₂ | 3-F | 4-Me | 5-F |
| N(CH₃)CH₂CH₃ | 3-F | 4-Me | 5-F |
| N(CH2CH₃)CH₂CH₃ | 3-F | 4-Me | 5-F |
| NHC(Me)₃ | H | H | H |
| N(CH₃)₂ | H | H | H |
| N(CH₃)CH₂CH₃ | H | H | H |
| N(CH₂CH₃)CH₂CH₃ | H | H | H |

TABLE 2

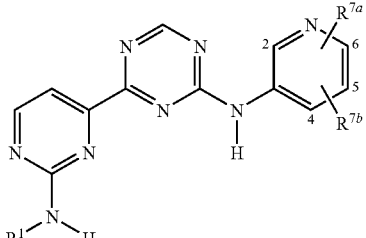

| R¹ | $R^{7a}$ | $R^{7b}$ | R¹ | $R^{7a}$ | $R^{7b}$ |
|---|---|---|---|---|---|
| t-butyl | H | 6-F | t-butyl | H | 6-Cl |
| cyclopropyl | H | 6-F | cyclopropyl | H | 6-Cl |
| cyclohexyl | H | 6-F | cyclohexyl | H | 6-Cl |
| CH-c-Pr | H | 6-F | CH-c-Pr | H | 6-Cl |
| 4-tetrahydropyranyl | H | 6-F | 4-tetrahydropyranyl | H | 6-Cl |
| 3-tetrahydropyranyl | H | 6-F | 3-tetrahydropyranyl | H | 6-Cl |
| (R)-3-tetrahydropyranyl | H | 6-F | (R)-3-tetrahydropyranyl | H | 6-Cl |
| (S)-3-tetrahydropyranyl | H | 6-F | (S)-3-tetrahydropyranyl | H | 6-Cl |
| 3-tetrahydrofuranyl | H | 6-F | 3-tetrahydrofuranyl | H | 6-Cl |
| (R)-3-tetrahydrofuranyl | H | 6-F | (R)-3-tetrahydrofuranyl | H | 6-Cl |
| (S)-3-tetrahydrofuranyl | H | 6-F | (S)-3-tetrahydrofuranyl | H | 6-Cl |
| 2-pyridinyl | H | 6-F | 2-pyridinyl | H | 6-Cl |
| $CH_2$-2-tetrahydrofuranyl | H | 6-F | $CH_2$-2-tetrahydrofuranyl | H | 6-Cl |
| $CH_2$-2-tetrahydropyranyl | H | 6-F | $CH_2$-2-tetrahydropyranyl | H | 6-Cl |
| $CH_2OMe$ | H | 6-F | $CH_2OMe$ | H | 6-Cl |
| $CH_2CH_2OMe$ | H | 6-F | $CH_2CH_2OMe$ | H | 6-Cl |
| $CH_2CH_2CH_2OMe$ | H | 6-F | $CH_2CH_2CH_2OMe$ | H | 6-Cl |
| $CH_2CH(Me)OMe$ | H | 6-F | $CH_2CH(Me)OMe$ | H | 6-Cl |
| $CH(Me)OMe$ | H | 6-F | $CH(Me)OMe$ | H | 6-Cl |
| $CH(Me)OEt$ | H | 6-F | $CH(Me)OEt$ | H | 6-Cl |
| $CH(Me)CH_2OMe$ | H | 6-F | $CH(Me)CH_2OMe$ | H | 6-Cl |
| $C(Me)_2CH_2OMe$ | H | 6-F | $C(Me)_2CH_2OMe$ | H | 6-Cl |
| $CH(Me)CH_2CH_2OMe$ | H | 6-F | $CH(Me)CH_2CH_2OMe$ | H | 6-Cl |
| (R)—$CH(Me)CH_2OMe$ | H | 6-F | (R)—$CH(Me)CH_2OMe$ | H | 6-Cl |
| (S)-$CH(Me)CH_2OMe$ | H | 6-F | (S)-$CH(Me)CH_2OMe$ | H | 6-Cl |
| $CH(Me)CH_2OH$ | H | 6-F | $CH(Me)CH_2OH$ | H | 6-Cl |
| $CH(Me)CH_2OC(=O)Me$ | H | 6-F | $CH(Me)CH_2OC(=O)Me$ | H | 6-Cl |
| $CH_2CH_2OCF_3$ | H | 6-F | $CH_2CH_2OCF_3$ | H | 6-Cl |
| $NH_2$ | H | 6-F | $NH_2$ | H | 6-Cl |
| $NHCH_3$ | H | 6-F | $NHCH_3$ | H | 6-Cl |
| $NHCH_2CF_3$ | H | 6-F | $NHCH_2CF_3$ | H | 6-Cl |
| $NHCH_2CH_3$ | H | 6-F | $NHCH_2CH_3$ | H | 6-Cl |
| $NHCH(Me)CH_3$ | H | 6-F | $NHCH(Me)CH_3$ | H | 6-Cl |
| $NHC(Me)_3$ | H | 6-F | $NHC(Me)_3$ | H | 6-Cl |
| $N(CH_3)_2$ | H | 6-F | $N(CH_3)_2$ | H | 6-Cl |
| t-butyl | H | 5-F | t-butyl | H | 6-CN |
| cyclopropyl | H | 5-F | cyclopropyl | H | 6-CN |
| cyclohexyl | H | 5-F | cyclohexyl | H | 6-CN |
| CH-c-Pr | H | 5-F | CH-c-Pr | H | 6-CN |
| 4-tetrahydropyranyl | H | 5-F | 4-tetrahydropyranyl | H | 6-CN |
| 3-tetrahydropyranyl | H | 5-F | 3-tetrahydropyranyl | H | 6-CN |
| (R)-3-tetrahydropyranyl | H | 5-F | (R)-3-tetrahydropyranyl | H | 6-CN |
| (S)-3-tetrahydropyranyl | H | 5-F | (S)-3-tetrahydropyranyl | H | 6-CN |
| 3-tetrahydrofuranyl | H | 5-F | 3-tetrahydrofuranyl | H | 6-CN |
| (R)-3-tetrahydrofuranyl | H | 5-F | (R)-3-tetrahydrofuranyl | H | 6-CN |
| (S)-3-tetrahydrofuranyl | H | 5-F | (S)-3-tetrahydrofuranyl | H | 6-CN |
| 2-pyridinyl | H | 5-F | 2-pyridinyl | H | 6-CN |
| $CH_2$-2-tetrahydrofuranyl | H | 5-F | $CH_2$-2-tetrahydrofuranyl | H | 6-CN |
| $CH_2$-2-tetrahydropyranyl | H | 5-F | $CH_2$-2-tetrahydropyranyl | H | 6-CN |
| $CH_2OMe$ | H | 5-F | $CH_2OMe$ | H | 6-CN |
| $CH_2CH_2OMe$ | H | 5-F | $CH_2CH_2OMe$ | H | 6-CN |
| $CH_2CH_2CH_2OMe$ | H | 5-F | $CH_2CH_2CH_2OMe$ | H | 6-CN |
| $CH_2CH(Me)OMe$ | H | 5-F | $CH_2CH(Me)OMe$ | H | 6-CN |
| $CH(Me)OMe$ | H | 5-F | $CH(Me)OMe$ | H | 6-CN |
| $CH(Me)OEt$ | H | 5-F | $CH(Me)OEt$ | H | 6-CN |
| $CH(Me)CH_2OMe$ | H | 5-F | $CH(Me)CH_2OMe$ | H | 6-CN |
| $C(Me)_2CH_2OMe$ | H | 5-F | $C(Me)_2CH_2OMe$ | H | 6-CN |
| $CH(Me)CH_2CH_2OMe$ | H | 5-F | $CH(Me)CH_2CH_2OMe$ | H | 6-CN |
| (R)—$CH(Me)CH_2OMe$ | H | 5-F | (R)—$CH(Me)CH_2OMe$ | H | 6-CN |
| (S)-$CH(Me)CH_2OMe$ | H | 5-F | (S)-$CH(Me)CH_2OMe$ | H | 6-CN |
| $CH(Me)CH_2OH$ | H | 5-F | $CH(Me)CH_2OH$ | H | 6-CN |
| $CH(Me)CH_2OC(=O)Me$ | H | 5-F | $CH(Me)CH_2OC(=O)Me$ | H | 6-CN |
| $CH_2CH_2OCF_3$ | H | 5-F | $CH_2CH_2OCF_3$ | H | 6-CN |
| $NH_2$ | H | 5-F | $NH_2$ | H | 6-CN |
| $NHCH_3$ | H | 5-F | $NHCH_3$ | H | 6-CN |

TABLE 2-continued

| R¹ | R⁷ᵃ | R⁷ᵇ | R¹ | R⁷ᵃ | R⁷ᵇ |
|---|---|---|---|---|---|
| NHCH₂CF₃ | H | 5-F | NHCH₂CF₃ | H | 6-CN |
| NHCH₂CH₃ | H | 5-F | NHCH₂CH₃ | H | 6-CN |
| NHCH(Me)CH₃ | H | 5-F | NHCH(Me)CH₃ | H | 6-CN |
| NHC(Me)₃ | H | 5-F | NHC(Me)₃ | H | 6-CN |
| N(CH₃)₂ | H | 5-F | N(CH₃)₂ | H | 6-CN |
| t-butyl | 5-F | 6-CN | t-butyl | H | H |
| cyclopropyl | 5-F | 6-CN | cyclopropyl | H | H |
| cyclohexyl | 5-F | 6-CN | cyclohexyl | H | H |
| CH-c-Pr | 5-F | 6-CN | CH-c-Pr | H | H |
| 4-tetrahydropyranyl | 5-F | 6-CN | 4-tetrahydropyranyl | H | H |
| 3-tetrahydropyranyl | 5-F | 6-CN | 3-tetrahydropyranyl | H | H |
| (R)-3-tetrahydropyranyl | 5-F | 6-CN | (R)-3-tetrahydropyranyl | H | H |
| (S)-3-tetrahydropyranyl | 5-F | 6-CN | (S)-3-tetrahydropyranyl | H | H |
| 3-tetrahydrofuranyl | 5-F | 6-CN | 3-tetrahydrofuranyl | H | H |
| (R)-3-tetrahydrofuranyl | 5-F | 6-CN | (R)-3-tetrahydrofuranyl | H | H |
| (S)-3-tetrahydrofuranyl | 5-F | 6-CN | (S)-3-tetrahydrofuranyl | H | H |
| 2-pyridinyl | 5-F | 6-CN | 2-pyridinyl | H | H |
| CH₂-2-tetrahydrofuranyl | 5-F | 6-CN | CH₂-2-tetrahydrofuranyl | H | H |
| CH₂-2-tetrahydropyranyl | 5-F | 6-CN | CH₂-2-tetrahydropyranyl | H | H |
| CH₂OMe | 5-F | 6-CN | CH₂OMe | H | H |
| CH₂CH₂OMe | 5-F | 6-CN | CH₂CH₂OMe | H | H |
| CH₂CH₂CH₂OMe | 5-F | 6-CN | CH₂CH₂CH₂OMe | H | H |
| CH₂CH(Me)OMe | 5-F | 6-CN | CH₂CH(Me)OMe | H | H |
| CH(Me)OMe | 5-F | 6-CN | CH(Me)OMe | H | H |
| CH(Me)OEt | 5-F | 6-CN | CH(Me)OEt | H | H |
| CH(Me)CH₂OMe | 5-F | 6-CN | CH(Me)CH₂OMe | H | H |
| C(Me)₂CH₂OMe | 5-F | 6-CN | C(Me)₂CH₂OMe | H | H |
| CH(Me)CH₂CH₂OMe | 5-F | 6-CN | CH(Me)CH₂CH₂OMe | H | H |
| (R)—CH(Me)CH₂OMe | 5-F | 6-CN | (R)—CH(Me)CH₂OMe | H | H |
| (S)-CH(Me)CH₂OMe | 5-F | 6-CN | (S)-CH(Me)CH₂OMe | H | H |
| CH(Me)CH₂OH | 5-F | 6-CN | CH(Me)CH₂OH | H | H |
| CH(Me)CH₂OC(=O)Me | 5-F | 6-CN | CH(Me)CH₂OC(=O)Me | H | H |
| CH₂CH₂OCF₃ | 5-F | 6-CN | CH₂CH₂OCF₃ | H | H |
| NH₂ | 5-F | 6-CN | NH₂ | H | H |
| NHCH₃ | 5-F | 6-CN | NHCH₃ | H | H |
| NHCH₂CF₃ | 5-F | 6-CN | NHCH₂CF₃ | H | H |
| NHCH₂CH₃ | 5-F | 6-CN | NHCH₂CH₃ | H | H |
| NHCH(Me)CH₃ | 5-F | 6-CN | NHCH(Me)CH₃ | H | H |
| NHC(Me)₃ | 5-F | 6-CN | NHC(Me)₃ | H | H |
| N(CH₃)₂ | 5-F | 6-CN | N(CH₃)₂ | H | H |

TABLE 3

| R¹ | R⁷ᵃ | R⁷ᵇ | R¹ | R⁷ᵃ | R⁷ᵇ |
|---|---|---|---|---|---|
| t-butyl | 2-F | H | t-butyl | 2-CN | H |
| cyclopropyl | 2-F | H | cyclopropyl | 2-CN | H |
| cyclohexyl | 2-F | H | cyclohexyl | 2-CN | H |
| CH-c-Pr | 2-F | H | CH-c-Pr | 2-CN | H |
| 4-tetrahydropyranyl | 2-F | H | 4-tetrahydropyranyl | 2-CN | H |

TABLE 3-continued

| R¹ | R⁷ᵃ | R⁷ᵇ | R¹ | R⁷ᵃ | R⁷ᵇ |
|---|---|---|---|---|---|
| 3-tetrahydropyranyl | 2-F | H | 3-tetrahydropyranyl | 2-CN | H |
| (R)-3-tetrahydropyranyl | 2-F | H | (R)-3-tetrahydropyranyl | 2-CN | H |
| (S)-3-tetrahydropyranyl | 2-F | H | (S)-3-tetrahydropyranyl | 2-CN | H |
| 3-tetrahydrofuranyl | 2-F | H | 3-tetrahydrofuranyl | 2-CN | H |
| (R)-3-tetrahydrofuranyl | 2-F | H | (R)-3-tetrahydrofuranyl | 2-CN | H |
| (S)-3-tetrahydrofuranyl | 2-F | H | (S)-3-tetrahydrofuranyl | 2-CN | H |
| 2-pyridinyl | 2-F | H | 2-pyridinyl | 2-CN | H |
| CH₂-2-tetrahydrofuranyl | 2-F | H | CH₂-2-tetrahydrofuranyl | 2-CN | H |
| CH₂-2-tetrahydropyranyl | 2-F | H | CH₂-2-tetrahydropyranyl | 2-CN | H |
| CH₂OMe | 2-F | H | CH₂OMe | 2-CN | H |
| CH₂CH₂OMe | 2-F | H | CH₂CH₂OMe | 2-CN | H |
| CH₂CH₂CH₂OMe | 2-F | H | CH₂CH₂CH₂OMe | 2-CN | H |
| CH₂CH(Me)OMe | 2-F | H | CH₂CH(Me)OMe | 2-CN | H |
| CH(Me)OMe | 2-F | H | CH(Me)OMe | 2-CN | H |
| CH(Me)OEt | 2-F | H | CH(Me)OEt | 2-CN | H |
| CH(Me)CH₂OMe | 2-F | H | CH(Me)CH₂OMe | 2-CN | H |
| C(Me)₂CH₂OMe | 2-F | H | C(Me)₂CH₂OMe | 2-CN | H |
| CH(Me)CH₂CH₂OMe | 2-F | H | CH(Me)CH₂CH₂OMe | 2-CN | H |
| (R)—CH(Me)CH₂OMe | 2-F | H | (R)—CH(Me)CH₂OMe | 2-CN | H |
| (S)-CH(Me)CH₂OMe | 2-F | H | (S)-CH(Me)CH₂OMe | 2-CN | H |
| CH(Me)CH₂OH | 2-F | H | CH(Me)CH₂OH | 2-CN | H |
| CH(Me)CH₂OC(=O)Me | 2-F | H | CH(Me)CH₂OC(=O)Me | 2-CN | H |
| CH₂CH₂OCF₃ | 2-F | H | CH₂CH₂OCF₃ | 2-CN | H |
| NH₂ | 2-F | H | NH₂ | 2-CN | H |
| NHCH₃ | 2-F | H | NHCH₃ | 2-CN | H |
| NHCH₂CF₃ | 2-F | H | NHCH₂CF₃ | 2-CN | H |
| NHCH₂CH₃ | 2-F | H | NHCH₂CH₃ | 2-CN | H |
| NHCH(Me)CH₃ | 2-F | H | NHCH(Me)CH₃ | 2-CN | H |
| NHC(Me)₃ | 2-F | H | NHC(Me)₃ | 2-CN | H |
| N(CH₃)₂ | 2-F | H | N(CH₃)₂ | 2-CN | H |
| t-butyl | 2-CN | 6-Cl | t-butyl | H | H |
| cyclopropyl | 2-CN | 6-Cl | cyclopropyl | H | H |
| cyclohexyl | 2-CN | 6-Cl | cyclohexyl | H | H |
| CH-c-Pr | 2-CN | 6-Cl | CH-c-Pr | H | H |
| 4-tetrahydropyranyl | 2-CN | 6-Cl | 4-tetrahydropyranyl | H | H |
| 3-tetrahydropyranyl | 2-CN | 6-Cl | 3-tetrahydropyranyl | H | H |
| (R)-3-tetrahydropyranyl | 2-CN | 6-Cl | (R)-3-tetrahydropyranyl | H | H |
| (S)-3-tetrahydropyranyl | 2-CN | 6-Cl | (S)-3-tetrahydropyranyl | H | H |
| 3-tetrahydrofuranyl | 2-CN | 6-Cl | 3-tetrahydrofuranyl | H | H |
| (R)-3-tetrahydrofuranyl | 2-CN | 6-Cl | (R)-3-tetrahydrofuranyl | H | H |
| (S)-3-tetrahydrofuranyl | 2-CN | 6-Cl | (S)-3-tetrahydrofuranyl | H | H |
| 2-pyridinyl | 2-CN | 6-Cl | 2-pyridinyl | H | H |
| CH₂-2-tetrahydrofuranyl | 2-CN | 6-Cl | CH₂-2-tetrahydrofuranyl | H | H |
| CH₂-2-tetrahydropyranyl | 2-CN | 6-Cl | CH₂-2-tetrahydropyranyl | H | H |
| CH₂OMe | 2-CN | 6-Cl | CH₂OMe | H | H |
| CH₂CH₂OMe | 2-CN | 6-Cl | CH₂CH₂OMe | H | H |
| CH₂CH₂CH₂OMe | 2-CN | 6-Cl | CH₂CH₂CH₂OMe | H | H |
| CH₂CH(Me)OMe | 2-CN | 6-Cl | CH₂CH(Me)OMe | H | H |
| CH(Me)OMe | 2-CN | 6-Cl | CH(Me)OMe | H | H |
| CH(Me)OEt | 2-CN | 6-Cl | CH(Me)OEt | H | H |
| CH(Me)CH₂OMe | 2-CN | 6-Cl | CH(Me)CH₂OMe | H | H |
| C(Me)₂CH₂OMe | 2-CN | 6-Cl | C(Me)₂CH₂OMe | H | H |
| CH(Me)CH₂CH₂OMe | 2-CN | 6-Cl | CH(Me)CH₂CH₂OMe | H | H |
| (R)—CH(Me)CH₂OMe | 2-CN | 6-Cl | (R)—CH(Me)CH₂OMe | H | H |
| (S)-CH(Me)CH₂OMe | 2-CN | 6-Cl | (S)-CH(Me)CH₂OMe | H | H |
| CH(Me)CH₂OH | 2-CN | 6-Cl | CH(Me)CH₂OH | H | H |
| CH(Me)CH₂OC(=O)Me | 2-CN | 6-Cl | CH(Me)CH₂OC(=O)Me | H | H |
| CH₂CH₂OCF₃ | 2-CN | 6-Cl | CH₂CH₂OCF₃ | H | H |
| NH₂ | 2-CN | 6-Cl | NH₂ | H | H |
| NHCH₃ | 2-CN | 6-Cl | NHCH₃ | H | H |
| NHCH₂CF₃ | 2-CN | 6-Cl | NHCH₂CF₃ | H | H |
| NHCH₂CH₃ | 2-CN | 6-Cl | NHCH₂CH₃ | H | H |
| NHCH(Me)CH₃ | 2-CN | 6-Cl | NHCH(Me)CH₃ | H | H |

TABLE 3-continued

| R¹ | R⁷ᵃ | R⁷ᵇ | R¹ | R⁷ᵃ | R⁷ᵇ |
|---|---|---|---|---|---|
| NHC(Me)₃ | 2-CN | 6-Cl | NHC(Me)₃ | H | H |
| N(CH₃)₂ | 2-CN | 6-Cl | N(CH₃)₂ | H | H |

TABLE 4

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| Me | H | 3-F | H | Me | 3-F | 4-F | H |
| Et | H | 3-F | H | Et | 3-F | 4-F | H |
| i-Pr | H | 3-F | H | i-Pr | 3-F | 4-F | H |
| n-Pr | H | 3-F | H | n-Pr | 3-F | 4-F | H |
| i-Bu | H | 3-F | H | i-Bu | 3-F | 4-F | H |
| n-Bu | H | 3-F | H | n-Bu | 3-F | 4-F | H |
| s-Bu | H | 3-F | H | s-Bu | 3-F | 4-F | H |
| t-butyl | H | 3-F | H | t-butyl | 3-F | 4-F | H |
| n-Hex | H | 3-F | H | n-Hex | 3-F | 4-F | H |
| cyclopropyl | H | 3-F | H | cyclopropyl | 3-F | 4-F | H |
| cyclopentyl | H | 3-F | H | cyclopentyl | 3-F | 4-F | H |
| cyclohexyl | H | 3-F | H | cyclohexyl | 3-F | 4-F | H |
| 2-cyclohexenyl | H | 3-F | H | 2-cyclohexenyl | 3-F | 4-F | H |
| 3-cyclohexenyl | H | 3-F | H | 3-cyclohexenyl | 3-F | 4-F | H |
| CH-c-Pr | H | 3-F | H | CH-c-Pr | 3-F | 4-F | H |
| 4-tetrahydropyranyl | H | 3-F | H | 4-tetrahydropyranyl | 3-F | 4-F | H |
| 3-tetrahydropyranyl | H | 3-F | H | 3-tetrahydropyranyl | 3-F | 4-F | H |
| (R)-3-tetrahydropyranyl | H | 3-F | H | (R)-3-tetrahydropyranyl | 3-F | 4-F | H |
| (S)-3-tetrahydropyranyl | H | 3-F | H | (S)-3-tetrahydropyranyl | 3-F | 4-F | H |
| 3-tetrahydrofuranyl | H | 3-F | H | 3-tetrahydrofuranyl | 3-F | 4-F | H |
| (R)-3-tetrahydrofuranyl | H | 3-F | H | (R)-3-tetrahydrofuranyl | 3-F | 4-F | H |
| (S)-3-tetrahydrofuranyl | H | 3-F | H | (S)-3-tetrahydrofuranyl | 3-F | 4-F | H |
| 2-pyridinyl | H | 3-F | H | 2-pyridinyl | 3-F | 4-F | H |
| 2-pyrimidinyl | H | 3-F | H | 2-pyrimidinyl | 3-F | 4-F | H |
| 2-pyrazinyl | H | 3-F | H | 2-pyrazinyl | 3-F | 4-F | H |
| 2-thiazolyl | H | 3-F | H | 2-thiazolyl | 3-F | 4-F | H |
| 2-oxazolyl | H | 3-F | H | 2-oxazolyl | 3-F | 4-F | H |
| 2-chloro-2-propenyl | H | 3-F | H | 2-chloro-2-propenyl | 3-F | 4-F | H |
| 3,3-dichloro-2-propenyl | H | 3-F | H | 3,3-dichloro-2-propenyl | 3-F | 4-F | H |
| CH₂-2-tetrahydrofuranyl | H | 3-F | H | CH₂-2-tetrahydrofuranyl | 3-F | 4-F | H |
| CH₂-2-tetrahydropyranyl | H | 3-F | H | CH₂-2-tetrahydropyranyl | 3-F | 4-F | H |
| CH₂CH₂OH | H | 3-F | H | CH₂CH₂OH | 3-F | 4-F | H |
| CH₂OMe | H | 3-F | H | CH₂OMe | 3-F | 4-F | H |
| CH₂CH₂OMe | H | 3-F | H | CH₂CH₂OMe | 3-F | 4-F | H |
| CH₂CH₂CH₂OMe | H | 3-F | H | CH₂CH₂CH₂OMe | 3-F | 4-F | H |
| CH₂CH(Me)OMe | H | 3-F | H | CH₂CH(Me)OMe | 3-F | 4-F | H |
| CH(Me)OMe | H | 3-F | H | CH(Me)OMe | 3-F | 4-F | H |
| CH(Me)OEt | H | 3-F | H | CH(Me)OEt | 3-F | 4-F | H |
| CH(Me)CH₂OMe | H | 3-F | H | CH(Me)CH₂OMe | 3-F | 4-F | H |
| C(Me)₂CH₂OMe | H | 3-F | H | C(Me)₂CH₂OMe | 3-F | 4-F | H |
| CH(Me)CH₂CH₂OMe | H | 3-F | H | CH(Me)CH₂CH₂OMe | 3-F | 4-F | H |
| (R)—CH(Me)CH₂OMe | H | 3-F | H | (R)—CH(Me)CH₂OMe | 3-F | 4-F | H |
| (S)-CH(Me)CH₂OMe | H | 3-F | H | (S)-CH(Me)CH₂OMe | 3-F | 4-F | H |

TABLE 4-continued

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| CH(Me)CH₂OH | H | 3-F | H | CH(Me)CH₂OH | 3-F | 4-F | H |
| CH(Me)CH₂OC(=O)Me | H | 3-F | H | CH(Me)CH₂OC(=O)Me | 3-F | 4-F | H |
| CH(Me)CH(OMe)₂ | H | 3-F | H | CH(Me)CH(OMe)₂ | 3-F | 4-F | H |
| CH₂-2-dioxolanyl | H | 3-F | H | CH₂-2-dioxolanyl | 3-F | 4-F | H |
| CH₂CH₂OCF₃ | H | 3-F | H | CH₂CH₂OCF₃ | 3-F | 4-F | H |
| CH₂CH(Me)SMe | H | 3-F | H | CH₂CH(Me)SMe | 3-F | 4-F | H |
| CH₂-2-thienyl | H | 3-F | H | CH₂-2-thienyl | 3-F | 4-F | H |
| CH₂-2-pyridinyl | H | 3-F | H | CH₂-2-pyridinyl | 3-F | 4-F | H |
| CH₂-3-pyridinyl | H | 3-F | H | CH₂-3-pyridinyl | 3-F | 4-F | H |
| NH₂ | H | 3-F | H | NH₂ | 3-F | 4-F | H |
| NHCH₃ | H | 3-F | H | NHCH₃ | 3-F | 4-F | H |
| NHCH₂CF₃ | H | 3-F | H | NHCH₂CF₃ | 3-F | 4-F | H |
| NHCH₂CH₃ | H | 3-F | H | NHCH₂CH₃ | 3-F | 4-F | H |
| NHCH(Me)CH₃ | H | 3-F | H | NHCH(Me)CH₃ | 3-F | 4-F | H |
| NHCH₂CH(Me)₂ | H | 3-F | H | NHCH₂CH(Me)₂ | 3-F | 4-F | H |
| NHC(Me)₃ | H | 3-F | H | NHC(Me)₃ | 3-F | 4-F | H |
| N(CH₃)₂ | H | 3-F | H | N(CH₃)₂ | 3-F | 4-F | H |
| N(CH₃)CH₂CH₃ | H | 3-F | H | N(CH₃)CH₂CH₃ | 3-F | 4-F | H |
| N(CH₂CH₃)CH₂CH₃ | H | 3-F | H | N(CH₂CH₃)CH₂CH₃ | 3-F | 4-F | H |
| Me | 3-CN | 5-F | H | Me | H | 3-Cl | H |
| Et | 3-CN | 5-F | H | Et | H | 3-Cl | H |
| i-Pr | 3-CN | 5-F | H | i-Pr | H | 3-Cl | H |
| n-Pr | 3-CN | 5-F | H | n-Pr | H | 3-Cl | H |
| i-Bu | 3-CN | 5-F | H | i-Bu | H | 3-Cl | H |
| n-Bu | 3-CN | 5-F | H | n-Bu | H | 3-Cl | H |
| s-Bu | 3-CN | 5-F | H | s-Bu | H | 3-Cl | H |
| t-butyl | 3-CN | 5-F | H | t-butyl | H | 3-Cl | H |
| n-Hex | 3-CN | 5-F | H | n-Hex | H | 3-Cl | H |
| cyclopropyl | 3-CN | 5-F | H | cyclopropyl | H | 3-Cl | H |
| cyclopentyl | 3-CN | 5-F | H | cyclopentyl | H | 3-Cl | H |
| cyclohexyl | 3-CN | 5-F | H | cyclohexyl | H | 3-Cl | H |
| 2-cyclohexenyl | 3-CN | 5-F | H | 2-cyclohexenyl | H | 3-Cl | H |
| 3-cyclohexenyl | 3-CN | 5-F | H | 3-cyclohexenyl | H | 3-Cl | H |
| CH-c-Pr | 3-CN | 5-F | H | CH-c-Pr | H | 3-Cl | H |
| 4-tetrahydropyranyl | 3-CN | 5-F | H | 4-tetrahydropyranyl | H | 3-Cl | H |
| 3-tetrahydropyranyl | 3-CN | 5-F | H | 3-tetrahydropyranyl | H | 3-Cl | H |
| (R)-3-tetrahydropyranyl | 3-CN | 5-F | H | (R)-3-tetrahydropyranyl | H | 3-Cl | H |
| (S)-3-tetrahydropyranyl | 3-CN | 5-F | H | (S)-3-tetrahydropyranyl | H | 3-Cl | H |
| 3-tetrahydrofuranyl | 3-CN | 5-F | H | 3-tetrahydrofuranyl | H | 3-Cl | H |
| (R)-3-tetrahydrofuranyl | 3-CN | 5-F | H | (R)-3-tetrahydrofuranyl | H | 3-Cl | H |
| (S)-3-tetrahydrofuranyl | 3-CN | 5-F | H | (S)-3-tetrahydrofuranyl | H | 3-Cl | H |
| 2-pyridinyl | 3-CN | 5-F | H | 2-pyridinyl | H | 3-Cl | H |
| 2-pyrimidinyl | 3-CN | 5-F | H | 2-pyrimidinyl | H | 3-Cl | H |
| 2-pyrazinyl | 3-CN | 5-F | H | 2-pyrazinyl | H | 3-Cl | H |
| 2-thiazolyl | 3-CN | 5-F | H | 2-thiazolyl | H | 3-Cl | H |
| 2-oxazolyl | 3-CN | 5-F | H | 2-oxazolyl | H | 3-Cl | H |
| 2-chloro-2-propenyl | 3-CN | 5-F | H | 2-chloro-2-propenyl | H | 3-Cl | H |
| 3,3-dichloro-2-propenyl | 3-CN | 5-F | H | 3,3-dichloro-2-propenyl | H | 3-Cl | H |
| CH₂-2-tetrahydrofuranyl | 3-CN | 5-F | H | CH₂-2-tetrahydrofuranyl | H | 3-Cl | H |
| CH₂-2-tetrahydropyranyl | 3-CN | 5-F | H | CH₂-2-tetrahydropyranyl | H | 3-Cl | H |
| CH₂CH₂OH | 3-CN | 5-F | H | CH₂CH₂OH | H | 3-Cl | H |
| CH₂OMe | 3-CN | 5-F | H | CH₂OMe | H | 3-Cl | H |
| CH₂CH₂OMe | 3-CN | 5-F | H | CH₂CH₂OMe | H | 3-Cl | H |
| CH₂CH₂CH₂OMe | 3-CN | 5-F | H | CH₂CH₂CH₂OMe | H | 3-Cl | H |
| CH₂CH(Me)OMe | 3-CN | 5-F | H | CH₂CH(Me)OMe | H | 3-Cl | H |
| CH(Me)OMe | 3-CN | 5-F | H | CH(Me)OMe | H | 3-Cl | H |
| CH(Me)OEt | 3-CN | 5-F | H | CH(Me)OEt | H | 3-Cl | H |
| CH(Me)CH₂OMe | 3-CN | 5-F | H | CH(Me)CH₂OMe | H | 3-Cl | H |
| C(Me)₂CH₂OMe | 3-CN | 5-F | H | C(Me)₂CH₂OMe | H | 3-Cl | H |
| CH(Me)CH₂OMe | 3-CN | 5-F | H | CH(Me)CH₂OMe | H | 3-Cl | H |
| (R)—CH(Me)CH₂OMe | 3-CN | 5-F | H | (R)—CH(Me)CH₂OMe | H | 3-Cl | H |
| (S)-CH(Me)CH₂OMe | 3-CN | 5-F | H | (S)-CH(Me)CH₂OMe | H | 3-Cl | H |
| CH(Me)CH₂OH | 3-CN | 5-F | H | CH(Me)CH₂OH | H | 3-Cl | H |
| CH(Me)CH₂OC(=O)Me | 3-CN | 5-F | H | CH(Me)CH₂OC(=O)Me | H | 3-Cl | H |
| CH(Me)CH(OMe)₂ | 3-CN | 5-F | H | CH(Me)CH(OMe)₂ | H | 3-Cl | H |

TABLE 4-continued

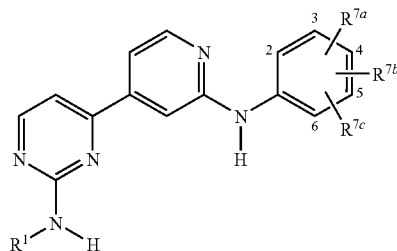

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| CH₂-2-dioxolanyl | 3-CN | 5-F | H | CH₂-2-dioxolanyl | H | 3-Cl | H |
| CH₂CH₂OCF₃ | 3-CN | 5-F | H | CH₂CH₂OCF₃ | H | 3-Cl | H |
| CH₂CH(Me)SMe | 3-CN | 5-F | H | CH₂CH(Me)SMe | H | 3-Cl | H |
| CH₂-2-thienyl | 3-CN | 5-F | H | CH₂-2-thienyl | H | 3-Cl | H |
| CH₂-2-pyridinyl | 3-CN | 5-F | H | CH₂-2-pyridinyl | H | 3-Cl | H |
| CH₂-3-pyridinyl | 3-CN | 5-F | H | CH₂-3-pyridinyl | H | 3-Cl | H |
| NH₂ | 3-CN | 5-F | H | NH₂ | H | 3-Cl | H |
| NHCH₃ | 3-CN | 5-F | H | NHCH₃ | H | 3-Cl | H |
| NHCH₂CF₃ | 3-CN | 5-F | H | NHCH₂CF₃ | H | 3-Cl | H |
| NHCH₂CH₃ | 3-CN | 5-F | H | NHCH₂CH₃ | H | 3-Cl | H |
| NHCH(Me)CH₃ | 3-CN | 5-F | H | NHCH(Me)CH₃ | H | 3-Cl | H |
| NHCH₂CH(Me)₂ | 3-CN | 5-F | H | NHCH₂CH(Me)₂ | H | 3-Cl | H |
| NHC(Me)₃ | 3-CN | 5-F | H | NHC(Me)₃ | H | 3-Cl | H |
| N(CH₃)₂ | 3-CN | 5-F | H | N(CH₃)₂ | H | 3-Cl | H |
| N(CH₃)CH₂CH₃ | 3-CN | 5-F | H | N(CH₃)CH₂CH₃ | H | 3-Cl | H |
| N(CH₂CH₃)CH₂CH₃ | 3-CN | 5-F | H | N(CH₂CH₃)CH₂CH₃ | H | 3-Cl | H |
| t-butyl | H | 3-CN | H | t-butyl | H | 3-NO₂ | H |
| cyclopropyl | H | 3-CN | H | cyclopropyl | H | 3-NO₂ | H |
| cyclohexyl | H | 3-CN | H | cyclohexyl | H | 3-NO₂ | H |
| CH-c-Pr | H | 3-CN | H | CH-c-Pr | H | 3-NO₂ | H |
| 4-tetrahydropyranyl | H | 3-CN | H | 4-tetrahydropyranyl | H | 3-NO₂ | H |
| 3-tetrahydropyranyl | H | 3-CN | H | 3-tetrahydropyranyl | H | 3-NO₂ | H |
| (R)-3-tetrahydropyranyl | H | 3-CN | H | (R)-3-tetrahydropyranyl | H | 3-NO₂ | H |
| (S)-3-tetrahydropyranyl | H | 3-CN | H | (S)-3-tetrahydropyranyl | H | 3-NO₂ | H |
| 3-tetrahydrofuranyl | H | 3-CN | H | 3-tetrahydrofuranyl | H | 3-NO₂ | H |
| (R)-3-tetrahydrofuranyl | H | 3-CN | H | (R)-3-tetrahydrofuranyl | H | 3-NO₂ | H |
| (S)-3-tetrahydrofuranyl | H | 3-CN | H | (S)-3-tetrahydrofuranyl | H | 3-NO₂ | H |
| 2-pyridinyl | H | 3-CN | H | 2-pyridinyl | H | 3-NO₂ | H |
| CH₂-2-tetrahydrofuranyl | H | 3-CN | H | CH₂-2-tetrahydrofuranyl | H | 3-NO₂ | H |
| CH₂-2-tetrahydropyranyl | H | 3-CN | H | CH₂-2-tetrahydropyranyl | H | 3-NO₂ | H |
| CH₂OMe | H | 3-CN | H | CH₂OMe | H | 3-NO₂ | H |
| CH₂CH₂OMe | H | 3-CN | H | CH₂CH₂OMe | H | 3-NO₂ | H |
| CH₂CH₂CH₂OMe | H | 3-CN | H | CH₂CH₂CH₂OMe | H | 3-NO₂ | H |
| CH₂CH(Me)OMe | H | 3-CN | H | CH₂CH(Me)OMe | H | 3-NO₂ | H |
| CH(Me)OMe | H | 3-CN | H | CH(Me)OMe | H | 3-NO₂ | H |
| CH(Me)OEt | H | 3-CN | H | CH(Me)OEt | H | 3-NO₂ | H |
| CH(Me)CH₂OMe | H | 3-CN | H | CH(Me)CH₂OMe | H | 3-NO₂ | H |
| C(Me)₂CH₂OMe | H | 3-CN | H | C(Me)₂CH₂OMe | H | 3-NO₂ | H |
| CH(Me)CH₂OMe | H | 3-CN | H | CH(Me)CH₂OMe | H | 3-NO₂ | H |
| (R)—CH(Me)CH₂OMe | H | 3-CN | H | (R)—CH(Me)CH₂OMe | H | 3-NO₂ | H |
| (S)-CH(Me)CH₂OMe | H | 3-CN | H | (S)-CH(Me)CH₂OMe | H | 3-NO₂ | H |
| CH(Me)CH₂OH | H | 3-CN | H | CH(Me)CH₂OH | H | 3-NO₂ | H |
| CH(Me)CH₂OC(=O)Me | H | 3-CN | H | CH(Me)CH₂OC(=O)Me | H | 3-NO₂ | H |
| CH₂CH₂OCF₃ | H | 3-CN | H | CH₂CH₂OCF₃ | H | 3-NO₂ | H |
| NH₂ | H | 3-CN | H | NH₂ | H | 3-NO₂ | H |
| NHCH₃ | H | 3-CN | H | NHCH₃ | H | 3-NO₂ | H |
| NHCH₂CF₃ | H | 3-CN | H | NHCH₂CF₃ | H | 3-NO₂ | H |
| NHCH₂CH₃ | H | 3-CN | H | NHCH₂CH₃ | H | 3-NO₂ | H |
| NHCH(Me)CH₃ | H | 3-CN | H | NHCH(Me)CH₃ | H | 3-NO₂ | H |
| NHC(Me)₃ | H | 3-CN | H | NHC(Me)₃ | H | 3-NO₂ | H |
| N(CH₃)₂ | H | 3-CN | H | N(CH₃)₂ | H | 3-NO₂ | H |
| t-butyl | H | 3-Br | H | t-butyl | H | 3-Me | H |
| cyclopropyl | H | 3-Br | H | cyclopropyl | H | 3-Me | H |
| cyclohexyl | H | 3-Br | H | cyclohexyl | H | 3-Me | H |
| CH-c-Pr | H | 3-Br | H | CH-c-Pr | H | 3-Me | H |
| 4-tetrahydropyranyl | H | 3-Br | H | 4-tetrahydropyranyl | H | 3-Me | H |
| 3-tetrahydropyranyl | H | 3-Br | H | 3-tetrahydropyranyl | H | 3-Me | H |
| (R)-3-tetrahydropyranyl | H | 3-Br | H | (R)-3-tetrahydropyranyl | H | 3-Me | H |
| (S)-3-tetrahydropyranyl | H | 3-Br | H | (S)-3-tetrahydropyranyl | H | 3-Me | H |
| 3-tetrahydrofuranyl | H | 3-Br | H | 3-tetrahydrofuranyl | H | 3-Me | H |
| (R)-3-tetrahydrofuranyl | H | 3-Br | H | (R)-3-tetrahydrofuranyl | H | 3-Me | H |
| (S)-3-tetrahydrofuranyl | H | 3-Br | H | (S)-3-tetrahydrofuranyl | H | 3-Me | H |
| 2-pyridinyl | H | 3-Br | H | 2-pyridinyl | H | 3-Me | H |
| CH₂-2-tetrahydrofuranyl | H | 3-Br | H | CH₂-2-tetrahydrofuranyl | H | 3-Me | H |
| CH₂-2-tetrahydropyranyl | H | 3-Br | H | CH₂-2-tetrahydropyranyl | H | 3-Me | H |

TABLE 4-continued

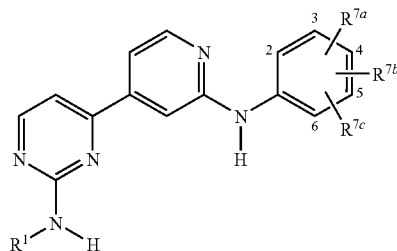

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| CH₂OMe | H | 3-Br | H | CH₂OMe | H | 3-Me | H |
| CH₂CH₂OMe | H | 3-Br | H | CH₂CH₂OMe | H | 3-Me | H |
| CH₂CH₂CH₂OMe | H | 3-Br | H | CH₂CH₂CH₂OMe | H | 3-Me | H |
| CH₂CH(Me)OMe | H | 3-Br | H | CH₂CH(Me)OMe | H | 3-Me | H |
| CH(Me)OMe | H | 3-Br | H | CH(Me)OMe | H | 3-Me | H |
| CH(Me)OEt | H | 3-Br | H | CH(Me)OEt | H | 3-Me | H |
| CH(Me)CH₂OMe | H | 3-Br | H | CH(Me)CH₂OMe | H | 3-Me | H |
| C(Me)₂CH₂OMe | H | 3-Br | H | C(Me)₂CH₂OMe | H | 3-Me | H |
| CH(Me)CH₂CH₂OMe | H | 3-Br | H | CH(Me)CH₂CH₂OMe | H | 3-Me | H |
| (R)—CH(Me)CH₂OMe | H | 3-Br | H | (R)—CH(Me)CH₂OMe | H | 3-Me | H |
| (S)-CH(Me)CH₂OMe | H | 3-Br | H | (S)-CH(Me)CH₂OMe | H | 3-Me | H |
| CH(Me)CH₂OH | H | 3-Br | H | CH(Me)CH₂OH | H | 3-Me | H |
| CH(Me)CH₂OC(=O)Me | H | 3-Br | H | CH(Me)CH₂OC(=O)Me | H | 3-Me | H |
| CH₂CH₂OCF₃ | H | 3-Br | H | CH₂CH₂OCF₃ | H | 3-Me | H |
| NH₂ | H | 3-Br | H | NH₂ | H | 3-Me | H |
| NHCH₃ | H | 3-Br | H | NHCH₃ | H | 3-Me | H |
| NHCH₂CF₃ | H | 3-Br | H | NHCH₂CF₃ | H | 3-Me | H |
| NHCH₂CH₃ | H | 3-Br | H | NHCH₂CH₃ | H | 3-Me | H |
| NHCH(Me)CH₃ | H | 3-Br | H | NHCH(Me)CH₃ | H | 3-Me | H |
| NHC(Me)₃ | H | 3-Br | H | NHC(Me)₃ | H | 3-Me | H |
| N(CH₃)₂ | H | 3-Br | H | N(CH₃)₂ | H | 3-Me | H |
| t-butyl | H | 4-Me | H | t-butyl | 2-Cl | 6-Me | H |
| cyclopropyl | H | 4-Me | H | cyclopropyl | 2-Cl | 6-Me | H |
| cyclohexyl | H | 4-Me | H | cyclohexyl | 2-Cl | 6-Me | H |
| CH-c-Pr | H | 4-Me | H | CH-c-Pr | 2-Cl | 6-Me | H |
| 4-tetrahydropyranyl | H | 4-Me | H | 4-tetrahydropyranyl | 2-Cl | 6-Me | H |
| 3-tetrahydropyranyl | H | 4-Me | H | 3-tetrahydropyranyl | 2-Cl | 6-Me | H |
| (R)-3-tetrahydropyranyl | H | 4-Me | H | (R)-3-tetrahydropyranyl | 2-Cl | 6-Me | H |
| (S)-3-tetrahydropyranyl | H | 4-Me | H | (S)-3-tetrahydropyranyl | 2-Cl | 6-Me | H |
| 3-tetrahydrofuranyl | H | 4-Me | H | 3-tetrahydrofuranyl | 2-Cl | 6-Me | H |
| (R)-3-tetrahydrofuranyl | H | 4-Me | H | (R)-3-tetrahydrofuranyl | 2-Cl | 6-Me | H |
| (S)-3-tetrahydrofuranyl | H | 4-Me | H | (S)-3-tetrahydrofuranyl | 2-Cl | 6-Me | H |
| 2-pyridinyl | H | 4-Me | H | 2-pyridinyl | 2-Cl | 6-Me | H |
| CH₂-2-tetrahydrofuranyl | H | 4-Me | H | CH₂-2-tetrahydrofuranyl | 2-Cl | 6-Me | H |
| CH₂-2-tetrahydropyranyl | H | 4-Me | H | CH₂-2-tetrahydropyranyl | 2-Cl | 6-Me | H |
| CH₂OMe | H | 4-Me | H | CH₂OMe | 2-Cl | 6-Me | H |
| CH₂CH₂OMe | H | 4-Me | H | CH₂CH₂OMe | 2-Cl | 6-Me | H |
| CH₂CH₂CH₂OMe | H | 4-Me | H | CH₂CH₂CH₂OMe | 2-Cl | 6-Me | H |
| CH₂CH(Me)OMe | H | 4-Me | H | CH₂CH(Me)OMe | 2-Cl | 6-Me | H |
| CH(Me)OMe | H | 4-Me | H | CH(Me)OMe | 2-Cl | 6-Me | H |
| CH(Me)OEt | H | 4-Me | H | CH(Me)OEt | 2-Cl | 6-Me | H |
| CH(Me)CH₂OMe | H | 4-Me | H | CH(Me)CH₂OMe | 2-Cl | 6-Me | H |
| C(Me)₂CH₂OMe | H | 4-Me | H | C(Me)₂CH₂OMe | 2-Cl | 6-Me | H |
| CH(Me)CH₂CH₂OMe | H | 4-Me | H | CH(Me)CH₂CH₂OMe | 2-Cl | 6-Me | H |
| (R)—CH(Me)CH₂OMe | H | 4-Me | H | (R)—CH(Me)CH₂OMe | 2-Cl | 6-Me | H |
| (S)-CH(Me)CH₂OMe | H | 4-Me | H | (S)-CH(Me)CH₂OMe | 2-Cl | 6-Me | H |
| CH(Me)CH₂OH | H | 4-Me | H | CH(Me)CH₂OH | 2-Cl | 6-Me | H |
| CH(Me)CH₂OC(=O)Me | H | 4-Me | H | CH(Me)CH₂OC(=O)Me | 2-Cl | 6-Me | H |
| CH₂CH₂OCF₃ | H | 4-Me | H | CH₂CH₂OCF₃ | 2-Cl | 6-Me | H |
| NH₂ | H | 4-Me | H | NH₂ | 2-Cl | 6-Me | H |
| NHCH₃ | H | 4-Me | H | NHCH₃ | 2-Cl | 6-Me | H |
| NHCH₂CF₃ | H | 4-Me | H | NHCH₂CF₃ | 2-Cl | 6-Me | H |
| NHCH₂CH₃ | H | 4-Me | H | NHCH₂CH₃ | 2-Cl | 6-Me | H |
| NHCH(Me)CH₃ | H | 4-Me | H | NHCH(Me)CH₃ | 2-Cl | 6-Me | H |
| NHC(Me)₃ | H | 4-Me | H | NHC(Me)₃ | 2-Cl | 6-Me | H |
| N(CH₃)₂ | H | 4-Me | H | N(CH₃)₂ | 2-Cl | 6-Me | H |
| t-butyl | 2-CN | 6-Me | H | t-butyl | 2-Me | 6-NO₂ | H |
| cyclopropyl | 2-CN | 6-Me | H | cyclopropyl | 2-Me | 6-NO₂ | H |
| cyclohexyl | 2-CN | 6-Me | H | cyclohexyl | 2-Me | 6-NO₂ | H |
| CH-c-Pr | 2-CN | 6-Me | H | CH-c-Pr | 2-Me | 6-NO₂ | H |
| 4-tetrahydropyranyl | 2-CN | 6-Me | H | 4-tetrahydropyranyl | 2-Me | 6-NO₂ | H |
| 3-tetrahydropyranyl | 2-CN | 6-Me | H | 3-tetrahydropyranyl | 2-Me | 6-NO₂ | H |
| (R)-3-tetrahydropyranyl | 2-CN | 6-Me | H | (R)-3-tetrahydropyranyl | 2-Me | 6-NO₂ | H |
| (S)-3-tetrahydropyranyl | 2-CN | 6-Me | H | (S)-3-tetrahydropyranyl | 2-Me | 6-NO₂ | H |
| 3-tetrahydrofuranyl | 2-CN | 6-Me | H | 3-tetrahydrofuranyl | 2-Me | 6-NO₂ | H |

TABLE 4-continued

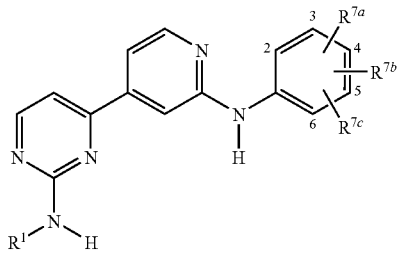

| R$^1$ | R$^{7a}$ | R$^{7b}$ | R$^{7c}$ | R$^1$ | R$^{7a}$ | R$^{7b}$ | R$^{7c}$ |
|---|---|---|---|---|---|---|---|
| (R)-3-tetrahydrofuranyl | 2-CN | 6-Me | H | (R)-3-tetrahydrofuranyl | 2-Me | 6-NO$_2$ | H |
| (S)-3-tetrahydrofuranyl | 2-CN | 6-Me | H | (S)-3-tetrahydrofuranyl | 2-Me | 6-NO$_2$ | H |
| 2-pyridinyl | 2-CN | 6-Me | H | 2-pyridinyl | 2-Me | 6-NO$_2$ | H |
| CH$_2$-2-tetrahydrofuranyl | 2-CN | 6-Me | H | CH$_2$-2-tetrahydrofuranyl | 2-Me | 6-NO$_2$ | H |
| CH$_2$-2-tetrahydropyranyl | 2-CN | 6-Me | H | CH$_2$-2-tetrahydropyranyl | 2-Me | 6-NO$_2$ | H |
| CH$_2$OMe | 2-CN | 6-Me | H | CH$_2$OMe | 2-Me | 6-NO$_2$ | H |
| CH$_2$CH$_2$OMe | 2-CN | 6-Me | H | CH$_2$CH$_2$OMe | 2-Me | 6-NO$_2$ | H |
| CH$_2$CH$_2$CH$_2$OMe | 2-CN | 6-Me | H | CH$_2$CH$_2$CH$_2$OMe | 2-Me | 6-NO$_2$ | H |
| CH$_2$CH(Me)OMe | 2-CN | 6-Me | H | CH$_2$CH(Me)OMe | 2-Me | 6-NO$_2$ | H |
| CH(Me)OMe | 2-CN | 6-Me | H | CH(Me)OMe | 2-Me | 6-NO$_2$ | H |
| CH(Me)OEt | 2-CN | 6-Me | H | CH(Me)OEt | 2-Me | 6-NO$_2$ | H |
| CH(Me)CH$_2$OMe | 2-CN | 6-Me | H | CH(Me)CH$_2$OMe | 2-Me | 6-NO$_2$ | H |
| C(Me)$_2$CH$_2$OMe | 2-CN | 6-Me | H | C(Me)$_2$CH$_2$OMe | 2-Me | 6-NO$_2$ | H |
| CH(Me)CH$_2$CH$_2$OMe | 2-CN | 6-Me | H | CH(Me)CH$_2$CH$_2$OMe | 2-Me | 6-NO$_2$ | H |
| (R)—CH(Me)CH$_2$OMe | 2-CN | 6-Me | H | (R)—CH(Me)CH$_2$OMe | 2-Me | 6-NO$_2$ | H |
| (S)-CH(Me)CH$_2$OMe | 2-CN | 6-Me | H | (S)-CH(Me)CH$_2$OMe | 2-Me | 6-NO$_2$ | H |
| CH(Me)CH$_2$OH | 2-CN | 6-Me | H | CH(Me)CH$_2$OH | 2-Me | 6-NO$_2$ | H |
| CH(Me)CH$_2$OC(=O)Me | 2-CN | 6-Me | H | CH(Me)CH$_2$OC(=O)Me | 2-Me | 6-NO$_2$ | H |
| CH$_2$CH$_2$OCF$_3$ | 2-CN | 6-Me | H | CH$_2$CH$_2$OCF$_3$ | 2-Me | 6-NO$_2$ | H |
| NH$_2$ | 2-CN | 6-Me | H | NH$_2$ | 2-Me | 6-NO$_2$ | H |
| NHCH$_3$ | 2-CN | 6-Me | H | NHCH$_3$ | 2-Me | 6-NO$_2$ | H |
| NHCH$_2$CF$_3$ | 2-CN | 6-Me | H | NHCH$_2$CF$_3$ | 2-Me | 6-NO$_2$ | H |
| NHCH$_2$CH$_3$ | 2-CN | 6-Me | H | NHCH$_2$CH$_3$ | 2-Me | 6-NO$_2$ | H |
| NHCH(Me)CH$_3$ | 2-CN | 6-Me | H | NHCH(Me)CH$_3$ | 2-Me | 6-NO$_2$ | H |
| NHC(Me)$_3$ | 2-CN | 6-Me | H | NHC(Me)$_3$ | 2-Me | 6-NO$_2$ | H |
| N(CH$_3$)$_2$ | 2-CN | 6-Me | H | N(CH$_3$)$_2$ | 2-Me | 6-NO$_2$ | H |
| t-butyl | 2-Cl | 6-F | H | t-butyl | 2-Cl | 4-Me | 6-Me |
| cyclopropyl | 2-Cl | 6-F | H | cyclopropyl | 2-Cl | 4-Me | 6-Me |
| cyclohexyl | 2-Cl | 6-F | H | cyclohexyl | 2-Cl | 4-Me | 6-Me |
| CH-c-Pr | 2-Cl | 6-F | H | CH-c-Pr | 2-Cl | 4-Me | 6-Me |
| 4-tetrahydropyranyl | 2-Cl | 6-F | H | 4-tetrahydropyranyl | 2-Cl | 4-Me | 6-Me |
| 3-tetrahydropyranyl | 2-Cl | 6-F | H | 3-tetrahydropyranyl | 2-Cl | 4-Me | 6-Me |
| (R)-3-tetrahydropyranyl | 2-Cl | 6-F | H | (R)-3-tetrahydropyranyl | 2-Cl | 4-Me | 6-Me |
| (S)-3-tetrahydropyranyl | 2-Cl | 6-F | H | (S)-3-tetrahydropyranyl | 2-Cl | 4-Me | 6-Me |
| 3-tetrahydrofuranyl | 2-Cl | 6-F | H | 3-tetrahydrofuranyl | 2-Cl | 4-Me | 6-Me |
| (R)-3-tetrahydrofuranyl | 2-Cl | 6-F | H | (R)-3-tetrahydrofuranyl | 2-Cl | 4-Me | 6-Me |
| (S)-3-tetrahydrofuranyl | 2-Cl | 6-F | H | (S)-3-tetrahydrofuranyl | 2-Cl | 4-Me | 6-Me |
| 2-pyridinyl | 2-Cl | 6-F | H | 2-pyridinyl | 2-Cl | 4-Me | 6-Me |
| CH$_2$-2-tetrahydrofuranyl | 2-Cl | 6-F | H | CH$_2$-2-tetrahydrofuranyl | 2-Cl | 4-Me | 6-Me |
| CH$_2$-2-tetrahydropyranyl | 2-Cl | 6-F | H | CH$_2$-2-tetrahydropyranyl | 2-Cl | 4-Me | 6-Me |
| CH$_2$OMe | 2-Cl | 6-F | H | CH$_2$OMe | 2-Cl | 4-Me | 6-Me |
| CH$_2$CH$_2$OMe | 2-Cl | 6-F | H | CH$_2$CH$_2$OMe | 2-Cl | 4-Me | 6-Me |
| CH$_2$CH$_2$CH$_2$OMe | 2-Cl | 6-F | H | CH$_2$CH$_2$CH$_2$OMe | 2-Cl | 4-Me | 6-Me |
| CH$_2$CH(Me)OMe | 2-Cl | 6-F | H | CH$_2$CH(Me)OMe | 2-Cl | 4-Me | 6-Me |
| CH(Me)OMe | 2-Cl | 6-F | H | CH(Me)OMe | 2-Cl | 4-Me | 6-Me |
| CH(Me)OEt | 2-Cl | 6-F | H | CH(Me)OEt | 2-Cl | 4-Me | 6-Me |
| CH(Me)CH$_2$OMe | 2-Cl | 6-F | H | CH(Me)CH$_2$OMe | 2-Cl | 4-Me | 6-Me |
| C(Me)$_2$CH$_2$OMe | 2-Cl | 6-F | H | C(Me)$_2$CH$_2$OMe | 2-Cl | 4-Me | 6-Me |
| CH(Me)CH$_2$CH$_2$OMe | 2-Cl | 6-F | H | CH(Me)CH$_2$CH$_2$OMe | 2-Cl | 4-Me | 6-Me |
| (R)—CH(Me)CH$_2$OMe | 2-Cl | 6-F | H | (R)—CH(Me)CH$_2$OMe | 2-Cl | 4-Me | 6-Me |
| (S)-CH(Me)CH$_2$OMe | 2-Cl | 6-F | H | (S)-CH(Me)CH$_2$OMe | 2-Cl | 4-Me | 6-Me |
| CH(Me)CH$_2$OH | 2-Cl | 6-F | H | CH(Me)CH$_2$OH | 2-Cl | 4-Me | 6-Me |
| CH(Me)CH$_2$OC(=O)Me | 2-Cl | 6-F | H | CH(Me)CH$_2$OC(=O)Me | 2-Cl | 4-Me | 6-Me |
| CH$_2$CH$_2$OCF$_3$ | 2-Cl | 6-F | H | CH$_2$CH$_2$OCF$_3$ | 2-Cl | 4-Me | 6-Me |
| NH$_2$ | 2-Cl | 6-F | H | NH$_2$ | 2-Cl | 4-Me | 6-Me |
| NHCH$_3$ | 2-Cl | 6-F | H | NHCH$_3$ | 2-Cl | 4-Me | 6-Me |
| NHCH$_2$CF$_3$ | 2-Cl | 6-F | H | NHCH$_2$CF$_3$ | 2-Cl | 4-Me | 6-Me |
| NHCH$_2$CH$_3$ | 2-Cl | 6-F | H | NHCH$_2$CH$_3$ | 2-Cl | 4-Me | 6-Me |
| NHCH(Me)CH$_3$ | 2-Cl | 6-F | H | NHCH(Me)CH$_3$ | 2-Cl | 4-Me | 6-Me |
| NHC(Me)$_3$ | 2-Cl | 6-F | H | NHC(Me)$_3$ | 2-Cl | 4-Me | 6-Me |
| N(CH$_3$)$_2$ | 2-Cl | 6-F | H | N(CH$_3$)$_2$ | 2-Cl | 4-Me | 6-Me |
| t-butyl | 2-F | 3-F | 6-F | t-butyl | 2-F | 4-Me | 6-F |
| cyclopropyl | 2-F | 3-F | 6-F | cyclopropyl | 2-F | 4-Me | 6-F |
| cyclohexyl | 2-F | 3-F | 6-F | cyclohexyl | 2-F | 4-Me | 6-F |
| CH-c-Pr | 2-F | 3-F | 6-F | CH-c-Pr | 2-F | 4-Me | 6-F |

TABLE 4-continued

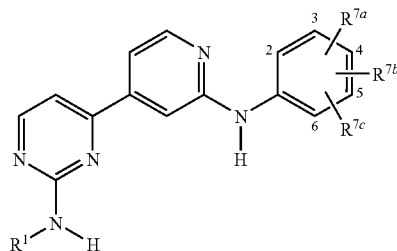

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| 4-tetrahydropyranyl | 2-F | 3-F | 6-F | 4-tetrahydropyranyl | 2-F | 4-Me | 6-F |
| 3-tetrahydropyranyl | 2-F | 3-F | 6-F | 3-tetrahydropyranyl | 2-F | 4-Me | 6-F |
| (R)-3-tetrahydropyranyl | l2-F | 3-F | 6-F | (R)-3-tetrahydropyranyl | 2-F | 4-Me | 6-F |
| (S)-3-tetrahydropyranyl | 2-F | 3-F | 6-F | (S)-3-tetrahydropyranyl | 2-F | 4-Me | 6-F |
| 3-tetrahydrofuranyl | 2-F | 3-F | 6-F | 3-tetrahydrofuranyl | 2-F | 4-Me | 6-F |
| (R)-3-tetrahydrofuranyl | 2-F | 3-F | 6-F | (R)-3-tetrahydrofuranyl | 2-F | 4-Me | 6-F |
| (S)-3-tetrahydrofuranyl | 2-F | 3-F | 6-F | (S)-3-tetrahydrofuranyl | 2-F | 4-Me | 6-F |
| 2-pyridinyl | 2-F | 3-F | 6-F | 2-pyridinyl | 2-F | 4-Me | 6-F |
| CH₂-2-tetrahydrofuranyl | 2-F | 3-F | 6-F | CH₂-2-tetrahydrofuranyl | 2-F | 4-Me | 6-F |
| CH₂-2-tetrahydropyranyl | 2-F | 3-F | 6-F | CH₂-2-tetrahydropyranyl | 2-F | 4-Me | 6-F |
| CH₂OMe | 2-F | 3-F | 6-F | CH₂OMe | 2-F | 4-Me | 6-F |
| CH₂CH₂OMe | 2-F | 3-F | 6-F | CH₂CH₂OMe | 2-F | 4-Me | 6-F |
| CH₂CH₂CH₂OMe | 2-F | 3-F | 6-F | CH₂CH₂CH₂OMe | 2-F | 4-Me | 6-F |
| CH₂CH(Me)OMe | 2-F | 3-F | 6-F | CH₂CH(Me)OMe | 2-F | 4-Me | 6-F |
| CH(Me)OMe | 2-F | 3-F | 6-F | CH(Me)OMe | 2-F | 4-Me | 6-F |
| CH(Me)OEt | 2-F | 3-F | 6-F | CH(Me)OEt | 2-F | 4-Me | 6-F |
| CH(Me)CH₂OMe | 2-F | 3-F | 6-F | CH(Me)CH₂OMe | 2-F | 4-Me | 6-F |
| C(Me)₂CH₂OMe | 2-F | 3-F | 6-F | C(Me)₂CH₂OMe | 2-F | 4-Me | 6-F |
| CH(Me)CH₂CH₂OMe | 2-F | 3-F | 6-F | CH(Me)CH₂CH₂OMe | 2-F | 4-Me | 6-F |
| (R)—CH(Me)CH₂OMe | 2-F | 3-F | 6-F | (R)—CH(Me)CH₂OMe | 2-F | 4-Me | 6-F |
| (S)-CH(Me)CH₂OMe | 2-F | 3-F | 6-F | (S)-CH(Me)CH₂OMe | 2-F | 4-Me | 6-F |
| CH(Me)CH₂OH | 2-F | 3-F | 6-F | CH(Me)CH₂OH | 2-F | 4-Me | 6-F |
| CH(Me)CH₂OC(=O)Me | 2-F | 3-F | 6-F | CH(Me)CH₂OC(=O)Me | 2-F | 4-Me | 6-F |
| CH₂CH₂OCF₃ | 2-F | 3-F | 6-F | CH₂CH₂OCF₃ | 2-F | 4-Me | 6-F |
| NH₂ | 2-F | 3-F | 6-F | NH₂ | 2-F | 4-Me | 6-F |
| NHCH₃ | 2-F | 3-F | 6-F | NHCH₃ | 2-F | 4-Me | 6-F |
| NHCH₂CF₃ | 2-F | 3-F | 6-F | NHCH₂CF₃ | 2-F | 4-Me | 6-F |
| NHCH₂CH₃ | 2-F | 3-F | 6-F | NHCH₂CH₃ | 2-F | 4-Me | 6-F |
| NHCH(Me)CH₃ | 2-F | 3-F | 6-F | NHCH(Me)CH₃ | 2-F | 4-Me | 6-F |
| NHC(Me)₃ | 2-F | 3-F | 6-F | NHC(Me)₃ | 2-F | 4-Me | 6-F |
| N(CH₃)₂ | 2-F | 3-F | 6-F | N(CH₃)₂ | 2-F | 4-Me | 6-F |
| t-butyl | 2-Me | 5-Cl | 6-Me | t-butyl | 2-Cl | 4-Cl | 6-Me |
| cyclopropyl | 2-Me | 5-Cl | 6-Me | cyclopropyl | 2-Cl | 4-Cl | 6-Me |
| cyclohexyl | 2-Me | 5-Cl | 6-Me | cyclohexyl | 2-Cl | 4-Cl | 6-Me |
| CH-c-Pr | 2-Me | 5-Cl | 6-Me | CH-c-Pr | 2-Cl | 4-Cl | 6-Me |
| 4-tetrahydropyranyl | 2-Me | 5-Cl | 6-Me | 4-tetrahydropyranyl | 2-Cl | 4-Cl | 6-Me |
| 3-tetrahydropyranyl | 2-Me | 5-Cl | 6-Me | 3-tetrahydropyranyl | 2-Cl | 4-Cl | 6-Me |
| (R)-3-tetrahydropyranyl | 2-Me | 5-Cl | 6-Me | (R)-3-tetrahydropyranyl | 2-Cl | 4-Cl | 6-Me |
| (S)-3-tetrahydropyranyl | 2-Me | 5-Cl | 6-Me | (S)-3-tetrahydropyranyl | 2-Cl | 4-Cl | 6-Me |
| 3-tetrahydrofuranyl | 2-Me | 5-Cl | 6-Me | 3-tetrahydrofuranyl | 2-Cl | 4-Cl | 6-Me |
| (R)-3-tetrahydrofuranyl | 2-Me | 5-Cl | 6-Me | (R)-3-tetrahydrofuranyl | 2-Cl | 4-Cl | 6-Me |
| (S)-3-tetrahydrofuranyl | 2-Me | 5-Cl | 6-Me | (S)-3-tetrahydrofuranyl | 2-Cl | 4-Cl | 6-Me |
| 2-pyridinyl | 2-Me | 5-Cl | 6-Me | 2-pyridinyl | 2-Cl | 4-Cl | 6-Me |
| CH₂-2-tetrahydrofuranyl | 2-Me | 5-Cl | 6-Me | CH₂-2-tetrahydrofuranyl | 2-Cl | 4-Cl | 6-Me |
| CH₂-2-tetrahydropyranyl | 2-Me | 5-Cl | 6-Me | CH₂-2-tetrahydropyranyl | 2-Cl | 4-Cl | 6-Me |
| CH₂OMe | 2-Me | 5-Cl | 6-Me | CH₂OMe | 2-Cl | 4-Cl | 6-Me |
| CH₂CH₂OMe | 2-Me | 5-Cl | 6-Me | CH₂CH₂OMe | 2-Cl | 4-Cl | 6-Me |
| CH₂CH₂CH₂OMe | 2-Me | 5-Cl | 6-Me | CH₂CH₂CH₂OMe | 2-Cl | 4-Cl | 6-Me |
| CH₂CH(Me)OMe | 2-Me | 5-Cl | 6-Me | CH₂CH(Me)OMe | 2-Cl | 4-Cl | 6-Me |
| CH(Me)OMe | 2-Me | 5-Cl | 6-Me | CH(Me)OMe | 2-Cl | 4-Cl | 6-Me |
| CH(Me)OEt | 2-Me | 5-Cl | 6-Me | CH(Me)OEt | 2-Cl | 4-Cl | 6-Me |
| CH(Me)CH₂OMe | 2-Me | 5-Cl | 6-Me | CH(Me)CH₂OMe | 2-Cl | 4-Cl | 6-Me |
| C(Me)₂CH₂OMe | 2-Me | 5-Cl | 6-Me | C(Me)₂CH₂OMe | 2-Cl | 4-Cl | 6-Me |
| CH(Me)CH₂CH₂OMe | 2-Me | 5-Cl | 6-Me | CH(Me)CH₂CH₂OMe | 2-Cl | 4-Cl | 6-Me |
| (R)—CH(Me)CH₂OMe | 2-Me | 5-Cl | 6-Me | (R)—CH(Me)CH₂OMe | 2-Cl | 4-Cl | 6-Me |
| (S)-CH(Me)CH₂OMe | 2-Me | 5-Cl | 6-Me | (S)-CH(Me)CH₂OMe | 2-Cl | 4-Cl | 6-Me |
| CH(Me)CH₂OH | 2-Me | 5-Cl | 6-Me | CH(Me)CH₂OH | 2-Cl | 4-Cl | 6-Me |
| CH(Me)CH₂OC(=O)Me | 2-Me | 5-Cl | 6-Me | CH(Me)CH₂OC(=O)Me | 2-Cl | 4-Cl | 6-Me |
| CH₂CH₂OCF₃ | 2-Me | 5-Cl | 6-Me | CH₂CH₂OCF₃ | 2-Cl | 4-Cl | 6-Me |
| NH₂ | 2-Me | 5-Cl | 6-Me | NH₂ | 2-Cl | 4-Cl | 6-Me |
| NHCH₃ | 2-Me | 5-Cl | 6-Me | NHCH₃ | 2-Cl | 4-Cl | 6-Me |
| NHCH₂CF₃ | 2-Me | 5-Cl | 6-Me | NHCH₂CF₃ | 2-Cl | 4-Cl | 6-Me |
| NHCH₂CH₃ | 2-Me | 5-Cl | 6-Me | NHCH₂CH₃ | 2-Cl | 4-Cl | 6-Me |
| NHCH(Me)CH₃ | 2-Me | 5-Cl | 6-Me | NHCH(Me)CH₃ | 2-Cl | 4-Cl | 6-Me |
| NHC(Me)₃ | 2-Me | 5-Cl | 6-Me | NHC(Me)₃ | 2-Cl | 4-Cl | 6-Me |

TABLE 4-continued

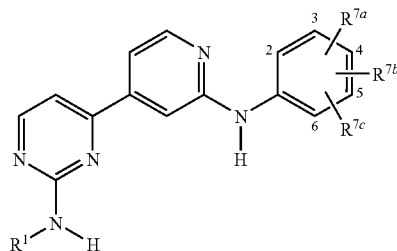

| R¹ | R⁷ᵃ | R⁷ᵇ | R⁷ᶜ | R¹ | R⁷ᵃ | R⁷ᵇ | R⁷ᶜ |
|---|---|---|---|---|---|---|---|
| N(CH₃)₂ | 2-Me | 5-Cl | 6-Me | N(CH₃)₂ | 2-Cl | 4-Cl | 6-Me |
| t-butyl | H | H | H | t-butyl | 2-Cl | 4-Cl | 6-Cl |
| cyclopropyl | H | H | H | cyclopropyl | 2-Cl | 4-Cl | 6-Cl |
| cyclohexyl | H | H | H | cyclohexyl | 2-Cl | 4-Cl | 6-Cl |
| CH-c-Pr | H | H | H | CH-c-Pr | 2-Cl | 4-Cl | 6-Cl |
| 4-tetrahydropyranyl | H | H | H | 4-tetrahydropyranyl | 2-Cl | 4-Cl | 6-Cl |
| 3-tetrahydropyranyl | H | H | H | 3-tetrahydropyranyl | 2-Cl | 4-Cl | 6-Cl |
| (R)-3-tetrahydropyranyl | H | H | H | (R)-3-tetrahydropyranyl | 2-Cl | 4-Cl | 6-Cl |
| (S)-3-tetrahydropyranyl | H | H | H | (S)-3-tetrahydropyranyl | 2-Cl | 4-Cl | 6-Cl |
| 3-tetrahydrofuranyl | H | H | H | 3-tetrahydrofuranyl | 2-Cl | 4-Cl | 6-Cl |
| (R)-3-tetrahydrofuranyl | H | H | H | (R)-3-tetrahydrofuranyl | 2-Cl | 4-Cl | 6-Cl |
| (S)-3-tetrahydrofuranyl | H | H | H | (S)-3-tetrahydrofuranyl | 2-Cl | 4-Cl | 6-Cl |
| 2-pyridinyl | H | H | H | 2-pyridinyl | 2-Cl | 4-Cl | 6-Cl |
| CH₂-2-tetrahydrofuranyl | H | H | H | CH₂-2-tetrahydrofuranyl | 2-Cl | 4-Cl | 6-Cl |
| CH₂-2-tetrahydropyranyl | H | H | H | CH₂-2-tetrahydropyranyl | 2-Cl | 4-Cl | 6-Cl |
| CH₂OMe | H | H | H | CH₂OMe | 2-Cl | 4-Cl | 6-Cl |
| CH₂CH₂OMe | H | H | H | CH₂CH₂OMe | 2-Cl | 4-Cl | 6-Cl |
| CH₂CH₂CH₂OMe | H | H | H | CH₂CH₂CH₂OMe | 2-Cl | 4-Cl | 6-Cl |
| CH₂CH(Me)OMe | H | H | H | CH₂CH(Me)OMe | 2-Cl | 4-Cl | 6-Cl |
| CH(Me)OMe | H | H | H | CH(Me)OMe | 2-Cl | 4-Cl | 6-Cl |
| CH(Me)OEt | H | H | H | CH(Me)OEt | 2-Cl | 4-Cl | 6-Cl |
| CH(Me)CH₂OMe | H | H | H | CH(Me)CH₂OMe | 2-Cl | 4-Cl | 6-Cl |
| C(Me)₂CH₂OMe | H | H | H | C(Me)₂CH₂OMe | 2-Cl | 4-Cl | 6-Cl |
| CH(Me)CH₂CH₂OMe | H | H | H | CH(Me)CH₂CH₂OMe | 2-Cl | 4-Cl | 6-Cl |
| (R)—CH(Me)CH₂OMe | H | H | H | (R)—CH(Me)CH₂OMe | 2-Cl | 4-Cl | 6-Cl |
| (S)-CH(Me)CH₂OMe | H | H | H | (S)-CH(Me)CH₂OMe | 2-Cl | 4-Cl | 6-Cl |
| CH(Me)CH₂OH | H | H | H | CH(Me)CH₂OH | 2-Cl | 4-Cl | 6-Cl |
| CH(Me)CH₂OC(=O)Me | H | H | H | CH(Me)CH₂OC(=O)Me | 2-Cl | 4-Cl | 6-Cl |
| CH₂CH₂OCF₃ | H | H | H | CH₂CH₂OCF₃ | 2-Cl | 4-Cl | 6-Cl |
| NH₂ | H | H | H | NH₂ | 2-Cl | 4-Cl | 6-Cl |
| NHCH₃ | H | H | H | NHCH₃ | 2-Cl | 4-Cl | 6-Cl |
| NHCH₂CF₃ | H | H | H | NHCH₂CF₃ | 2-Cl | 4-Cl | 6-Cl |
| NHCH₂CH₃ | H | H | H | NHCH₂CH₃ | 2-Cl | 4-Cl | 6-Cl |
| NHCH(Me)CH₃ | H | H | H | NHCH(Me)CH₃ | 2-Cl | 4-Cl | 6-Cl |
| NHC(Me)₃ | H | H | H | NHC(Me)₃ | 2-Cl | 4-Cl | 6-Cl |
| N(CH₃)₂ | H | H | H | N(CH₃)₂ | 2-Cl | 4-Cl | 6-Cl |

TABLE 5

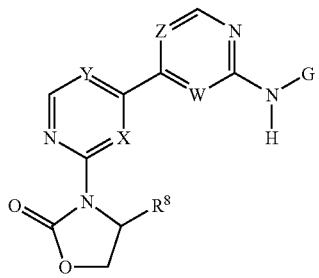

| G | R⁸ | X | Y | W | Z |
|---|---|---|---|---|---|
| 3-F—Ph | H | N | CH | N | N |
| 3-Cl—Ph | H | N | CH | N | N |
| 3,5-di-F—Ph | H | N | CH | N | N |
| 3,5-di-Cl—Ph | H | N | CH | N | N |
| 3-CN—Ph | H | N | CH | N | N |
| 3-NO₂—Ph | H | N | CH | N | N |
| 3-Cl-5-F—Ph | H | N | CH | N | N |
| 3-F-5-CN—Ph | H | N | CH | N | N |

TABLE 5-continued

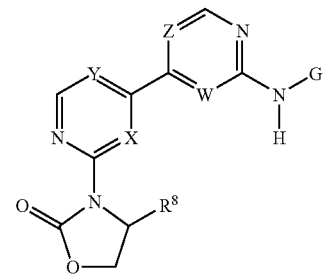

| G | R⁸ | X | Y | W | Z |
|---|---|---|---|---|---|
| 3-F-5-NO₂—Ph | H | N | CH | N | N |
| 3-Cl-5-CN—Ph | H | N | CH | N | N |
| 3-Cl-5-NO₂—Ph | H | N | CH | N | N |
| 3-F-4-Me—Ph | H | N | CH | N | N |
| 3-Cl-4-Me—Ph | H | N | CH | N | N |
| 3,4,5-tri-F—Ph | H | N | CH | N | N |
| 3-F—Ph | H | N | CH | CH | CH |
| 3-Cl—Ph | H | N | CH | CH | CH |

TABLE 5-continued

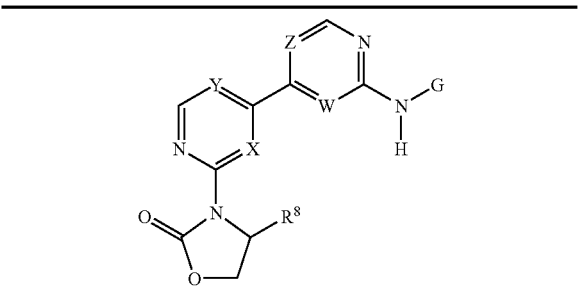

| G | R⁸ | X | Y | W | Z |
|---|---|---|---|---|---|
| 2,6-di-F—Ph | H | N | CH | CH | CH |
| 2,6-di-Cl—Ph | H | N | CH | CH | CH |
| 3-CN—Ph | H | N | CH | CH | CH |
| 3-NO₂—Ph | H | N | CH | CH | CH |
| 2-F-6-Me—Ph | H | N | CH | CH | CH |
| 2-F-6-MeO—Ph | H | N | CH | CH | CH |
| 2-Cl-6-Me—Ph | H | N | CH | CH | CH |
| 2-Cl-6-MeO—Ph | H | N | CH | CH | CH |
| 2,6-di-Cl-4-Me—Ph | H | N | CH | CH | CH |
| 2,4-di-Cl-6-Me—Ph | H | N | CH | CH | CH |
| 2,4,6-tri-Cl—Ph | H | N | CH | CH | CH |
| 3-F—Ph | H | CH | N | CH | N |
| 3-F—Ph | H | N | N | N | CH |
| 3-Cl—Ph | H | N | N | N | CH |
| 3,5-di-F—Ph | H | N | N | N | CH |
| 3,5-di-Cl—Ph | H | N | N | N | CH |
| 3-CN—Ph | H | N | N | N | CH |
| 3-NO₂—Ph | H | N | N | N | CH |
| 3-Cl-5-F—Ph | H | N | N | N | CH |
| 3-F-5-CN—Ph | H | N | N | N | CH |
| 3-F-5-NO₂—Ph | H | N | N | N | CH |
| 3-Cl-5-CN—Ph | H | N | N | N | CH |
| 3-Cl-5-NO₂—Ph | H | N | N | N | CH |
| 3-F-4-Me—Ph | H | N | N | N | CH |
| 3-Cl-4-Me—Ph | H | N | N | N | CH |
| 3,4,5-tri-F—Ph | H | N | N | N | CH |
| 3-F—Ph | H | N | CH | CH | N |
| 3-Cl—Ph | H | N | CH | CH | N |
| 2,6-di-F—Ph | H | N | CH | CH | N |
| 2,6-di-Cl—Ph | H | N | CH | CH | N |
| 3-CN—Ph | H | N | CH | CH | N |
| 3-NO₂—Ph | H | N | CH | CH | N |
| 2-F-6-Me—Ph | H | N | CH | CH | N |
| 2-F-6-MeO—Ph | H | N | CH | CH | N |
| 2-Cl-6-Me—Ph | H | N | CH | CH | N |
| 2-Cl-6-MeO—Ph | H | N | CH | CH | N |
| 2,6-di-Cl-4-Me—Ph | H | N | CH | CH | N |
| 2,4-di-Cl-6-Me—Ph | H | N | CH | CH | N |
| 2,4,6-tri-Cl—Ph | H | N | CH | CH | N |
| 3-F—Ph | Me | N | CH | N | N |
| 3-Cl—Ph | H | CH | N | CH | N |
| 2,6-di-F—Ph | H | CH | N | CH | N |
| 2,6-di-Cl—Ph | H | CH | N | CH | N |
| 3-CN—Ph | H | CH | N | CH | N |
| 3-NO₂—Ph | H | CH | N | CH | N |
| 2-F-6-Me—Ph | H | CH | N | CH | N |
| 2-F-6-MeO—Ph | H | CH | N | CH | N |
| 2-Cl-6-Me—Ph | H | CH | N | CH | N |
| 2-Cl-6-MeO—Ph | H | CH | N | CH | N |
| 2,6-di-Cl-4-Me—Ph | H | CH | N | CH | N |
| 2,4-di-Cl-6-Me—Ph | H | CH | N | CH | N |
| 2,4,6-tri-Cl—Ph | H | CH | N | CH | N |
| 3-F—Ph | Me | N | N | N | CH |
| 3-Cl—Ph | Me | N | N | N | CH |
| 3,5-di-F—Ph | Me | N | N | N | CH |
| 3,5-di-Cl—Ph | Me | N | N | N | CH |
| 3-CN—Ph | Me | N | N | N | CH |
| 3-NO₂—Ph | Me | N | N | N | CH |
| 3-F-5-CN—Ph | Me | N | N | N | CH |
| 3-F-5-NO₂—Ph | Me | N | N | N | CH |
| 3-Cl-5-CN—Ph | Me | N | N | N | CH |
| 3-Cl-5-NO₂—Ph | Me | N | N | N | CH |
| 3-F-4-Me—Ph | Me | N | N | N | CH |
| 3-Cl-4-Me—Ph | Me | N | N | N | CH |
| 3,4,5-tri-F—Ph | Me | N | N | N | CH |
| 3-F—Ph | Me | N | CH | CH | N |
| 3-Cl—Ph | Me | N | CH | CH | N |
| 2,6-di-F—Ph | Me | N | CH | CH | N |
| 2,6-di-Cl—Ph | Me | N | CH | CH | N |
| 3-CN—Ph | Me | N | CH | CH | N |
| 3-NO₂—Ph | Me | N | CH | CH | N |
| 3-Cl—Ph | Me | N | CH | N | N |
| 3,5-di-F—Ph | Me | N | CH | N | N |
| 3,5-di-Cl—Ph | Me | N | CH | N | N |
| 3-CN—Ph | Me | N | CH | N | N |
| 3-NO₂—Ph | Me | N | CH | N | N |
| 3-F-5-CN—Ph | Me | N | CH | N | N |
| 3-F-5-NO₂—Ph | Me | N | CH | N | N |
| 3-Cl-5-CN—Ph | Me | N | CH | N | N |
| 3-Cl-5-NO₂—Ph | Me | N | CH | N | N |
| 3-F-4-Me—Ph | Me | N | CH | N | N |
| 3-Cl-4-Me—Ph | Me | N | CH | N | N |
| 3,4,5-tri-F—Ph | Me | N | CH | N | N |
| 3-F—Ph | Me | N | CH | CH | CH |
| 3-Cl—Ph | Me | N | CH | CH | CH |
| 2,6-di-F—Ph | Me | N | CH | CH | CH |
| 2,6-di-Cl—Ph | Me | N | CH | CH | CH |
| 3-CN—Ph | Me | N | CH | CH | CH |
| 3-NO₂—Ph | Me | N | CH | CH | CH |
| 2-F-6-Me—Ph | Me | N | CH | CH | CH |
| 2-F-6-MeO—Ph | Me | N | CH | CH | CH |
| 2-Cl-6-Me—Ph | Me | N | CH | CH | CH |
| 2-Cl-6-MeO—Ph | Me | N | CH | CH | CH |
| 2,6-di-Cl-4-Me—Ph | Me | N | CH | CH | CH |
| 2,4-di-Cl-6-Me—Ph | Me | N | CH | CH | CH |
| 2,4,6-tri-Cl—Ph | Me | N | CH | CH | CH |
| 3-F—Ph | Me | CH | N | CH | N |
| 3-Cl—Ph | Me | CH | N | CH | N |
| 2,6-di-F—Ph | Me | CH | N | CH | N |
| 2,6-di-Cl—Ph | Me | CH | N | CH | N |
| 3-CN—Ph | Me | CH | N | CH | N |
| 3-NO₂—Ph | Me | CH | N | CH | N |
| 2-F-6-Me—Ph | Me | N | CH | CH | N |
| 2-F-6-MeO—Ph | Me | N | CH | CH | N |
| 2-Cl-6-Me—Ph | Me | N | CH | CH | N |
| 2-Cl-6-MeO—Ph | Me | N | CH | CH | N |
| 2,6-di-Cl-4-Me—Ph | Me | N | CH | CH | N |
| 2,4-di-Cl-6-Me—Ph | Me | N | CH | CH | N |
| 2,4,6-tri-Cl—Ph | Me | N | CH | CH | N |
| 2-F-6-Me—Ph | Me | CH | N | CH | N |
| 2-F-6-MeO—Ph | Me | CH | N | CH | N |
| 2-Cl-6-Me—Ph | Me | CH | N | CH | N |
| 2-Cl-6-MeO—Ph | Me | CH | N | CH | N |
| 2,6-di-Cl-4-Me—Ph | Me | CH | N | CH | N |
| 2,4-di-Cl-6-Me—Ph | Me | CH | N | CH | N |
| 2,4,6-tri-Cl—Ph | Me | CH | N | CH | N |

TABLE 6

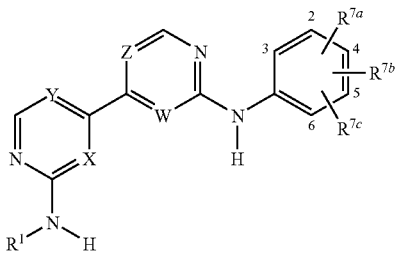

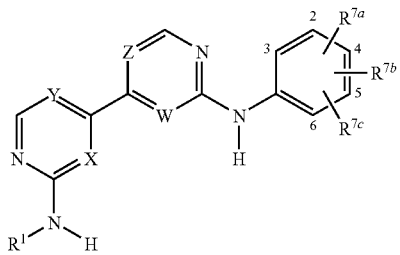

| R¹ | X | Y | W | Z | R⁷ᵃ | R⁷ᵇ | R⁷ᶜ |
|---|---|---|---|---|---|---|---|
| t-butyl | N | N | N | CH | 3-F | H | H |
| cyclopropyl | N | N | N | CH | 3-F | H | H |
| 4-tetrahydropyranyl | N | N | N | CH | 3-F | H | H |
| (R)-3-tetrahydropyranyl | N | N | N | CH | 3-F | H | H |
| (S)-3-tetrahydropyranyl | N | N | N | CH | 3-F | H | H |
| CH₂OMe | N | N | N | CH | 3-F | H | H |
| CH₂CH₂OMe | N | N | N | CH | 3-F | H | H |
| CH₂CH₂CH₂OMe | N | N | N | CH | 3-F | H | H |
| CH₂CH(Me)OMe | N | N | N | CH | 3-F | H | H |
| CH(Me)OMe | N | N | N | CH | 3-F | H | H |
| CH(Me)OEt | N | N | N | CH | 3-F | H | H |
| CH(Me)CH₂OMe | N | N | N | CH | 3-F | H | H |
| C(Me)₂CH₂OMe | N | N | N | CH | 3-F | H | H |
| CH(Me)CH₂CH₂OMe | N | N | N | CH | 3-F | H | H |
| (R)—CH(Me)CH₂OMe | N | N | N | CH | 3-F | H | H |
| (S)—CH(Me)CH₂OMe | N | N | N | CH | 3-F | H | H |
| CH(Me)CH₂OC(O)Me | N | N | N | CH | 3-F | H | H |
| CH₂CH₂OCF₃ | N | N | N | CH | 3-F | H | H |
| t-butyl | N | N | N | CH | 3-Cl | H | H |
| cyclopropyl | N | N | N | CH | 3-Cl | H | H |
| 4-tetrahydropyranyl | N | N | N | CH | 3-Cl | H | H |
| (R)-3-tetrahydropyranyl | N | N | N | CH | 3-Cl | H | H |
| (S)-3-tetrahydropyranyl | N | N | N | CH | 3-Cl | H | H |
| CH₂OMe | N | N | N | CH | 3-Cl | H | H |
| CH₂CH₂OMe | N | N | N | CH | 3-Cl | H | H |
| CH₂CH₂CH₂OMe | N | N | N | CH | 3-Cl | H | H |
| CH₂CH(Me)OMe | N | N | N | CH | 3-Cl | H | H |
| CH(Me)OMe | N | N | N | CH | 3-Cl | H | H |
| CH(Me)OEt | N | N | N | CH | 3-Cl | H | H |
| CH(Me)CH₂OMe | N | N | N | CH | 3-Cl | H | H |
| C(Me)₂CH₂OMe | N | N | N | CH | 3-Cl | H | H |
| CH(Me)CH₂CH₂OMe | N | N | N | CH | 3-Cl | H | H |
| (R)—CH(Me)CH₂OMe | N | N | N | CH | 3-Cl | H | H |
| (S)—CH(Me)CH₂OMe | N | N | N | CH | 3-Cl | H | H |
| CH(Me)CH₂OC(O)Me | N | N | N | CH | 3-Cl | H | H |
| CH₂CH₂OCF₃ | N | N | N | CH | 3-Cl | H | H |
| t-butyl | N | N | N | CH | 3-CN | H | H |
| cyclopropyl | N | N | N | CH | 3-CN | H | H |
| 4-tetrahydropyranyl | N | N | N | CH | 3-CN | H | H |
| (R)-3-tetrahydropyranyl | N | N | N | CH | 3-CN | H | H |
| (S)-3-tetrahydropyranyl | N | N | N | CH | 3-CN | H | H |
| CH₂OMe | N | N | N | CH | 3-CN | H | H |
| CH₂CH₂OMe | N | N | N | CH | 3-CN | H | H |
| CH₂CH₂CH₂OMe | N | N | N | CH | 3-CN | H | H |
| CH₂CH(Me)OMe | N | N | N | CH | 3-CN | H | H |
| CH(Me)OMe | N | N | N | CH | 3-CN | H | H |
| CH(Me)OEt | N | N | N | CH | 3-CN | H | H |
| CH(Me)CH₂OMe | N | N | N | CH | 3-CN | H | H |
| C(Me)₂CH₂OMe | N | N | N | CH | 3-CN | H | H |
| CH(Me)CH₂CH₂OMe | N | N | N | CH | 3-CN | H | H |
| (R)—CH(Me)CH₂OMe | N | N | N | CH | 3-CN | H | H |
| (S)—CH(Me)CH₂OMe | N | N | N | CH | 3-CN | H | H |
| CH(Me)CH₂OC(O)Me | N | N | N | CH | 3-CN | H | H |
| CH₂CH₂OCF₃ | N | N | N | CH | 3-CN | H | H |
| t-butyl | N | N | N | CH | 3-CN | 5-F | H |
| cyclopropyl | N | N | N | CH | 3-CN | 5-F | H |
| 4-tetrahydropyranyl | N | N | N | CH | 3-CN | 5-F | H |
| (R)-3-tetrahydropyranyl | N | N | N | CH | 3-CN | 5-F | H |
| (S)-3-tetrahydropyranyl | N | N | N | CH | 3-CN | 5-F | H |
| CH₂OMe | N | N | N | CH | 3-CN | 5-F | H |
| CH₂CH₂OMe | N | N | N | CH | 3-CN | 5-F | H |
| CH₂CH₂CH₂OMe | N | N | N | CH | 3-CN | 5-F | H |
| CH₂CH(Me)OMe | N | N | N | CH | 3-CN | 5-F | H |
| CH(Me)OMe | N | N | N | CH | 3-CN | 5-F | H |
| CH(Me)OEt | N | N | N | CH | 3-CN | 5-F | H |
| CH(Me)CH₂OMe | N | N | N | CH | 3-CN | 5-F | H |
| C(Me)₂CH₂OMe | N | N | N | CH | 3-CN | 5-F | H |
| CH(Me)CH₂CH₂OMe | N | N | N | CH | 3-CN | 5-F | H |
| (R)—CH(Me)CH₂OMe | N | N | N | CH | 3-CN | 5-F | H |
| (S)—CH(Me)CH₂OMe | N | N | N | CH | 3-CN | 5-F | H |
| CH(Me)CH₂OC(O)Me | N | N | N | CH | 3-CN | 5-F | H |
| CH₂CH₂OCF₃ | N | N | N | CH | 3-CN | 5-F | H |
| t-butyl | N | N | N | CH | 3-F | 5-F | H |
| cyclopropyl | N | N | N | CH | 3-F | 5-F | H |
| 4-tetrahydropyranyl | N | N | N | CH | 3-F | 5-F | H |
| (R)-3-tetrahydropyranyl | N | N | N | CH | 3-F | 5-F | H |
| (S)-3-tetrahydropyranyl | N | N | N | CH | 3-F | 5-F | H |
| CH₂OMe | N | N | N | CH | 3-F | 5-F | H |
| CH₂CH₂OMe | N | N | N | CH | 3-F | 5-F | H |
| CH₂CH₂CH₂OMe | N | N | N | CH | 3-F | 5-F | H |
| CH₂CH(Me)OMe | N | N | N | CH | 3-F | 5-F | H |
| CH(Me)OMe | N | N | N | CH | 3-F | 5-F | H |
| CH(Me)OEt | N | N | N | CH | 3-F | 5-F | H |
| CH(Me)CH₂OMe | N | N | N | CH | 3-F | 5-F | H |
| C(Me)₂CH₂OMe | N | N | N | CH | 3-F | 5-F | H |
| CH(Me)CH₂CH₂OMe | N | N | N | CH | 3-F | 5-F | H |
| (R)—CH(Me)CH₂OMe | N | N | N | CH | 3-F | 5-F | H |
| (S)—CH(Me)CH₂OMe | N | N | N | CH | 3-F | 5-F | H |
| CH(Me)CH₂OC(O)Me | N | N | N | CH | 3-F | 5-F | H |
| CH₂CH₂OCF₃ | N | N | N | CH | 3-F | 5-F | H |
| t-butyl | N | N | N | CH | 3-Cl | 5-F | H |
| cyclopropyl | N | N | N | CH | 3-Cl | 5-F | H |
| 4-tetrahydropyranyl | N | N | N | CH | 3-Cl | 5-F | H |
| (R)-3-tetrahydropyranyl | N | N | N | CH | 3-Cl | 5-F | H |
| (S)-3-tetrahydropyranyl | N | N | N | CH | 3-Cl | 5-F | H |
| CH₂OMe | N | N | N | CH | 3-Cl | 5-F | H |
| CH₂CH₂OMe | N | N | N | CH | 3-Cl | 5-F | H |
| CH₂CH₂CH₂OMe | N | N | N | CH | 3-Cl | 5-F | H |
| CH₂CH(Me)OMe | N | N | N | CH | 3-Cl | 5-F | H |
| CH(Me)OMe | N | N | N | CH | 3-Cl | 5-F | H |
| CH(Me)OEt | N | N | N | CH | 3-Cl | 5-F | H |
| CH(Me)CH₂OMe | N | N | N | CH | 3-Cl | 5-F | H |
| C(Me)₂CH₂OMe | N | N | N | CH | 3-Cl | 5-F | H |
| CH(Me)CH₂CH₂OMe | N | N | N | CH | 3-Cl | 5-F | H |
| (R)—CH(Me)CH₂OMe | N | N | N | CH | 3-Cl | 5-F | H |
| (S)—CH(Me)CH₂OMe | N | N | N | CH | 3-Cl | 5-F | H |
| CH(Me)CH₂OC(O)Me | N | N | N | CH | 3-Cl | 5-F | H |
| CH₂CH₂OCF₃ | N | N | N | CH | 3-Cl | 5-F | H |
| t-butyl | N | N | N | CH | 3-Cl | 5-Cl | H |
| cyclopropyl | N | N | N | CH | 3-Cl | 5-Cl | H |
| 4-tetrahydropyranyl | N | N | N | CH | 3-Cl | 5-Cl | H |
| (R)-3-tetrahydropyranyl | N | N | N | CH | 3-Cl | 5-Cl | H |
| (S)-3-tetrahydropyranyl | N | N | N | CH | 3-Cl | 5-Cl | H |
| CH₂OMe | N | N | N | CH | 3-Cl | 5-Cl | H |
| CH₂CH₂OMe | N | N | N | CH | 3-Cl | 5-Cl | H |
| CH₂CH₂CH₂OMe | N | N | N | CH | 3-Cl | 5-Cl | H |
| CH₂CH(Me)OMe | N | N | N | CH | 3-Cl | 5-Cl | H |
| CH(Me)OMe | N | N | N | CH | 3-Cl | 5-Cl | H |
| CH(Me)OEt | N | N | N | CH | 3-Cl | 5-Cl | H |
| CH(Me)CH₂OMe | N | N | N | CH | 3-Cl | 5-Cl | H |
| C(Me)₂CH₂OMe | N | N | N | CH | 3-Cl | 5-Cl | H |
| CH(Me)CH₂CH₂OMe | N | N | N | CH | 3-Cl | 5-Cl | H |
| (R)—CH(Me)CH₂OMe | N | N | N | CH | 3-Cl | 5-Cl | H |
| (S)—CH(Me)CH₂OMe | N | N | N | CH | 3-Cl | 5-Cl | H |
| CH(Me)CH₂OC(O)Me | N | N | N | CH | 3-Cl | 5-Cl | H |
| CH₂CH₂OCF₃ | N | N | N | CH | 3-Cl | 5-Cl | H |
| t-butyl | N | CH | CH | N | 3-F | H | H |
| cyclopropyl | N | CH | CH | N | 3-F | H | H |
| 4-tetrahydropyranyl | N | CH | CH | N | 3-F | H | H |
| (R)-3-tetrahydropyranyl | N | CH | CH | N | 3-F | H | H |

TABLE 6-continued

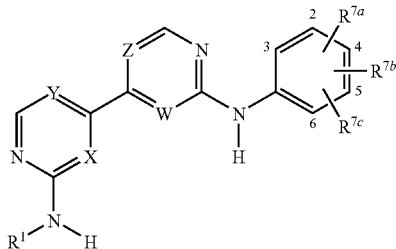

| R¹ | X | Y | W | Z | R⁷ᵃ | R⁷ᵇ | R⁷ᶜ |
|---|---|---|---|---|---|---|---|
| (S)-3-tetrahydropyranyl | N | CH | CH | N | 3-F | H | H |
| CH₂OMe | N | CH | CH | N | 3-F | H | H |
| CH₂CH₂OMe | N | CH | CH | N | 3-F | H | H |
| CH₂CH₂CH₂OMe | N | CH | CH | N | 3-F | H | H |
| CH₂CH(Me)OMe | N | CH | CH | N | 3-F | H | H |
| CH(Me)OMe | N | CH | CH | N | 3-F | H | H |
| CH(Me)OEt | N | CH | CH | N | 3-F | H | H |
| CH(Me)CH₂OMe | N | CH | CH | N | 3-F | H | H |
| C(Me)₂CH₂OMe | N | CH | CH | N | 3-F | H | H |
| CH(Me)CH₂CH₂OMe | N | CH | CH | N | 3-F | H | H |
| (R)—CH(Me)CH₂OMe | N | CH | CH | N | 3-F | H | H |
| (S)—CH(Me)CH₂OMe | N | CH | CH | N | 3-F | H | H |
| CH(Me)CH₂OC(O)Me | N | CH | CH | N | 3-F | H | H |
| CH₂CH₂OCF₃ | N | CH | CH | N | 3-F | H | H |
| t-butyl | N | CH | CH | N | 3-Cl | H | H |
| cyclopropyl | N | CH | CH | N | 3-Cl | H | H |
| 4-tetrahydropyranyl | N | CH | CH | N | 3-Cl | H | H |
| (R)-3-tetrahydropyranyl | N | CH | CH | N | 3-Cl | H | H |
| (S)-3-tetrahydropyranyl | N | CH | CH | N | 3-Cl | H | H |
| CH₂OMe | N | CH | CH | N | 3-Cl | H | H |
| CH₂CH₂OMe | N | CH | CH | N | 3-Cl | H | H |
| CH₂CH₂CH₂OMe | N | CH | CH | N | 3-Cl | H | H |
| CH₂CH(Me)OMe | N | CH | CH | N | 3-Cl | H | H |
| CH(Me)OMe | N | CH | CH | N | 3-Cl | H | H |
| CH(Me)OEt | N | CH | CH | N | 3-Cl | H | H |
| CH(Me)CH₂OMe | N | CH | CH | N | 3-Cl | H | H |
| C(Me)₂CH₂OMe | N | CH | CH | N | 3-Cl | H | H |
| CH(Me)CH₂CH₂OMe | N | CH | CH | N | 3-Cl | H | H |
| (R)—CH(Me)CH₂OMe | N | CH | CH | N | 3-Cl | H | H |
| (S)—CH(Me)CH₂OMe | N | CH | CH | N | 3-Cl | H | H |
| CH(Me)CH₂OC(O)Me | N | CH | CH | N | 3-Cl | H | H |
| CH₂CH₂OCF₃ | N | CH | CH | N | 3-Cl | H | H |
| t-butyl | N | CH | CH | N | 2-Cl | 6-Me | H |
| cyclopropyl | N | CH | CH | N | 2-Cl | 6-Me | H |
| 4-tetrahydropyranyl | N | CH | CH | N | 2-Cl | 6-Me | H |
| (R)-3-tetrahydropyranyl | N | CH | CH | N | 2-Cl | 6-Me | H |
| (S)-3-tetrahydropyranyl | N | CH | CH | N | 2-Cl | 6-Me | H |
| CH₂OMe | N | CH | CH | N | 2-Cl | 6-Me | H |
| CH₂CH₂OMe | N | CH | CH | N | 2-Cl | 6-Me | H |
| CH₂CH₂CH₂OMe | N | CH | CH | N | 2-Cl | 6-Me | H |
| CH₂CH(Me)OMe | N | CH | CH | N | 2-Cl | 6-Me | H |
| CH(Me)OMe | N | CH | CH | N | 2-Cl | 6-Me | H |
| CH(Me)OEt | N | CH | CH | N | 2-Cl | 6-Me | H |
| CH(Me)CH₂OMe | N | CH | CH | N | 2-Cl | 6-Me | H |
| C(Me)₂CH₂OMe | N | CH | CH | N | 2-Cl | 6-Me | H |
| CH(Me)CH₂CH₂OMe | N | CH | CH | N | 2-Cl | 6-Me | H |
| (R)—CH(Me)CH₂OMe | N | CH | CH | N | 2-Cl | 6-Me | H |
| (S)—CH(Me)CH₂OMe | N | CH | CH | N | 2-Cl | 6-Me | H |
| CH(Me)CH₂OC(O)Me | N | CH | CH | N | 2-Cl | 6-Me | H |
| CH₂CH₂OCF₃ | N | CH | CH | N | 2-Cl | 6-Me | H |
| t-butyl | N | CH | CH | N | 2-Cl | 6-Cl | H |
| cyclopropyl | N | CH | CH | N | 2-Cl | 6-Cl | H |
| 4-tetrahydropyranyl | N | CH | CH | N | 2-Cl | 6-Cl | H |
| (R)-3-tetrahydropyranyl | N | CH | CH | N | 2-Cl | 6-Cl | H |
| (S)-3-tetrahydropyranyl | N | CH | CH | N | 2-Cl | 6-Cl | H |
| CH₂OMe | N | CH | CH | N | 2-Cl | 6-Cl | H |
| CH₂CH₂OMe | N | CH | CH | N | 2-Cl | 6-Cl | H |
| CH₂CH₂CH₂OMe | N | CH | CH | N | 2-Cl | 6-Cl | H |
| CH₂CH(Me)OMe | N | CH | CH | N | 2-Cl | 6-Cl | H |
| CH(Me)OMe | N | CH | CH | N | 2-Cl | 6-Cl | H |
| CH(Me)OEt | N | CH | CH | N | 2-Cl | 6-Cl | H |
| CH(Me)CH₂OMe | N | CH | CH | N | 2-Cl | 6-Cl | H |
| C(Me)₂CH₂OMe | N | CH | CH | N | 2-Cl | 6-Cl | H |
| CH(Me)CH₂CH₂OMe | N | CH | CH | N | 2-Cl | 6-Cl | H |
| (R)—CH(Me)CH₂OMe | N | CH | CH | N | 2-Cl | 6-Cl | H |

TABLE 6-continued

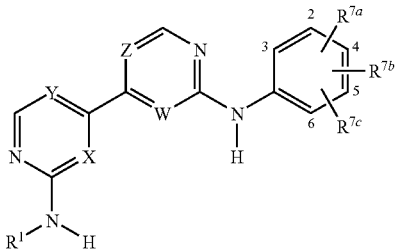

| R¹ | X | Y | W | Z | R⁷ᵃ | R⁷ᵇ | R⁷ᶜ |
|---|---|---|---|---|---|---|---|
| (S)—CH(Me)CH₂OMe | N | CH | CH | N | 2-Cl | 6-Cl | H |
| CH(Me)CH₂OC(O)Me | N | CH | CH | N | 2-Cl | 6-Cl | H |
| CH₂CH₂OCF₃ | N | CH | CH | N | 2-Cl | 6-Cl | H |
| t-butyl | N | CH | CH | N | 2-Cl | 4-Cl | 6-Me |
| cyclopropyl | N | CH | CH | N | 2-Cl | 4-Cl | 6-Me |
| 4-tetrahydropyranyl | N | CH | CH | N | 2-Cl | 4-Cl | 6-Me |
| (R)-3-tetrahydropyranyl | N | CH | CH | N | 2-Cl | 4-Cl | 6-Me |
| (S)-3-tetrahydropyranyl | N | CH | CH | N | 2-Cl | 4-Cl | 6-Me |
| CH₂OMe | N | CH | CH | N | 2-Cl | 4-Cl | 6-Me |
| CH₂CH₂OMe | N | CH | CH | N | 2-Cl | 4-Cl | 6-Me |
| CH₂CH₂CH₂OMe | N | CH | CH | N | 2-Cl | 4-Cl | 6-Me |
| CH₂CH(Me)OMe | N | CH | CH | N | 2-Cl | 4-Cl | 6-Me |
| CH(Me)OMe | N | CH | CH | N | 2-Cl | 4-Cl | 6-Me |
| CH(Me)OEt | N | CH | CH | N | 2-Cl | 4-Cl | 6-Me |
| CH(Me)CH₂OMe | N | CH | CH | N | 2-Cl | 4-Cl | 6-Me |
| C(Me)₂CH₂OMe | N | CH | CH | N | 2-Cl | 4-Cl | 6-Me |
| CH(Me)CH₂CH₂OMe | N | CH | CH | N | 2-Cl | 4-Cl | 6-Me |
| (R)—CH(Me)CH₂OMe | N | CH | CH | N | 2-Cl | 4-Cl | 6-Me |
| (S)—CH(Me)CH₂OMe | N | CH | CH | N | 2-Cl | 4-Cl | 6-Me |
| CH(Me)CH₂OC(O)Me | N | CH | CH | N | 2-Cl | 4-Cl | 6-Me |
| CH₂CH₂OCF₃ | N | CH | CH | N | 2-Cl | 4-Cl | 6-Me |
| t-butyl | CH | N | N | CH | 3-F | H | H |
| cyclopropyl | CH | N | N | CH | 3-F | H | H |
| 4-tetrahydropyranyl | CH | N | N | CH | 3-F | H | H |
| (R)-3-tetrahydropyranyl | CH | N | N | CH | 3-F | H | H |
| (S)-3-tetrahydropyranyl | CH | N | N | CH | 3-F | H | H |
| CH₂OMe | CH | N | N | CH | 3-F | H | H |
| CH₂CH₂OMe | CH | N | N | CH | 3-F | H | H |
| CH₂CH₂CH₂OMe | CH | N | N | CH | 3-F | H | H |
| CH₂CH(Me)OMe | CH | N | N | CH | 3-F | H | H |
| CH(Me)OMe | CH | N | N | CH | 3-F | H | H |
| CH(Me)OEt | CH | N | N | CH | 3-F | H | H |
| CH(Me)CH₂OMe | CH | N | N | CH | 3-F | H | H |
| C(Me)₂CH₂OMe | CH | N | N | CH | 3-F | H | H |
| CH(Me)CH₂CH₂OMe | CH | N | N | CH | 3-F | H | H |
| (R)—CH(Me)CH₂OMe | CH | N | N | CH | 3-F | H | H |
| (S)—CH(Me)CH₂OMe | CH | N | N | CH | 3-F | H | H |
| CH(Me)CH₂OC(O)Me | CH | N | N | CH | 3-F | H | H |
| CH₂CH₂OCF₃ | CH | N | N | CH | 3-F | H | H |
| t-butyl | CH | N | N | CH | 3-Cl | H | H |
| cyclopropyl | CH | N | N | CH | 3-Cl | H | H |
| 4-tetrahydropyranyl | CH | N | N | CH | 3-Cl | H | H |
| (R)-3-tetrahydropyranyl | CH | N | N | CH | 3-Cl | H | H |
| (S)-3-tetrahydropyranyl | CH | N | N | CH | 3-Cl | H | H |
| CH₂OMe | CH | N | N | CH | 3-Cl | H | H |
| CH₂CH₂OMe | CH | N | N | CH | 3-Cl | H | H |
| CH₂CH₂CH₂OMe | CH | N | N | CH | 3-Cl | H | H |
| CH₂CH(Me)OMe | CH | N | N | CH | 3-Cl | H | H |
| CH(Me)OMe | CH | N | N | CH | 3-Cl | H | H |
| CH(Me)OEt | CH | N | N | CH | 3-Cl | H | H |
| CH(Me)CH₂OMe | CH | N | N | CH | 3-Cl | H | H |
| C(Me)₂CH₂OMe | CH | N | N | CH | 3-Cl | H | H |
| CH(Me)CH₂CH₂OMe | CH | N | N | CH | 3-Cl | H | H |
| (R)—CH(Me)CH₂OMe | CH | N | N | CH | 3-Cl | H | H |
| (S)—CH(Me)CH₂OMe | CH | N | N | CH | 3-Cl | H | H |
| CH(Me)CH₂OC(O)Me | CH | N | N | CH | 3-Cl | H | H |
| CH₂CH₂OCF₃ | CH | N | N | CH | 3-Cl | H | H |
| t-butyl | CH | N | N | CH | 2-Cl | 6-Me | H |
| cyclopropyl | CH | N | N | CH | 2-Cl | 6-Me | H |
| 4-tetrahydropyranyl | CH | N | N | CH | 2-Cl | 6-Me | H |
| (R)-3-tetrahydropyranyl | CH | N | N | CH | 2-Cl | 6-Me | H |
| (S)-3-tetrahydropyranyl | CH | N | N | CH | 2-Cl | 6-Me | H |
| CH₂OMe | CH | N | N | CH | 2-Cl | 6-Me | H |
| CH₂CH₂OMe | CH | N | N | CH | 2-Cl | 6-Me | H |
| CH₂CH₂CH₂OMe | CH | N | N | CH | 2-Cl | 6-Me | H |

TABLE 6-continued

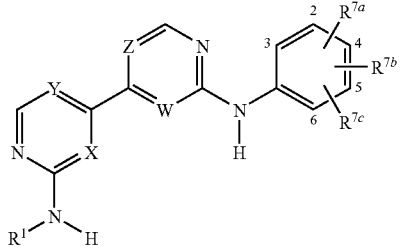

| R¹ | X | Y | W | Z | R⁷ᵃ | R⁷ᵇ | R⁷ᶜ |
|---|---|---|---|---|---|---|---|
| CH₂CH(Me)OMe | CH | N | N | CH | 2-Cl | 6-Me | H |
| CH(Me)OMe | CH | N | N | CH | 2-Cl | 6-Me | H |
| CH(Me)OEt | CH | N | N | CH | 2-Cl | 6-Me | H |
| CH(Me)CH₂OMe | CH | N | N | CH | 2-Cl | 6-Me | H |
| C(Me)₂CH₂OMe | CH | N | N | CH | 2-Cl | 6-Me | H |
| CH(Me)CH₂CH₂OMe | CH | N | N | CH | 2-Cl | 6-Me | H |
| (R)—CH(Me)CH₂OMe | CH | N | N | CH | 2-Cl | 6-Me | H |
| (S)—CH(Me)CH₂OMe | CH | N | N | CH | 2-Cl | 6-Me | H |
| CH(Me)CH₂OC(O)Me | CH | N | N | CH | 2-Cl | 6-Me | H |
| CH₂CH₂OCF₃ | CH | N | N | CH | 2-Cl | 6-Me | H |
| t-butyl | CH | N | N | CH | 2-Cl | 6-Cl | H |
| cyclopropyl | CH | N | N | CH | 2-Cl | 6-Cl | H |
| 4-tetrahydropyranyl | CH | N | N | CH | 2-Cl | 6-Cl | H |
| (R)-3-tetrahydropyranyl | CH | N | N | CH | 2-Cl | 6-Cl | H |
| (S)-3-tetrahydropyranyl | CH | N | N | CH | 2-Cl | 6-Cl | H |
| CH₂OMe | CH | N | N | CH | 2-Cl | 6-Cl | H |
| CH₂CH₂OMe | CH | N | N | CH | 2-Cl | 6-Cl | H |
| CH₂CH₂CH₂OMe | CH | N | N | CH | 2-Cl | 6-Cl | H |
| CH₂CH(Me)OMe | CH | N | N | CH | 2-Cl | 6-Cl | H |
| CH(Me)OMe | CH | N | N | CH | 2-Cl | 6-Cl | H |
| CH(Me)OEt | CH | N | N | CH | 2-Cl | 6-Cl | H |
| CH(Me)CH₂OMe | CH | N | N | CH | 2-Cl | 6-Cl | H |
| C(Me)₂CH₂OMe | CH | N | N | CH | 2-Cl | 6-Cl | H |
| CH(Me)CH₂CH₂OMe | CH | N | N | CH | 2-Cl | 6-Cl | H |
| (R)—CH(Me)CH₂OMe | CH | N | N | CH | 2-Cl | 6-Cl | H |
| (S)—CH(Me)CH₂OMe | CH | N | N | CH | 2-Cl | 6-Cl | H |
| CH(Me)CH₂OC(O)Me | CH | N | N | CH | 2-Cl | 6-Cl | H |
| CH₂CH₂OCF₃ | CH | N | N | CH | 2-Cl | 6-Cl | H |
| t-butyl | CH | N | N | CH | 2-Cl | 4-Cl | 6-Me |
| cyclopropyl | CH | N | N | CH | 2-Cl | 4-Cl | 6-Me |
| 4-tetrahydropyranyl | CH | N | N | CH | 2-Cl | 4-Cl | 6-Me |
| (R)-3-tetrahydropyranyl | CH | N | N | CH | 2-Cl | 4-Cl | 6-Me |
| (S)-3-tetrahydropyranyl | CH | N | N | CH | 2-Cl | 4-Cl | 6-Me |
| CH₂OMe | CH | N | N | CH | 2-Cl | 4-Cl | 6-Me |
| CH₂CH₂OMe | CH | N | N | CH | 2-Cl | 4-Cl | 6-Me |
| CH₂CH₂CH₂OMe | CH | N | N | CH | 2-Cl | 4-Cl | 6-Me |
| CH₂CH(Me)OMe | CH | N | N | CH | 2-Cl | 4-Cl | 6-Me |
| CH(Me)OMe | CH | N | N | CH | 2-Cl | 4-Cl | 6-Me |
| CH(Me)OEt | CH | N | N | CH | 2-Cl | 4-Cl | 6-Me |
| CH(Me)CH₂OMe | CH | N | N | CH | 2-Cl | 4-Cl | 6-Me |
| C(Me)₂CH₂OMe | CH | N | N | CH | 2-Cl | 4-Cl | 6-Me |
| CH(Me)CH₂CH₂OMe | CH | N | N | CH | 2-Cl | 4-Cl | 6-Me |
| (R)—CH(Me)CH₂OMe | CH | N | N | CH | 2-Cl | 4-Cl | 6-Me |
| (S)—CH(Me)CH₂OMe | CH | N | N | CH | 2-Cl | 4-Cl | 6-Me |
| CH(Me)CH₂OC(O)Me | CH | N | N | CH | 2-Cl | 4-Cl | 6-Me |
| CH₂CH₂OCF₃ | CH | N | N | CH | 2-Cl | 4-Cl | 6-Me |

TABLE 7

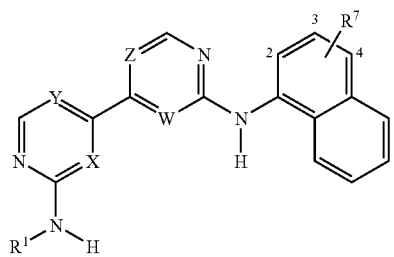

| R¹ | X | Y | W | Z | R⁷ |
|---|---|---|---|---|---|
| t-butyl | CH | N | N | CH | 2-Cl |
| cyclopropyl | CH | N | N | CH | 2-Cl |
| 4-tetrahydropyranyl | CH | N | N | CH | 2-Cl |
| (R)-3-tetrahydropyranyl | CH | N | N | CH | 2-Cl |
| (S)-3-tetrahydropyranyl | CH | N | N | CH | 2-Cl |
| CH₂OMe | CH | N | N | CH | 2-Cl |
| CH₂CH₂OMe | CH | N | N | CH | 2-Cl |
| CH₂CH₂CH₂OMe | CH | N | N | CH | 2-Cl |
| CH₂CH(Me)OMe | CH | N | N | CH | 2-Cl |
| CH(Me)OMe | CH | N | N | CH | 2-Cl |
| CH(Me)OEt | CH | N | N | CH | 2-Cl |
| CH(Me)CH₂OMe | CH | N | N | CH | 2-Cl |
| C(Me)₂CH₂OMe | CH | N | N | CH | 2-Cl |
| CH(Me)CH₂CH₂OMe | CH | N | N | CH | 2-Cl |
| (R)—CH(Me)CH₂OMe | CH | N | N | CH | 2-Cl |
| (S)—CH(Me)CH₂OMe | CH | N | N | CH | 2-Cl |
| CH(Me)CH₂OC(O)Me | CH | N | N | CH | 2-Cl |
| CH₂CH₂OCF₃ | CH | N | N | CH | 2-Cl |
| t-butyl | N | CH | N | N | 2-Cl |
| cyclopropyl | N | CH | N | N | 2-Cl |
| t-butyl | N | CH | CH | CH | 2-Cl |
| cyclopropyl | N | CH | CH | CH | 2-Cl |
| 4-tetrahydropyranyl | N | CH | CH | CH | 2-Cl |
| (R)-3-tetrahydropyranyl | N | CH | CH | CH | 2-Cl |
| (S)-3-tetrahydropyranyl | N | CH | CH | CH | 2-Cl |
| CH₂OMe | N | CH | CH | CH | 2-Cl |
| CH₂CH₂OMe | N | CH | CH | CH | 2-Cl |
| CH₂CH₂CH₂OMe | N | CH | CH | CH | 2-Cl |
| CH₂CH(Me)OMe | N | CH | CH | CH | 2-Cl |
| CH(Me)OMe | N | CH | CH | CH | 2-Cl |
| CH(Me)OEt | N | CH | CH | CH | 2-Cl |
| CH(Me)CH₂OMe | N | CH | CH | CH | 2-Cl |
| C(Me)₂CH₂OMe | N | CH | CH | CH | 2-Cl |
| CH(Me)CH₂CH₂OMe | N | CH | CH | CH | 2-Cl |
| (R)—CH(Me)CH₂OMe | N | CH | CH | CH | 2-Cl |
| (S)—CH(Me)CH₂OMe | N | CH | CH | CH | 2-Cl |
| CH(Me)CH₂OC(O)Me | N | CH | CH | CH | 2-Cl |
| CH₂CH₂OCF₃ | N | CH | CH | CH | 2-Cl |
| t-butyl | CH | N | N | CH | 2-Me |
| cyclopropyl | CH | N | N | CH | 2-Me |
| 4-tetrahydropyranyl | N | CH | N | N | 2-Cl |
| (R)-3-tetrahydropyranyl | N | CH | N | N | 2-Cl |
| (S)-3-tetrahydropyranyl | N | CH | N | N | 2-Cl |
| CH₂OMe | N | CH | N | N | 2-Cl |
| CH₂CH₂OMe | N | CH | N | N | 2-Cl |
| CH₂CH₂CH₂OMe | N | CH | N | N | 2-Cl |
| CH₂CH(Me)OMe | N | CH | N | N | 2-Cl |
| CH(Me)OMe | N | CH | N | N | 2-Cl |
| CH(Me)OEt | N | CH | N | N | 2-Cl |
| CH(Me)CH₂OMe | N | CH | N | N | 2-Cl |
| C(Me)₂CH₂OMe | N | CH | N | N | 2-Cl |
| CH(Me)CH₂CH₂OMe | N | CH | N | N | 2-Cl |
| (R)—CH(Me)CH₂OMe | N | CH | N | N | 2-Cl |
| (S)—CH(Me)CH₂OMe | N | CH | N | N | 2-Cl |
| CH(Me)CH₂OC(O)Me | N | CH | N | N | 2-Cl |
| CH₂CH₂OCF₃ | N | CH | N | N | 2-Cl |
| t-butyl | N | CH | CH | CH | 2-Me |
| cyclopropyl | N | CH | CH | CH | 2-Me |
| 4-tetrahydropyranyl | N | CH | CH | CH | 2-Me |
| (R)-3-tetrahydropyranyl | N | CH | CH | CH | 2-Me |
| (S)-3-tetrahydropyranyl | N | CH | CH | CH | 2-Me |
| CH₂OMe | N | CH | CH | CH | 2-Me |
| CH₂CH₂OMe | N | CH | CH | CH | 2-Me |
| CH₂CH₂CH₂OMe | N | CH | CH | CH | 2-Me |
| CH₂CH(Me)OMe | N | CH | CH | CH | 2-Me |

TABLE 7-continued

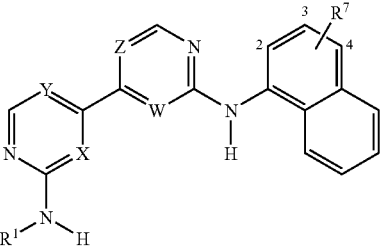

| R¹ | X | Y | W | Z | R⁷ |
|---|---|---|---|---|---|
| CH(Me)OMe | N | CH | CH | CH | 2-Me |
| CH(Me)OEt | N | CH | CH | CH | 2-Me |
| CH(Me)CH₂OMe | N | CH | CH | CH | 2-Me |
| C(Me)₂CH₂OMe | N | CH | CH | CH | 2-Me |
| CH(Me)CH₂CH₂OMe | N | CH | CH | CH | 2-Me |
| (R)—CH(Me)CH₂OMe | N | CH | CH | CH | 2-Me |
| (S)—CH(Me)CH₂OMe | N | CH | CH | CH | 2-Me |
| 4-tetrahydropyranyl | CH | N | N | CH | 2-Me |
| (R)-3-tetrahydropyranyl | CH | N | N | CH | 2-Me |
| (S)-3-tetrahydropyranyl | CH | N | N | CH | 2-Me |
| CH₂OMe | CH | N | N | CH | 2-Me |
| CH₂CH₂OMe | CH | N | N | CH | 2-Me |
| CH₂CH₂CH₂OMe | CH | N | N | CH | 2-Me |
| CH₂CH(Me)OMe | CH | N | N | CH | 2-Me |
| CH(Me)OMe | CH | N | N | CH | 2-Me |
| CH(Me)OEt | CH | N | N | CH | 2-Me |
| CH(Me)CH₂OMe | CH | N | N | CH | 2-Me |
| C(Me)₂CH₂OMe | CH | N | N | CH | 2-Me |
| CH(Me)CH₂CH₂OMe | CH | N | N | CH | 2-Me |
| (R)—CH(Me)CH₂OMe | CH | N | N | CH | 2-Me |
| (S)—CH(Me)CH₂OMe | CH | N | N | CH | 2-Me |
| CH(Me)CH₂OC(O)Me | CH | N | N | CH | 2-Me |
| CH₂CH₂OCF₃ | CH | N | N | CH | 2-Me |
| t-butyl | N | CH | N | N | 2-Me |
| cyclopropyl | N | CH | N | N | 2-Me |
| 4-tetrahydropyranyl | N | CH | N | N | 2-Me |
| (R)-3-tetrahydropyranyl | N | CH | N | N | 2-Me |
| (S)-3-tetrahydropyranyl | N | CH | N | N | 2-Me |
| CH₂OMe | N | CH | N | N | 2-Me |
| CH₂CH₂OMe | N | CH | N | N | 2-Me |
| CH₂CH₂CH₂OMe | N | CH | N | N | 2-Me |
| CH₂CH(Me)OMe | N | CH | N | N | 2-Me |
| CH(Me)OMe | N | CH | N | N | 2-Me |
| CH(Me)OEt | N | CH | N | N | 2-Me |
| CH(Me)CH₂OMe | N | CH | N | N | 2-Me |
| C(Me)₂CH₂OMe | N | CH | N | N | 2-Me |
| CH(Me)CH₂CH₂OMe | N | CH | N | N | 2-Me |
| (R)—CH(Me)CH₂OMe | N | CH | N | N | 2-Me |
| (S)—CH(Me)CH₂OMe | N | CH | N | N | 2-Me |
| CH(Me)CH₂OC(O)Me | N | CH | CH | CH | 2-Me |
| CH₂CH₂OCF₃ | N | CH | CH | CH | 2-Me |
| t-butyl | N | CH | CH | CH | 3-Cl |
| cyclopropyl | N | CH | CH | CH | 3-Cl |
| 4-tetrahydropyranyl | N | CH | CH | CH | 3-Cl |
| (R)-3-tetrahydropyranyl | N | CH | CH | CH | 3-Cl |
| (S)-3-tetrahydropyranyl | N | CH | CH | CH | 3-Cl |
| CH₂OMe | N | CH | CH | CH | 3-Cl |
| CH₂CH₂OMe | N | CH | CH | CH | 3-Cl |
| CH₂CH₂CH₂OMe | N | CH | CH | CH | 3-Cl |
| CH₂CH(Me)OMe | N | CH | CH | CH | 3-Cl |
| CH(Me)OMe | N | CH | CH | CH | 3-Cl |
| CH(Me)OEt | N | CH | CH | CH | 3-Cl |
| CH(Me)CH₂OMe | N | CH | CH | CH | 3-Cl |
| C(Me)₂CH₂OMe | N | CH | CH | CH | 3-Cl |
| CH(Me)CH₂CH₂OMe | N | CH | CH | CH | 3-Cl |
| (R)—CH(Me)CH₂OMe | N | CH | CH | CH | 3-Cl |
| (S)—CH(Me)CH₂OMe | N | CH | CH | CH | 3-Cl |
| CH(Me)CH₂OC(O)Me | N | CH | CH | CH | 3-Cl |
| CH₂CH₂OCF₃ | N | CH | CH | CH | 3-Cl |
| t-butyl | N | CH | CH | CH | 3-F |
| cyclopropyl | N | CH | CH | CH | 3-F |
| 4-tetrahydropyranyl | N | CH | CH | CH | 3-F |
| (R)-3-tetrahydropyranyl | N | CH | CH | CH | 3-F |
| (S)-3-tetrahydropyranyl | N | CH | CH | CH | 3-F |
| CH₂OMe | N | CH | CH | CH | 3-F |

TABLE 7-continued

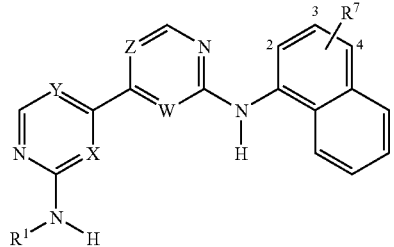

| R¹ | X | Y | W | Z | R⁷ |
|---|---|---|---|---|---|
| CH₂CH₂OMe | N | CH | CH | CH | 3-F |
| CH₂CH₂CH₂OMe | N | CH | CH | CH | 3-F |
| CH₂CH(Me)OMe | N | CH | CH | CH | 3-F |
| CH(Me)OMe | N | CH | CH | CH | 3-F |
| CH(Me)CH₂OC(O)Me | N | CH | N | N | 2-Me |
| CH₂CH₂OCF₃ | N | CH | N | N | 2-Me |
| t-butyl | N | CH | N | N | 3-Cl |
| cyclopropyl | N | CH | N | N | 3-Cl |
| 4-tetrahydropyranyl | N | CH | N | N | 3-Cl |
| (R)-3-tetrahydropyranyl | N | CH | N | N | 3-Cl |
| (S)-3-tetrahydropyranyl | N | CH | N | N | 3-Cl |
| CH₂OMe | N | CH | N | N | 3-Cl |
| CH₂CH₂OMe | N | CH | N | N | 3-Cl |
| CH₂CH₂CH₂OMe | N | CH | N | N | 3-Cl |
| CH₂CH(Me)OMe | N | CH | N | N | 3-Cl |
| CH(Me)OMe | N | CH | N | N | 3-Cl |
| CH(Me)OEt | N | CH | N | N | 3-Cl |
| CH(Me)CH₂OMe | N | CH | N | N | 3-Cl |
| C(Me)₂CH₂OMe | N | CH | N | N | 3-Cl |
| CH(Me)CH₂CH₂OMe | N | CH | N | N | 3-Cl |
| (R)—CH(Me)CH₂OMe | N | CH | N | N | 3-Cl |
| (S)—CH(Me)CH₂OMe | N | CH | N | N | 3-Cl |
| CH(Me)CH₂OC(O)Me | N | CH | N | N | 3-Cl |
| CH₂CH₂OCF₃ | N | CH | N | N | 3-Cl |
| t-butyl | N | CH | N | N | 3-F |
| cyclopropyl | N | CH | N | N | 3-F |
| 4-tetrahydropyranyl | N | CH | N | N | 3-F |
| (R)-3-tetrahydropyranyl | N | CH | N | N | 3-F |
| (S)-3-tetrahydropyranyl | N | CH | N | N | 3-F |
| CH₂OMe | N | CH | N | N | 3-F |
| CH₂CH₂OMe | N | CH | N | N | 3-F |
| CH₂CH₂CH₂OMe | N | CH | N | N | 3-F |
| CH₂CH(Me)OMe | N | CH | N | N | 3-F |
| CH(Me)OMe | N | CH | N | N | 3-F |
| CH(Me)OEt | N | CH | CH | CH | 3-F |
| CH(Me)CH₂OMe | N | CH | CH | CH | 3-F |
| C(Me)₂CH₂OMe | N | CH | CH | CH | 3-F |
| CH(Me)CH₂CH₂OMe | N | CH | CH | CH | 3-F |
| (R)—CH(Me)CH₂OMe | N | CH | CH | CH | 3-F |
| (S)—CH(Me)CH₂OMe | N | CH | CH | CH | 3-F |
| CH(Me)CH₂OC(O)Me | N | CH | CH | CH | 3-F |
| CH₂CH₂OCF₃ | N | CH | CH | CH | 3-F |
| t-butyl | N | N | CH | N | 3-F |
| cyclopropyl | N | N | CH | N | 2-F |
| 4-tetrahydropyranyl | N | N | CH | N | 3-F |
| (R)-3-tetrahydropyranyl | N | N | CH | N | 2-F |
| (S)-3-tetrahydropyranyl | N | N | CH | N | 3-F |
| CH₂OMe | N | N | CH | N | 2-F |
| CH₂CH₂OMe | N | N | CH | N | 3-F |
| CH₂CH₂CH₂OMe | N | N | CH | N | 3-F |
| CH₂CH(Me)OMe | N | N | CH | N | 3-F |
| CH(Me)OMe | N | N | CH | N | 2-F |
| CH(Me)OEt | N | N | CH | N | 3-F |
| CH(Me)CH₂OMe | N | N | CH | N | 2-F |
| C(Me)₂CH₂OMe | N | N | CH | N | 3-F |
| CH(Me)CH₂CH₂OMe | N | N | CH | N | 2-F |
| (R)—CH(Me)CH₂OMe | N | N | CH | N | 3-F |
| (S)—CH(Me)CH₂OMe | N | N | CH | N | 2-F |
| CH(Me)CH₂OC(O)Me | N | N | CH | N | 3-F |
| CH₂CH₂OCF₃ | N | N | CH | N | 2-F |
| CH(Me)OEt | N | CH | N | N | 3-F |
| CH(Me)CH₂OMe | N | CH | N | N | 3-F |
| C(Me)₂CH₂OMe | N | CH | N | N | 3-F |
| CH(Me)CH₂CH₂OMe | N | CH | N | N | 3-F |
| (R)—CH(Me)CH₂OMe | N | CH | N | N | 3-F |

TABLE 7-continued

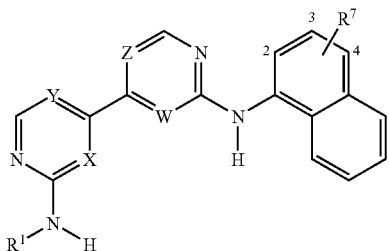

| R[1] | X | Y | W | Z | R[7] |
|---|---|---|---|---|---|
| (S)—CH(Me)CH$_2$OMe | N | CH | N | N | 3-F |
| CH(Me)CH$_2$OC(O)Me | N | CH | N | N | 3-F |
| CH$_2$CH$_2$OCF$_3$ | N | CH | N | N | 3-F |
| t-butyl | N | CH | N | N | — |
| cyclopropyl | N | CH | N | N | — |
| 4-tetrahydropyranyl | N | CH | N | N | — |
| (R)-3-tetrahydropyranyl | N | CH | N | N | — |
| (S)-3-tetrahydropyranyl | N | CH | N | N | — |
| CH$_2$OMe | N | CH | N | N | — |
| CH$_2$CH$_2$OMe | N | CH | N | N | — |
| CH$_2$CH$_2$CH$_2$OMe | N | CH | N | N | — |
| CH$_2$CH(Me)OMe | N | CH | N | N | — |
| CH(Me)OMe | N | CH | N | N | — |
| CH(Me)OEt | N | CH | N | N | — |
| CH(Me)CH$_2$OMe | N | CH | N | N | — |
| C(Me)$_2$CH$_2$OMe | N | CH | N | N | — |
| CH(Me)CH$_2$CH$_2$OMe | N | CH | N | N | — |
| (R)—CH(Me)CH$_2$OMe | N | CH | N | N | — |
| (S)—CH(Me)CH$_2$OMe | N | CH | N | N | — |
| CH(Me)CH$_2$OC(O)Me | N | CH | N | N | — |
| CH$_2$CH$_2$OCF$_3$ | N | CH | N | N | — |

A dash (—) in the R[7] column means that no R[7] substituent is present.

Formulation/Utility

A compound of this invention will generally be used as a fungicidal active ingredient in a composition, i.e., formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, pills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto vegetable seeds as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids. Such formulation auxiliaries and additives may control: pH (buffers), foaming during processing (antifoams such polyorganosiloxanes (e.g., Rhodorsil® 416)), sedimentation of active ingredients (suspending agents), viscosity (thixotropic thickeners), in-container microbial growth (antimicrobials), product freezing (antifreezes), color (dyes/pigment dispersions (e.g., Pro-lzed® Colorant Red)), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and, usually, grinding as in a hammer mill or fluid-energy mill. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. Nos. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-C.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 2 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 4 | 10.0% |
| attapulgite granules (low volatile matter, 0.71/0.30 mm; U.S.S. No. 25-50 sieves) | 90.0% |

Example D

| Extruded Pellet | |
|---|---|
| Compound 3 | 25.0% |
| hydrated attapulgite | 3.0% |
| crude calcium ligninsulfonate | 10.0% |
| sodium dihydrogen phosphate | 0.5% |
| water | 61.5% |

Example E

| Extruded Pellet | |
|---|---|
| Compound 6 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example F

| Microemulsion | |
|---|---|
| Compound 4 | 1.0% |
| triacetine | 30.0% |
| $C_8$-$C_{10}$ alkylpolyglycoside | 30.0% |
| glyceryl monooleate | 19.0% |
| water | 20.0% |

Example G

| Emulsifiable Concentrate | |
|---|---|
| Compound 21 | 10.0% |
| $C_8$-$C_{10}$ fatty acid methyl ester | 70.0% |
| polyoxyethylene sorbitol hexoleate | 20.0% |

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans*, *Phytophthora megasperma*, *Phytophthora parasitica*, *Phytophthora cinnamomi* and *Phytophthora capsici*, *Pythium* diseases such as *Pythium aphanidermatum*, and diseases in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae*, *Guignardia* diseases such as *Guignardia bidwell*, *Venturia* diseases such as *Venturia inaequalis*, *Septoria* diseases such as *Septoria nodorum* and *Septoria tritici*, powdery mildew diseases such as *Erysiphe* spp. (including *Erysiphe graminis* and *Erysiphe polygoni*), *Uncinula necatur*, *Sphaerotheca fuligena* and *Podosphaera leucot-*

*richa, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondite, Puccinia striiformis, Puccinia hordei, Puccinia graminis* and *Puccinia arachidis*), *Hemileia vastatrix* and *Phakopsora pachyrhizi*; other pathogens including *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species. Of note is control provided of disease caused by the Ascomycete and Basidiomycete classes.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Rates of application for these compounds can be influenced by many factors of the environment and should be determined under actual use conditions. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other insecticides, fungicides, nematocides, bactericides, acaricides, growth regulators, chemosterilants, semiochemicals, repellents, attractants, pheromones, feeding stimulants or other biologically active compounds to form a multi-component pesticide giving an even broader spectrum of agricultural protection. Examples of such agricultural protectants with which compounds of this invention can be formulated are: insecticides such as abamectin, acephate, acetamiprid, amidoflumet (S-1955), avermectin, azadirachtin, azinphos-methyl, bifenthrin, bifenazate, 3-bromo-1-(3-chloro-2-pyridinyl)-N-[4-cyano-2-methyl-6-[(methylamino) carbonyl]phenyl]-1H-pyrazole-5-carboxamide, buprofezin, carbofuran, cartap, chlorantraniliprole (DPX-E2Y45), chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, enestroburin (SYP-Z071), esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, rynaxypyr, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; fungicides such as acibenzolar-S-methyl, aldimorph, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, Bordeaux mixture (tribasic copper sulfate), boscalid, bromuconazole, bupirimate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, etridiazole, famoxadone, fenamidone, fenarimol, fenbuconazole, fenfuram, fenhexamid, fenoxanil, fenpiclonil, fenpropidin, fenpropimorph, fentin acetate, fentin chloride, fentin hydroxide, ferbam, ferimzone, fluazinam, fludioxonil, flumetover, flumorph, fluopicolide, fluopyram, fluoroimide, fluoxastrobin, fluquinconazole, flusilazole, flusulfamide, flutolanil, flutriafol, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neoasozin (ferric methanearsonate), nuarimol, octhilinone, ofurace, orysastrobin, oxadixyl, oxolinic acid, oxpoconazole, oxycarboxin, oxytetracycline, penconazole, pencycuron, penthiopyrad, pefurazoate, phosphorous acid and salts, phthalide, picobenzamid, picoxystrobin, piperalin, polyoxin, probenazole, prochloraz, procymidone, propamocarb, propamocarb-hydrochloride, propiconazole, propineb, proquinazid, prothioconazole, pyraclostrobin, pryazophos, pyribencarb, pyrifenox, pyrimethanil, pyrolnitrine, pyroquilon, quinomethionate, quinoxyfen, quintozene, silthiofam, simeconazole, spiroxamine, streptomycin, sulfur, tebuconazole, tecloftalam, tecnazene, terbinafine, tetraconazole, thiabendazole, thifluzamide, thiophanate, thiophanate-methyl, thiram, tiadinil, tolclofos-methyl, tolyfluanid, triadimefon, triadimenol, triazoxide, tricyclazole, tridemorph, triflumizole, tricyclazole, trifloxystrobin, triforine, triticonazole, uniconazole, validamycin, valiphenal, vinclozolin, zineb, ziram, zoxamide, 5-chloro-6-(2,4,6-trifluorophenyl)-7-(4-methylpiperidin-1-yl) [1,2,4]triazolo[1,5-a]pyrimidine (BAS600), N-[2-(1,3-dimethylbutyl)phenyl]-5-fluoro-1,3-dimethyl-1H-pyrazol-4-carboxamide, N-[2-[4-[[3-(4-chlorophenyl)-2-propyn-1-yl]oxy]-3-methoxyphenyl]ethyl]-3-methyl-2-[(ethylsulfonyl)amino]butanamide, N-[2-[4-[[3-(4-chlorophenyl)-2-propyn-1-yl]oxy]-3-methoxyphenyl] ethyl]-3-methyl-2-[(ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]-benzeneacetamide, α-[methoxyimino]-N-methyl-2-[[[1-[3-(trifluoromethyl)phenyl]-ethoxy]imino]methyl]benzeneacetamide, N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile, N-[2-(1S,2R)-[1,1'-bicyclopropyl]-2-ylphenyl]-3-(difluoromethyl)-1-methyl-1H-pyrazole-4-carboxamide, and N-(4-chloro-2-nitrophenyl)-N-ethyl-4-methylbenzenesulfonamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. aizawai, *Bacillus thuringiensis* subsp. kurstaki, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e., insecticides, fungicides, nematocides, acaricides, herbicides and biological agents) include *The Pesticide Manual, 13th Edition*, C. D. S. Tomlin, Ed., British Crop Protection Council, Farnham, Surrey, U. K., 2003 and *The BioPesticide Manual, 2nd Edition*, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:100 and about 3000:1. Of note are weight ratios between about 1:30 and about 300:1 (for example ratios between about 1:1 and about 30:1). It will be evident that including these additional components may expand the spectrum of diseases controlled beyond the spectrum controlled by the compound of Formula 1 alone.

In one mixture embodiment, granules of a solid composition comprising a compound of Formula 1 is mixed with granules of a solid composition comprising another agricultural protectant. These granule mixtures can be in accordance with the general granule mixture disclosure of PCT Patent Publication WO 94/24861 or more preferably the homogenous granule mixture teaching of U.S. Pat. No. 6,022,552.

Of note are combinations (e.g., in the form of compositions) of (a) a compound of Formula 1 with (b) at least one other fungicide. Of particular note are such combinations where the other fungicide has different site of action from the compound of Formula 1. In certain instances, combinations with other fungicides having a similar spectrum of control but a different site of action will be particularly advantageous for resistance management. Of particular note are compositions which in addition to a compound of Formula 1 include at least one compound selected from the group consisting of
(b1) methyl benzimidazole carbamate (MBC) fungicides;
(b2) dicarboximide fungicides;
(b3) demethylation inhibitor (DMI) fungicides;
(b4) phenylamide fungicides;
(b5) amine/morpholine fungicides;
(b6) phospholipid biosynthesis inhibitor fungicides;
(b7) carboxamide fungicides;
(b8) hydroxy(2-amino-)pyrimidine fungicides;
(b9) anilinopyrimidine fungicides;
(b10) N-phenyl carbamate fungicides;
(b11) quinone outside inhibitor (QoI) fungicides;
(b12) phenylpyrrole fungicides;
(b13) quinoline fungicides;
(b14) lipid peroxidation inhibitor fungicides;
(b15) melanin biosynthesis inhibitors-reductase (MBI-R) fungicides;
(b16) melanin biosynthesis inhibitors-dehydratase (MBI-D) fungicides;
(b17) hydroxyanilide fungicides;
(b18) squalene-epoxidase inhibitor fungicides;
(b19) polyoxin fungicides;
(b20) phenylurea fungicides;
(b21) quinone inside inhibitor (QiI) fungicides;
(b22) benzamide fungicides;
(b23) enopyranuronic acid antibiotic fungicides;
(b24) hexopyranosyl antibiotic fungicides;
(b25) glucopyranosyl antibiotic: protein synthesis fungicides;
(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide (CAA) fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicides other than fungicides of components (b1) through (b45); and salts of compounds of (b1) through (b46).

"Methyl benzimidazole carbamate (MBC) fungicides (b1)" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

"Dicarboximide fungicides (b2)" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

"Demethylation inhibitor (DMI) fungicides (b3)" (Fungicide Resistance Action Committee (FRAC) code 3) inhibit C14-demethylase which plays a role in sterol production.

Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

"Phenylamide fungicides (b4)" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M/mefenoxam. The oxazolidinones include oxadixyl. The butyrolactones include ofurace.

"Amine/morpholine fungicides (b5)" (Fungicide Resistance Action Committee (FRAC) code 5) inhibit two target sites within the sterol biosynthetic pathway, $\Delta^8 \to \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketalamine fungicides. The morpholines include aldimorph, dodemorph, fenpropimorph, tridemorph and trimorphamide. The piperidines include fenpropidin and piperalin. The spiroketalamines include spiroxamine.

"Phospholipid biosynthesis inhibitor fungicides (b6)" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

"Carboxamide fungicides (b7)" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The Benzamides include benodanil, flutolanil and mepronil. The furan carboxamides include fenfuram. The oxathiin carboxamide include carboxin and oxycarboxin. The thiazole carboxamides include thifluzamide. The pyrazole carboxamides include furametpyr, penthiopyrad, bixafen, N-[2-(1S,2R)-[1,1'-bicyclopropyl]-2-ylphenyl]-3-(difluoromethyl)-1-methyl-1H-pyrazole-4-carboxamide and N-[2-(1,3-dimethylbutyl)phenyl]-5-fluoro-1,3-dimethyl-1H-pyrazole-4-carboxamide (PCT Patent Publication WO 2003/010149). The pyridine carboxamide include boscalid.

"Hydroxy(2-amino-)pyrimidine fungicides (b8)" (Fungicide Resistance Action Committee (FRAC) code 8) inhibit nucleic acid synthesis by interfering with adenosine deaminase. Examples include bupirimate, dimethirimol and ethirimol.

"Anilinopyrimidine fungicides (b9)" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

"N-Phenyl carbamate fungicides (b10)" (Fungicide Resistance Action Committee (FRAC) code 10) inhibit mitosis by binding to β-tubulin and disrupting microtubule assembly Inhibition of microtubule assembly can disrupt cell division, transport within the cell and cell structure. Examples include diethofencarb.

"Quinone outside inhibitor (QoI) fungicides (b11)" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_O$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin and α-[methoxyimino]-N-methyl-2-[[[1-[3-(trifluoromethyl)phenyl]-ethoxy]imino]methyl]benzeneacetamide. The oxazolidinediones include famoxadone. The dihydrodioxazines include fluoxastrobin. The imidazolinones include fenamidone. The benzylcarbamates include pyribencarb.

"Phenylpyrrole fungicides (b12)" (Fungicide Resistance Action Committee (FRAC) code 12) inhibit a MAP protein kinase associated with osmotic signal transduction in fungi. Fenpiclonil and fludioxonil are examples of this fungicide class.

"Quinoline fungicides (b13)" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

"Lipid peroxidation inhibitor fungicides (b14)" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbons include biphenyl, chloroneb, dicloran, quintozene, tecnazene and tolclofos-methyl. The 1,2,4-thiadiazoles include etridiazole.

"Melanin biosynthesis inhibitors-reductase (MBI-R) fungicides (b15)" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

"Melanin biosynthesis inhibitors-dehydratase (MBI-D) fungicides (b16)" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

"Hydroxyanilide fungicides (b17)" (Fungicide Resistance Action Committee (FRAC) code 17) inhibit C4-demethylase which plays a role in sterol production. Examples include fenhexamid.

"Squalene-epoxidase inhibitor fungicides (b18)" (Fungicide Resistance Action Committee (FRAC) code 18) inhibit squalene-epoxidase in ergosterol biosynthesis pathway. Sterols such as ergosterol are needed for membrane structure and function making them essential for the development of functional cell walls. Therefore exposure to these fungicides result in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

"Polyoxin fungicides (b19)" (Fungicide Resistance Action Committee (FRAC) code 19) inhibit chitin synthase. Examples include polyoxin.

"Phenylurea fungicides (b20)" (Fungicide Resistance Action Committee (FRAC) code 20) are proposed to affect cell division. Examples include pencycuron.

"Quinone inside inhibitor (QiI) fungicides (b21)" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

"Benzamide fungicides (b22)" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

"Enopyranuronic acid antibiotic fungicides (b23)" (Fungicide Resistance Action Committee (FRAC) code 23) inhibit growth of fungi by affecting protein biosynthesis. Examples include blasticidin-S.

"Hexopyranosyl antibiotic fungicides (b24)" (Fungicide Resistance Action Committee (FRAC) code 24) inhibit growth of fungi by affecting protein biosynthesis. Examples include kasugamycin.

"Glucopyranosyl antibiotic: protein synthesis fungicides (b25)" (Fungicide Resistance Action Committee (FRAC) code 25) inhibit growth of fungi by affecting protein biosynthesis. Examples include streptomycin.

"Glucopyranosyl antibiotic: trehalase and inositol biosynthesis fungicides (b26)" (Fungicide Resistance Action Committee (FRAC) code 26) inhibit trehalase in inositol biosynthesis pathway. Examples include validamycin.

"Cyanoacetamideoxime fungicides (b27)" (Fungicide Resistance Action Committee (FRAC) code 27) include cymoxanil.

"Carbamate fungicides (b28)" (Fungicide Resistance Action Committee (FRAC) code 28) are considered multi-site inhibitors of fungal growth. They are proposed to interfere with the synthesis of fatty acids in cell membranes, which then disrupts cell membrane permeability. propamacarb, propamacarb-hydrochloride, iodocarb, and prothiocarb are examples of this fungicide class.

"Oxidative phosphorylation uncoupling fungicides (b29)" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

"Organo tin fungicides (b30)" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

"Carboxylic acid fungicides (b31)" (Fungicide Resistance Action Committee (FRAC) code 31) inhibit growth of fungi by affecting deoxyribonucleic acid (DNA) topoisomerase type II (gyrase). Examples include oxolinic acid.

"Heteroaromatic fungicides (b32)" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

"Phosphonate fungicides (b33)" (Fungicide Resistance Action Committee (FRAC) code 33) include phosphorous acid and its various salts, including fosetyl-aluminum.

"Phthalamic acid fungicides (b34)" (Fungicide Resistance Action Committee (FRAC) code 34) include teclofthalam.

"Benzotriazine fungicides (b35)" (Fungicide Resistance Action Committee (FRAC) code 35) include triazoxide.

"Benzene-sulfonamide fungicides (b36)" (Fungicide Resistance Action Committee (FRAC) code 36) include flusulfamide.

"Pyridazinone fungicides (b37)" (Fungicide Resistance Action Committee (FRAC) code 37) include diclomezine.

"Thiophene-carboxamide fungicides (b38)" (Fungicide Resistance Action Committee (FRAC) code 38) are proposed to affect ATP production. Examples include silthiofam.

"Pyrimidinamide fungicides (b39)" (Fungicide Resistance Action Committee (FRAC) code 39) inhibit growth of fungi by affecting phospholipid biosynthesis and include diflumetorim.

"Carboxylic acid amide (CAA) fungicides (b40)" (Fungicide Resistance Action Committee (FRAC) code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]-ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

"Tetracycline antibiotic fungicides (b41)" (Fungicide Resistance Action Committee (FRAC) code 41) inhibit growth of fungi by affecting complex 1 nicotinamide adenine dinucleotide (NADH) oxidoreductase. Examples include oxytetracycline.

"Thiocarbamate fungicides (b42)" (Fungicide Resistance Action Committee (FRAC) code 42) include methasulfocarb.

"Benzamide fungicides (b43)" (Fungicide Resistance Action Committee (FRAC) code 43) inhibit growth of fungi by delocalization of spectrin-like proteins. Examples include acylpicolide fungicides such as fluopicolide and fluopyram.

"Host plant defense induction fungicides (b44)" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-5-methyl. The benzisothiazoles include probenazole. The thiadiazole-carboxamides include tiadinil and isotianil.

"Multi-site contact fungicides (b45)" inhibit fungal growth through multiple sites of action and have contact/preventive activity. This class of fungicides includes: "copper fungicides (b45.1) (Fungicide Resistance Action Committee (FRAC) code M1)", "sulfur fungicides (b45.2) (Fungicide Resistance Action Committee (FRAC) code M2)", "dithiocarbamate fungicides (b45.3) (Fungicide Resistance Action Committee (FRAC) code M3)", "phthalimide fungicides (b45.4) (Fungicide Resistance Action Committee (FRAC) code M4)", "chloronitrile fungicides (b45.5) (Fungicide Resistance Action Committee (FRAC) code M5)", "sulfamide fungicides (b45.6) (Fungicide Resistance Action Committee (FRAC) code M6)", "guanidine fungicides (b45.7) (Fungicide Resistance Action Committee (FRAC) code M7)" "triazines fungicides (b45.8) (Fungicide Resistance Action Committee (FRAC) code M8)" and "quinone fungicides (b45.9) (Fungicide Resistance Action Committee (FRAC) code M9)". "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazines fungicides" include anilazine. "Quinone fungicides" include dithianon.

"Fungicides other than fungicides of component (a) and components (b1) through (b45); (b46)" include certain fungicides considered to have an unknown mode of action. These include: "thiazole carboxamide fungicide (b46.1) (Fungicide Resistance Action Committee (FRAC) code U5)", "phenyl-acetamide fungicide (b46.2) (Fungicide Resistance Action Committee (FRAC) code U6)", "quinazolinone fungicide (b46.3) (Fungicide Resistance Action Committee (FRAC) code U7)" and "benzophenone fungicide (b46.4) (Fungicide Resistance Action Committee (FRAC) code U8)". The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid, 6-bromo-3-propyl-2-propyloxy-4(3H)-quinazolinone, 6,8-diiodo-3-propyl-2-propyloxy-4-(3H)-quinazolinone, 6-chloro-2-propoxy-3-propylthieno[2,3-d]pyrimidin-4(3H)-one, 2,3-dibutyl-6-chlorothieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, 3-(cyclopropylmethyl)-6-iodo-2-(propylthio)pyrido[2,3-d]pyrimidin-4(3H)-one, 2-butoxy-6-iodo-3-propyl-4H-1-benzopyran-4-one, 2-ethoxy-6-iodo-3-propyl-4H-1-benzopyran-4-one, 6-iodo-2-propoxy-3-propyl-4H-1-benzopyran-4-one, 2-(2-butynyloxy)-6-iodo-3-propyl-4H-1-benzopyran-4-one, 6-iodo-2-(1-methylbutoxy)-3-propyl-4H-1-benzopyran-4-one, 2-(3-butenyloxy)-6-iodo-3-propyl-4H-1-benzopyran-4-one, 3-butyl-6-iodo-2-(1-methylethoxy)-4H-1-benzopyran-4-one, and 6-iodo-3-propyl-2H-1,3-benzoxazine-2,4(3H)-dione 2-(O-methyloxime). The benzophenones include metrafenone. The (b46) group also includes 5-chloro-6-(2,4,6-trifluorophenyl)-7-(4-methylpiperidin-1-yl)[1,2,4]triazolo[1,5-a]pyrimidine (BAS600), 3-[5-(4-chlorophenyl)-2,3-dimethyl-3-isoxazolidinyl]pyridine (SYP-Z048), 4-fluorophenyl N-[1-[[[1-(4-cyanophenyl)ethyl]sulfonyl]methyl]propyl] carbamate (XR-539), N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (OK-5203) and N-(4-chloro-2-nitrophenyl)-N-ethyl-4-methylbenzenesulfonamide (TF-991).

Embodiments of the present invention include:

Embodiment B1

The composition described in the Summary of the Invention (including but not limited to composition of Embodiments 1 through 37 and A1 through A4) wherein component (b) includes at least one compound selected from (b1) methyl benzimidazole carbamate fungicides such as benomyl, carbendazim and thiophanate-methyl.

Embodiment B2

The composition described in the Summary of the Invention (including but not limited to composition of Embodiments 1 through 37 and A1 through A4) wherein component (b) includes at least one compound selected from (b2) dicarboximide fungicides such as procymidone, iprodione and vinclozolin.

Embodiment B3

The composition described in the Summary of the Invention (including but not limited to composition of Embodiments 1 through 37 and A1 through A4) wherein component (b) includes at least one compound selected from (b3) demethylation inhibitor fungicides such as epoxiconazole, fluquinconazole, triadimenol, simeconazole, ipconazole, triforine, cyproconazole, difenoconazole, flusilazole, flutriafol, metconazole, myclobutanil, prochloraz, propiconazole, prothioconazole, tebuconazole and tetraconazole.

Embodiment B4

The composition described in the Summary of the Invention (including but not limited to composition of Embodiments 1 through 37 and A1 through A4) wherein component (b) includes at least one compound selected from (b4) phenylamide fungicides such as mefenoxam, metalaxyl, metalaxyl-M, benalaxyl, benalaxyl-M, furalaxyl, ofurace and oxadixyl.

Embodiment B5

The composition described in the Summary of the Invention (including but not limited to composition of Embodiments 1 through 37 and A1 through A4) wherein component (b) includes at least one compound selected from (b5) amine/morpholine fungicides such as aldimorph, dodemorph, fenpropimorph, tridemorph, trimorphamide. fenpropidin, piperalin and spiroxamine.

Embodiment B6

The composition described in the Summary of the Invention (including but not limited to composition of Embodiments 1 through 37 and A1 through A4) wherein component (b) includes at least one compound selected from (b6) phospholipid biosynthesis inhibitor fungicides such as edifenphos and isoprothiolane.

Embodiment B7

The composition described in the Summary of the Invention (including but not limited to composition of Embodiments 1 through 37 and A1 through A4) wherein component (b) includes at least one compound selected from (b7) carboxamide fungicides such as boscalid, penthiopyrad, bixafen, carboxin and oxycarboxin.

Embodiment B8

The composition described in the Summary of the Invention (including but not limited to composition of Embodiments 1 through 37 and A1 through A4) wherein component (b) includes at least one compound selected from (b8) hydroxy(2-amino-)pyrimidine fungicides such as ethirimol.

Embodiment B9

The composition described in the Summary of the Invention (including but not limited to composition of Embodiments 1 through 37 and A1 through A4) wherein component (b) includes at least one compound selected from (b9) anilinopyrimidine fungicides such as cyprodinil.

Embodiment B10

The composition described in the Summary of the Invention (including but not limited to composition of Embodiments 1 through 37 and A1 through A4) wherein component (b) includes at least one compound selected from (b10) N-phenyl carbamate fungicides such as diethofencarb.

Embodiment B11

The composition described in the Summary of the Invention (including but not limited to composition of Embodiments 1 through 37 and A1 through A4) wherein component (b) includes at least one compound selected from (b11) quinone outside inhibitor fungicides such as azoxystrobin, pyraclostrobin, kresoxim-methyl, trifloxystrobin, picoxystrobin, pyribencarb, famoxadone, fenamidone, discostrobin, enestrobin, dimoxystrobin, metominostrobin, orysastrobin and fluoxastrobin.

Embodiment B12

The composition described in the Summary of the Invention (including but not limited to composition of Embodiments 1 through 37 and A1 through A4) wherein component (b) includes at least one compound selected from (b12) phenylpyrrole fungicides compound such as fenpiclonil and fludioxonil.

Embodiment B13

The composition described in the Summary of the Invention (including but not limited to composition of Embodiments 1 through 37 and A1 through A4) wherein component (b) includes at least one compound selected from (b13) quinoline fungicides such as quinoxyfen.

Embodiment B14

The composition described in the Summary of the Invention (including but not limited to composition of Embodiments 1 through 37 and A1 through A4) wherein component (b) includes at least one compound selected from (b14) lipid peroxidation inhibitor fungicides such as chloroneb.

Embodiment B15

The composition described in the Summary of the Invention (including but not limited to composition of Embodiments 1 through 37 and A1 through A4) wherein component (b) includes at least one compound selected from (b15) melanin biosynthesis inhibitors-reductase fungicides such as pyroquilon and tricyclazole.

Embodiment B16

The composition described in the Summary of the Invention (including but not limited to composition of Embodiments 1 through 37 and A1 through A4) wherein component (b) includes at least one compound selected from (b16) melanin biosynthesis inhibitors-dehydratase fungicides such as carpropamid.

Embodiment B17

The composition described in the Summary of the Invention (including but not limited to composition of Embodiments 1 through 37 and A1 through A4) wherein component (b) includes at least one compound selected from (b17) hydroxyanilide fungicides such as fenhexamid.

Embodiment B18

The composition described in the Summary of the Invention (including but not limited to composition of Embodiments 1 through 37 and A1 through A4) wherein component (b) includes at least one compound selected from (b18) squalene-epoxidase inhibitor fungicides such as pyributicarb.

Embodiment B19

The composition described in the Summary of the Invention (including but not limited to composition of Embodiments 1 through 37 and A1 through A4) wherein component (b) includes at least one compound selected from (b19) polyoxin fungicides such as polyoxin.

Embodiment B20

The composition described in the Summary of the Invention (including but not limited to composition of Embodiments 1 through 37 and A1 through A4) wherein component (b) includes at least one compound selected from (b20) phenylurea fungicides such as pencycuron.

Embodiment B21

The composition described in the Summary of the Invention (including but not limited to composition of Embodiments 1 through 37 and A1 through A4) wherein component (b) includes at least one compound selected from (b21) quinone inside inhibitor fungicides such as cyazofamid and amisulbrom.

Embodiment B22

The composition described in the Summary of the Invention (including but not limited to composition of Embodiments 1 through 37 and A1 through A4) wherein component (b) includes at least one compound selected from (b22) benzamide fungicides such as zoxamide.

Embodiment B23

The composition described in the Summary of the Invention (including but not limited to composition of Embodiments 1 through 37 and A1 through A4) wherein component (b) includes at least one compound selected from (b23) enopyranuronic acid antibiotic fungicides such as blasticidin-S.

Embodiment B24

The composition described in the Summary of the Invention (including but not limited to composition of Embodiments 1 through 37 and A1 through A4) wherein component (b) includes at least one compound selected from (b24) hexopyranosyl antibiotic fungicides such as kasugamycin.

Embodiment B25

The composition described in the Summary of the Invention (including but not limited to composition of Embodiments 1 through 37 and A1 through A4) wherein component (b) includes at least one compound selected from (b25) glucopyranosyl antibiotic: protein synthesis fungicides such as streptomycin.

Embodiment B26

The composition described in the Summary of the Invention (including but not limited to composition of Embodiments 1 through 37 and A1 through A4) wherein component (b) includes at least one compound selected from (b26) glucopyranosyl antibiotic: trehalase and inositol biosynthesis fungicides such as validamycin.

Embodiment B27

The composition described in the Summary of the Invention (including but not limited to composition of Embodiments 1 through 37 and A1 through A4) wherein component (b) includes at least one compound selected from (b27) cyanoacetylamideoxime fungicides such as cymoxanil.

Embodiment B28

The composition described in the Summary of the Invention (including but not limited to composition of Embodiments 1 through 37 and A1 through A4) wherein component (b) includes at least one compound selected from (b28) carbamate fungicides such as propamacarb, propamacarb-hydrochloride, prothiocarb and iodocarb.

Embodiment B29

The composition described in the Summary of the Invention (including but not limited to composition of Embodiments 1 through 37 and A1 through A4) wherein component (b) includes at least one compound selected from (b29) oxidative phosphorylation uncoupling fungicides such as fluazinam, binapacryl, ferimzone, meptyldinocap and dinocap.

Embodiment B30

The composition described in the Summary of the Invention (including but not limited to composition of Embodiments 1 through 37 and A1 through A4) wherein component (b) includes at least one compound selected from (b30) organo tin fungicides such as fentin acetate.

Embodiment B31

The composition described in the Summary of the Invention (including but not limited to composition of Embodiments 1 through 37 and A1 through A4) wherein component (b) includes at least one compound selected from (b31) carboxylic acid fungicides such as oxolinic acid.

Embodiment B32

The composition described in the Summary of the Invention (including but not limited to composition of Embodiments 1 through 37 and A1 through A4) wherein component (b) includes at least one compound selected from (b32) heteroaromatic fungicides such as hymexazole.

Embodiment B33

The composition described in the Summary of the Invention (including but not limited to composition of Embodiments 1 through 37 and A1 through A4) wherein component (b) includes at least one compound selected from (b33) phosphonate fungicides such as phosphorous acid and its various salts, including fosetyl-aluminum.

Embodiment B34

The composition described in the Summary of the Invention (including but not limited to composition of Embodiments 1 through 37 and A1 through A4) wherein component (b) includes at least one compound selected from (b34) phthalamic acid fungicides such as teclofthalam.

Embodiment B35

The composition described in the Summary of the Invention (including but not limited to composition of Embodiments 1 through 37 and A1 through A4) wherein component (b) includes at least one compound selected from (b35) benzotriazine fungicides such as triazoxide.

Embodiment B36

The composition described in the Summary of the Invention (including but not limited to composition of Embodiments 1 through 37 and A1 through A4) wherein component (b) includes at least one compound selected from (b36) benzene-sulfonamide fungicides such as flusulfamide.

Embodiment B37

The composition described in the Summary of the Invention (including but not limited to composition of Embodiments 1 through 37 and A1 through A4) wherein component (b) includes at least one compound selected from (b37) pyridazinone fungicides such as diclomezine.

Embodiment B38

The composition described in the Summary of the Invention (including but not limited to composition of Embodiments 1 through 37 and A1 through A4) wherein component (b) includes at least one compound selected from (b38) thiophene-carboxamide fungicides such as silthiofam.

Embodiment B39

The composition described in the Summary of the Invention (including but not limited to composition of Embodiments 1 through 37 and A1 through A4) wherein component (b) includes at least one compound selected from (b39) pyrimidinamide fungicides such as diflumetorim.

Embodiment B40

The composition described in the Summary of the Invention (including but not limited to composition of Embodiments 1 through 37 and A1 through A4) wherein component (b) includes at least one compound selected from (b40) carboxylic acid amide fungicides such as dimethomorph, benthiavalicarb, benthiavalicarb-isopropyl, iprovalicarb, valiphenal, mandipropamid and flumorph.

Embodiment B41

The composition described in the Summary of the Invention (including but not limited to composition of Embodiments 1 through 37 and A1 through A4) wherein component (b) includes at least one compound selected from (b41) tetracycline antibiotic fungicides such as oxytetracycline.

Embodiment B42

The composition described in the Summary of the Invention (including but not limited to composition of Embodiments 1 through 37 and A1 through A4) wherein component (b) includes at least one compound selected from (b42) thiocarbamate fungicides such as methasulfocarb.

Embodiment B43

The composition described in the Summary of the Invention (including but not limited to composition of Embodiments 1 through 37 and A1 through A4) wherein component (b) includes at least one compound selected from (b43) benzamide fungicides such as fluopicolide and fluopyram.

Embodiment B44

The composition described in the Summary of the Invention (including but not limited to composition of Embodiments 1 through 37 and A1 through A4) wherein component (b) includes at least one compound selected from (b44) host plant defense induction fungicides such as acibenzolar-S-methyl.

Embodiment B45

The composition described in the Summary of the Invention (including but not limited to composition of Embodiments 1 through 37 and A1 through A4) wherein component (b) includes at least one compound selected from (b45) multi-site contact fungicides such as copper oxychloride, copper sulfate, copper hydroxide, Bordeaux composition (tribasic copper sulfide), elemental sulfur, mancozeb, metiram, propineb, ferbam, maneb, thiram, zineb, ziram, folpet, captan, captafol and chlorothalonil.

Embodiment B46

The composition described in the Summary of the Invention (including but not limited to composition of Embodiments 1 through 37 and A1 through A4) wherein component (b) includes at least one compound selected from (b46) fungicides other than fungicides of component (a) and components (b1) through (b45) such as ethaboxam, cyflufenamid, proquinazid, metrafenone, 5-chloro-6-(2,4,6-trifluorophenyl)-7-(4-methylpiperidin-1-yl)[1,2,4]triazolo[1,5-a]pyrimidine (BAS600), 2-butoxy-6-iodo-3-propyl-4H-1-benzopyran-4-one, 3-[5-(4-chlorophenyl)-2,3-dimethyl-3-isoxazolidinyl]pyridine (SYP-Z048), 4-fluorophenyl N-[1-[[[1-(4-cyanophenyl)ethyl]sulfonyl]methyl]propyl] carbamate (XR-539), N-[[(cyclopropylmethoxy)amino][6-(difluoromethoxy)-2,3-difluorophenyl]methylene] benzeneacetamide, N'-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene] acetonitrile (OK-5203) and N-(4-chloro-2-nitrophenyl)-N-ethyl-4-methylbenzenesulfonamide (TF-991).

The following TESTS demonstrate the control efficacy of compounds of this invention on specific pathogens. The pathogen control protection afforded by the compounds is not limited, however, to these species See Index Tables A-C for compound descriptions. See Index Table D for $^1$H NMR data. The following abbreviations are used in the Index Tables A-C which follow: Cmpd means Compound, Me is methyl, Et is ethyl, Pr is propyl, Bu is butyl, c-Pr is cyclopropyl, i-Pr is isopropyl, c-Pn is cyclopentyl, t-Bu is tertiary-butyl, Ph is phenyl, OMe is methoxy, CN is cyano and $NO_2$ is nitro. (R) or (S) denotes the absolute chirality of the asymmetric carbon center. The abbreviation "Ex." stands for "Example" and is followed by a number indicating in which example the compound is prepared.

INDEX TABLE A

| Cmpd | R¹ | G | m.p. (° C.) |
|---|---|---|---|
| 1 (Ex. 1) | CH(CH₃)CH₂OCH₃ | 3-Cl—Ph | ** |
| 2 | CH(CH₃)CH₂OCH₃ | 3-F—Ph | * |
| 3 | 4-tetrahydropyranyl | 3-F—Ph | * |
| 4 (Ex. 2) | 4-tetrahydropyranyl | 3-Cl—Ph | ** |
| 5 | (S)—CH(CH₃)CH₂OCH₃ | 3-F—Ph | * |
| 6 | C(CH₃)₂CH₂OCH₃ | 3-F—Ph | * |
| 7 | CH(CH₃)CH₂OH | 3-F—Ph | * |
| 8 | CH(CH₃)CH₂OC(=O)CH₃ | 3-F—Ph | * |
| 9 | c-Pr | 3-F—Ph | * |
| 10 | t-Bu | 3-F—Ph | * |
| 11 | (S)—CH(CH₃)CH₂OCH₃ | 3-Br—Ph | * |
| 12 | (S)—CH(CH₃)CH₂OCH₃ | 3-I—Ph | * |
| 13 | (S)—CH(CH₃)CH₂OCH₃ | 4-F—Ph | * |
| 14 | (S)—CH(CH₃)CH₂OCH₃ | 3,4-di-Cl—Ph | * |
| 15 | (S)—CH(CH₃)CH₂OCH₃ | 4-Cl—Ph | * |
| 16 | (S)—CH(CH₃)CH₂OCH₃ | 3-Cl—Ph | * |
| 17 | (S)—CH(CH₃)CH₂OCH₃ | 2-F—Ph | * |
| 18 | (S)—CH(CH₃)CH₂OCH₃ | 3-CN—Ph | * |
| 19 | (S)—CH(CH₃)CH₂OCH₃ | 3-Me—Ph | * |

INDEX TABLE A-continued

| Cmpd | R¹ | G | m.p. (° C.) |
|---|---|---|---|
| 20 | (S)—CH(CH₃)CH₂OCH₃ | 4-Me—Ph | * |
| 21 | (S)—CH(CH₃)CH₂OCH₃ | 3-NO₂—Ph | * |
| 22 | (S)—CH(CH₃)CH₂OCH₃ | 3,5-di-F—Ph | * |
| 23 | (S)—CH(CH₃)CH₂OCH₃ | 3-Cl-4-F—Ph | * |
| 24 | (S)—CH(CH₃)CH₂OCH₃ | 3,4-di-Me—Ph | * |
| 25 | (S)—CH(CH₃)CH₂OCH₃ | 3-F-4-Me—Ph | * |
| 26 | (S)—CH(CH₃)CH₂OCH₃ | 4-Me-3-NO₂—Ph | * |
| 27 | (S)—CH(CH₃)CH₂OCH₃ | 2-Cl-4-pyridinyl | * |
| 28 | (S)—CH(CH₃)CH₂OCH₃ | 3,5-di-Cl—Ph | * |
| 29 | (S)—CH(CH₃)CH₂OCH₃ | 3,4-di-F—Ph | * |
| 30 | C(CH₃)₂CH₂OCH₃ | 3,5-di-F—Ph | * |
| 31 | (S)—CH(CH₃)CH₂OCH₃ | 2-F-4-pyridinyl | * |
| 32 | C(CH₃)₂OCH₃ | 3,5-di-F—Ph | * |
| 33 | t-Bu | 3,5-di-F—Ph | * |
| 34 | 4-tetrahydropyranyl | 3,5-di-F—Ph | * |
| 35 | (S)—CH(CH₃)CH₂OCH₃ | 5-F-3-pyridinyl | * |
| 36 | (S)—CH(CH₃)CH₂OCH₃ | 3-CN-5-F—Ph | * |
| 37 (Ex. 3) | (S)—CH(CH₃)CH₂OCH₃ | 2-CN-5-pyridinyl | ** |
| 38 | (S)—CH(CH₃)CH₂OCH₃ | 2-Cl-pyridinyl | * |
| 39 (Ex. 4) | (S)—CH(CH₃)CH₂OCH₃ | 3-F-5-NO₂—Ph | ** |

* See Index Table D for ¹H NMR data.
** See synthesis example for ¹H NMR data.

INDEX TABLE B

| Cmpd | R¹ | G | m.p. (° C.) |
|---|---|---|---|
| 40 | CH(CH₃)CH₂OCH₃ | 3-Cl—Ph | * |
| 41 | CH(CH₃)CH₂OCH₃ | 3-F—Ph | * |
| 42 | CH(CH₃)CH₂OCH₃ | 3-CN—Ph | * |
| 43 | CH(CH₃)CH₂OCH₃ | Ph | * |
| 44 | CH(CH₃)CH₂OCH₃ | 3-NO₂—Ph | * |
| 45 | t-Bu | 3-F—Ph | * |
| 46 | CH(CH₃)CH₂OCH₃ | 2-F-3-Cl—Ph | * |
| 47 | CH(CH₃)CH₂OCH₃ | 2,4-di-F—Ph | * |
| 48 | CH(CH₃)CH₂OH | 3-F—Ph | * |
| 49 | CH(CH₃)CH₂OCH₃ | 2,6-di-F—Ph | * |
| 50 | CH(CH₃)CH₂OCH₃ | 4-F—Ph | * |
| 51 | CH(CH₃)CH₂OCH₃ | 3-Me—Ph | * |
| 52 | CH(CH₃)CH₂OCH₃ | 3-MeOC(=O)—Ph | * |
| 53 | CH(CH₃)CH₂OCH₃ | 2-F—Ph | * |
| 54 | CH(CH₃)CH₂OCH₃ | 2-Cl-4-pyridinyl | * |
| 55 | CH₂CH₂SCH₃ | 3-F—Ph | * |
| 56 | (S)—CH(CH₃)CH₂OCH₃ | 3-F—Ph | * |
| 57 | (R)—CH(CH₃)CH₂OH | 3-F—Ph | * |
| 58 | CH₂CH₂OCH₃ | 3-F—Ph | * |
| 59 | CH(CH₃)CH₂CH₂CH₃ | 3-F—Ph | * |
| 60 | i-Pr | 3-F—Ph | * |
| 61 | Et | 3-F—Ph | * |
| 62 (Ex. 9) | c-Pn | 3-F—Ph | ** |
| 63 | CH(CH₃)CH₂OCH₃ | 4-CN—Ph | * |

INDEX TABLE B-continued

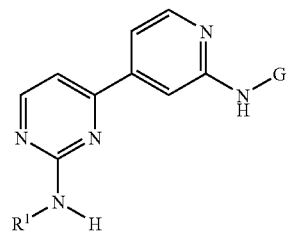

| Cmpd | R$^1$ | G | m.p. (° C.) |
|---|---|---|---|
| 64 | CH$_2$CH$_2$CH$_2$OCH$_3$ | 3-F—Ph | * |
| 65 | c-Pr | 3-F—Ph | * |
| 66 | NHCH$_2$CH$_3$ | 3-F—Ph | * |
| 67 (Ex. 10) | 4-tetrahydropyranyl | 3-F—Ph | ** |
| 68 | (R)—CH(CH$_3$)CH$_2$OCH$_3$ | 3-F—Ph | * |
| 69 (Ex. 11) | 4-tetrahydropyranyl | 3-Cl—Ph | ** |
| 70 | CH(CH$_3$)CH$_2$OCH$_3$ | 2,3,6-tri-F—Ph | * |
| 71 | (S)-3-tetrahydrofuranyl | 3-F—Ph | * |
| 72 | (S)-3-tetrahydrofuranyl | 3-Cl—Ph | * |
| 73 | 4-tetrahydropyranyl | 2,3,6-tri-F—Ph | * |
| 74 | 3-tetrahydrofuranyl | 3-F—Ph | * |
| 75 | 3-tetrahydropyranyl | 3-F—Ph | * |
| 76 (Ex. 6) | CH(CH$_3$)CH$_2$OCH$_3$ | 2-Cl-6-Me—Ph | ** |
| 77 | CH(CH$_3$)CH$_2$OCH$_3$ | 2,6-di-Me—Ph | * |
| 78 | CH(CH$_3$)CH$_2$OCH$_3$ | 2,6,-di-Cl—Ph | * |
| 79 | CH(CH$_3$)CH$_2$OCH$_3$ | 2-Cl-6-F—Ph | * |
| 80 | 4-tetrahydropyranyl | 2-Cl-6-Me—Ph | * |
| 81 | 4-tetrahydropyranyl | 2,6-di-Cl—Ph | * |
| 82 (Ex. 15) | tetrahydrofuran-3-yl-methyl | 3-F—Ph | ** |
| 83 (Ex. 16) | tetrahydrofuran-2-yl-methyl | 3-F—Ph | ** |
| 84 (Ex. 18) | CH(CH$_3$)CH$_2$CH$_2$OCH$_3$ | 3-F—Ph | ** |
| 85 | CH(CH$_3$)CH$_2$OCH$_3$ | 2-MeO-6-Me—Ph | * |
| 86 | CH(CH$_3$)CH$_2$OCH$_3$ | 2-Me-1-naphthalenyl | * |
| 87 | CH(CH$_3$)CH$_2$OCH$_3$ | 2-Cl-4,6-di-Me—Ph | * |
| 88 | 4-tetrahydropyranyl | 2-MeO-6-Me—Ph | * |
| 89 | 4-tetrahydropyranyl | 2-Me-1-naphthalenyl | * |
| 90 | 4-tetrahydropyranyl | 2-Cl-4,6-di-Me—Ph | * |
| 91 | CH(CH$_3$)CH$_2$OCH$_3$ | 2-Me-5-F—Ph | * |
| 92 | CH(CH$_3$)CH$_2$OCH$_3$ | 5-Cl-2,6-di-Me—Ph | * |
| 93 | CH(CH$_3$)CH$_2$OCH$_3$ | 2,4-di-Cl-6-Me—Ph | * |
| 94 (Ex. 7) | CH(CH$_3$)CH$_2$SCH$_3$ | 3-F—Ph | ** |
| 95 (Ex. 8) | CH(CH$_3$)CH$_2$SCH$_3$ | 3-Cl—Ph | ** |
| 96 (Ex. 17) | CH$_2$CH(CH$_3$)OCH$_3$ | 3-F—Ph | ** |
| 97 | CH(CH$_3$)CH$_2$OCH$_3$ | 2-Cl-6-CF$_3$—Ph | * |
| 98 | 4-tetrahydropyranyl | 2-Cl-6-CF$_3$—Ph | * |
| 99 | 4-tetrahydropyranyl | 2,4,6-tri-Cl—Ph | * |
| 100 | 4-tetrahydropyranyl | 2,4,-di-Cl-6-Me—Ph | * |
| 101 (Ex. 12) | 4-tetrahydropyranyl | 2-Cl—Ph | ** |
| 102 (Ex. 14) | 4-tetrahydropyranyl | 2-Cl-4-Me—Ph | ** |
| 103 (Ex. 13) | 4-tetrahydropyranyl | 2-Me-4-Cl—Ph | ** |

\* See Index Table D for $^1$H NMR data.

\*\* See synthesis example for $^1$H NMR data.

INDEX TABLE C

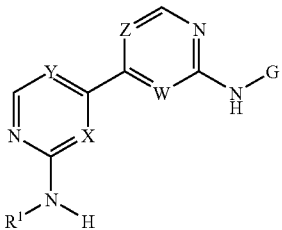

| Cmpd | X | Y | W | Z | R¹ | G | m.p. (° C.) |
|---|---|---|---|---|---|---|---|
| 104 (Ex. 5) | N | N | N | CH | 4-tetrahydropyranyl | 2-Cl-6-Me—Ph | ** |
| 105 (Ex. 19) | CH | N | N | CH | CH(CH₃)CH₂OCH₃ | 3-Cl—Ph | ** |
| 106 (Ex. 20) | CH | N | N | CH | CH(CH₃)CH₂OCH₃ | 3-F—Ph | ** |
| 107 (Ex. 21) | CH | N | N | CH | CH(CH₃)CH₂OCH₃ | 3-NO₂—Ph | ** |
| 108 (Ex. 22) | CH | N | N | CH | CH(CH₃)CH₂OCH₃ | Ph | ** |
| 109 (Ex. 24) | N | CH | CH | N | CH(CH₃)CH₂OCH₃ | 3-F—Ph | ** |
| 110 (Ex. 23) | CH | N | N | CH | CH(CH₃)CH₂OCH₃ | 2-Cl-6-Me—Ph | ** |

** See synthesis example for $^1$H NMR data.

INDEX TABLE D

| Cmpd | $^1$H NMR data (CDCl₃ solution unless indicated otherwise)$^a$ |
|---|---|
| 2 | δ 8.97 (s, 1H), 8.54 (d, 1H), 8.15 (br s, 1H), 7.71 (br s, 1H), 7.54 (d, 1H), 7.30 (m, 2H), 6.84 (m, 1H), 5.85 (br s, 1H), 4.36 (br s, 1H), 3.48 (m, 2H), 3.37 (s, 3H), 1.30 (d, 3H). |
| 3 | δ 8.94 (s, 1H), 8.56 (d, 1H), 7.75 (br s, 2H), 7.58 (d, 1H), 7.33 (m, 1H), 7.23 (m, 1H), 6.85 (m, 1H), 5.47 (br s, 1H), 4.16 (br s, 1H), 4.00 (m, 2H), 3.57 (m, 2H), 2.05 (m, 2H), 1.59 (m, 2H). |
| 5 | δ 8.97 (s, 1H), 8.54 (d, 1H), 8.15 (br s, 1H), 7.71 (br s, 1H), 7.54 (d, 1H), 7.30 (m, 2H), 6.84 (m, 1H), 5.85 (br s, 1H), 4.36 (br s, 1H), 3.48 (m, 2H), 3.37 (s, 3H), 1.30 (d, 3H). |
| 6 | δ 8.92 (s, 1H), 8.56 (d, 1H), 7.81 (br s, 1H), 7.71 (br s, 1H), 7.55 (d, 1H), 7.35 (m, 2H), 6.85 (m, 1H), 5.78 (s, 1H), 3.52 (s, 2H), 3.36 (s, 3H), 1.48 (s, 6H). |
| 7 | δ 8.90 (s, 1H), 8.53 (d, 1H), 8.25 (br s, 1H), 7.69 (br s, 1H), 7.62 (s, 1H), 7.30 (m, 2H), 6.83 (m, 1H), 5.64 (br s, 1H0, 3.80 (m, 1H), 3.71 (br s, 1H), 3.50 (m, 2H), 1.23 (d, 3H). |
| 8 | δ 8.93 (s, 1H), 8.55 (d, 1H), 7.88 (br s, 1H), 7.72 (br s, 1H), 7.60 (d, 1H), 7.30 (m, 2H), 6.86 (t, 1H), 5.58 (br s, 1H), 4.50 (br s, 1H), 4.20 (s, 2H), 2.06 (s, 3H), 1.30 (d, 3H) |
| 9 | δ 8.94 (s, 1H), 8.56 (d, 1H), 7.75 (br s, 2H), 7.58 (d, 1H), 7.32 (m, 1H), 7.25 (m, 1H), 6.87 (t, 1H), 5.46 (br s, 1H), 4.16 (br s, 1H), 4.00 (m, 1H), 3.57 (m, 1H), 2.07 (m, 1H), 1.59 (m, 1H) |
| 10 | δ 8.92 (s, 1H), 8.53 (d, 1H), 7.83 (br s, 1H), 7.20 (br s, 1H), 7.54 (d, 1H), 7.32 (m, 2H), 6.86 (t, 1H), 5.56 (br s, 1H), 1.48 (s, 9H). |
| 11 | δ 8.96 (s, 1H), 8.54 (d, 1H), 8.10 (br s, 1H), 8.01 (br s, 1H), 7.54 (d, 1H), 7.48 (br s, 1H) 7.23 (m, 2H), 5.85 (br s, 1H), 4.35 (br s, 1H), 3.45 (m, 2H), 3.37 (s, 3H), 1.28 (d, 3H). |
| 12 | δ 8.96 (s, 1H), 8.54 (d, 1H), 8.16 (br s, 1H), 7.54 (d, 2H), 7.45 (d, 1H) 7.07 (t, 1H), 5.88 (br s, 1H), 4.35 (br s, 1H), 3.46 (m, 2H), 3.37 (s, 3H), 1.28 (d, 3H). |
| 13 | δ 8.89 (s, 1H), 8.52 (d, 1H), 8.38 (br s, 1H), 8.03 (br s, 1H), 7.57 (d, 2H), 7.06 (t, 2H), 5.85 (br s, 1H), 4.34 (br s, 1H), 3.47 (m, 2H), 3.36 (s, 3H), 1.28 (d, 3H). |
| 14 | δ 8.98 (s, 1H), 8.54 (d, 1H), 8.11 (br s, 1H), 7.99 (s, 1H), 7.55 (d, 1H), 7.42 (m, 2H), 5.81 (br s, 1H), 4.36 (br s, 1H), 3.47 (m, 2H), 3.37 (s, 3H), 1.28 (d, 3H). |
| 15 | δ 8.93 (s, 1H), 8.53 (d, 1H), 7.94 (br s, 1H), 7.60 (br s, 2H), 7.52 (d, 2H), 7.36 (m, 2H), 5.78 (br s, 1H), 4.34 (br s, 1H), 3.47 (m, 2H), 3.36 (s, 3H), 1.28 (d, 3H). |
| 16 | δ 8.96 (s, 1H), 8.53 (d, 1H), 8.11 (br s, 1H), 7.87 (br s, 1H), 7.55 (d, 1H), 7.45 (d, 1H), 7.27 (t, 1H), 7.11 (d, 1H), 5.83 (br s, 1H), 4.36 (br s, 1H), 3.47 (m, 2H), 3.37 (s, 3H), 1.28 (d, 3H). |
| 17 | δ 8.94 (s, 1H), 8.54d, 1H), 8.38 (br s, 1H), 7.90 (br s, 1H), 7.23 (m, 1H), 7.13 (m, 2H), 5.75 (br s, 1H), 4.35 (br s, 1H), 3.48 (m, 2H), 3.36 (s, 3H), 1.28 (d, 3H). |
| 18 | δ 9.00 (s, 1H), 8.55 (d, 1H), 8.25 (br s, 2H), 7.79 (br s, 1H), 7.55 (d, 1H), 7.45 (m, 2H), 5.82 (br s, 1H), 4.36 (br s, 1H), 3.49 (m, 2H), 3.38 (s, 3H), 1.28 (d, 3H). |
| 19 | δ 8.90 (s, 1H), 8.53 (d, 1H), 7.77 (br s, 1H), 7.56 (br s, 2H), 7.43 (br s, 1H), 7.41 (s, 1H), 7.27 (m, 1H), 6.99 (d, 1H), 5.74 (br s, 1H), 4.35 (br s, 1H), 3.48 (m, 2H), 3.38 (s, 3H), 2.39 (s, 3H), 1.28 (d, 3H). |
| 20 | δ 8.88 (s, 1H), 8.52 (d, 1H), 7.97 (br s, 1H), 7.53 (br s, 1H), 7.48 (br s, 2H), 7.18 (m, 2H), 5.81 (br s, 1H), 4.35 (br s, 1H), 3.48 (m, 2H), 3.36 (s, 3H), 2.31 (s, 3H), 1.28 (d, 3H). |
| 21 | δ 9.02 (s, 1H), 8.05 (br s, 1H), 8.56 (d, 1H), 8.44 (br s, 1H), 7.98 (dd, 1H), 7.84 (br s, 1H), 7.60 (s, 1H), 7.52 (t, 1H), 5.84 (br s, 1H), 4.36 (br s, 1H), 3.48 (m, 2H), 3.38 (s, 3H), 1.29 (d, 3H). |
| 22 | δ 8.98 (s, 1H), 8.56 (d, 1H), 7.79 (s, 1H), 7.57 (d, 1H), 7.35 (br s, 2H), 6.60 (m, 1H), 5.74 (br s, 1H), 4.37 (br s, 1H), 3.47 (m, 2H), 3.36 (s, 3H), 1.29 (d, 3H). |
| 23 | δ 8.98 (s, 1H), 8.56 (d, 1H), 7.80 (s, 1H), 7.57 (br s, 1H), 7.55 (br s, 2H), 7.47 (s, 1H), 6.87 (dt, 1H), 5.74 (br s, 1H), 4.35 (br s, 1H), 3.47 (m, 2H), 3.36 (s, 3H), 1.29 (d, 3H). |
| 24 | δ 8.87 (s, 1H), 8.54 (d, 1H), 7.87 (s, 1H), 7.55 (d, 1H), 7.45 (br s, 1H), 7.34 (s, 1H), 7.15 (d, 1H), 5.95 (br s, 1H), 4.35 (br s, 1H), 3.47 (m, 2H), 3.36 (s, 3H), 1.29 (d, 3H). |
| 25 | δ 8.93 (s, 1H), 8.54 (d, 1H), 7.87 (br s, 1H), 7.61 (br s, 1H), 7.55 (d, 1H), 7.14 (m, 2H), 5.79 (br s, 1H), 4.35 (br s, 1H), 3.47 (m, 2H), 3.36 (s, 3H), 1.29 (d, 3H). |

INDEX TABLE D-continued

| Cmpd | ¹H NMR data (CDCl₃ solution unless indicated otherwise)ᵃ |
|---|---|
| 26 | δ 8.98 (s, 1H), 8.84 (br s, 1H), 8.54 (d, 1H), 8.31 (br s, 1H), 7.66 (br s, 1H), 7.55 (d, 1H), 7.31 (d, 1H), 5.84 (br s, 1H), 4.35 (br s, 1H), 3.47 (m, 2H), 3.36 (s, 3H), 1.29 (d, 3H). |
| 27 | δ 9.07 (s, 1H), 8.64 (br s, 1H), 8.57 (d, 1H), 8.32 (d, 1H), 7.99 (br s, 1H), 7.57 (d, 1H), 7.54 (d, 1H), 5.80 (d, 1H), 4.39 (br s, 1H), 3.49 (m, 2H), 3.36 (s, 3H), 1.31 (d, 3H). |
| 28 | δ 8.99 (s, 1H), 8.57 (d, 1H), 8.05 (br s, 1H), 7.67 (br s, 2H), 7.54 (d, 1H), 7.31 (s, 1H), 5.78 (br s, 1H), 4.36 (br s, 1H), 3.47 (m, 2H), 3.36 (s, 3H), 1.29 (d, 3H). |
| 29 | δ 8.94 (s, 1H), 8.55 (d, 1H), 7.77 (br s, 2H), 7.55 (d, 1H), 7.15 (m, 2H), 5.73 (br s, 1H), 4.36 (br s, 1H), 3.48 (m, 2H), 3.37 (s, 3H), 1.29 (d, 3H). |
| 30 | δ 8.95 (s, 1H), 8.52 (d, 1H), 7.79 (br s, 1H), 7.54 (d, 1H), 7.36 (br s, 2H), 6.60 (m, 1H), 5.82 (s, 1H), 3.52 (s, 2H), 3.36 (s, 3H), 1.48 (d, 6H). |
| 31 | δ 9.07 (s, 1H), 8.57 (d, 1H), 8.41 (s, 1H), 8.16 (d, 1H), 7.70 (br s, 1H), 7.58 (d, 1H), 7.36 (d, 2H), 6.98 (s, 1H), 5.78 (d, 1H), 4.39 (br s, 1H), 3.49 (m, 2H), 3.39 (s, 3H), 1.30 (d, 3H). |
| 32 | δ 8.96 (s, 1H), 8.56 (d, 1H), 8.14 (s, 1H), 7.57 (d, 1H), 7.36 (br s, 2H), 6.60 (t, 1H), 5.70 (br s, 1H), 4.26 (br s, 1H), 3.37 (s, 3H), 1.23 (s, 6H). |
| 33 | δ 8.95 (s, 1H), 8.54 (d, 1H), 7.69 (br s, 1H), 7.54 (d, 1H), 7.33 (d, 2H), 6.59 (t, 1H), 5.54 (s, 1H), 1.49 (s, 9H). |
| 34 | δ 8.96 (s, 1H), 8.57 (d, 1H), 7.71 (s, 1H), 7.60 (d, 1H), 7.35 (br s, 2H), 6.60 (t, 1H), 5.45 (br s, 1H), 4.16 (br s, 1H), 4.00 (m, 2H), 3.57 (m, 2H), 2.05 (m, 2H), 1.59 (m, 2H) |
| 35 | δ 9.08 (s, 1H), 8.56 (d, 1H), 8.37 (br s, 3H), 8.29 (s, 1H), 7.56 (d, 1H), 5.84 (s, 1H), 4.38 (s, 1H), 3.50 (d, 2H), 3.39 (s, 3H), 1.30 (d, 3H). |
| 36 | δ 9.00 (s, 1H), 8.57 (d, 1H), 7.88 (br s, 1H), 7.82 (s, 1H), 7.70 (s, 1H), 7.58 (d, 1H), 7.14 (d, 1H), 5.70 (s, 1H), 4.37 (s, 1H), 3.49 (d, 2H), 3.38 (s, 3H), 1.30 (d, 3H). |
| 38 | δ 9.00 (s, 1H), 8.68 (s, 1H), 8.54 (d, 1H), 8.22 (s, 1H), 8.14 (s, 1H), 7.54 (s, 1H), 7.38 (d, 1H), 5.86 (s, 1H), 4.36 (m, 1H), 3.49 (m, 2H), 3.39 (s, 3H), 1.30 (d, 3H). |
| 40 | δ 8.4 (d, 1H), 8.3 (d, 1H), 7.58 (s, 1H), 7.5 (s, 1H), 7.3 (d, 1H), ) 7.2 (1H), 7.0 (m, 1H), 6.9 (d, 1H), 6.6 (s, 1H), 5.4 (d, 1H), 4.3 (m, 1H), 3.48 (d, 2H), 3.89 (s, 3H), 1.3 (d, 3H). |
| 41 | δ 8.39 (d, 1H), 8.34 (d, 1H), 7.53 (s, 1H), 7.33 (d, 1H), 7.24 (m, 2H), 7.10 (d, 1H), 6.92 (d, 1H), 6.82 (s, 1H), 6.71 (t, 1H), 5.42 (d, 1H), 4.34 (m, 1H), 3.48 (d, 2H), 3.39 (s, 3H), 1.30 (d, 3H). |
| 42 | (DMSO-d₆) δ 9.67 (s, 1H), 8.44 (d, 1H), 8.35 (m, 2H), 7.88 (d, 1H), 7.55 (s, 1H), 7.48 (t, 1H), 7.41 (d, 1H), 7.32 (d, 1H), 7.11 (d, 2H), 4.31 (br s, 1H), 3.47 (m, 1H), 3.32 (m, 1H), 3.28 (s, 3H), 1.19 (d, 3H). |
| 43 | δ 8.36 (d, 1H), 8.28 (d, 1H), 7.54 (s, 1H), 7.36 (d, 5H), 7.24 (m, 1H), 7.06 (d, 1H), 6.88 (d, 1H), 6.71 (t, 1H), 5.42 (d, 1H), 4.30 (m, 1H), 3.47 (d, 2H), 3.36 (s, 3H), 1.28 (d, 3H). |
| 44 | (acetone-d₆) δ 8.96 (m, 2H), 8.42 (m, 2H), 8.06 (d, 1H), 7.77 (d, 1H), 7.64 (s, 1H), 7.55 (t, 1H), 7.49 (d, 1H), 7.13 (d, 1H), 6.18 (br s, 1H), 4.38 (m, 1H), 3.55 (m, 1H), 3.44 (m, 1H), 3.35 (s, 3H), 1.29 (d, 3H). |
| 45 | δ 8.33 (m, 2H), 7.64 (s, 1H), 7.48 (s, 1H), 7.28 (, 3H), 7.09 (m, 1H) 6.89 (d, 1H), 6.73 (t, 1H), 5.43 (s, 1H), 1.48 (s, 9H). |
| 46 | δ 8.39 (d, 1H), 8.34 (d, 1H), 8.07 (t, 1H), 7.47 (s, 1H), 7.32 (d, 1H), 7.04 (m, 3H), 6.93 (d, 1H), 5.57 (d, 1H), 4.33 (m, 1H), 3.48 (d, 2H), 3.39 (s, 3H), 1.30 (d, 3H) |
| 47 | 8.38 (d, 1H), 8.29 (d, 1H), 7.98 (m, 1H), 7.35 (s, 1H), 7.27 (d, 1H), 6.91 (m, 4H), 5.57 (d, 1H), 4.35 (m, 1H), 3.48 (d, 2H), 3.39 (s, 3H), 1.30 (d, 3H). |
| 48 | δ 8.33 (d, 1H), 8.29 (d, 1H), 7.45 (s, 2H), 7.35 (d, 1H), 7.20 (m, 2H), 7.08 (d, 1H), 6.71 (t, 1H), 5.63 (d, 1H), 4.22 (m, 1H), 3.76 (d, 1H), 3.65 (m, 1H), 1.25 (d, 3H). |
| 49 | δ 8.36 (d, 1H), 8.28 (d, 1H), 7.32 (d, 1H), 7.14 (m, 2H), 7.03 (t, 2H), 6.90 (d, 1H), 6.61 (s, 1H), 5.46 (d, 1H), 4.30 (m, 1H), 3.47 (d, 2H), 3.36 (s, 3H), 1.28 (d, 3H). |
| 50 | δ 8.35 (d, 1H), 8.27 (d, 1H), 7.36 (d, 3H), 7.24 (m, 1H), 7.05 (d, 2H), 6.92 (s, 1H), 6.88 (d, 1H), 5.42 (d, 1H), 4.30 (m, 1H), 3.47 (d, 2H), 3.36 (s, 3H), 1.28 (d, 3H). |
| 51 | δ 8.35 (d, 1H), 8.29 (d, 1H), 7.52 (s, 1H), 7.20 (m, 4H), 6.89 (d, 1H), 6.88 (s, 1H), 6.80 (s, 1H), 5.45 (d, 1H), 4.30 (m, 1H), 3.47 (d, 2H), 3.36 (s, 3H), 1.28 (d, 3H). |
| 52 | δ 8.38 (d, 1H), 8.35 (d, 1H), 8.05 (s, 1H), 7.73 (d, 2H), 7.49 (s, 1H), 7.42 (t, 1H), 7.31 (d, 1H), 6.93 (d, 1H), 6.76 (s, 1H), 5.39 (d, 1H), 4.30 (m, 1H), 3.47 (d, 2H), 3.36 (s, 3H), 1.28 (d, 3H). |
| 53 | δ 8.37 (d, 1H), 8.33 (d, 1H), 8.09 (t, 1H), 7.46 (s, 1H), 7.30 (t, 1H), 7.14 (m, 2H), 6.99 (m, 1H), 6.93 (d, 1H), 6.85 (s, 1H), 5.49 (d, 1H), 4.30 (m, 1H), 3.47 (d, 2H), 3.36 (s, 3H), 1.28 (d, 3H). |
| 54 | δ 8.42 (d, 1H), 8.36 (d, 1H), 8.11 (d, 1H), 7.73 (d, 1H), 7.49 (s, 1H), 7.49 (s, 1H), 7.41 (d, 1H), 7.23 (d, 1H), 6.86 (d, 1H), 6.73 (d, 1H), 5.49 (d, 1H), 4.35 (m, 1H), 3.47 (d, 2H), 3.38 (s, 3H), 1.30 (d, 3H). |
| 55 | δ 8.41 (d, 1H), 8.35 (d, 1H), 7.52 (s, 1H), 7.36 (m, 1H), 7.30 (m, 1H), 7.25 (m, 1H), 7.08 (d, 1H), 6.97 (d, 1H), 6.78 (s, 1H), 6.72 (t, 1H), 5.63 (m, 1H), 3.73 (m, 2H), 2.81 (t, 2H), 2.15 (s, 3H) |
| 56 | δ 8.39 (d, 1H), 8.34 (d, 1H), 7.53 (s, 1H), 7.33 (d, 1H), 7.24 (m, 2H), 7.10 (d, 1H), 6.92 (d, 1H), 6.82 (s, 1H), 6.71 (t, 1H), 5.42 (d, 1H), 4.34 (m, 1H), 3.48 (d, 2H), 3.39 (s, 3H), 1.30 (d, 3H). |
| 57 | (DMSO-d₆) δ 9.54 (s, 1H), 8.43 (d, 1H), 8.34 (d, 2H), 7.89 (d, 1H), 7.54 (s, 1H), 7.38 (m, 2H), 7.30 (m, 1H), 7.11 (d, 2H), 6.96 (t, 1H), 4.75 (d, 1H), 3.86 (m, 1H), 3.34 (m 1H) 1.10 (d, 3H). |
| 58 | δ 8.39 (d, 1H), 8.33 (d, 1H), 7.53 (s, 1H), 7.28 (m, 4H), 7.09 (d, 1H), 6.93 (d, 1H), 6.72 (t, 1H), 5.81 (br s, 1H), 3.69 (m, 2H), 3.60 (m, 2H), 3.39 (s, 3H). |
| 59 | δ 8.37 (d, 1H), 8.33 (d, 1H), 7.56 (s, 1H), 7.28 (m, 4H), 7.07 (d, 1H), 6.89 (d, 1H), 6.73 (t, 1H), 5.28 (br s, 1H), 4.15 (m, 1H), 3.69 (m, 2H), 1.53 (m, 2H), 1.42 (m, 2H), 1.22 (d, 3H), 0.91 (t, 3H). |
| 60 | δ 8.38 (d, 1H), 8.33 (d, 1H), 7.56 (s, 1H), 7.28 (m, 3H), 7.07 (d, 1H), 7.03 (s, 1H), 6.91 (d, 1H), 6.73 (t, 1H), 5.20 (br s, 1H), 4.23 (m, 1H), 1.29 (d, 6H). |

INDEX TABLE D-continued

| Cmpd | ¹H NMR data (CDCl₃ solution unless indicated otherwise)[a] |
|---|---|
| 61 | (acetone-d₆) δ 8.68 (s, 1H), 8.40 (d, 1H), 8.36 (d, 1H), 7.96 (d, 1H), 7.62 (s, 1H), 7.43 (d, 1H), 7.36 (d, 1H), 7.27 (m 1H), 7.10 (d, 1H), 6.67 (t, 1H), 6.43 (s, 1H), 3.52 (m, 2H), 1.25 (t, 3H). |
| 63 | δ 8.38 (m, 2H), 7.68 (s, 1H), 7.60 (m, 5H), 7.37 (d, 1H), 6.93 (d, 1H), 5.67 (d, 1H), 4.36 (m, 1H), 3.48 (m, 2H), 3.38 (s, 3H), 1.31 (d, 3H) |
| 64 | δ 8.37 (d, 1H), 8.32 (d, 1H), 7.56 (s, 1H), 7.47 (s, 1H), 7.28 (m, 3H), 7.09 (d, 1H), 6.89 (d, 1H), 6.71 (t, 1H), 5.91 (br s, 1H), 3.59 (m, 2H), 3.49 (t, 2H), 3.34 (s, 3H), 1.91 (m, 2H). |
| 65 | (DMSO-d₆) δ 9.57 (s, 1H), 8.46 (s, 1H), 8.34 (d, 1H), 8.13 (s, 1H), 7.85 (d, 1H), 7.57 (s, 1H), 7.52 (s, 1H), 7.40 (m 2H), 7.30 (m, 2H), 7.15 (d, 1H), 6.71 (m, 1H), 2.82 (br s, 1H), 0.70 (m, 2H), 0.53 (s, 2H). |
| 66 | δ 8.39 (d, 1H), 8.33 (d, 1H), 7.54 (s, 1H), 7.31 (m, 3H), 7.09 (d, 1H), 6.92 (d, 1H), 6.90 (s, 1H), 6.73 (t, 1H), 5.28 (br s, 1H), 3.54 (m, 2H), 1.28 (t, 3H). |
| 68 | δ 8.39 (d, 1H), 8.33 (d, 1H), 7.54 (s, 1H), 7.39 (s, 1H), 7.33 (m, 3H), 7.09 (d, 1H), 6.90 (d, 1H), 6.73 (t, 1H), 5.67 (br s, 1H), 4.34 (m 1H), 3.48 (m, 2H), 3.37 (s, 3H), 1.29 (d, 3H). |
| 70 | δ 8.36 (d, 1H), 8.30 (d, 1H), 7.35 (d, 1H), 7.22 (s, 1H), 7.00 (m, 2H), 6.91 (d, 1H), 6.81 (s, 1H), 5.49 (br d, 1H), 4.29 (m 1H), 3.46 (d, 2H), 3.37 (s, 3H), 1.29 (d, 3H). |
| 71 | δ 8.41 (d, 1H), 8.36 (d, 1H), 7.57 (s, 1H), 7.30 (m, 4H), 7.09 (d, 1H), 6.97 (d, 1H), 6.73 (t, 1H), 5.92 (br s, 1H), 4.65 (m 1H), 3.99 (m, 2H), 3.87 (m, 1H), 3.79 (m, 1H), 2.33 (m, 1H), 1.93 (m, 1H). |
| 72 | δ 8.41 (d, 1H), 8.36 (d, 1H), 7.56 (s, 1H), 7.51 (s, 1H), 7.23 (m, 4H), 7.01 (m, 1H), 6.97 (d, 1H), 5.90 (br s, 1H), 4.67 (m 1H), 3.99 (m, 2H), 3.87 (m, 1H), 3.79 (m, 1H), 2.33 (m, 1H), 1.93 (m, 1H). |
| 73 | δ 8.39 (d, 1H), 8.32 (d, 1H), 7.33 (d, 1H), 7.21 (s, 1H), 6.99 (m, 2H), 6.95 (d, 1H), 6.45 (s, 1H), 5.19 (d, 1H), 4.11 (m, 1H), 4.02 (m, 2H), 3.53 (t, 2H), 2.05 (m, 2H), 1.55 (m, 2H). |
| 74 | δ 8.41 (d, 1H), 8.36 (d, 1H), 7.57 (s, 1H), 7.30 (m, 4H), 7.09 (d, 1H), 6.97 (d, 1H), 6.73 (t, 1H), 5.92 (br s, 1H), 4.65 (m 1H), 3.99 (m, 2H), 3.87 (m, 1H), 3.79 (m, 1H), 2.33 (m, 1H), 1.93 (m, 1H). |
| 75 | δ 8.38 (d, 1H), 8.34 (d, 1H), 7.54 (s, 2H), 7.32 (d, 1H), 7.25 (m, 2H), 7.11 (d, 1H), 6.93 (d, 1H), 6.73 (t, 1H), 5.82 (br s, 1H), 4.15 (m, 1H), 4.02 (d, 1H), 3.75 (m, 1H), 3.61 (m, 1H), 3.46 (m 1H), 2.00 (m, 1H), 1.82 (m, 1H), 1.68 (m, 2H). |
| 77 | δ 8.30 (d, 1H), 8.23 (d, 1H), 7.16 (m, 4H), 6.78 (d, 1H), 6.63 (s, 1H), 6.45 (s, 1H), 5.43 (d, 1H), 4.24 (m, 1H), 3.42 (m, 2H), 3.36 (s, 3H), 2.25 (s, 6H), 1.24 (d, 2H). |
| 78 | 8.33 (d, 1H), 8.30 (d, 1H), 7.43 (s, 1H), 7.42 (d, 2H), 7.15 (d, 1H), 6.97 (s, 1H), 6.86 (d, 1H), 6.85 (s, 1H), 5.52 (d, 1H), 4.27 (m, 1H), 3.46 (d, 2H), 3.36 (s, 3H), 1.27 (d, 2H). |
| 79 | 8.34 (d, 1H), 8.29 (d, 1H), 7.30 (m, 2H), 7.12 (m, 3H), 6.96 (s, 1H), 6.89 (d, 1H), 5.62 (d, 1H), 4.27 (m, 1H), 3.46 (d, 2H), 3.36 (s, 3H), 1.27 (d, 2H). |
| 80 | δ 8.34 (d, 1H), 8.31 (d, 1H), 7.37 (d, 1H), 7.16 (m, 3H), 6.88 (d, 1H), 6.81 (s, 1H), 6.49 (s, 1H), 5.18 (d, 1H), 4.05 (m, 1H), 3.97 (m, 2H), 3.47 (t, 2H), 2.30 (s, 3H), 2.00 (m, 2H), 1.52 (m, 2H). |
| 81 | δ 8.35 (d, 1H), 8.31 (d, 1H), 7.44 (d, 2H), 7.28 (m, 1H), 7.16 (t, 1H), 6.95 (s, 2H), 6.91 (d, 1H), 5.43 (d, 1H), 4.05 (m, 1H), 3.97 (m, 2H), 3.47 (t, 2H), 2.00 (m, 2H), 1.52 (m, 2H). |
| 85 | δ 8.32 (d, 1H), 8.25 (d, 1H), 7.21 (d, 1H), 7.15 (t, 1H), 6.92 (d, 1H), 6.81 (m, 3H), 6.46 (s, 1H), 5.39 (d, 1H), 4.25 (m, 1H), 3.78 (s, 3H), 3.44 (m, 2H), 3.36 (s, 3H), 2.26 (s, 3H), 1.28 (d, 3H). |
| 86 | δ 8.23 (d, 1H), 8.19 (d, 1H), 8.04 (m, 1H), 7.86 (m, 1H), 7.75 (d, 1H), 7.43 (m, 3H), 7.30 (s, 1H), 7.17 (d, 1H), 6.65 (d, 1H), 6.56 (s, 1H), 5.46 (br s, 1H), 4.06 (m, 1H), 3.34 (m, 2H), 3.29 (s, 3H), 2.44 (s, 3H), 1.13 (d, 3H). |
| 87 | δ 8.33 (d, 1H), 8.27 (d, 1H), 7.22 (d, 1H), 7.17 (s, 1H), 7.02 (s, 1H), 6.84 (d, 1H), 6.78 (s, 1H), 6.48 (s, 1H), 5.41 (d, 1H), 4.25 (m, 1H), 3.44 (d, 2H), 3.37 (s, 3H), 2.33 (s, 3H), 2.25 (s, 3H), 1.25 (d, 3H). |
| 88 | δ 8.32 (d, 1H), 8.26 (d, 1H), 7.17 (m, 2H), 6.92 (d, 1H), 6.84 (m, 3H), 6.55 (s, 1H), 5.36 (s, 1H), 4.05 (m, 1H), 3.98 (m, 2H), 3.78 (s, 3H), 3.49 (t, 2H), 2.26 (s, 3H), 1.98 (m, 2H), 1.52 (m, 2H). |
| 89 | δ 8.25 (d, 1H), 8.19 (d, 1H), 8.05 (m, 1H), 7.87 (m, 1H), 7.78 (d, 1H), 7.46 (m, 3H), 7.38 (s, 1H), 7.13 (d, 1H), 6.71 (d, 1H), 6.57 (s, 1H), 5.42 (s, 1H), 4.06 (m, 1H), 3.90 (m, 3H), 3.33 (m, 2H), 2.43 (s, 3H), 1.83 (m, 2H), 1.42 (m, 2H). |
| 90 | δ 8.33 (d, 1H), 8.27 (d, 1H), 7.19 (m, 2H), 7.02 (s, 1H), 6.87 (d, 1H), 6.78 (s, 1H), 6.61 (s, 1H), 5.35 (d, 1H), 4.00 (m, 3H), 3.48 (t, 2H), 2.33 (s, 3H), 2.25 (s, 3H), 1.99 (m, 2H), 1.56 (m, 2H). |
| 91 | δ 8.37 (d, 1H), 8.30 (d, 1H), 7.41 (m, 2H), 7.26 (m, 1H), 7.16 (t, 1H), 6.89 (d, 1H), 6.73 (m, 2H), 5.63 (d, 1H), 4.31 (m 1H), 3.47 (d, 2H), 3.37 (s, 3H), 2.25 (s, 3H), 1.29 (d, 3H). |
| 92 | δ 8.30 (d, 1H), 8.23 (d, 1H), 7.27 (d, 1H), 7.19 (d, 1H), 7.10 (d, 1H), 6.82 (m, 2H), 6.66 (s, 1H), 5.55 (d, 1H), 4.22 (m 1H), 3.44 (d, 2H), 3.35 (s, 3H), 2.32 (s, 3H), 2.23 (s, 3H), 1.25 (d, 3H). |
| 93 | δ 8.35 (d, 1H), 8.26 (d, 1H), 7.36 (m, 1H), 7.24 (m, 1H), 7.22 (s, 1H), 6.86 (d, 2H), 6.72 (s, 1H), 5.54 (d, 1H), 4.26 (m 1H), 3.46 (d, 2H), 3.37 (s, 3H), 2.25 (s, 3H), 1.29 (d, 3H). |
| 97 | δ 8.34 (d, 1H), 8.27 (d, 1H), 7.71 (m, 2H), 7.37 (m, 1H), 7.31 (d, 1H), 6.92 (s, 1H), 6.85 (d, 1H), 6.61 (s, 2H), 5.44 (d, 1H), 4.25 (m 1H), 3.45 (m, 2H), 3.37 (s, 3H), 1.27 (d, 3H). |
| 98 | δ 8.35 (d, 1H), 8.29 (d, 1H), 7.72 (m, 2H), 7.39 (t, 1H), 7.29 (d, 1H), 6.90 (d, 1H), 6.89 (d, 1H), 6.53 (s, 2H), 5.17 (d, 1H), 4.00 (m, 3H), 3.50 (t, 2H), 2.03 (m, 2H), 1.57 (m, 2H). |
| 99 | δ 8.37 (d, 1H), 8.32 (d, 1H), 7.45 (s, 2H), 7.30 (d, 1H), 6.97 (s, 1H), 6.92 (d, 1H), 6.72 (s, 1H), 5.32 (d, 1H), 4.00 (m, 3H), 3.53 (t, 2H), 2.05 (m, 2H), 1.57 (m, 2H). |
| 100 | δ 8.36 (d, 1H), 8.28 (d, 1H), 7.38 (s, 1H), 7.23 (m, 2H), 6.89 (d, 1H), 6.83 (s, 1H), 6.51 (s, 1H), 5.24 (d, 1H), 4.00 (m, 3H), 3.53 (t, 2H), 2.31 (s, 3H), 2.01 (m, 2H), 1.57 (m, 2H). |

[a]¹H NMR data are in ppm downfield from tetramethylsilane. Couplings are designated by (s)—singlet, (d)—doublet, (t)—triplet, (q)—quartet, (dd)—doublet of doublets, (dt)—doublet of triplets, (br s)—broad singlet, (m)—multiplet.

Biological Examples of the Invention

General protocol for preparing test suspensions for Tests A-R: The test compounds were first dissolved in acetone in an amount equal to 3% of the final volume and then suspended at the desired concentration (in ppm) in acetone and purified water (50/50 mix) containing 250 ppm of the surfactant Trem® 014 (polyhydric alcohol esters). The resulting test suspensions were then used in tests A-R. In Tests A-M, compounds were sprayed as a 200 ppm test suspension (equivalent to a rate of 500 g/ha) or as a 40 ppm test suspension to the point of runoff on the test plants. In Tests N-R, compounds were sprayed as a 100 g/ha test suspension (equivalent to a rate of 100 ppm) on the test plants at an application volume of 1000 L/ha.

Test A

The test suspension was sprayed to the point of run-off on wheat seedlings. The following day the seedlings were inoculated with a spore dust of *Erysiphe graminis* f. sp. *tritici* (the causal agent of wheat powdery mildew) and incubated in a growth chamber at 20° C. for 8 days, after which time disease ratings were made.

Test B

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 7 days, after which time disease ratings were made.

Test C

The test suspension was sprayed to the point of run-off on wheat seedlings. The following day the seedlings were inoculated with a spore suspension of *Septoria nodorum* (the causal agent of wheat glume blotch) and incubated in a saturated atmosphere at 20° C. for 48 h, and then moved to a growth chamber at 20° C. for 7 days, after which time disease ratings were made.

Test D

The test suspension was sprayed to the point of run-off on wheat seedlings. The following day the seedlings were inoculated with a spore suspension of *Septoria tritici* (the causal agent of wheat leaf blotch) and incubated in saturated atmosphere at 20° C. for 48 h, and moved to a growth chamber at 20° C. for 19 additional days, after which time disease ratings were made.

Test E

The test suspension was sprayed to the point of run-off on wheat seedlings. The following day the seedlings were inoculated with a spore suspension of *Fusarium graminearum* (the causal agent of wheat head scab) and incubated in a saturated atmosphere at 20° C. for 72 h, and then moved to a growth chamber at 20° C. for 5 days, after which time disease ratings were made.

Test F

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time disease ratings were made.

Test G

The test suspension was sprayed to the point of run-off on cucumber seedlings. The following day the seedlings were inoculated with a spore suspension of *Sclerotinia sclerotiorum* (the causal agent of cucumber white mold) and incubated in saturated atmosphere at 24° C. for 72 h, and then moved to a growth chamber at 24° C. for 3 additional days, after which time disease ratings were made.

Test H

The test suspension was sprayed to the point of run-off on wheat seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time disease ratings were made.

Test I

The test suspension was sprayed to the point of run-off on cucumber seedlings. The following day the seedlings were inoculated with a spore suspension of *Colletotrichum orbiculare* (the causal agent of cucumber *Colletotrichum* anthracnose) and incubated in saturated atmosphere at 20° C. for 24 h, and moved to a growth chamber at 24° C. for 5 additional days, after which time disease ratings were made.

Test J

The test suspension was sprayed to the point of run-off on creeping bent grass seedlings. The following day the seedlings were inoculated with a blended mix of wheat bran and mycelium of *Rhizoctonia oryzae* (the causal agent of turf brown patch) and incubated in a saturated atmosphere at 27° C. for 48 h, and then moved to a growth chamber at 27° C. for 3 days, after which time disease ratings were made.

Test K

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 4 days, after which time disease ratings were made.

Test L

Grape seedlings were inoculated with a spore suspension of *Plasmopara viticola* (the causal agent of grape downy mildew) and incubated in a saturated atmosphere at 20° C. for 24 h. After a short drying period, the test suspension was sprayed to the point of run-off on the grape seedlings and then moved to a growth chamber at 20° C. for 6 days, after which time the test units were placed back into a saturated atmosphere at 20° C. for 24 h. Upon removal, disease ratings were made.

Test M

The test suspension was sprayed to the point of run-off on bluegrass seedlings. The following day the seedlings were inoculated with a spore suspension of *Pythium aphanidermatum* (the causal agent of bluegrass pythium blight) and incubated in a covered containers to provide saturated atmosphere at 27° C. for 48 h, and then the covers were removed and the plants left at 27° C. for 3 additional days, after which time disease ratings were made.

Test N

The test suspension was sprayed on grape seedlings. The following day the seedlings were inoculated with a spore suspension of *Uncinula necator* (the causal agent of grape powdery mildew) and incubated in a greenhouse or growth chamber at 24° C. for 10-12 days, after which time disease ratings were made.

Test O

The test suspension was sprayed on apple seedlings. The following day the seedlings were inoculated with a spore suspension of *Venturia inaequalis* (the causal agent of apple scab) and incubated in a saturated atmosphere at 20° C. for 48 h, and then moved to a growth chamber at 22° C. for 12 days, after which time disease ratings were made.

Test P

The test suspension was sprayed on rice seedlings. The following day the seedlings were inoculated with a blended mix of wheat bran and mycelium of *Rhizoctonia oryzae* (the causal agent of rice sheath blight) and incubated in saturated atmosphere at 27° C. for 48 h, and moved to a growth chamber at 27° C. for 5 additional days, after which time disease ratings were made.

Test Q

The test suspension was sprayed on rice seedlings. The following day the seedlings were inoculated with a spore suspension of *Magnaporthe grisea* (the causal agent of rice blast) and incubated in a saturated atmosphere at 24° C. for 24 h, and then moved to a growth chamber at 27° C. for 7 days, after which time disease ratings were made.

Test R

The test suspension was sprayed on grape seedlings. The following day the seedlings were inoculated with a spore suspension of *Plasmopara viticola* (the causal agent of grape downy mildew) and incubated in a saturated atmosphere at 20° C. for 24 h, then moved to a growth chamber at 20° C. for 7 days, after which time the test units were placed back into a saturated atmosphere at 20° C. for 24 h. Upon removal, disease ratings were made.

Results for Tests A-M are given in Table A1. In the table, a rating of 100 indicates 100% disease control and a rating of 0 indicates no disease control (relative to the controls). A dash (-) indicates no test results. All results are for 200 ppm except where followed by "*" which indicates 40 ppm.

TABLE A1

| Cmpd No. | Test A | Test B | Test C | Test D | Test E | Test F | Test G | Test H | Test I | Test J | Test K | Test L | Test M |
|---|---|---|---|---|---|---|---|---|---|---|---|---|---|
| 1 | 76 | 96 | 100 | 0 | 98 | 98 | — | — | 99 | — | — | — | — |
| 2 | 94 | 99 | 99 | 71 | 95 | 93 | — | 97 | 99 | — | — | — | — |
| 3 | 64 | 96 | 100 | 67 | 27 | 0 | — | — | 94 | — | — | — | — |
| 4 | 0 | 91 | 99 | 11 | 0 | 0 | — | — | 66 | — | — | — | — |
| 5 | — | 100 | 100 | 98 | 98 | 80 | — | 0 | 99 | — | — | — | — |
| 6 | — | 97 | 100 | 58 | 84 | 85 | — | 98 | 0 | — | — | — | — |
| 7 | — | 99 | 100 | 87 | 0 | 0 | — | 0 | 96 | — | — | — | — |
| 8 | — | 97 | 95 | 42 | 77 | 0 | — | 41 | 0 | — | — | — | — |
| 9 | — | 100 | 99 | 20 | 80 | 73 | — | 99 | 100 | — | — | — | — |
| 10 | — | 93 | 100 | 10 | 61 | 0 | — | 97 | 99 | — | — | — | — |
| 11 | — | 96 | 100 | 0 | 99 | 96 | — | 98 | — | — | — | — | — |
| 12 | — | 79 | 100 | 0 | 96 | 37 | — | 98 | — | — | — | — | — |
| 13 | — | 100 | 100 | 26 | 96 | 87 | — | 98* | — | — | — | — | — |
| 14 | — | 79 | 100 | 0 | 92 | 55 | — | 95 | — | — | — | — | — |
| 15 | — | 32 | 92 | 0 | 0 | 0 | — | 90 | 93 | — | — | — | — |
| 16 | — | 99 | 99 | 71 | 99 | 96 | — | 98 | 97 | — | — | — | — |
| 17 | — | 86 | 99 | 66 | 0 | 97 | — | 90 | 98 | — | — | — | — |
| 18 | — | 100 | 100 | 0 | 85 | 95 | — | 89* | 99 | — | — | — | — |
| 19 | — | 97 | 100 | 87 | 97 | 99 | — | 93 | 99 | — | — | — | — |
| 20 | — | 74 | 100 | 20 | 91 | 99 | — | 96 | 0 | — | — | — | — |
| 21 | — | 99 | 97 | 13 | 87 | 72 | — | — | 96 | — | — | — | — |
| 22 | 69* | 99 | 100 | 36 | 99 | 99* | — | 100* | 100 | — | — | — | — |
| 23 | 0* | 98 | 100 | 13 | 98 | 90 | — | 100* | 99 | — | — | — | — |
| 24 | — | 97 | 100 | 24 | 99 | 70 | — | 100 | — | — | — | — | — |
| 25 | — | 99 | 100 | 16 | 99 | 63 | — | 99 | — | — | — | — | — |
| 26 | — | 98 | 100 | 2 | 98 | 17 | — | 91 | — | — | — | — | — |
| 27 | 0 | 100 | 99 | 75 | 97 | 94 | — | 100* | — | — | — | — | — |
| 28 | — | 73 | 99 | 0 | 90 | 84* | — | 85 | 96 | — | — | — | — |
| 29 | — | 100 | 100 | 90 | 99 | 91 | — | 97* | — | — | — | — | — |
| 30 | 67 | 99 | 100 | 88 | 91 | 96 | — | 87* | — | — | — | — | — |
| 31 | 0 | 100 | 100 | 88 | 89 | 99 | — | 92 | — | — | — | — | — |
| 32 | 0 | 99 | 100 | 39 | 38 | 94 | — | 99 | — | — | — | — | — |
| 33 | 0 | 87 | 99 | 22 | 83* | 0 | — | 94 | — | — | — | — | — |
| 34 | 0 | 98 | 100 | 59 | 68 | 0 | — | 94 | — | — | — | — | — |
| 35 | 72 | 100 | 98 | 7 | 98 | 91 | — | — | — | — | — | — | — |
| 36 | 0* | 99* | 100* | 29* | 91* | 99* | — | 99* | — | — | — | — | — |
| 37 | 79 | 99 | 98 | 0 | 41 | 0 | — | 72 | — | — | — | — | — |
| 38 | 0 | 98 | 100 | 0 | 65 | 13 | — | 93 | — | — | — | — | — |

TABLE A1-continued

| Cmpd No. | Test A | Test B | Test C | Test D | Test E | Test F | Test G | Test H | Test I | Test J | Test K | Test L | Test M |
|---|---|---|---|---|---|---|---|---|---|---|---|---|---|
| 39 | 0* | 98* | 99* | 24* | 82* | 60* | — | 99* | — | — | — | — | — |
| 40 | 63 | 90 | 99 | 27 | 48 | 99 | 83 | — | 84 | 0 | 0 | 0 | 0 |
| 41 | 57 | 98 | 99 | 15 | 45 | 96 | 94 | — | 54 | 34 | 0 | 0 | 0 |
| 42 | 0 | 88 | 94 | 9 | 0 | 75 | — | — | 92 | 0 | 0 | 16 | 0 |
| 43 | 29 | 99 | 99 | — | 100 | 92 | — | — | 90 | 9 | 0 | 0 | 0 |
| 44 | 0 | 89 | 98 | — | 99 | 0 | — | — | 40 | 0 | 0 | 0 | 0 |
| 45 | 77 | 79 | 98 | — | 90 | 20 | — | — | 8 | 0 | 0 | 0 | 0 |
| 46 | 0 | 91 | 97 | — | 94 | 7 | — | — | 0 | 0 | 0 | 0 | 0 |
| 47 | 0 | 85 | 0 | — | 92 | 0 | — | — | 40 | 0 | 0 | 0 | 0 |
| 48 | 0 | 99 | 87 | — | 0 | 15 | — | — | 26 | 0 | 0 | 0 | 0 |
| 49 | 86 | 99 | 92 | — | 81 | 90 | — | — | 67 | 0 | 0 | 0 | 0 |
| 50 | 0 | 99 | 84 | — | 72 | 94 | — | — | 96 | 0 | 0 | 0 | 0 |
| 51 | 88 | 99 | 98 | — | 48 | 99 | — | — | 92 | 0 | 0 | 0 | 0 |
| 52 | 0 | 94 | 90 | 31 | 0 | 98 | — | — | 0 | — | — | — | — |
| 53 | 88 | 98 | 96 | 41 | 0 | 99 | — | — | 26 | — | — | — | — |
| 54 | 0 | 96 | 64 | 35 | 0 | 85 | — | — | 0 | — | — | — | — |
| 55 | 0 | 95 | 78 | 20 | 0 | 0 | — | — | 0 | — | — | — | — |
| 56 | 84 | 99 | 99 | 82 | 90 | 99 | — | — | 90 | — | — | — | — |
| 57 | 0 | 95 | 51 | 9 | 0 | 0 | — | — | 0 | — | — | — | — |
| 58 | 44 | 98 | 99 | 36 | 0 | 86 | — | — | 24 | — | — | — | — |
| 59 | 87 | — | 99 | 0 | 0 | 57 | — | — | 0 | — | — | — | — |
| 60 | 97 | 95 | 100 | 18 | 0 | 61 | — | — | 0 | — | — | — | — |
| 61 | 0 | 96 | 99 | 32 | 0 | 0 | — | — | 0 | — | — | — | — |
| 62 | 0 | 94 | 0 | 14 | 0 | 0 | — | — | 0 | — | — | — | — |
| 63 | 0 | 80 | 0 | 41 | 0 | 0 | — | — | 90 | — | — | — | — |
| 64 | 0 | 94 | 97 | 95 | 0 | 0 | — | — | 92 | — | — | — | — |
| 65 | 46 | 80 | 96 | 0 | 0 | 0 | — | — | 83 | — | — | — | — |
| 66 | 0 | 85 | 99 | 92 | 64 | 84 | — | — | — | — | — | — | — |
| 67 | 17 | 97 | 99 | 52 | 0 | 95 | — | — | 79 | — | — | — | — |
| 68 | 0 | 95 | 99 | 96 | 0 | 93 | — | — | — | — | — | — | — |
| 69 | 91 | 94 | 97 | 77 | 0 | 85 | — | — | 0 | — | — | — | — |
| 70 | 95 | 98 | 99 | 17 | 84 | 97 | — | — | 98 | — | — | — | — |
| 71 | 0 | 94 | 99 | 25 | 0 | 77 | — | — | 46 | — | — | — | — |
| 72 | 0 | 80 | 95 | 11 | 0 | 0 | — | — | 0 | — | — | — | — |
| 73 | 43 | 96 | 99 | 40 | 0 | 57 | — | — | 85 | — | 0 | — | 0 |
| 74 | 0 | 94 | 99 | 72 | 0 | 48 | — | — | 17 | — | — | — | — |
| 75 | 0 | 83 | 89 | 28 | 0 | 90 | — | — | 9 | — | — | — | — |
| 76 | 36 | 99 | 99 | 87 | 93 | 97 | — | — | 72 | — | — | — | — |
| 77 | 95 | 99 | 99 | 61 | 92 | 88 | — | — | 96 | — | — | — | — |
| 78 | 39 | 99 | 99 | 60 | 0 | 93 | — | — | 98 | — | — | — | — |
| 79 | 0 | 99 | 99 | 5 | 0 | 94 | — | — | 96 | — | — | — | — |
| 80 | 86 | 100 | 99 | 93 | 98 | 99 | — | — | 98 | — | — | — | — |
| 81 | 95 | 100 | 99 | 92 | 97 | 99 | — | — | 91 | — | — | — | — |
| 82 | 0 | 98 | 91 | 68 | 0 | 0 | — | — | 29 | — | — | — | — |
| 83 | 0 | 95 | 99 | 92 | 0 | 53 | — | — | 0 | — | — | — | — |
| 84 | 28 | 91 | 99 | 59 | 0 | 99 | — | — | 0 | — | — | — | — |
| 85 | 56 | 94 | 99 | 0 | 0 | 93 | — | — | 96 | — | — | — | — |
| 86 | 27 | 55 | 94 | 0 | 0 | 96 | — | — | 0 | — | — | — | — |
| 87 | 87 | 95 | 100 | 49 | 0 | 96 | — | — | 88 | — | — | — | — |
| 88 | 99 | 100 | 97 | 0 | 91 | 0 | — | — | 0 | — | — | — | — |
| 89 | 74 | 95 | 100 | 0 | 89 | 99 | — | — | 0 | — | — | — | — |
| 90 | 98 | 99 | 100 | 47 | 100 | 99 | — | — | 93 | — | — | — | — |
| 91 | 97 | 99 | 94 | 7 | 19 | 98 | — | — | 0 | — | — | — | — |
| 92 | 91 | 94 | 100 | 65 | 0 | 99 | — | — | 0 | — | — | — | — |
| 93 | 84 | 99 | 100 | 78 | 66 | 98 | — | — | 0 | — | — | — | — |
| 94 | — | 89 | 95 | 69 | 0 | 72 | — | 0 | 0 | — | — | — | — |
| 95 | — | 88 | 94 | 77 | 0 | 0 | — | 0 | 0 | — | — | — | — |
| 96 | — | 85 | 99 | 28 | 0 | 86 | — | 0 | 0 | — | — | — | — |
| 97 | 0 | 97 | 100 | 67 | 48 | 99 | — | — | 93 | — | — | — | — |
| 98 | 89 | 99 | 99 | 83 | 97 | 91 | — | — | 0 | — | — | — | — |
| 99 | 0 | 95 | 100 | 30 | 92 | 0 | — | — | 0 | — | — | — | — |
| 100 | 0 | 98 | 98 | 77 | 96 | 0 | — | 99 | 0 | — | — | — | — |
| 101 | — | 99 | 100 | 53 | 97 | 99 | — | 92 | 97 | — | — | — | — |
| 102 | — | 93 | 100 | 3 | 27 | 83 | — | 41 | 0 | — | — | — | — |
| 103 | — | 97 | 100 | 1 | 0 | 0 | — | 99 | 0 | — | — | — | — |
| 104 | — | 99 | 94 | 10 | 0 | 0 | — | 0 | 0 | — | — | — | — |
| 105 | 0 | 97 | 92 | — | 73 | 78 | — | — | 0 | 0 | 0 | 0 | 0 |
| 106 | 24 | 94 | 99 | 17 | 32 | 85 | — | — | 37 | 0 | 0 | 0 | 0 |
| 107 | 0 | 94 | 100 | 8 | 89 | 28 | — | — | 72 | 0 | 0 | 0 | 0 |
| 108 | 0 | 80 | 0 | — | 98 | 38 | — | — | 0 | 0 | 0 | 0 | 0 |
| 109 | 0 | 96 | 94 | 5 | 0 | 0 | — | — | 9 | — | — | — | — |
| 110 | — | 89 | 60 | 9 | 0 | 65 | — | 89 | 97 | — | — | — | — |

Results for Tests N-R are given in Table A2. In the table, a rating of 100 indicates 100% disease control and a rating of 0 indicates no disease control (relative to the controls). A dash (-) indicates no test results. All results are for 100 ppm.

TABLE A2

| Cmpd. No. | Test N | Test O | Test P | Test Q | Test R |
|---|---|---|---|---|---|
| 1 | 90 | 78 | — | — | 26 |
| 2 | 89 | 95 | 100 | 93 | 60 |
| 11 | 85 | 92 | — | — | 27 |
| 16 | 99 | 76 | — | — | 40 |
| 18 | 99 | 83 | 100 | 100 | 86 |
| 19 | 95 | 33 | — | — | 73 |
| 21 | 57 | 99 | — | — | 79 |
| 22 | 99 | 99 | 100 | 100 | 83 |
| 23 | 61 | 99 | — | — | 30 |
| 25 | 99 | 59 | — | — | 86 |
| 26 | 69 | 96 | — | — | 96 |
| 56 | 64 | 75 | 100 | 98 | 97 |
| 67 | 55 | 73 | — | — | 94 |
| 81 | 97 | 69 | — | — | 97 |
| 90 | 98 | — | — | — | 98 |
| 99 | 30 | 83 | — | — | 99 |

What is claimed is:
1. A compound selected from Formula 1, or an N-oxide or salt thereof,

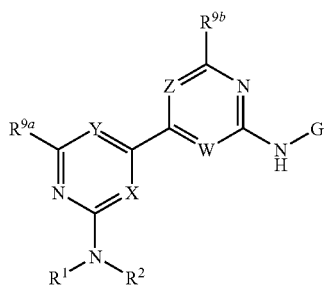

wherein
$R^1$ is H, halogen, cyano, hydroxy, amino, nitro, —CHO or —C(=O)NH$_2$; or $C_1$-$C_6$ alkyl, $C_2$-$C_6$ alkenyl, $C_2$-$C_6$ alkynyl, $C_2$-$C_8$ alkylcarbonyl, $C_2$-$C_8$ alkoxycarbonyl, $C_2$-$C_8$ alkylaminocarbonyl, $C_3$-$C_{10}$ dialkylaminocarbonyl, $C_1$-$C_6$ alkoxy, $C_3$-$C_8$ cycloalkoxy, $C_2$-$C_8$ alkylcarbonyloxy, $C_4$-$C_{10}$ cycloalkylcarbonyloxy, $C_1$-$C_6$ alkylthio, $C_3$-$C_8$ cycloalkylthio, $C_1$-$C_6$ alkylsulfinyl, $C_1$-$C_6$ alkylsulfonyl, $C_3$-$C_8$ cycloalkylsulfonyl, $C_1$-$C_6$ alkylamino, $C_2$-$C_8$ dialkylamino, $C_3$-$C_8$ cycloalkylamino, $C_2$-$C_8$ alkylcarbonylamino, $C_1$-$C_6$ alkylsulfonylamino, $G^A$, $G^N$ or naphthalenyl, each optionally substituted with one or more substituents selected from the group consisting of halogen, cyano, hydroxy, amino, nitro, —CHO, —C(=O)OH, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_4$-$C_{10}$ cycloalkylcarbonyl, $C_2$-$C_8$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_6$ alkylthio, $C_1$-$C_6$ haloalkylthio, $C_3$-$C_8$ cycloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_3$-$C_8$ cycloalkylsulfonyl, $C_3$-$C_{10}$ trialkylsilyl, $C_1$-$C_6$ alkylamino, $C_2$-$C_8$ dialkylamino, $C_1$-$C_6$ haloalkylamino, $C_2$-$C_8$ halodialkylamino, $C_3$-$C_8$ cycloalkylamino, $C_2$-$C_8$ alkylcarbonylamino, $C_2$-$C_8$ haloalkylcarbonylamino, $C_1$-$C_6$ alkylsulfonylamino, $C_1$-$C_6$ haloalkylsulfonylamino, $G^A$, $G^N$ and phenyl;
$R^2$ is H, cyano, hydroxy, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_2$-$C_8$ alkoxyalkyl, $C_4$-$C_{10}$ cycloalkoxyalkyl or $C_3$-$C_{10}$ alkoxyalkoxyalkyl; or
$R^1$ and $R^2$ are taken together with the nitrogen to which they are attached to form a 3- to 7-membered ring, containing ring members in addition to the nitrogen selected from the group consisting of C($R^8$)$_2$, O, S, NR$^3$, —C($R^8$)=C(CR$^8$)—, —C($R^8$)=N—, —N=N—, C(=O), C(=S), C(=NR$^4$), S(=O)$_p$(=NR$^4$)$_q$ and SiR$^{5a}$R$^{5b}$;
each $G^A$ is independently a benzoyl, phenoxy or phenylsulfonyl or a 5- or 6-membered heteroaromatic ring;
each $G^N$ is independently a 3- to 7-membered nonaromatic carbocyclic or heterocyclic ring, containing ring members selected from the group consisting of C($R^8$)$_2$, O, S, NR$^3$, —C($R^8$)=C(CR$^8$)—, —C($R^8$)—N—, —N=N—, C(=O), C(=S), C(=NR$^4$), S(=O)$_p$(=NR$^4$)$_q$ and SiR$^{5a}$R$^{5b}$;
each $R^3$ is independently H, cyano, hydroxy, —C(=O)NH$_2$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, $C_3$-$C_8$ cycloalkyl, $C_3$-$C_8$ halocycloalkyl, $C_4$-$C_{10}$ alkylcycloalkyl, $C_4$-$C_{10}$ cycloalkylalkyl, $C_5$-$C_{12}$ alkylcycloalkylalkyl, $C_3$-$C_8$ cycloalkenyl, $C_2$-$C_8$ alkoxyalkyl, $C_4$-$C_{10}$ cycloalkoxyalkyl, $C_3$-$C_{10}$ alkoxyalkoxyalkyl, $C_2$-$C_8$ alkylthioalkyl, $C_2$-$C_8$ alkylsulfinylalkyl, $C_2$-$C_8$ alkylsulfonylalkyl, $C_2$-$C_8$ alkylaminoalkyl, $C_4$-$C_{10}$ dialkylaminoalkyl, $C_3$-$C_8$ haloalkylaminoalkyl, $C_4$-$C_{10}$ cycloalkylaminoalkyl, $C_2$-$C_{10}$ alkylcarbonyl, $C_2$-$C_{10}$ haloalkylcarbonyl, $C_4$-$C_{10}$ cycloalkylcarbonyl, $C_2$-$C_{10}$ alkoxycarbonyl, $C_4$-$C_{10}$ cycloalkoxycarbonyl, $C_2$-$C_{10}$ alkylaminocarbonyl, $C_3$-$C_{10}$ dialkylaminocarbonyl, $C_4$-$C_{10}$ cycloalkylaminocarbonyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkoxyalkoxy, $C_1$-$C_6$ alkylthio, $C_1$-$C_6$ haloalkylthio, $C_3$-$C_8$ cycloalkylthio, $C_1$-$C_6$ alkylsulfonyl, $C_1$-$C_6$ haloalkylsulfonyl, $C_3$-$C_8$ cycloalkylsulfonyl, $C_3$-$C_5$ trialkylsilyl or $C_3$-$C_5$ halotrialkylsilyl;
each $R^4$ is independently H, cyano, amino, hydroxy, $C_1$-$C_6$ alkyl, $C_3$-$C_{10}$ cycloalkyl, $C_2$-$C_6$ alkylcarbonyl, $C_2$-$C_6$ haloalkylcarbonyl, $C_1$-$C_6$ alkoxy, phenyl or benzoyl;
each $R^{5a}$ and $R^{5b}$ is independently $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_4$-$C_{10}$ cycloalkylalkyl, $C_4$-$C_{10}$ alkylcycloalkyl, $C_5$-$C_{12}$ alkylcycloalkylalkyl, $C_1$-$C_6$ haloalkyl, $C_1$-$C_6$ alkoxy or $C_1$-$C_6$ haloalkoxy;
G is benzoyl, phenoxy, phenylethynyl, phenylsulfonyl or —(CR$^{6a}$R$^{6b}$)$_n$G$^B$;
$G^B$ is a phenyl ring, naphthalenyl or 5- to 6-membered heteroaromatic ring, each ring optionally substituted with 1 to 5 substituents independently selected from $R^7$;
each $R^{6a}$ and $R^{6b}$ is independently H, halogen, —C(=O)OH, $C_1$-$C_6$ alkyl, $C_2$-$C_6$ alkenyl, $C_2$-$C_6$ alkynyl, $C_3$-$C_8$ cycloalkyl, $C_3$-$C_8$ halocycloalkyl, $C_4$-$C_{10}$ cycloalkylalkyl, $C_4$-$C_8$ alkylcycloalkyl, $C_5$-$C_{12}$ alkylcycloalkylalkyl, $C_1$-$C_6$ haloalkyl, $C_2$-$C_8$ alkoxycarbonyl, $C_1$-$C_6$ alkoxy or $C_1$-$C_6$ haloalkoxy; or $R^{6a}$ and $R^{6b}$ in geminal configuration are taken together with the carbon atom to which they are attached to form a 3- to 7-membered ring, containing ring members in addition to the carbon atom selected from the group consisting of $C(R^8)_2$, O, S, $NR^3$, —$C(R^8)$=$C(CR^8)$—, —$C(R^8)$=N—, —N=N—, C(=O), C(=S), C(=$NR^4$), S(=O)$_p$(=$NR^4$)$_q$ and $SiR^{5a}R^{5b}$;

$R^7$ is halogen, cyano, hydroxy, amino, nitro, —CHO, —C(=O)OH, —C(=O)$NH_2$, —$SO_2NH_2$, $C_1$-$C_6$ alkyl, $C_2$-$C_6$ alkenyl, $C_2$-$C_6$ alkynyl, $C_1$-$C_6$ haloalkyl, $C_2$-$C_8$ alkylcarbonyl, $C_2$-$C_8$ haloalkylcarbonyl, $C_2$-$C_8$ alkoxycarbonyl, $C_4$-$C_{10}$ cycloalkoxycarbonyl, $C_5$-$C_{12}$ cycloalkylalkoxycarbonyl, $C_2$-$C_8$ alkylaminocarbonyl, $C_3$-$C_{10}$ dialkylaminocarbonyl, $C_1$-$C_6$ alkoxy, $C_1$-$C_6$ haloalkoxy, $C_2$-$C_8$ alkylcarbonyloxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylaminosulfonyl, $C_2$-$C_8$ dialkylaminosulfonyl, $C_3$-$C_{10}$ trialkylsilyl, $C_1$-$C_6$ alkylamino, $C_2$-$C_8$ dialkylamino, $C_2$-$C_8$ alkylcarbonylamino, $C_1$-$C_6$ alkylsulfonylamino, phenyl, pyridinyl or thienyl;

each $R^8$ is independently H, halogen, CN, $C_1$-$C_3$ alkyl or $C_1$-$C_3$ alkoxy;

X is N or $CR^{9c}$;

Y is N or $CR^{9d}$;

W is N;

Z is N;

each $R^{9a}$, $R^{9b}$, $R^{9c}$, $R^{9d}$, $R^{9e}$ and $R^{9f}$ is independently H, halogen, nitro, CN, $C_1$-$C_3$ alkyl, $C_1$-$C_3$ haloalkyl, $C_3$-$C_6$ cycloalkyl, $C_1$-$C_3$ alkoxy or $C_1$-$C_3$ haloalkoxy;

n is an integer selected from 0 through 6; and p and q are independently 0, 1 or 2 in each instance of S(=O)$_p$(=$NR^4$)$_q$, provided that the sum of p and q is 0, 1 or 2;

provided that:
  (a) when $R^1$ is hydroxy, then $R^2$ is other than hydroxy; and
  (b) at least one of X or Y is N.

2. A compound of claim 1 wherein
$R^1$ is $C_1$-$C_6$ alkyl, $C_2$-$C_6$ alkenyl, $C_2$-$C_6$ alkynyl or $G^N$, each optionally substituted with one or more substituents selected from the group consisting of halogen, cyano, hydroxy, amino, nitro, —CHO, —C(=O)OH, —C(=O)$NH_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_8$ cycloalkoxy, $C_3$-$C_8$ halocycloalkoxy, $C_4$-$C_{10}$ cycloalkylalkoxy, $C_2$-$C_6$ alkenyloxy, $C_2$-$C_6$ haloalkenyloxy, $C_2$-$C_6$ alkynyloxy, $C_3$-$C_6$ haloalkynyloxy, $C_2$-$C_8$ alkoxyalkoxy and $G^N$;

$R^2$ is H or $C_1$-$C_6$ alkyl;

G is $G^B$;

X is N;

and Y is CH.

3. A compound of claim 2 wherein
$R^1$ is 2-methoxy-1-methylethyl, 2-ethoxy-1-methylethyl, 2-methoxy-1-ethylethyl, 2-ethoxy-1-ethylethyl, 3-methoxy-1-methylpropyl, 3-ethoxy-1-methylpropyl, 1-ethyl-3-methoxypropyl, 3-ethoxy-1-ethylpropyl or tetrahydro-2H-pyran-4-yl;

$R^2$ is H; and $G^B$ is naphthalenyl or a phenyl or pyridinyl ring, each optionally substituted with up to 3 substituents independently selected from halogen, $C_1$-$C_6$ alkyl, $C_1$-$C_6$ haloalkyl and $C_1$-$C_6$ alkoxy.

4. A compound of claim 3 wherein
$R^1$ is 2-methoxy-1-methylethyl or tetrahydro-2H-pyran-4-yl; and $G^B$ is phenyl optionally substituted at the 3 and 5 positions with halogen.

5. A compound of claim 4 wherein
$G^B$ is phenyl optionally substituted at the 3 position with halogen.

6. A method for controlling plant diseases caused by Ascomycete or Basidiomycete fungal plant pathogens comprising applying to the plant or portion thereof, or to the plant seed or seedling, a fungicidally effective amount of a compound of claim 1.

7. A fungicidal composition comprising (a) a fungicidally effective amount of a compound of claim 1; and (b) a fungicidally effective amount of at least one other fungicide.

8. A fungicidal composition comprising (1) a fungicidally effective amount of a compound of claim 1; and (2) at least one additional component selected from the group consisting of surfactants, solid diluents and liquid diluents.

9. A compound selected from the group consisting of:
N-(3,5-difluorophenyl)-4-[2-[[(1S)-2-methoxy-1-methylethyl]amino]-4-pyrimidinyl]-1,3,5-triazin-2-amine;
N-(3-fluorophenyl)-4-[2-[[(1S)-2-methoxy-1-methylethyl]amino]-4-pyrimidinyl]-1,3,5-triazin-2-amine; and
N-(3-fluorophenyl)-4-[2-[2-methoxy-1-methylethyl)amino]-4-pyrimidinyl]-1,3,5-triazin-2-amine.

10. A compound selected from the group consisting of:
N-(3-chlorophenyl)-4-[2-[(2-methoxy-1-methylethyl)amino]-4-pyrimidinyl]-1,3,5-triazin-2-amine;
N-(3-chlorophenyl)-4-[2-[[(1S)-2-methoxy-1-methylethyl]amino]-4-pyrimidinyl]-1,3,5-triazin-2-amine;
3-[[4-[2-[[(1S)-2-methoxy-1-methylethyl]amino]-4-pyrimidinyl]-1,3,5-triazin-2-yl]amino]benzonitrile;
4-[2-[[(1S)-2-methoxy-1-methylethyl]amino]-4-pyrimidinyl]-N-(3-methylphenyl)-1,3,5-triazin-2-amine; and
N-(3-chloro-4-fluorophenyl)-4-[2-[[(1S)-2-methoxy-1-methylethyl]amino]-4-pyrimidinyl]-1,3,5-triazin-2-amine.

* * * * *

UNITED STATES PATENT AND TRADEMARK OFFICE
CERTIFICATE OF CORRECTION

PATENT NO. : 8,026,359 B2 Page 1 of 1
APPLICATION NO. : 12/741047
DATED : September 27, 2011
INVENTOR(S) : Yuzhong Chen It is certified that error appears in the above-identified patent and that said Letters Patent is hereby corrected as shown below:

Front page "(22) PCT Filed: May 14, 2009" should read --(22) PCT Filed: November 5, 2008--

Column 156, line 27, "–C($R^8$)–N–" should read ---C($R^8$)=N---

Signed and Sealed this
Twenty-fourth Day of January, 2012

David J. Kappos
*Director of the United States Patent and Trademark Office*